United States Patent
Coffin

(10) Patent No.: US 11,274,312 B2
(45) Date of Patent: Mar. 15, 2022

(54) GENES AND USES FOR PLANT ENHANCEMENT

(71) Applicant: Monsanto Technology LLC, St. Louis, MO (US)

(72) Inventor: Marie Coffin, Cary, NC (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 16/873,608

(22) Filed: May 21, 2020

(65) Prior Publication Data

US 2021/0032647 A1    Feb. 4, 2021

Related U.S. Application Data

(63) Continuation of application No. 15/732,766, filed on Dec. 22, 2017, now Pat. No. 10,696,975, which is a continuation of application No. 14/544,230, filed on Dec. 10, 2014, now abandoned, which is a continuation of application No. 12/386,976, filed on Apr. 24, 2009, now abandoned.

(60) Provisional application No. 61/125,908, filed on Apr. 29, 2008.

(51) Int. Cl.
   *C12N 15/82*    (2006.01)

(52) U.S. Cl.
   CPC ..... *C12N 15/8241* (2013.01); *C12N 15/8271* (2013.01)

(58) Field of Classification Search
   None
   See application file for complete search history.

(56) References Cited

U.S. PATENT DOCUMENTS

| | | | |
|---|---|---|---|
| 7,101,712 | B1 | 9/2006 | Kondorosi et al. |
| 7,989,676 | B2 | 8/2011 | Troukhan et al. |
| 10,696,975 | B2 | 6/2020 | Coffin et al. |
| 2003/0233675 | A1 | 12/2003 | Cao et al. |
| 2004/0031072 | A1 | 2/2004 | La Rosa |
| 2005/0138691 | A1 | 6/2005 | Orozco et al. |
| 2006/0048240 | A1 | 3/2006 | Alexandrov et al. |
| 2006/0107345 | A1 | 5/2006 | Alexandrov et al. |
| 2006/0168696 | A1 | 7/2006 | Feldmann et al. |
| 2007/0124833 | A1 | 5/2007 | Abad et al. |
| 2008/0072340 | A1 | 3/2008 | Troukhan et al. |
| 2009/0265815 | A1 | 10/2009 | Alexandrov et al. |
| 2013/0333068 | A1 | 12/2013 | Coffin |
| 2016/0122783 | A1 | 5/2016 | Coffin |
| 2019/0249198 | A1 | 8/2019 | Coffin |

FOREIGN PATENT DOCUMENTS

| | | | | |
|---|---|---|---|---|
| EP | 1033405 | A2 | 9/2000 | |
| EP | 1586645 | A2 | 10/2005 | |
| WO | WO-9964451 | | 12/1999 | |
| WO | WO-9964451 | A2 | 12/1999 | |
| WO | WO-1999064451 | A2 | 12/1999 | |
| WO | WO-0210210 | A2 | 2/2002 | |
| WO | WO-0216655 | A2 | 2/2002 | |
| WO | WO-2002016655 | A2 | 2/2002 | |
| WO | WO-03070901 | A2 | 8/2003 | |
| WO | WO-2003070901 | A | 8/2003 | |
| WO | WO-2005019425 | A | 3/2005 | |
| WO | WO-2006076423 | A | 7/2006 | |
| WO | WO-2006076423 | A2 | 7/2006 | |
| WO | WO-2006081029 | A2 | 8/2006 | |
| WO | WO-2006138005 | A2 * | 12/2006 | ......... C12N 15/8243 |
| WO | WO-2007138070 | | 12/2007 | |
| WO | WO-2007138070 | A2 | 12/2007 | |
| WO | WO-2009009142 | A2 | 1/2009 | |
| WO | WO-09134339 | A2 | 11/2009 | |
| WO | WO-2009134339 | A8 | 11/2009 | |
| WO | WO-2009134339 | A3 | 3/2010 | |
| WO | WO-2010099083 | A1 | 9/2010 | |

OTHER PUBLICATIONS

"U.S. Appl. No. 12/386,976, Examiner Interview Summary dated Aug. 11, 2014", 2 pgs.
"U.S. Appl. No. 12/386,976, Final Office Action dated Aug. 11, 2014", 16 pgs.
"U.S. Appl. No. 12/386,976, Non Final Office Action dated Apr. 2, 2014", 15 pgs.
"U.S. Appl. No. 12/386,976, Response filed Feb. 10, 2014 to Restriction Requirement dated Dec. 17, 2013", 14 pgs.
"U.S. Appl. No. 12/386,976, Response filed Jul. 2, 2014 to Non Final Office Action dated Apr. 2, 2014", 10 pgs.
"U.S. Appl. No. 12/386,976, Restriction Requirement dated Dec. 17, 2013", 11 pgs.
"U.S. Appl. No. 14/544,230, Final Office Action dated Sep. 29, 2017", 11 pgs.
"U.S. Appl. No. 14/544,230, Non Final Office Action dated Jun. 22, 2017", 17 pgs.
"U.S. Appl. No. 14/544,230, Response filed Mar. 26, 2015 to Non Final Office Action dated Jan. 26, 2015", 5 pgs.
"U.S. Appl. No. 14/544,230, Response filed May 25, 2017 to Restriction Requirement dated Apr. 5, 2017", 12 pgs.
"U.S. Appl. No. 14/544,230, Response filed Sep 21, 2017 to Non Final Office Action dated Jun. 22, 2017", 7 pgs.
"U.S. Appl. No. 14/544,230, Restriction Requirement dated Apr. 5, 2017", 6 pgs.
"U.S. Appl. No. 15/732,766, 312 Amendment filed May 22, 2020", 3 pgs.
"U.S. Appl. No. 15/732,766, Final Office Action dated Nov. 22, 2019", 13 pgs.

(Continued)

Primary Examiner — Matthew R Keogh
(74) Attorney, Agent, or Firm — Morrison & Foerster LLP

(57) ABSTRACT

Transgenic seed for crops with enhanced agronomic traits are provided by trait-improving recombinant DNA in the nucleus of cells of the seed where plants grown from such transgenic seed exhibit one or more enhanced traits as compared to a control plant. Of particular interest are transgenic plants that have increased yield. The present invention also provides recombinant DNA molecules for expression of a protein, and recombinant DNA molecules for suppression of a protein.

10 Claims, 13 Drawing Sheets

Specification includes a Sequence Listing.

(56) References Cited

OTHER PUBLICATIONS

"U.S. Appl. No. 15/732,766, Non Final Office Action dated Aug. 14, 2019", 13 pgs.
"U.S. Appl. No. 15/732,766, Notice of Allowability dated Mar. 26, 2020", 6 pgs.
"U.S. Appl. No. 15/732,766, Notice of Allowance dated Feb. 6, 2020", 11 pgs.
"U.S. Appl. No. 15/732,766, PTO Response to Rule 312 Communication dated Jun. 2, 2020", 2 pgs.
"U.S. Appl. No. 15/732,766, Response filed Jan. 17, 2020 to Final Office Action dated Nov. 22, 2019", 8 pgs.
"U.S. Appl. No. 15/732,766, Response filed Nov. 18, 2019 to Non-Final Office Action dated Aug. 14, 2019", 7 pgs.
"U.S. Appl. No. 15/732,766, Response filed Jul. 9, 2019 to Restriction Requirement dated May 17, 2019", 10 pgs.
"U.S. Appl. No. 15/732,766, Restriction Requirement dated May 17, 2019", 6 pgs.
"Brazil Application Serial No. PI 0911501-3, Office Action dated Apr. 4, 2018", with machine translation, 3 pgs.
"Brazil Application Serial No. PI 0911501-3, Office Action dated Sep. 5, 2018", w/ English translation, 4 pgs.
"Brazil Application Serial No. PI 0911501-3, Response filed Jun. 8, 2018", with machine translation, 18 pgs.
"Brazil Application Serial No. PI 0911501-3, Voluntary Amendment filed Jun. 13, 2012", with machine translation, 11 pgs.
"European Application Serial No. 12166547.5, Partial Search Report dated Nov. 22, 2012", 6 pgs.
"European Application Serial No. 09739142.9, Office Action dated Dec. 7, 2010", 2 pgs.
"European Application Serial No. 12166547.5, European Search Report dated Mar. 11, 2013", 10 pgs.
"European Application Serial No. 12166547.5, Office Action dated May 21, 2012", 1 pg.
"European Application Serial No. 12166547.5, Response filed Jul. 5, 2012 to Office Action dated May 21, 2012", 6 pgs.
"European Application Serial No. 13187670.8, Extended European Search Report dated Jun. 3, 2014", 9 pgs.
"European Application Serial No. 11150290.2, Partial European Search Report dated Jun. 24, 2011", 6 pgs.
"European Application Serial No. 11150290.2, Extended European Search Report dated Oct. 10, 2011", 8 pgs.
"F7H2.18 protein—WD40 domain-containing protein", EBI Database Uniprot Q9LMQ0, (Oct. 1, 2000), 1 pg.
"Friedberg", Briefings in Bioinformatics 7:3, (2006), 225-242.
"International Application Serial No. PCT/US2009/002547, International Report on Patentability dated Nov. 11, 2010", (Nov. 11, 2010), 9 pgs.
"International Application Serial No. PCT/US2009/002547, Written Opinion dated Jan. 21, 2010", 8 pgs.
"Internnational Application Serial No. PCT/US2009/002547, International Search Report and Written Opinion dated Jan. 21, 2010", 7 pgs.
"SubName: Full=Centromere protein 0; SubName: Full=Putative uncharacterized protein At5g10710", DATABASE UniProt [Online], XP002719741, retrieved from EBI accession No. Uniprot: Q8GUP4, (Mar. 1, 2003), 4 pgs.
Eddy, Sean R, "Profile Hidden Markov models.", Bioinformatics, 14(9), (1998), 755-763.
Hanke, Guy Thomas, et al., "A Post Genomic Characterization of Arabidopsis Ferredoxins", Plant Physiology, vol. 134, (Jan. 2004), 255-264.
Hori, Tetsuya, et al., "CENP-O Class Proteins Form a Stable Complex and Are Required for Proper Kinetochore Function", Molecular Biology of the Cell, vol. 19, 843-854, Mar. 2008, (Mar. 2008), 843-854.
Penaloza-Vasquez, "", Plant Cell Reports 14, (1995), 482-487.
Petrasek, et al., "", Science 312, (2006), 914-919.

\* cited by examiner

```
SEQ ID No 35795---------------------------------------------------------MS--
SEQ ID No 59830--------------------------------------------------------MSKN
SEQ ID No 23175--------------------------------------------------------MSKN
SEQ ID No 93133--------------------------------------------------------MSKN
SEQ ID No 19860------------------------------------------------------------
SEQ ID No 57392------------------------------------------------------------
SEQ ID No 91490------------------------------------------------------------
SEQ ID No 20139MLSVKPKKWLNRFNWSTGCARPIEDRLREAKKFLSLPVASSSRSRLNLNRLRSSQDLSRS
SEQ ID No 88784------------------------------------------------------------
SEQ ID No 17591------------------------------------------------------------
SEQ ID No 43370------------------------------------------------------------
SEQ ID No 60203------------------------------------------------------------
SEQ ID No  1325------------------------------------------------------------
SEQ ID No 21321------------------------------------------------------------
SEQ ID No 45211---------------MAVTTLRKKSASQGMLRTPSCPYPISSAASSSSASMHGSFSSP
SEQ ID No 50671-----------------------------MTQTPTP------------------------
SEQ ID No 78019-----------------------------MALSPTP------------------------
SEQ ID No 45047------------------------------------------------------------
SEQ ID No 69645------------------------------------------------------------
SEQ ID No 13488------------------------------------------------------------
SEQ ID No 83296------------------------------------------------------------
SEQ ID No 58057------------------------------------------------------------
SEQ ID No 25554------------------------------------------------------------
SEQ ID No  4744------------------------------------------------------------
SEQ ID No 80927------------------------------------------------------------
SEQ ID No 68166------------------------------------------------------------
SEQ ID No 31956------------------------------------------------------------
SEQ ID No 29566------------------------------------------------------------
SEQ ID No 67810------------------------------------------------------------
SEQ ID No 36150------------------------------------------------------------
SEQ ID No 94673------------------------------------------------------------
```

FIG. 4A

```
----------NGA--------GEFELPQEMLAVLPSDPY---------EQLDVARRITAM
ESSYAGV-VGNGG--------GEFELPQEVFSVLPSDPY---------EQLDVARRITAM
GSLYAGS-MGNG---------GEFELPQEVLSVLPSDPY---------EQLDVARRITAM
RGFNAGSSMGNGG--------GEFEISQELLSVLPSDPY---------EQLEVARRITGM
--------MGNG---------GEFELSQEVLAVLPSDPY---------EQLDVARRITAM
--------MGNG---------GEFELSQEVVSVLPSDPY---------EQIDIASRITAM
--------MGSG---------GQGELPQDLVSVLPSDPY---------EQLDVARRITAM
GCRLRPNGMSQNSN-YNSGSGPDFNITDDILAVIPTDPY---------DQLDLARKITSM
--------MSQLT----TG-GTDFSLPDEILAVIPMDPY---------DQLDLARKITSM
--------MSSQG----TGSVVDFDLPDEILSVIPTDPY---------QQLDLARKITSM
--------MAHGG-----GGAPDFDLPDEILSVMPTDPY---------DQLDLARKITSM
--------MGDDQ--------LDFELPEEVLSVIPMDPF---------EQLDLARKITSM
--------MGDDQ--------LDFELPEEVLSVIPMDPF---------EQLDLARKITSM
--------MGDDR--------LDLELSDEVLSVIPMDPF---------EQLDLARKITSM
TGTRNLVAASPPPP---PLFPTSTGTYPAFISATTPDECPAAALVMLPGKLEVARKITAV
-------AAAAPAP---AVAVSEAGLPDAIAAALPPDPY---------EQLEVARKITAV
----TAVAAPPPEPGPEPAPSAELPLPDAIAAALPPDPY---------EQLEVARKITAV
--------MPLAEG--------EFALPDEVLAVMPRDPY---------EQLDLARRITAL
--------MPLAEG--------EFALPDEVLAVMPRDPY---------EQLDLARRITAL
--------MPLAEG--------EFALPDEVLAVMPRDPY---------EQLDLARRITAL
--------MPPAEGAAAGLGVSEFALPDGVLAVLPRDPY---------EQLDLARRITAL
--------MPLGD-----DAAADFALPDELLAALPRDPY---------EQLDLARRITAL
--------MPLGD-----DAAADFALPDELLAALPRDPY---------EQLDLARRITAL
--------MPLGDG----AEAADFVLPDELLAALPRDPY---------EQLDLARRITAL
--------MARHEAA---AGVVDFHLPDEILAVIPTDPY---------EQLDVARKITSM
--------MARHEAA---AGVVDFHLPDEILAVIPTDPY---------EQLDVARKITSM
--------MARQEAVG-AATGVDFHLPDEILAVIPTDPY---------EQLDVARKITSM
--------MSKGANYG-PDNASDFELPEELLGILPTDPY---------EQLELARRITSI
--------MSKAG---------EMQLADGILMNLPEHPD---------QQLEIAQQITRF
------------------------------------------------------------
--------mxxxxx----xxxxxfxlpxexlxvxpxdpy---------eqldxarxitxx
```

FIG. 4B

```
AVAARVSKLESETGKLRQKLAEKEHLTYGLQERVVEAENTL-QETSSRLSHALDEQ----
AVAARVSKLESETGKLRQKLTEKERLISGLQERASEAEGTL-QETSARLSHALDEQ----
AVAARVSKLESETGKLRQKLSEKEHVIYGLQDRVVEAENTL-QETSARLSHALDEQ----
AVAARVSKLEGETVKLRQKLTEKEHLIYGLQERIGEAQSTL-QETSARLSVALDVQ----
AISTRMSKLESETGKLRQRLAEKEHVILGLQERVAEAQSTL-QETNSKITQSMDEQ----
AVSTRVSKLETEAGKLRQKMTEKEHVIHGLQERISKATGAL-QEQSAKLSHSEAEQ----
AVATSMSKLESETGKLRQKLTEKEQVIHGLQGRVLEAEAAL-QVLNAKLSQSEAEQ----
AIASRVSKLESEVGRLRQMMYEKDRVAFDLEEKVSQLERAY-QESESRLKMVIDEN----
AIASRVSYLESERGRMKQRMFDKDRIIFELREKLGHLQRVC-QESESKLSLALDEN----
AIASRVSSLESDASRLRQKLLEKDRIILDLEDRLSSLTRAS-HQTDSTLNTALNEN----
AIASRVTKLETEAGTLRQRLREKDELIQELEDKVSQLDGAH-QDAELRLKILREDN----
AIASRVSNLDSEVVELRQKLLGKESVVRELEEKASRLERDC-READSRLKVVLEDNIQDF
AIASRVSNLDSEVVELRQKLLGKESVVRELEEKASRLERDC-READSRLKVVLEDN----
AIASRVSNLDSEVVELRQKLQGKETVVRELVDKASRLEKDR-READSRLKTVLEEN----
AVAARASRLELEAARLRQKLADKDRLAAELADRAASLEQAL-RDSDARLRAALDDN----
AVAARASRLELEAARLRQKLADKDRLAAELADRAASLEQAL-RDSDARLRAALDDN----
AVASRASRLELEAARLRQRLADRDRLAAELADRAAKLEQAL-RDADARLRSALDDN----
AVAGRVTGLEREAARLRESAADKDRENGELRERVALLDRAL-QETNSRLRAALEDN----
AVAGRVTGLEREAARLRESAADKDRENGELRERVALLDRALXQETNSRLRAALEDN----
AVAGRVTGLEREAARLRESPADKDRENGELRERVALLDRAL-QETNSRLRAALEDN----
AVAGRVTGLEREAARLREGAAERDRENAELRDRVALLDRAL-QETNARLRAALEDN----
AVAGRVSGLEREAGRLRAEAAGKDRESAELRERVALLDAAL-QETNARLRAALEDN----
AVAGRVSGLEREAGRLRAEAAGKDRESAELRERVALLDAAL-QETNARLRAALEDN----
AVSGRVSGLEREAGRLRAEAAGKDRENAELRERVVLLDTAL-QETNARLRAALEDN----
AIASRVSRLEADAARLRRDLADRDRAEADLRARLA--------DSDARLLAALDEN----
AIASRVSRLEADAARLRRDLADRDRAEADLRARLA--------DSDARLLAALDEN----
AIASRVSRLEADVARLRRDLADRDRGEADLRARLA--------DSDARLLAALDEN----
AVGSRVSKLEAEASKFKIKITEKDQRIYELEEKINQLEKAL-NETDERLSHSLEEQ----
AVSGRVANLEGELDCLTLKLVEKAAIVEDLQARVSAVESML-GGITAKLAVALQDQ----
MLERRVSTLELELQDMAAKS---------------------KQAVEEA--------
axaxrvsxLexexxxlrxxxxkxxxxxlxxrxxxxxxxx-xxxxxrlxxalxxx----
```

FIG. 4C

```
--------TKLANEKNALAAQVKKLMRDVAKLETFKRTLMQSLQEDDDHPYVK------
--------AKLANEKNALAAQVKKLMRDVAKLETFKRTLMQSLQEDDDNPKAEGGDKRGV
--------NKLANDKNMLAAQVKKLMRDVAKLETFKRTLMNSLQEDDENPNGEG-ERRGV
--------NKLASEKNALVAQVKKLTRDVAKLETFKRTLMNSLQEDDESPNGEG-GKRGV
--------AKLATEKNSLALQVKKLMRDVAKLETFKRTLMQSLQEEDDKHGGEGGNNRGE
--------VKLVNEKNALATQVKNLLRDVAKLETFKRALMKSLEQEDENP---------
--------TKLVDEKNSLALQVKGLLRDVAKLETFKRTLMHSLEQEEDDN--------L
--------TRLSKERDSLAMTAKKMGRDLAK---------------------QTE
--------VKLSKEKDSLAMTAKKLGRDLAKLETFKRQLMQSLSDDNS-S------QAE
--------IKLSKERDQLAATVKKLSRDFAKLETFKKQLMQSLTDDNA-S------HAE
--------MKLLKERDSLALTANKLNRDLAKLEAFKRQLMQSLNEENSKQ------QTE
LGVTGYLRMNLTKEKDSLAMTVTKLTRDLAKLETFKRQLIKSLSDESGP-------QTE
--------MNLTKEKDSLAMTVTKLTRDLAKLETFKRQLIKSLSDESGP-------QTE
--------MILTKEKDSLAMTVTKLTRDLAKLETFKRQLIKSLSDESAPP-------QTE
--------AKLAKERDSLAHTSKKLARDLAKLETFKRHLMQSLGDDNPPI--------QE
--------AKLAKERDSLAHTSKKLARDLAKLETFKRHLMQSLGDDNPP----------E
--------AKLAKERDSLAQTSKKLARDLAKLETFKRHLMQSLGDDNSQTH------HQE
--------IKLSKERDSLAQTSKKLARDLQKLESFKRHLMQSLRDDSPSP--------QE
--------IKLSKERDSLAQTSKKLARDLQKLESFKRHLMQSLRDDSPSP--------QE
--------IKLSKERDSLAQTSKKLARDLQKLESFKRHLMQSLRDDSPS-----------
--------IQLSKERDSLAQTSKKQARDLHKLESFKRHLMQSLRDDSTSP--------QE
--------IKLSKERDSLAQTSKKLARDLHKLESFKRHLMQSLRDDSSST--------QE
--------IKLSKERDSLAQTSKKLARDLHKLESFKRHLMQSLRDDSSST--------QE.
--------IKLSXERDSLAQTSXKLARDLQKLESFXRHLMXSLRDDXXSP--------QE
--------AKLAKERDSLASTAKKMARNLAKLEAFKKQLMKSLSEDNLLQ------LSE
--------AKLAKERDSLASTAKKMARNLAKLEAFKKQLMKSLSEDNLLQ------LSE
--------AKLVKERDTLALTAKKLSRNLAKLEAFKKQLMKSLSEDNLLQ------LSE
--------AKLNHDKSVLAATVKKLNRDVAKLETFKKTLMQSLQEEDEAAQ-----ADV
--------AKLAEVKDALADQMKTLMCQVSVLDDFKKAVVRSLGPNSDFD--------D
--------HRLQSEKSLLAETVKRLHKEVARLDAFKKNLLNHLNSEDEPG----------
--------xkLxxexdxLaxtxkklxrdxaklexfkrxlmxslxxxxxxx------xxx
```

FIG. 4D

```
---------AESTVSRAQ--LLDDDGQSAK-SFSTSSSGTTEERGYREGAALKPPTRYQS
SSNLAIRRASQAESSLSR--ALDDDGQSTK-SFSTSSSVNTEERGFREGGASKPPTSYQT
NSSLAIIRASQAESTVSRSPILDDDHQPGKLSYESDSSVITEERGYRQGAVLKPPTSHQG
NPSLAIKRASQAESTVSRTPVSDDDYQSEKSSYDTDSSLTSEERGYQH--ASRPPTSYQN
PQSLALYKATQAETLSKAQI-FEDDGRYARASFSANPPQYHDDADSKS----ATPTSQSA
PANSAMWKASRGTTR-------------------------------------PKSQSA
APNSAIWKASQAESAVVKAQNFEDHGRYAKTSSRPDPPKYQGDLDAVSDGRTTPPKSRNG
TVDIGTCDQS---IPKAYPD---IDDGTNGYVVNQPLSGFTEYRNSTDEASRLAVQRFSV
TVDIGTCDQS---VPRAYSE---KDEGMNVYVAHHNFNGSTDMGN-TDEAPRHAGQRYSI
TIDIGTCDQS---VPKAYPD---KDDDGSGYMVHHSYNGPADVGKTNDEASRYSGQRFSL
TVDIGTYDQT---VPKAYYT---GDE-PNGYTKHHSYSGSTESASLNDDVSKQTGQKHSI
PVDIRTCDQP-----GSYPG---KDGRINAHSIKQAYSGSTDTNNPVVEASKYTGNKFSM
PVDIRTCDQP-----GSYPG---KDGRINAHSIKQAYSGSTDTNNPVVEASKYTGNKFSM
PVDIKACDQSSIGSTGSYTG---KDERTTVHSTHRSYSGSSDMNNPIVEASKYAGNKFSM
TVDIRTCEQSVA-KASSWKDGVAHSRHHHPVSSLADGSTEIES-VNQEVA-RPFEQKLSV
TVDIRTCEQSVA-KASSWKDGVAHSRHHHPVSSLADGSTEIES-VNQEVA-RPFEQKLSV
TVDIRTYEQSVA-KANSWKDGLEKN--SHPVSSLSDESVEADS-VNQEVTTRPFEQKLTI
TVDITTCDQSISSKASSCGD---GDSITHTTTNLLSTSLDVGSTVQE--VSKPPIQKYAL
TVDITTCDQSISSKASSCGD---GDSITHTTTNLLSTSLDVGSTVQEGTVXKPPIQKYAL
--KMSGTNLSLIFSLN-IAD---GDSITHTTTNLLSTSLDVGSTVQEGTVSKPPIQKYAL
TVDITTCDQSVSSKTSSCGD---G-SISHTAANLLNGSGDLGSTTRE--AARTPVQKYAL
TVDITTCDQPVASKASSSAD---GGSVSNPATNIFTESLDVGSTNRDGAAARPPIQKYSL
TVDITTCDQPVASKASSSAGYRYGGSVSNPATNIFTESLDVGSTNRDGTAARPPIQKYSL
TVDITTCDQSVATKASSSGD---GGSGSHPTTNIFSESLDAGSTNRDGTASRPPIQKYAP
IGDDRDFDAN----NNLTAR------VPSWEDEVSSSRTSADSSSRSTMTESAQEHQFSV
IGDDRDFDAN----NNLTAR------VPSWK---------------------EHQFSV
TGEDRDVDAE----NNGTAR------IPSWKDEVSSSHTSSNTSSRSTITESAQGYQFSI
TQNTATRRVTSAKLSFSLSS-RDDSNVPIGETNQVSSAVSETNSTLDGDNQASRHGKSK
NPGDATYAYAPEASASTYCS--------SEKSLLQLPLIMSKSTEPPTPTKRKQQGQYSC
------------------------LEPSVAAADVAGERLVSEVLSSISKPPPPQMGV
xxxxxxxxxxxxxxxxxxx-xxxxxxxxxxxxxxxxxxxxxxxxxxxxxxxxxx
```

FIG. 4E

```
--------SAHNSARG--TPHLSPKLTP--SGSP-RGSGRTSPRRSMSLTDNSHRISLPS
--------SAHNSAQG--TPHLSPKLTS--SG-----SGRASPRRSMSLTDNSHRISLPS
--------SAHNSARG--TPHLSPRLTP--SGSPKRQSARTSPRRSMSSSENSHRISLPS
--------SAQNSARG--TPRLSPRLTP--SVSPKQQSARGSPQRSMSLTENSHRISLPS
RNSPKQIIRGTSSARG--TPSLTPRLTP--TGSPKPQPKKGSPLPSS-YTLDSQHIQIPT
HTSPKQIMRGIDSARGSMTPRLTPLHTS--MTSPQPKPKK-EALPR------ASVTQIPS
RTVPKQIVGGSTTLRP------SSQLIP--IGSRLPKNVD-SPLNS--------MIQLPS
TPYITPR-FTPSGTPKIFSTGGSPRGYS-AVASPNKTSGATSPTKSQYDGRGALSSWYPS
TPYITPR-LTPSGTPKIISTSASPKGYS-AAGSPQKTSGATSPTKPQYDGRASLSSWYPS
TPYITPR-LTPTGTPKVISTAGSPREYS-AAGSPKKTSGATSPTKLPYDGRTSLSSWYSS
TPYISPR-LTPTGTPKVISTSVSPRRYS-AAGSPQKTSGITSPTR--HEGRGSLSSWYPS
TSYISPR-LTPTATPKIISTSVSPRGYS-AAGSPKRTSGAVSPTK-------ATLWYPS
TSYISPR-LTPTATPKIISTSVSPRGYS-AAGSPKRTSGAVSPTK-------ATLWYPS
TPY---------------------------------------------------------
T-HISPR-LTSDPAAKTRTAATSPRRYS-TAVSPKLAASATSP---R-------------
T-HISPR-LTSDPAAKTRTAATSPRRYS-TAVSPKLAASATSP---RLEGHMAMQPWLPS
T-HITPR-LTSDPAPKLRTAATSPRRYS-TAVSPKLASGATSP---RLEGHMAMSPWLPS
SSHITPR-LTPEATPKIMSTSASPRRMS-TTATPKLMSGTTSPSKTRIEGYMSMTPWYPS
SSHITPR-LTPEATPKIMSTSASPRRMS-TTATPKLMSGTTSPSKTRIEGYMSMTPWYPS
SSHITPR-LTPEATPKIMSTSASPRRMS-TTATPKLMSGTTSPSKTRIEGYMSMTPWYPS
SPHINQR-LTPEATPNIMSTSASPRGMS-TTATPKLVSGATSPSRTRIEGHMSMTPWY-S
TTHITPR-LTPEATPKVMSTSASPRRMS-TTGTPKLMSGSTSPSKTRIESHMSMTPWYPS
TTHITPR-LTPEATPKIMSTSASPRRMS-TTGTPKLMSGSTSPSKTRIEAHMSMTPWYPS
SSHITPW-LTPKATPKIMSTSASPRQIS-TTATPKLMSGATSPTKSRMEAHMSMTPWYPS
TPYTAPK-LTPG------------------STPKFLSGPTSPTKSLSEVHSTFSSWHGS
TPYTAPK-LTPG------------------STPKFLSGPTSPTKSLSEVHSTFSSWHGS
TPYVAPQ-ITPGSTPIISSSSGSPLAYSTGPSTPKFYSGPTSPTRSREDQSAFSSWNGS
GIPLTPHNNTPPELTPKLTPNGSPKRLS-PPQSPRRHSASMSPTRHQFEGRLSSYSSLPA
MMLTSQD--------------SPRDSAKGEESGKAMEDDKWTDNYKSAGAISEKSQWEC
GGAYGLRGMATAAATPAFPSTSGRPLYGASTPQAGQPPAASGPPYAAMTGMGMPAQAPPP
xxxxxxx-xxxxxxxxxxxxxspxxxx-xxxxpxxxsxxxspxxxxxxxxxxxxxxxps
```

FIG. 4F

```
SKPTSQSTTAPNSPPSHGSDPS-------------------RTPRVDGKDFFR-----Q
SKPTSQSTTAPNSPPSHGSAPS-------------------RTPRVDGKDFFR-----Q
SKPTSQSTTAPNSPPSSGSMPS-------------------RTPRVDGKDFFR-----Q
SKATSQSTTAPNSPPSSGSMPS-------------------RTPRVDGKDFFR-----Q
SQPTSRSS----SPPSSGSGQS-------------------RTTRLDGKEFFR-----Q
SLPTSGSS----SPNSGHETLQGFHDNRSAFMNARVSVFIAARTARLDGKEFFR-----Q
SQPTSGAS----SPPSHGSGQS-------------------RSTRLDGKEFFR-----Q
S----QQSSAANSPPRARPLPG-----------------------------------S
S----QQSSAANSPPRGHPIPG-------------------RAPRVDGKEFFR-----Q
S----QQSSAANSPPWGRSLPV-------------------RTPKIDGKEFFR-----Q
S----QQSSAANSPPRARPLPA-------------------RAPGIDGKEFFR-----Q
S----QQSSAANSPPRNRTLPA-------------------RTPRMDGKEFFR-----Q
S----QQSSAANSPPRNRTLPA-------------------RTPRMDGKEFFR-----Q
---------------------------------------------------------
-----------------------------------------RTTRVDGKEFFR-----Q
S----KMSSAANSPPRAHSISG-------------------RTTRVDGKEFFR-----Q
S----KMSSAANSPPRGQSISG-------------------RGTRVDGKEFFR-----Q
S----KQSSAANSPPRGRPNPG-------------------RTPRIDGKEFFR-----Q
S----KQSSAANSPPRGRPNPG-------------------RTPRIDGKEFFR-----Q
S----KQSSAANSPPRGRPNPG-------------------RTPRIDGKEFFR-----Q
S----KQSSAANSPPRGRPNPG-------------------RTPRIDGKEFFR-----Q
S----KQSSAANSPPRGRSNPG-------------------RTPRIDGKEFFR-----Q
S----KQSSAANSPPRGRSNPG-------------------RTPRIDGKEFFR-----Q
S----KQSSAASSPPRGGSNPG-------------------RTPRVDGKEFFR-----Q
SS---HQYSAPTSPPQHRSFAG-------------------R-PRIDGKEFFR-----Q
SS---HQYSAPTSPPQHRSFAG-------------------R-PRIDGKEFFR-----Q
S----HQYSAPVSP-QRRSFAG-------------------R-PRIDGKEFFR-----Q
S----HQATAPTSPPHSR--AQ-------------------AHVRIDGKEFFR-----Q
P-------LTPRLPSDTGPAKS-------------------RRIDGKEVFRRASQIQ
S------TYATPHPHAQYGAAPG------------------SPPRVDGKEFFR------
s----xxxxaxxsppxxxxxxx-------------------rxxrxdgkeffr-----q
```

FIG. 4G

```
ARNRLSYEQFSAFLANIKELNAHRQTREETLRKAEETFGPENKDLYAAFDGLLSRHLPS-
ARNRLSYEQFSAFLANIKELNAHRQTREETLRKAEETFGPDNKDLYAAFDGLLSRHLPF-
ARNRLSYEQFSAFLANIKELNAHRQTREETLQKAQETFGPDNKDLYSAFEGLLSRHLPS-
ARNRLSYEQFSAFLANIKELNAHRQTREETLRKAQETFGPDNKDLYSAFEGLLSRHLPS-
ARARLSYEQFSSFLANIKELNAHRQTREETLANAEDIFGPENRDLYAAFEGILSRHLPS-
ARSRLSYEKFSSFLANIKELNAHRQTREETLAKAEDIFGPEHMDLHSAFEEVLSRHLSA-
ARSRLSYEQFSSFLANIKELNAHRQTREDTLGQAERIFGPENRDLSIAFEAILSRHLPS-
EKSRLSYEQFSAFLANIKELNAQKQSREETLRKAEEIFGTDNKDLYLSFQGLLNRNPH--
ARSRLSYEQFSAFLANIKKLNGQEQTREETLRKAEEIFGTDNKDLYFSFRGLLNRNIH--
ARSRLSYEQFSAFLANIKELNAQKQTREETLRKADEIFGSDNKDLYLSFQGLLNRNAR--
ARSRLSLEQFGSFLANVKELNAQRQSREETLRKAEEIFGMDNKDLYISFQGLLNRNIH--
ARSRLSYEQFSSFLANIKELNAQKQTREETLRKADEIFGEENKDLYLSFQGLLNRNMR--
ARSRLSYEQFSSFLANIKELNAQKQTREETLRKADEIFGEENKDLYLSFQGLLNRNMR--
-------------------------------------------------------------
ARNRLSYEQFAAFLANIKELNAHRQSREETLQKADEIFGSENKDLFMSFQSLLSRSLSSG
ARNRLSYEQFAAFLANIKELNAHRQSREETLQKADEIFGSENKDLFMSFQSLLSRSLS--
ARHRLSYEQFAAFLSNIKELNAHRQSREETLRKADEIFGAENMDLFRSFQGLLSRSLS--
ARSRLSYEQFGAFLANIKELNAHKQSREDTLKKAEEIFGPDNKDLYLSFQGLLNRSLP--
ARSRLSYEQFGAFLANIKELNAHKQSREDTLKKAEEIFGPDNKDLYLSFQGLLNRSLP--
ARSRLSYEQFGAFLANIKELNAHKQSREDTLKKAEEIFGPDNKDLYLSFQGLLNRSLP--
ARSRLSYEQFGAFLANIKELNAHKQSREETLKKAEEIFGPDSKDLYLSFQGLLNLSLP--
ARSRLSYEQFGAFLANIKELNAHKQSREETLKKAEEIFGPDNKDLYLSFQGLLNRSMVA-
ARSRLSYEQFGAFLANIKELNAHKQSREETLKKAEEIFGPDNKDLYLSFQGLLNRSMVA-
ARSRLSYEQFGAFLANIKELNAHKQSREETLKKAEEIFGPENKDLYLSFRGLLNRSMP--
ARTRLSYEQFGAFLANIKEFNAQKQSREDTLSKAEEIFGTEHKDLYISFQNMLNRNHS--
ARTRLSYEQFGAFLANIKEFNAQKQSREDTLSKAEEIFGTEHKDLYISFQNMLNRNHS--
ARTRLSYEQFGAFLANIKEFNAQKQSREDTLSKAEEIFGTEHKDLYISFQNMLNRNQS--
ARNRLSFEQFSAFLANIKELNSHRQTREETLHKADEIFGSDNKDLYVIFDSLLHRHLS--
SRARWTCEQFSDFLNNIREVNALRRAEEFLVCASSRAAYAYNVVPQCQLYGLNPPNWNCP
-----QARYLSVYKENLH------------------------------------------
arxrlsyeqfxaflanikelnaxxqxrextlxkaxeifgxxnkdlyxxfxxllrxxxx-
```

FIG. 4H

```
VKVYQMMDLSTTSVVAAKAYKYRAESLVKDYLLADCYVSYTAVLGGILMCKMVYDITHLI
```

```
PANCRVYTR
```

FIG. 4I

```
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
SSLYYKGYGSLTKIQKLEWNNRGMSTVHAMFITLMSVYLVFFSNLFSDELDGPVTVRSSN
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
------------------------------------------------------------
```

FIG. 4J

GENES AND USES FOR PLANT ENHANCEMENT

CROSS REFERENCE TO RELATED APPLICATIONS

This application is a continuation of U.S. application Ser. No. 15/732,766, filed Dec. 22, 2017, which application is a continuation of U.S. application Ser. No. 14/544,230 filed Dec. 10, 2014, which application is a continuation of U.S. application Ser. No. 12/386,976, filed Apr. 24, 2009, which application claims the benefit and priority under 35 U.S.C. § 119(e) of U.S. Provisional Application Ser. No. 61/125,908 filed on Apr. 29, 2008 which are incorporated herein by reference in their entireties.

INCORPORATION OF SEQUENCE LISTING

Two copies of the sequence listing (Copy 1 and Copy 2) and a computer readable form (CRF) of the sequence listing, all on CD-Rs, each containing the file named 38-21_54976_000l_seqListing.txt, which is 319,330,304 bytes (measured in MS-WINDOWS) and recorded on CD-R on May 14, 2020, are incorporated herein by reference in their entirety.

INCORPORATION OF COMPUTER PROGRAM LISTING

A Computer Program Listing folder named "3126008US2 prgmlisting" containing folders "hmmer-2.3.2" and "495pfamdir" is contained on a CD-R and is incorporated herein by reference in their entirety. Folder hmmer-2.3.2 contains the source code and other associated file for implementing the HMMer software for Pfam analysis. Folder 495pfamdir contains 495 profile Hidden Markov Models. Both folders were recorded on CD-R on May 14, 2020 having a total size of 40,880,128 bytes when measured in MS-WINDOWS® operating system.

INCORPORATION OF TABLES

Two copies of Table 19 (Copy 1 and Copy 2) and a computer readable form (CRF), all on CD-Rs, each containing the file named 38-21_54976_0001_table19.txt, which is 886,784 bytes (measured in MS-WINDOWS®), were recorded on CD-R on May 14, 2020, and comprise 417 pages when viewed in MS Word, are herein incorporated by reference.

FIELD OF THE INVENTION

Disclosed herein are recombinant DNA for providing enhanced traits to transgenic plants, seeds, pollen, plant cells and plant nuclei of such transgenic plants, methods of making and using such recombinant DNA, plants, seeds, pollen, plant cells and plant nuclei. Also disclosed are methods of producing hybrid seed comprising such recombinant DNA.

SUMMARY OF THE INVENTION

This invention provides recombinant DNA comprising polynucleotides characterized by SEQ ID NO: 1-803 and the cognate amino acid sequences of SEQ ID NO: 804-1606. The recombinant DNA is used for providing enhanced traits when stably integrated into the chromosomes and expressed in the nuclei of transgenic plants cells. In some aspects the recombinant DNA encodes a protein; in other aspects the recombinant DNA is transcribed to RNA that suppresses the expression of a native gene.

Such recombinant DNA in a plant cell nucleus of this invention is provided in as a construct comprising a promoter that is functional in plant cells and that is operably linked to DNA that encodes a protein or to DNA that results in gene suppression. Such DNA in the construct is sometimes defined by protein domains of an encoded protein targeted for production or suppression e.g. a "Pfam domain module" (as defined herein below) from the group of Pfam domain modules identified in Table 20. Alternatively, e.g. where a Pfam domain module is not available, such DNA in the construct is defined a consensus amino acid sequence of an encoded protein that is targeted for production e.g. a protein having amino acid sequence with at least 90% identity to a consensus amino acid sequence in the group of SEQ ID NO: 94617 through SEQ ID NO: 94734. In a particular aspect of the invention the recombinant DNA is characterized by its cognate amino acid sequence that has at least 70% identity to any of SEQ ID NO: 804-1606.

This invention also provides transgenic plant cell nuclei comprising the recombinant DNA of the invention, transgenic plant cells comprising such nuclei, transgenic plants comprising a plurality of such transgenic plant cells, and transgenic seeds and transgenic pollen of such plants. Such transgenic plants are selected from a population of transgenic plants regenerated from plant cells transformed with recombinant DNA by screening transgenic plants for an enhanced trait as compared to control plants. The enhanced trait is one or more of enhanced water use efficiency, enhanced cold tolerance, increased yield, enhanced nitrogen use efficiency, enhanced heat tolerance, enhanced shade tolerance, enhanced high salinity tolerance, enhanced seed protein and enhanced seed oil. Such recombinant DNA in a plant cell nucleus of this invention is provided in as a construct comprising a promoter that is functional in plant cells and that is operably linked to DNA that encodes a protein or to DNA that results in gene suppression. Such DNA in the construct is sometimes defined by protein domains of an encoded protein targeted for production or suppression, e.g. a "Pfam domain module" (as defined herein below) from the group of Pfam domain modules identified in Table 20. Alternatively, e.g. where a Pfam domain module is not available, such DNA in the construct is defined a consensus amino acid sequence of an encoded protein that is targeted for production e.g. a protein having amino acid sequence with at least 90% identity to a consensus amino acid sequence in the group of SEQ ID NO: 94617 through SEQ ID NO: 94734.

In another aspect of the invention the plant cell nuclei, cells, plants, seeds, and pollen further comprise DNA expressing a protein that provides tolerance from exposure to an herbicide applied at levels that are lethal to a wild type plant cell.

This invention also provides methods for manufacturing non-natural, transgenic seed that can be used to produce a crop of transgenic plants with an enhanced trait resulting from expression of stably-integrated, recombinant DNA in the nucleus of the plant cells. More specifically the method comprises (a) screening a population of plants for an enhanced trait and recombinant DNA, where individual plants in the population can exhibit the trait at a level less than, essentially the same as or greater than the level that the trait is exhibited in control plants which do not express the recombinant DNA; (b) selecting from the population one or more plants that exhibit the trait at a level greater than the level that said trait is exhibited in control plants and (c) collecting seed from a selected plant. Such method further comprises steps (a) verifying that the recombinant DNA is stably integrated in said selected plants; and (b) analyzing tissue of a selected plant to determine the production of a protein having the function of a protein encoded by a recombinant DNA with a sequence of one of SEQ ID NO: 1-803; in one aspect of the invention the plants in the population further comprise DNA expressing a protein that provides tolerance to exposure to an herbicide applied at levels that are lethal to wild type plant cells and where the selecting is effected by treating the population with the herbicide, e.g. a glyphosate, dicamba, or glufosinate compound. In another aspect of the invention the plants are selected by identifying plants with the enhanced trait. The methods are used for manufacturing corn, soybean, cotton, canola, alfalfa, wheat, rice seed or any combinations thereof selected as having one of the enhanced traits described above.

Another aspect of the invention provides a method of producing hybrid corn seed comprising acquiring hybrid corn seed from a herbicide tolerant corn plant which also has a nucleus of this invention with stably-integrated, recombinant DNA. The method further comprises producing corn plants from said hybrid corn seed, where a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Still other aspects of this invention relate to transgenic plants with enhanced water use efficiency or enhanced nitrogen use efficiency. For instance, this invention provides methods of growing a corn, cotton, soybean, or canola crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton, soybean or canola crop without added nitrogen fertilizer comprising planting seed having plant cells of the invention which are selected for enhanced nitrogen use efficiency.

BRIEF DESCRIPTION OF THE DRAWINGS

FIGS. 4A-4J illustrate a consensus amino acid sequence of SEQ ID NO: 1325 and its homologs.

DETAILED DESCRIPTION OF THE INVENTION

Figure 1:
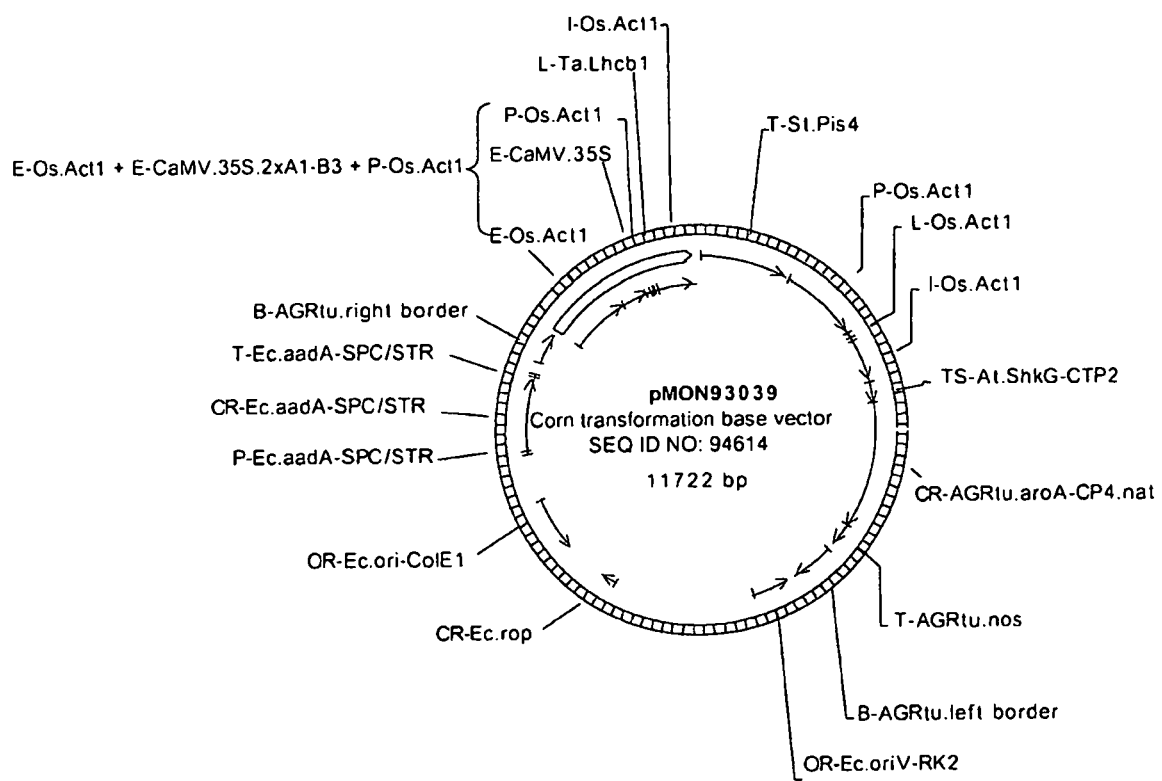
FIGS. 1, 2 and 3 illustrate plasmid maps.

In the attached sequence listing:
SEQ ID NO: 1-803 are nucleotide sequences of the coding strand of DNA for "genes" used in the recombinant DNA imparting an enhanced trait in plant cells, where each represents a coding sequence for a protein;

SEQ ID NO: 804-1606 are amino acid sequences of the cognate protein of the "genes" with nucleotide coding sequence 1-803;

SEQ ID NO: 1607-94613 are amino acid sequences of homologous proteins;

SEQ ID NO: 94614 is a nucleotide sequence of a plasmid base vector for corn transformation; and SEQ ID NO: 94615 is a DNA sequence of a plasmid base vector for soybean transformation.

SEQ ID NO: 94616 is a DNA sequence of a plasmid base vector for cotton transformation.

SEQ ID NO: 94617-94734 are consensus sequences.

Table 1 lists the protein SEQ ID NOs and their corresponding consensus SEQ ID NOs.

TABLE 1

| NUC SEQ ID NO | PEP SEQ ID NO | GENE ID | CONSENSUS SEQ ID NO |
|---|---|---|---|
| 5 | 808 | CGPG1067 | 94617 |
| 6 | 809 | CGPG1095 | 94618 |
| 7 | 810 | CGPG1101 | 94619 |
| 8 | 811 | CGPG1109 | 94620 |
| 10 | 813 | CGPG1155 | 94621 |
| 12 | 815 | CGPG1171 | 94622 |
| 13 | 816 | CGPG1177 | 94623 |
| 19 | 822 | CGPG1279 | 94624 |
| 20 | 823 | CGPG1304 | 94625 |
| 22 | 825 | CGPG1327 | 94626 |
| 57 | 860 | CGPG1723 | 94627 |
| 78 | 881 | CGPG1972 | 94628 |
| 88 | 891 | CGPG2041 | 94629 |
| 90 | 893 | CGPG2070 | 94630 |
| 98 | 901 | CGPG2126 | 94631 |
| 99 | 902 | CGPG213 | 94632 |
| 106 | 909 | CGPG2193 | 94633 |
| 108 | 911 | CGPG2224 | 94634 |
| 118 | 921 | CGPG2319 | 94635 |
| 121 | 924 | CGPG2359 | 94636 |
| 130 | 933 | CGPG2408 | 94637 |
| 133 | 936 | CGPG2414 | 94638 |
| 156 | 959 | CGPG2863 | 94639 |
| 172 | 975 | CGPG3183 | 94640 |
| 180 | 983 | CGPG3280 | 94641 |
| 191 | 994 | CGPG3405 | 94642 |
| 200 | 1003 | CGPG3598 | 94643 |
| 202 | 1005 | CGPG3606 | 94644 |
| 203 | 1006 | CGPG3610 | 94645 |
| 204 | 1007 | CGPG3620 | 94646 |
| 222 | 1025 | CGPG3820 | 94647 |
| 226 | 1029 | CGPG3958 | 94648 |
| 227 | 1030 | CGPG3981 | 94649 |
| 236 | 1039 | CGPG4083 | 94650 |
| 256 | 1059 | CGPG4347 | 94651 |
| 257 | 1060 | CGPG4354 | 94652 |
| 273 | 1076 | CGPG4559 | 94653 |
| 294 | 1097 | CGPG4802 | 94654 |
| 295 | 1098 | CGPG4822 | 94655 |
| 296 | 1099 | CGPG4826 | 94656 |
| 297 | 1100 | CGPG4833 | 94657 |
| 298 | 1101 | CGPG4841 | 94658 |
| 332 | 1135 | CGPG5208 | 94659 |
| 393 | 1196 | CGPG5750 | 94660 |
| 394 | 1197 | CGPG5751 | 94661 |
| 413 | 1216 | CGPG5922 | 94662 |
| 415 | 1218 | CGPG5964 | 94663 |
| 432 | 1235 | CGPG6137 | 94664 |
| 456 | 1259 | CGPG6358 | 94665 |
| 501 | 1304 | CGPG6803 | 94666 |
| 504 | 1307 | CGPG6812 | 94667 |
| 506 | 1309 | CGPG6827 | 94668 |
| 509 | 1312 | CGPG6859 | 94669 |
| 514 | 1317 | CGPG6886 | 94670 |
| 518 | 1321 | CGPG6903 | 94671 |

TABLE 1-continued

| NUC SEQ ID NO | PEP SEQ ID NO | GENE ID | CONSENSUS SEQ ID NO |
|---|---|---|---|
| 520 | 1323 | CGPG6933 | 94672 |
| 522 | 1325 | CGPG6944 | 94673 |
| 523 | 1326 | CGPG6949 | 94674 |
| 525 | 1328 | CGPG6989 | 94675 |
| 527 | 1330 | CGPG7003 | 94676 |
| 528 | 1331 | CGPG7009 | 94677 |
| 531 | 1334 | CGPG7062 | 94678 |
| 532 | 1335 | CGPG7064 | 94679 |
| 534 | 1337 | CGPG7109 | 94680 |
| 535 | 1338 | CGPG7123 | 94681 |
| 538 | 1341 | CGPG7159 | 94682 |
| 541 | 1344 | CGPG7224 | 94683 |
| 569 | 1372 | CGPG7505 | 94684 |
| 576 | 1379 | CGPG7540 | 94685 |
| 582 | 1385 | CGPG7568 | 94686 |
| 583 | 1386 | CGPG7571 | 94687 |
| 584 | 1387 | CGPG7587 | 94688 |
| 585 | 1388 | CGPG7591 | 94689 |
| 588 | 1391 | CGPG7633 | 94690 |
| 601 | 1404 | CGPG7774 | 94691 |
| 602 | 1405 | CGPG7777 | 94692 |
| 606 | 1409 | CGPG7792 | 94693 |
| 613 | 1416 | CGPG7851 | 94694 |
| 616 | 1419 | CGPG7865 | 94695 |
| 622 | 1425 | CGPG7934 | 94696 |
| 623 | 1426 | CGPG7949 | 94697 |
| 624 | 1427 | CGPG7954 | 94698 |
| 627 | 1430 | CGPG7969 | 94699 |
| 641 | 1444 | CGPG8072 | 94700 |
| 642 | 1445 | CGPG8075 | 94701 |
| 644 | 1447 | CGPG8100 | 94702 |
| 645 | 1448 | CGPG8101 | 94703 |
| 646 | 1449 | CGPG8104 | 94704 |
| 647 | 1450 | CGPG8108 | 94705 |
| 648 | 1451 | CGPG8116 | 94706 |
| 651 | 1454 | CGPG8138 | 94707 |
| 654 | 1457 | CGPG8163 | 94708 |
| 659 | 1462 | CGPG8204 | 94709 |
| 662 | 1465 | CGPG8234 | 94710 |
| 671 | 1474 | CGPG8345 | 94711 |
| 686 | 1489 | CGPG8515 | 94712 |
| 688 | 1491 | CGPG8518 | 94713 |
| 690 | 1493 | CGPG8523 | 94714 |
| 691 | 1494 | CGPG8528 | 94715 |
| 693 | 1496 | CGPG8553 | 94716 |
| 694 | 1497 | CGPG8562 | 94717 |
| 697 | 1500 | CGPG8589 | 94718 |
| 699 | 1502 | CGPG8592 | 94719 |
| 703 | 1506 | CGPG8648 | 94720 |
| 706 | 1509 | CGPG8678 | 94721 |
| 707 | 1510 | CGPG8694 | 94722 |
| 709 | 1512 | CGPG8737 | 94723 |
| 710 | 1513 | CGPG8745 | 94724 |
| 712 | 1515 | CGPG8749 | 94725 |
| 715 | 1518 | CGPG8781 | 94726 |
| 760 | 1563 | CGPG9075 | 94727 |
| 762 | 1565 | CGPG9094 | 94728 |
| 769 | 1572 | CGPG9136 | 94729 |
| 770 | 1573 | CGPG9156 | 94730 |
| 773 | 1576 | CGPG9173 | 94731 |
| 781 | 1584 | CGPG921 | 94732 |
| 788 | 1591 | CGPG19281 | 94733 |
| 792 | 1595 | CGPG9304 | 94734 |

The nuclei of this invention are identified by screening transgenic plants for one or more traits including enhanced drought stress tolerance, enhanced heat stress tolerance, enhanced cold stress tolerance, enhanced high salinity stress tolerance, enhanced low nitrogen availability stress tolerance, enhanced shade stress tolerance, enhanced plant growth and development at the stages of seed imbibition through early vegetative phase, and enhanced plant growth and development at the stages of leaf development, flower production and seed maturity.

"As used herein a "plant cell" means a plant cell that is transformed with stably-non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. Hence, a polynucleotide in the present invention can have any base sequence that has been changed from SEQ ID NO:1 through SEQ ID NO: 803 through substitution in accordance with degeneracy of the genetic code. Homologs are proteins that, when optimally aligned, have at least about 60% identity, about 70% or higher, at least about 80% and at least about 90% identity over the full length of a protein identified as being associated with imparting an enhanced trait when expressed in plant cells. Homologs include proteins with an amino acid sequence that has at least about 90% identity to a consensus amino acid sequence of proteins and homologs disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism could be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best hit is the query protein itself or a protein encoded by a duplicated gene after speciation. A further aspect of the homologs encoded by DNA in the transgenic plants of the invention are those proteins that differ from a disclosed protein as the result of deletion or insertion of one or more amino acids in a native sequence.

Homologous genes are genes which encode proteins with the same or similar biological function to the protein encoded by the second gene. Homologous genes can be generated by the event of speciation (see ortholog) or by the event of genetic duplication (see paralog). "Orthologs" refer to a set of homologous genes in different species that evolved from a common ancestral gene by specification. Normally, orthologs retain the same function in the course of evolution; and "paralogs" refer to a set of homologous genes in the same species that have diverged from each other as a consequence of genetic duplication. Thus, homologous genes can be from the same or a different organism. As used herein, "homolog" means a protein that performs the same biological function as a second protein including those identified by sequence identity search.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein, "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that can effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein, "operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression. In the examples illustrating the invention recombinant DNA for effecting gene suppression that imparts is identified by the term "antisense". It will be understood by a person of ordinary skill in the art that any of the ways of effecting gene suppression are contemplated and enabled by a showing of one approach to gene suppression.

As used herein "expressed" means produced, e.g. a protein is expressed in a plant cell when its cognate DNA is transcribed to mRNA that is translated to the protein.

As used herein "suppressed" means decreased, e.g. a protein is suppressed in a plant cell when there is a decrease in the amount and/or activity of the protein in the plant cell. The presence or activity of the protein can be decreased by any amount up to and including a total loss of protein expression and/or activity.

As used herein a "control plant" means a plant that does not contain the recombinant DNA that expressed a protein that imparts an enhanced trait. A control plant is to identify and select a transgenic plant that has an enhance trait. A suitable control plant can be a non-transgenic plant of the parental line used to generate a transgenic plant, e.g. devoid of recombinant DNA. A suitable control plant can in some cases be a progeny of a hemizygous transgenic plant line that is does not contain the recombinant DNA, known as a negative segregant.

"Trait enhancement" means a detectable and desirable difference in a characteristic in a transgenic plant relative to a control plant or a reference. In some cases, the trait enhancement can be measured quantitatively. For example, the trait enhancement can entail at least about 2% difference in an observed trait, at least about 5% desirable difference, at least about 10% difference, at least about 20% difference, at least about 30% difference, at least about 40%, at least about 50% difference, at least about 60%, at least about 70% difference, at least about 80% difference, at least about 90% difference, or at least about a 100% difference, or an even greater difference. In other cases, the trait enhancement is only measured qualitatively. It is known that there can be a natural variation in a trait. Therefore, the trait enhancement observed entails a change of the normal distribution of the trait in the transgenic plant compared with the trait distribution observed in a control plant or a reference, which is evaluated by statistical methods provided herein. Trait enhancement includes, but is not limited to, yield increase, including increased yield under non-stress conditions and increased yield under environmental stress conditions. Stress conditions can include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability, high plant density, or any combinations thereof.

"Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (e.g. seeds, or weight of seeds, per acre), bushels per acre, tonnes per acre, tons per acre, kilo per hectare. For example, maize yield can be measured as production of shelled corn kernels per unit of production area, for example in bushels per acre or metric tons per hectare, often reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that could correspond to an increase in overall plant yield. Such properties include enhancements in seed oil, seed molecules such as tocopherol, protein and starch, or oil particular oil components as can be manifest by alterations in the ratios of seed components.

"Stress condition" means a condition unfavorable for a plant, which adversely affect plant metabolism, growth and/or development. A plant under the stress condition typically shows reduced germination rate, retarded growth and development, reduced photosynthesis rate, and eventually leading to reduction in yield. Specifically, "water deficit stress" used herein refers to the sub-optimal conditions for water and humidity needed for normal growth of natural plants. Relative water content (RWC) can be used as a physiological measure of plant water deficit. It measures the effect of osmotic adjustment in plant water status, when a plant is under stressed conditions. Conditions which can result in water deficit stress include, but are not limited to, heat, drought, high salinity and PEG induced osmotic stress.

"Cold stress" means the exposure of a plant to a temperatures below (two or more degrees Celsius below) those normal for a particular species or particular strain of plant.

"Nitrogen nutrient" means any one or any mix of the nitrate salts commonly used as plant nitrogen fertilizer, including, but not limited to, potassium nitrate, calcium nitrate, sodium nitrate, ammonium nitrate. The term ammonium as used herein means any one or any mix of the ammonium salts commonly used as plant nitrogen fertilizer, e.g., ammonium nitrate, ammonium chloride, ammonium sulfate, etc.

"Low nitrogen availability stress" means a plant growth condition that does not contain sufficient nitrogen nutrient to maintain a healthy plant growth and/or for a plant to reach its typical yield under a sufficient nitrogen growth condition. For example, a limiting nitrogen condition can refers to a growth condition with 50% or less of the conventional nitrogen inputs. "Sufficient nitrogen growth condition" means a growth condition where the soil or growth medium contains or receives optimal amounts of nitrogen nutrient to sustain a healthy plant growth and/or for a plant to reach its typical yield for a particular plant species or a particular strain. One skilled in the art would recognize what constitute such soil, media and fertilizer inputs for most plant species.

"Shade stress" means a growth condition that has limited light availability that triggers the shade avoidance response in plant. Plants are subject to shade stress when localized at lower part of the canopy, or in close proximity of neighboring vegetation. Shade stress can become exacerbated when the planting density exceeds the average prevailing density for a particular plant species.

In some embodiments of the invention a constitutively active mutant, is constructed to achieve the desired effect. In other embodiments of the invention, a dominant negative gene is constructed to adversely affect the normal, wild-type gene product within the same cell.

DNA constructs are assembled using methods well known to persons of ordinary skill in the art and typically comprise a promoter operably linked to DNA, the expression of which provides the enhanced agronomic trait. Other construct components can include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Promoters derived from plant genes are found in U.S. Pat. No. 5,641,876, which discloses a rice actin promoter, U.S. Pat. No. 7,151,204, which discloses a maize chloroplast aldolase promoter and a maize aldolase (FDA) promoter, and U.S. Patent Application Publication 2003/0131377 A1, which discloses a maize nicotinamide synthase promoter, all of which are incorporated herein by reference. These and numerous other promoters that function in plant cells are known to those skilled in the art and available for use in recombinant polynucleotides of the present invention to provide for expression of desired genes in transgenic plant cells.

In other aspects of the invention, preferential expression in plant green tissues is desired. Promoters of interest for such uses include those from genes such as *Arabidopsis thaliana* ribulose-1,5-bisphosphate carboxylase (Rubisco) small subunit (Fischhoff et al. (1992) *Plant Mol Biol.* 20:81-93), aldolase and pyruvate orthophosphate dikinase (PPDK) (Taniguchi et al. (2000) *Plant Cell Physiol.* 41(1): 42-48).

Furthermore, the promoters can be altered to contain multiple "enhancer sequences" to assist in elevating gene expression. Such enhancers are known in the art. By including an enhancer sequence with such constructs, the expression of the selected protein can be enhanced. These enhancers often are found 5' to the start of transcription in a promoter that functions in eukaryotic cells, but can often be inserted upstream (5') or downstream (3') to the coding sequence. In some instances, these 5' enhancing elements are introns. In one embodiment, enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to affect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2):157-166), globulin 1 (Belanger et al (1991) *Genetics* 129:863-872), glutelin 1 (Russell (1997) supra), and peroxiredoxin antioxidant (Per1) (Stacy et al. (1996) *Plant Mol Biol.* 31(6):1205-1216).

Recombinant DNA constructs prepared in accordance with the invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose-1, 6-biphosphatase gene, a rice glutelin gene, a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3), and 3' elements from the genes within the host plant.

Constructs and vectors can also include a transit peptide for targeting of a gene to a plant organelle, particularly to a chloroplast, leucoplast or other plastid organelle. For descriptions of the use of chloroplast transit peptides see U.S. Pat. Nos. 5,188,642 and 5,728,925, incorporated herein by reference. For description of the transit peptide region of an *Arabidopsis* EPSPS gene can be in the present invention, see Klee, H. J. et al (*MGG* (1987) 210:437-442).

Gene suppression includes any of the well-known methods for suppressing transcription of a gene or the accumulation of the mRNA corresponding to that gene thereby preventing translation of the transcript into protein. Post-transcriptional gene suppression is mediated by transcription of RNA that forms double-stranded RNA (dsRNA) having homology to a gene targeted for suppression. Suppression can also be achieved by insertion mutations created by transposable elements can also prevent gene function. For example, in many di cot plants, transformation with the T-DNA of *Agrobacterium* can be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants can be screened with polynucleotides encoding the polypeptide of interest to detect mutated plants having an insertion in the gene encoding the polypeptide of interest.

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent Application publication 2003/0083480 A1 also for imparting glyphosate tolerance; dicamba monooxygenase disclosed in U.S. Patent Application publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxaflutole and glufosinate herbicides are disclosed in U.S. Pat. No. 6,376,754 and U.S. Patent Application Publication 2002/0112260, all of said U.S. patents and patent application Publications are incorporated herein by reference. Molecules and methods for imparting insect/nematode/vines resistance are disclosed in U.S. Pat. Nos. 5,250,515; 5,880,275; 6,506,599; 5,986,175 and U.S. Patent Application Publication 2003/0150017 A1, all of which are incorporated herein by reference.

A "consensus amino acid sequence" means an artificial, amino acid sequence indicating conserved amino acids in the sequence of homologous proteins as determined by statistical analysis of an optimal alignment, e.g. CLUSTALW, of amino acid sequence of homolog proteins. The consensus sequences listed in the sequence listing were created by identifying the most frequent amino acid at each position in a set of aligned protein sequences. When there was 100% identity in an alignment the amino acid is indicated by a capital letter. When the occurrence of an amino acid is at least about 70% in an alignment, the amino acid is indicated by a lower case letter. When there is no amino acid occurrence of at least about 70%, e.g. due to diversity or gaps, the amino acid is indicated by an "x". When used to defined embodiments of the invention, a consensus amino acid sequence will be aligned with a query protein amino acid sequence in an optimal alignment, e.g. CLUSTALW. An embodiment of the invention will have identity to the conserved amino acids indicated in the consensus amino acid sequence.

"*Arabidopsis*" means plants of *Arabidopsis thaliana*.

"Pfam" database is a large collection of multiple sequence alignments and hidden Markov models covering many common protein families, e.g. Pfam version 19.0 (December 2005) contains alignments and models for 8183 protein families and is based on the Swissprot 47.0 and SP-TrEMBL 30.0 protein sequence databases. See S. R. Eddy, "Profile Hidden Markov Models", *Bioinformatics* 14:755-763, 1998. The Pfam database is currently maintained and updated by the Pfam Consortium. The alignments represent some evolutionary conserved structure that has implications for the protein's function. Profile hidden Markov models (profile HMMs) built from the protein family alignments can be used for automatically recognizing that a new protein belongs to an existing protein family even if the homology by alignment appears to be low.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly- and broadly-defined domains, leading to identification of overlapping domains on some proteins. A Pfam domain module is characterized by non-overlapping domains. Where there is overlap, the domain having a function that is more closely associated with the function of the protein (based on the E value of the Pfam match) is selected.

Once one DNA is identified as encoding a protein which imparts an enhanced trait when expressed in transgenic plants, other DNA encoding proteins with the same Pfam domain module are identified by querying the amino acid sequence of protein encoded by candidate DNA against the Hidden Markov Models which characterizes the Pfam domains using HMMER software, a current version of which is provided in the appended computer listing. Candidate proteins meeting the same Pfam domain module are in the protein family and have cognate DNA that is used in constructing recombinant DNA for the use in the plant cells of this invention. Hidden Markov Model databases for use with MA ER software in identifying DNA expressing protein with a common Pfam domain module for recombinant DNA in the plant cells of this invention are also included in the appended computer listing.

Version 19.0 of the HMMER software and Pfam databases were used to identify known domains in the proteins corresponding to amino acid sequence of SEQ ID NO: 804 through SEQ ID NO:1606. All DNA encoding proteins that have scores higher than the gathering cutoff disclosed in Table 19 by Pfam analysis disclosed herein can be used in recombinant DNA of the plant cells of this invention, e.g. for selecting transgenic plants having enhanced agronomic traits. The relevant Pfam modules for use in this invention, as more specifically disclosed below, are Syntaxin::SNARE, Pro_isomerase, Pkinase, ATP-synt_G, Carboxyl_trans, CDC50, GATase::GMP_synt_C, F-box::WD40::WD40::WD40, dsrm::dsrm, Pyr_redox2::Pyr_redox_dim, WAK::Pkinase, Pkinase_Tyr, PTPA, Biotin_lipoyl::E3_binding::2-oxoacid_dh, AAA, LRRNT_2::LRR_1::LRR_1::LRR_1::LRR_1, PRA1, TIM, YTH, ThiF, Hep_59, Pkinase, PAT P::Thr_dehydrat_C::Thr_dehydrat_C, zf-Tim10_DDP, CAF1, Pkinase, Pyr_redox_2::Pyr_redox_dim, Response_reg, YIF1, NPH3, LRRNT_2::LRR_1::LRR_1::LRR_1::LRR_1::Pkinase_Tyr, NOI, Fer2, AA_permease, Caleosin, IF4E, Pkinase, Ribu_P_3_epim, F-box::WD40::WD40::WD40::WD40::WD40::WD40, MIP, p450, Ribosomal_S5::Ribosomal_S5_C, Hpt, TBC, Acyltransferase, Epimerase, Pkinase, Dus, SelR, PH, Tyr-DNA_phospho, RRM_1, Pkinase, ECH, SRPRB, DUF599, Pkinase::efhand::efhand::efhand::efhand, ORC2, PMEI, p450, GLTP, Suc_Fer-like, CBS::CBS, ADH_N::ADH_zinc_N, LRRNT_2::LRR_1::LRR_1::LRR_1::Pkinase, F-box, adh_short, polyprenyl_sync, GHMP_kinases_N::GHMP_kinases_C, PsbW, Na_H_Exchanger::TrkA_C, Ribosomal_L12, CDC50, DCP1, Pyr_redox_2::Pyr_redox_dim, Steroid_dh, tRNA-synt_1c::tRNA-synt_1c_C, Cupin_1::Cupin_1, peroxidase, Sugar_tr, Pro_isomerase, Iso_dh, PTS_2-RNA, Aminotran_5, ENOD93, KH_1::KH_1::KH_1::KH_1::KH_1, Mito_carr::Mito_carr::Mito_carr, DUF569::DUF569, C1_2::C1_2::C1_3::C1_2::C1_3::C1_2, DnaJ::zf-C2H2, Aldedh, AAA::Rep_fac_C, DUF641, Aminotran_1_2, TB2_DP1_HVA22, zf-C3HC4, RRM_1::RRM_2, Pkinase, PPR::PPR::PPR::PPR::PPR::PPR::PPR::PPR::PPR::PPR::PPR, Pyr_redox_2, IQ::IQ, SMP::SMP::SMP, AWPM-19, CLP_protease, Pkinase::NAF, PRMT5, PPR::PPR::PPR::PPR::PPR::PPR, Aldedh, ATP-synt_C::ATP-synt_C, adh_short, RCC1::RCC1::RCC1::RCC1::FYVE::DZC, p450, PfkB, PB1, Hexapep::Hexapep::Hexapep::Hexapep, Aminotran_1_2, DUF862, Aldedh, ADH_N::ADH_zinc_N, CDC48_N::AAA::AAA, AA_permease, UQ_con, Mem_trans, GFA, OPT, DUF887, Di19, U-box::Arm::Arm, DAO, G-alpha, Aminotran_3, 2OG-FeII_Oxy, Lectin_legB::Pkinase, NAC::UBA, efhand_like::PI-PLC-X::PI-PLC-Y::C2, TLC, ATP-grasp_2::Ligase_CoA, Pkinase, PRC::PRC, MFS_::Sugar_tr, Copine::zf-C3HC4, RRM_1::RRM_1::RRM_1, Pribosyltran, AA_kinase, PhzC-PhzF, Gp_dh_N::Gp_dh_C, Sugar_tr, Pre-SET::SET, Alpha-amylase::Alpha-amyl_C2, Cyclin_N, FAE1_CUT1_RppA::ACP_syn_III_C, RPE65, efhand_like::PI-PLC-X::PI-PLC-Y::C2, Mito_carr::Mito_carr::Mito_carr, Invertase_neut, DSPc, LANC_like, Aminotran_5, Glutaminase, PPR::PPR::PPR::PPR::PPR::PPR::PPR::PPR, PGI, SSB, p450, La::RRM_1::RRM_3, Methyltransf_11, SBF, NTP_transferase::Hexapep::Hexapep::Hexapep, Mov34, Hydrolase, AAA, RRM_1::RRM_1, Pkinase::NAF, F-box::FBA_1, p450, F-box::LRR_2, zf-DHHC, TBP::TBP, DUF607, FMO-like, adh_short, ATP-synt_ab_N::ATP-synt_ab, RNase_PH, PP2C, UQ_con, Aminotran_1_2, p450, FMO-like, Gp_dh_N::Gp_dh_C, Mito_carr::Mito_carr::Mito_carr, zf-CCCH::zf-CCCH::zf-CCCH::zf-CCCH::zf-CCCH, GST_C, GH3, PAP_fibrillin, ThiF, Ribul_P_3_epim, DUF260, p450, MACPF, Steroid_dh, Response_reg, Carb_anhydrase, Aldedh, Pkinase, Methyltransf_11, PK::PK_C, Pkinase, DEK_C::SWIB::SWIB, TATA_RF, Tryp_alpha_amyl, Y_phosphatase2, TATA_RF, NifU_N, ENT, Pkinase, F-box::Kelch_2::Kelch_2, WD40::WD40, MtN3_slv::MtN3_sly, TB2_DP1_HVA22, Pkinase, Aldedh, AAA, Pyridoxal_deC, zf-CCHC::zf-CCHC::zf-CCHC::zf-CCHC, Peptidase_M24, LRRNT_2::LRR_1::LRR_::LRR_1::LRR_1::Pkinase, Arf, DUF1279, UPF0185, Rhodanese, adh_short, Tryp_alpha_amyl, Pkinase, UPF0139, CBS, Glyco_transf_29, iPGM_N::Metalloenzyme, Proteasome, Pkinase, UBX, ELFV_dehydrog_N::ELFV_dehydrog, p450, ADH_N::ADH_zinc_N, zf-C3HC4, NDK, NAD_Gly3P_dh_N::NAD_Gy3P_dh_C, GlutR_N::Shikimate_DH::GlutR_dimer, p450, SNF5, p450, Pribosyltran, AIG1, Response_reg::CCT, mTERF, DUF220, Pkinase::NAF, zf-CCCH::zf-CCCH, Pkinase, Pkinase, MATH::MATH, Asparaginase, Pkinase, Gp_dh_N::Gp_dh_C, Pkinase, KH_1, Fcf1, PK::PK_C::PEP-utilizers, CRAL_TRIO_N::CRAL_TRIO, Raffinose_syn, DUF584, BT1, Aminotran_1_2, C1_2::C1_3::C1_3::C1_2::C1_3C3::C1_2, FMO-like, PLAC8, F-box::Kelch_2::Kelch_1::Kelch_2, XS::XH, STT3, ABC_tran::ABC_tran, Aldo_ket_red, NTF2::RRM_1, DUF594, Biotin_lipoyl::2-oxoacid_dh, RRM_1, FHA, Mov34, MT-A70, Brix, X8, Auxin_inducible, Peptidase_M18, Sec61_beta, F-box::Kelch_1::Kelch_1, Brix, TIM, CTP_transf_1, Tetraspannin, PALP, DUF822, Pkinase, B3::B3, MFS_1, SFT2, F-box::Kelch_1::Kelch_1, DUF588, Thioredoxin, Alba, Ion_trans_2::Ion_trans_2, Peptidase_C48, YDG_SRA::PreSET::SET, Aldedh, Abhydrolase_3, p450, U-box::Arm::Arm::Arm::Arm, AA_permease, LAG1, peroxidase, PAD_porph, Pkinase, F-box, AIG2, p450, AARP2CN::DUF663, UPF0153, NAD_binding_2::6PGD, Pkinase, B_lectin::S_locus_glycop::PAN_1::Pkinase, EMP24_GP25L, DUF6::DUF6, DUF163, Sina, adh_short, Rho_GDI, zf-CCHC::zf-CCHC::zf-CCHC::zf-CCHC::zf-CCHC::zf-CCHC::zf-CCHC, VHS::GAT, Pyrophosphatase, DMRL_synthase, Cyclin_N::Cyclin_C, NDK, TPP_enzyme_N::TPP_enzyme_M::TPP_enzyme_C, SH3_1, UDPG_MGDP_dh_N::UDPG_MGDP_dh::UDPG_MGDP_dh_C, UIM::efhand, DUF579, Pkinase, DHBP_synthase::GTP_cyclohydro2, Peptidase_C14, Glycolytic, Pkinase, Lipase_3, LRRNT_2::LRR_1::LRR_1::LRR_1::LRR_1, Snf7, BT1, PPDK_N::PEP-utilizers::PEP-utilizers_C, V-ATPase_G, RNA_pol_I_A49, Zip, WD40::WD40::WD40, Branch, RCC1::RCC1::RCC1::RCC1, TFIID-18 kDa, Pkinase, Cullin, TFIID-31 kDa, Asp, Pkinase, Ubie_methyltran, PPR::PPR::PPR::PPR::PPR::PPR::PPR::PPR, Fructosamin_kin, PPR::PPR::PPR::PPR::PPR::PPR, Pkinase_Tyr, p450, AA_permease, Glycos_transf_1, ECH::3HCDH_N::3HCDH, MIP, ADH_N::ADH_zinc_N, Aa_trans, DUF1517, Redoxin, RRS1, Pribosyltran, Sulfate_transp::STAS, DUF167, MMR_HSR1::DUF933, Aminotran_1_2, AA_permease, DUF620, Aldedh, Aminotran_1_2, LRR_1, CDP-OH_P_transf, DHBP_synthase::GTP_cyclohydro2, NHL::NHL, WD40::U3_snoRNA_C, Na_sulph_symp, adh_short, Thioredoxin, Ribosomal_L7Ae, OTCace_N::OTCace, Mito_carr::Mito_carr::Mito_carr, Pescadillo_N::BRCT, PPR::PPR::PPR::PPR::PPR::PPR::PPR::PPR::PPR::PPR, mTERF, Chalcone, Per1, PPR::PPR, Na_H_Exchanger::TrkA_N, DEAD::Helicase_C, Cyclin_N::Cyclin_C, PP-binding, SRF-TF, SATase_N::Hexapep::Hexapep::Hexapep, PK::PK_C, adh_short, DUF6::DUF6, Pyr_redox_2, G-patch, WD40::WD40::WD40::WD40, G-alpha, VQ, WD40::WD40::WD40::WD40, Aminotran_3, Pribosyltran, LRRNT_2::LRR_1::LRR_1::LRR_1::LRR_1::LRR_1, eIF3_subunit, H_PPase, Nodulin-like, Whi5, Tryp_alpha_amyl, NIR_SIR_ferr::NIR_SIR::NIR_SIR_ferr, RRM_1::RRM_1, Band_7, Asp, MFS_1, F420_oxidored, Pkinase, PRK, Na_Ca_ex::Na_Ca_ex, Bombesin, Pkinase, Epimerase, Pkinase, Inositol_P, Arm::Arm::Arm::Arm, PB1, Hin1, p450, RNA_pol_Rpb5_N::RNA_pol_Rpb5_C, Adap_comp_sub, Peptidase_M16::Peptidase_M16_C, Pkinase, PGK, Biotin_lipoyl::E3_binding::2-oxoacid_dh, Alg6_Alg8, F-box, MMR_HSR1, G6PD_N::G6PD_C, DAD, malic::Malic_M::PTA_PTB, ADH_N::ADH_zinc_N, LRR_1::LRR_1::LRR_1::LRR_::LRR_1::LRR_1::LRR_1, PfkB, PA, Pyr_redox_2::Pyr_redox_dim, SIP1, PP2C, BT1, AhpC-TSA, GASA, Aminotran_3, Sad1_UNC, Pkinase, zf-MYND::PDCD2_C, Pkinase, PGK, ArfGap, GATase::GMP_synt_C, p450, DUF1637, 2OG-FeII_Oxy, Aldedh, DUF231, Glyco_transf_8, Sec1, DUF1475, Cellulose_synt, RRM_::RRM_::RRM_1, Usp, AA_permease, Acetyltransf_1::Bromodomain, Glyco_tran_28_C, RNA_po_N, NTP_transferase, malic::Malic_M, Histone, Epimerase, UPF0061, ClpS, LEA_5, Auxin_inducible, PAP_fibrillin, Aldo_ket_red, Gln-synt_C, DREPP, p450, SFT2, eIF2A, Cenp-O, CPSase_sm_chain::GATase, WD40::WD40::WD40, Pkinase, Porin_3, Pkinase, Aminotran_1_2, GST_N::GST_C, F-box::Kelch_1::Kelch_1, IU_nuc_hydro, SYF2, PDT, Subtilisin_N::PA, Sugar_tr, WD40::WD40, p450, DUF829, Pyr_redox_2::Pyr_redox_dim, Aminotran_1_2, Cyclin_N::Cyclin_C, YgbB, Sugar_tr, SRF-TF, DUF231, DUF584, BT1, zf-C3HC4, Metallophos, FA_hydroxylase, p450, ACBP::Ank::Ank, LSM, SAM_1, LRR_1::LRR_1::Pkinase, Cullin, F-box::FBA_1, peroxidase, Rib_5-P_isom_A, zf-A20::zf-AN1, Dimerisation::Methyltransf_2, PGAM, PTR2, Copine, PALP, Exo_endo_phos, G6PD_N::G6PD_C, PLAC8, Aldo_ket_red, Ank::Ank, FBPase, zf-C3HC4, ACT::ACT, Suc_Fer-like, Pkinase_Tyr, G-alpha, RAMP4, Glutaredoxin, RRM_1::RRM_1, MT-A70, Response_reg::CCT, Arf, AP2, DUF177, 2OG-FeII_Oxy, LRRNT_2::LRR_1::LRR_1::LRR_1::LRR_1::LRR_1, LRR_1, Aldedh, DUF1350, FAE1_CUT1_RppA::ACP_syn_III_C, Sybindin, zf-C3HC4, Nfu_N::NifU, Rho_GDI, PK::PK_C, NOSIC::Nop, PK::PK_C, PRK::Pribosyltran, PfkB, p450, DUF231, TFIID_30 kDa, Aldedh, zf-AN1, GHMP_kinases_N::GHMP_kinases_C, DUF423, Pkinase, Cu-oxidase_3::Cu-oxidase::Cu-oxidase_2, PCI, RNase_PH::RNase_PH_C, DUF59, NTP_transferase, CH::EB1, Pkinase::Pkinase_C, DUF866, SMP::SMP::SMP, Aminotran_3, Transket_pyr::Transketolase_C, Copine, His_biosynth, Tbf5, DUF543, p450, C2, DUF616, Gp_dh_N::Gp_dh_C, Smg4_UPF3, DUF231, DUF89, WD40::WD40, Aldedh, ACT::ACT::ACT::ACT, Pkinase, Pyridoxal_deC, Skp1_POZ::Skp1, NAP, FolB, p450, Pentapeptide::Pentapeptide, NTP_transferase::MannoseP_isomer, SQS_PSY, Cyclase, GASA, Rick_17 kDa_Anti, FMO-like, B_lectin::S_locus_glycop::PAN_2, Peptidase_C12, Ribosomal_S6e, Glyoxalase, Response_reg::CCT, PHD::SET, Redoxin, G_glu_transpept, Synaptobrevin, p450, RALF, PALP, Branch, DUF579, Aminotran_3, Nramp, Enolase_N::Enolase_C, Str_synth, FAD_binding_3, MOSC_N::MOSC, Spc97_Spc98, Glycolytic, F-box::WD40::WD40::WD40::WD40, AA_kinase::ACT::ACT, RALF, and ATP_bind_1.

Plant Cell Transformation Methods

Numerous methods for transforming chromosomes in a plant cell nucleus with recombinant DNA are known in the art and are used in methods of preparing a transgenic plant cell nucleus cell, and plant. Two effective methods for such transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola, also known as rapeseed); U.S. Pat. No. 5,591,616 (corn); U.S. Pat. No. 6,384,301 (soybean), U.S. Pat. No. 7,026,528 (wheat) and U.S. Pat. No. 6,329,571 (rice), all of which are incorporated herein by reference for enabling the production of transgenic plants. Transformation of plant material is practiced in tissue culture on a nutrient media, e.g. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus can be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In practice, DNA is introduced into only a small percentage of target cell nuclei. Marker genes are used to provide an efficient system for identification of those cells with nuclei that are stably transformed by receiving and integrating a recombinant DNA molecule into their genomes. Some marker genes provide selective markers that confer resistance to a selective agent, such as an antibiotic or herbicide. Potentially transformed cells with a nucleus of the invention are exposed to the selective agent. In the population of surviving cells will be those cells where, generally, the resistance-conferring gene has been integrated and expressed at sufficient levels to permit cell survival. Cells can be tested further to confirm stable integration of the exogenous DNA in the nucleus. Explementary selective marker genes include those conferring resistance to antibiotics such as kanamycin (nptII), hygromycin B (aph IV), spectinomycin (aadA) and gentamycin (aac3 and aacC4) or resistance to herbicides such as glufosinate (bar or pat), dicamba (DMO) and glyphosate (EPSPS). Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a heir-glucuronidase or uidA gene (GUS) for which various chromogenic substrates are known. It is also contemplated that combinations of screenable and selectable markers can be used for identification of transformed cells. See PCT publication WO 99/61129 (herein incorporated by reference) which discloses use of a gene fusion between a selectable marker gene and a screenable marker gene, e.g., an NPTII gene and a GFP gene.

Plant cells that survive exposure to the selective agent, or plant cells that have been scored positive in a screening assay, can be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from transgenic plant cells having a transgenic nucleus of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

To identify nuclei with recombinant DNA that confer enhanced traits to plants, *Arabidopsis thaliana* was transformed with a candidate recombinant DNA construct and screened for an enhanced trait.

*Arabidopsis thaliana* is used a model for genetics and metabolism in plants. A two-step screening process was employed which included two passes of trait characterization to ensure that the trait modification was dependent on expression of the recombinant DNA, but not due to the chromosomal location of the integration of the transgene. Twelve independent transgenic lines for each recombinant DNA construct were established and assayed for the transgene expression levels. Five transgenic lines with high transgene expression levels were used in the first pass screen to evaluate the transgene's function in T2 transgenic plants. Subsequently, three transgenic events, which had been shown to have one or more enhanced traits, were further evaluated in the second pass screen to confirm the transgene's ability to impart an enhanced trait. The following Table 3 summarizes the enhanced traits that have been confirmed as provided by a recombinant DNA construct.

Table 2 provides a list of protein encoding DNA ("genes" as recombinant DNA for production of transgenic plants with enhanced agronomic trait, the elements of Table 2 are described by reference to:

PEP SEQ ID NO" identifies an amino acid sequence from SEQ ID NO: 804 to 1606.

"NIX SEQ ID NO" identifies a DNA sequence from SEQ ID NO:1 to 803

"construct_id" refers to an arbitrary number used to identify a particular recombinant DNA construct comprising the particular DNA.

"Gene ID" refers to an arbitrary name used to identify the particular DNA, "orientation" refers to the orientation of the particular DNA in a recombinant DNA construct relative to the promoter.

TABLE 2

| NUC SEQ ID NO | PEP SEQ ID NO | Gene ID | Construct ID | Orientation |
|---|---|---|---|---|
| 1 | 804 | CGPG10 | 70244 | SENSE |
| 2 | 805 | CGPG1008 | 71108 | SENSE |
| 3 | 806 | CGPG1023 | 12816 | SENSE |
| 4 | 807 | CGPG1038 | 12650 | ANTI-SENSE |
| 5 | 808 | CGPG1067 | 12031 | SENSE |
| 6 | 809 | CGPG1095 | 12217 | SENSE |
| 7 | 810 | CGPG1101 | 12043 | SENSE |
| 8 | 811 | CGPG1109 | 12147 | ANTI-SENSE |
| 9 | 812 | CGPG1113 | 13638 | ANTI-SENSE |
| 10 | 813 | CGPG1155 | 11860 | ANTI-SENSE |
| 11 | 814 | CGPG1163 | 72361 | SENSE |
| 12 | 815 | CGPG1171 | 12230 | SENSE |
| 13 | 816 | CGPG1177 | 71626 | SENSE |
| 14 | 817 | CGPG1205 | 13454 | ANTI-SENSE |
| 15 | 818 | CGPG1207 | 12173 | ANTI-SENSE |
| 16 | 819 | CGPG1215 | 17806 | ANTI-SENSE |
| 17 | 820 | CGPG1223 | 12011 | ANTI-SENSE |
| 18 | 821 | CGPG1250 | 72915 | SENSE |
| 19 | 822 | CGPG1279 | 13231 | SENSE |
| 20 | 823 | CGPG1304 | 13913 | SENSE |
| 21 | 824 | CGPG1319 | 12749 | ANTI-SENSE |
| 22 | 825 | CGPG1327 | 78901 | SENSE |
| 23 | 826 | CGPG1329 | 75969 | SENSE |
| 24 | 827 | CGPG133 | 15606 | SENSE |
| 25 | 828 | CGPG1332 | 75946 | SENSE |
| 26 | 829 | CGPG1343 | 13050 | ANTI-SENSE |
| 27 | 830 | CGPG1348 | 75958 | SENSE |
| 28 | 831 | CGPG1349 | 17333 | SENSE |
| 29 | 832 | CGPG1373 | 76002 | SENSE |
| 30 | 833 | CGPG1377 | 78735 | SENSE |
| 31 | 834 | CGPG1412 | 13914 | SENSE |
| 32 | 835 | CGPG1421 | 14405 | SENSE |
| 33 | 836 | CGPG1426 | 75983 | SENSE |
| 34 | 837 | CGPG1433 | 70721 | ANTI-SENSE |
| 35 | 838 | CGPG1453 | 13811 | SENSE |
| 35 | 838 | CGPG1453 | 13828 | ANTI-SENSE |
| 36 | 839 | CGPG1454 | 13614 | SENSE |
| 37 | 840 | CGPG1463 | 76050 | SENSE |
| 38 | 841 | CGPG1464 | 13038 | ANTI-SENSE |
| 39 | 842 | CGPG1471 | 13040 | ANTI-SENSE |
| 40 | 843 | CGPG1481 | 70716 | ANTI-SENSE |
| 40 | 843 | CGPG1481 | 76039 | SENSE |
| 41 | 844 | CGPG1499 | 71611 | SENSE |
| 42 | 845 | CGPG150 | 70253 | SENSE |
| 43 | 846 | CGPG1536 | 14415 | SENSE |
| 44 | 847 | CGPG1539 | 13718 | ANTI-SENSE |
| 45 | 848 | CGPG155 | 10706 | ANTI-SENSE |
| 45 | 848 | CGPG155 | 10709 | ANTI-SENSE |
| 46 | 849 | CGPG1583 | 14340 | ANTI-SENSE |
| 47 | 850 | CGPG1588 | 13471 | ANTI-SENSE |
| 48 | 851 | CGPG16 | 18304 | SENSE |
| 49 | 852 | CGPG1609 | 13623 | SENSE |
| 50 | 853 | CGPG1629 | 18302 | SENSE |
| 51 | 854 | CGPG1637 | 15053 | ANTI-SENSE |
| 52 | 855 | CGPG1653 | 15624 | SENSE |
| 53 | 856 | CGPG1658 | 70412 | SENSE |
| 54 | 857 | CGPG1663 | 17902 | SENSE |
| 55 | 858 | CGPG1682 | 14272 | ANTI-SENSE |
| 56 | 859 | CGPG1701 | 15122 | SENSE |
| 56 | 859 | CGPG1701 | 70723 | ANTI-SENSE |
| 57 | 860 | CGPG1723 | 14248 | SENSE |
| 58 | 861 | CGPG1724 | 13965 | ANTI-SENSE |
| 59 | 862 | CGPG1726 | 75912 | SENSE |
| 60 | 863 | CGPG1736 | 14344 | ANTI-SENSE |
| 61 | 864 | CGPG1741 | 14807 | ANTI-SENSE |
| 62 | 865 | CGPG1783 | 17307 | SENSE |
| 63 | 866 | CGPG1790 | 16431 | ANTI-SENSE |
| 64 | 867 | CGPG1797 | 73075 | SENSE |
| 65 | 868 | CGPG1845 | 16323 | SENSE |
| 66 | 869 | CGPG1855 | 14833 | ANTI-SENSE |
| 67 | 870 | CGPG1870 | 17030 | ANTI-SENSE |
| 68 | 871 | CGPG1879 | 76414 | SENSE |
| 69 | 872 | CGPG1886 | 16021 | SENSE |
| 70 | 873 | CGPG1903 | 78701 | SENSE |
| 71 | 874 | CGPG1905 | 78702 | SENSE |
| 72 | 875 | CGPG1914 | 15220 | ANTI-SENSE |
| 73 | 876 | CGPG193 | 15623 | SENSE |
| 74 | 877 | CGPG1939 | 19402 | SENSE |
| 75 | 878 | CGPG1949 | 70559 | SENSE |
| 76 | 879 | CGPG1959 | 15111 | ANTI-SENSE |
| 77 | 880 | CGPG197 | 70832 | SENSE |
| 78 | 881 | CGPG1972 | 15129 | SENSE |
| 79 | 882 | CGPG1981 | 76086 | SENSE |
| 80 | 883 | CGPG1999 | 15203 | ANTI-SENSE |
| 81 | 884 | CGPG2 | 70216 | SENSE |
| 82 | 885 | CGPG2006 | 14910 | ANTI-SENSE |
| 83 | 886 | CGPG2010 | 70318 | SENSE |
| 84 | 887 | CGPG2011 | 15207 | ANTI-SENSE |
| 85 | 888 | CGPG2014 | 14915 | ANTI-SENSE |
| 86 | 889 | CGPG2023 | 15132 | SENSE |
| 87 | 890 | CGPG2026 | 16229 | SENSE |
| 88 | 891 | CGPG2041 | 14932 | ANTI-SENSE |
| 89 | 892 | CGPG2064 | 76017 | SENSE |
| 90 | 893 | CGPG2070 | 15964 | ANTI-SENSE |
| 91 | 894 | CGPG2077 | 17227 | SENSE |
| 92 | 895 | CGPG2095 | 72952 | SENSE |
| 93 | 896 | CGPG2105 | 73706 | SENSE |
| 94 | 897 | CGPG2108 | 18203 | SENSE |
| 95 | 898 | CGPG2111 | 16309 | SENSE |
| 96 | 899 | CGPG2124 | 15986 | ANTI-SENSE |
| 97 | 900 | CGPG2125 | 15987 | ANTI-SENSE |

TABLE 2-continued

| NUC SEQ ID NO | PEP SEQ ID NO | Gene ID | Construct ID | Orientation |
|---|---|---|---|---|
| 98 | 901 | CGPG2126 | 16204 | SENSE |
| 99 | 902 | CGPG213 | 11133 | SENSE |
| 100 | 903 | CGPG2134 | 73977 | SENSE |
| 101 | 904 | CGPG2139 | 15995 | ANTI-SENSE |
| 101 | 904 | CGPG2139 | 18201 | SENSE |
| 102 | 905 | CGPG2140 | 16887 | SENSE |
| 103 | 906 | CGPG2153 | 16213 | SENSE |
| 104 | 907 | CGPG2163 | 15507 | ANTI-SENSE |
| 105 | 908 | CGPG2165 | 15508 | ANTI-SENSE |
| 106 | 909 | CGPG2193 | 15959 | ANTI-SENSE |
| 107 | 910 | CGPG2218 | 72427 | ANTI-SENSE |
| 108 | 911 | CGPG2224 | 19041 | ANTI-SENSE |
| 109 | 912 | CGPG2225 | 17802 | SENSE |
| 110 | 913 | CGPG2229 | 19042 | ANTI-SENSE |
| 111 | 914 | CGPG2243 | 76053 | SENSE |
| 112 | 915 | CGPG2254 | 16120 | SENSE |
| 113 | 916 | CGPG2268 | 15424 | ANTI-SENSE |
| 114 | 917 | CGPG227 | 16401 | SENSE |
| 115 | 918 | CGPG2312 | 72417 | SENSE |
| 116 | 919 | CGPG2315 | 73702 | SENSE |
| 117 | 920 | CGPG2316 | 70706 | ANTI-SENSE |
| 118 | 921 | CGPG2319 | 71145 | SENSE |
| 119 | 922 | CGPG235 | 11609 | ANTI-SENSE |
| 120 | 923 | CGPG2358 | 71706 | SENSE |
| 121 | 924 | CGPG2359 | 17325 | SENSE |
| 122 | 925 | CGPG2361 | 70102 | SENSE |
| 123 | 926 | CGPG2365 | 70106 | SENSE |
| 124 | 927 | CGPG2372 | 70113 | SENSE |
| 125 | 928 | CGPG2374 | 70115 | SENSE |
| 126 | 929 | CGPG2377 | 70118 | SENSE |
| 127 | 930 | CGPG2387 | 70128 | SENSE |
| 128 | 931 | CGPG2389 | 70130 | SENSE |
| 129 | 932 | CGPG2395 | 17103 | ANTI-SENSE |
| 130 | 933 | CGPG2408 | 72748 | SENSE |
| 131 | 934 | CGPG2409 | 17502 | SENSE |
| 132 | 935 | CGPG2410 | 17503 | SENSE |
| 133 | 936 | CGPG2414 | 78708 | SENSE |
| 134 | 937 | CGPG2416 | 17504 | SENSE |
| 135 | 938 | CGPG2441 | 17132 | ANTI-SENSE |
| 136 | 939 | CGPG2450 | 72965 | SENSE |
| 137 | 940 | CGPG2451 | 72796 | SENSE |
| 138 | 941 | CGPG2492 | 16617 | SENSE |
| 139 | 942 | CGPG2495 | 16640 | SENSE |
| 140 | 943 | CGPG2506 | 16603 | SENSE |
| 141 | 944 | CGPG2515 | 16612 | SENSE |
| 142 | 945 | CGPG2531 | 16614 | SENSE |
| 143 | 946 | CGPG2581 | 78354 | SENSE |
| 144 | 947 | CGPG2584 | 17818 | SENSE |
| 145 | 948 | CGPG2592 | 78370 | SENSE |
| 146 | 949 | CGPG2612 | 70411 | SENSE |
| 147 | 950 | CGPG2660 | 19154 | SENSE |
| 148 | 951 | CGPG2663 | 19155 | SENSE |
| 149 | 952 | CGPG2679 | 18307 | SENSE |
| 150 | 953 | CGPG2696 | 72030 | SENSE |
| 151 | 954 | CGPG2772 | 17916 | SENSE |
| 152 | 955 | CGPG2773 | 17917 | SENSE |
| 153 | 956 | CGPG281 | 17334 | SENSE |
| 154 | 957 | CGPG2846 | 71531 | SENSE |
| 155 | 958 | CGPG2852 | 18441 | SENSE |
| 156 | 959 | CGPG2863 | 19162 | SENSE |
| 157 | 960 | CGPG2870 | 73205 | SENSE |
| 158 | 961 | CGPG2877 | 18306 | SENSE |
| 159 | 962 | CGPG289 | 70808 | SENSE |
| 160 | 963 | CGPG2924 | 17653 | SENSE |
| 161 | 964 | CGPG2947 | 19535 | SENSE |
| 162 | 965 | CGPG2963 | 71719 | SENSE |
| 163 | 966 | CGPG2987 | 18546 | SENSE |
| 164 | 967 | CGPG3033 | 19534 | SENSE |
| 165 | 968 | CGPG3045 | 18421 | SENSE |
| 166 | 969 | CGPG3046 | 18422 | SENSE |
| 167 | 970 | CGPG3060 | 19539 | SENSE |
| 168 | 971 | CGPG3075 | 19244 | SENSE |
| 169 | 972 | CGPG310 | 15803 | SENSE |
| 170 | 973 | CGPG3103 | 19545 | SENSE |
| 171 | 974 | CGPG315 | 10222 | ANTI-SENSE |
| 171 | 974 | CGPG315 | 72356 | SENSE |
| 172 | 975 | CGPG3183 | 70425 | SENSE |
| 173 | 976 | CGPG3189 | 19237 | SENSE |
| 174 | 977 | CGPG3204 | 71303 | SENSE |
| 175 | 978 | CGPG3208 | 19240 | SENSE |
| 176 | 979 | CGPG3219 | 18535 | SENSE |
| 177 | 980 | CGPG3233 | 19450 | SENSE |
| 178 | 981 | CGPG3263 | 18221 | SENSE |
| 179 | 982 | CGPG3276 | 18233 | SENSE |
| 180 | 983 | CGPG3280 | 18236 | SENSE |
| 181 | 984 | CGPG3282 | 18238 | SENSE |
| 182 | 985 | CGPG3300 | 18309 | SENSE |
| 183 | 986 | CGPG3318 | 70337 | SENSE |
| 184 | 987 | CGPG3319 | 18319 | SENSE |
| 185 | 988 | CGPG3326 | 70338 | SENSE |
| 186 | 989 | CGPG333 | 10471 | SENSE |
| 187 | 990 | CGPG3338 | 18331 | SENSE |
| 188 | 991 | CGPG334 | 10228 | ANTI-SENSE |
| 188 | 991 | CGPG334 | 10473 | SENSE |
| 189 | 992 | CGPG3374 | 18261 | SENSE |
| 190 | 993 | CGPG3402 | 18848 | SENSE |
| 191 | 994 | CGPG3405 | 18268 | SENSE |
| 192 | 995 | CGPG3413 | 18345 | SENSE |
| 193 | 996 | CGPG3422 | 73607 | SENSE |
| 194 | 997 | CGPG3436 | 18352 | SENSE |
| 195 | 998 | CGPG3539 | 18357 | SENSE |
| 196 | 999 | CGPG3550 | 19423 | SENSE |
| 197 | 1000 | CGPG3551 | 78373 | SENSE |
| 198 | 1001 | CGPG3552 | 70603 | SENSE |
| 199 | 1002 | CGPG3572 | 19616 | SENSE |
| 200 | 1003 | CGPG3598 | 19425 | SENSE |
| 201 | 1004 | CGPG3599 | 19426 | SENSE |
| 202 | 1005 | CGPG3606 | 18382 | SENSE |
| 203 | 1006 | CGPG3610 | 71536 | SENSE |
| 204 | 1007 | CGPG3620 | 70419 | SENSE |
| 205 | 1008 | CGPG364 | 70827 | SENSE |
| 206 | 1009 | CGPG3676 | 19311 | SENSE |
| 207 | 1010 | CGPG3679 | 19323 | SENSE |
| 208 | 1011 | CGPG3686 | 19320 | SENSE |
| 209 | 1012 | CGPG3694 | 73613 | SENSE |
| 210 | 1013 | CGPG3696 | 70432 | SENSE |
| 211 | 1014 | CGPG3698 | 70433 | SENSE |
| 212 | 1015 | CGPG3699 | 70434 | SENSE |
| 213 | 1016 | CGPG3702 | 72614 | SENSE |
| 214 | 1017 | CGPG3703 | 70436 | SENSE |
| 215 | 1018 | CGPG3707 | 74226 | SENSE |
| 216 | 1019 | CGPG3710 | 70439 | SENSE |
| 217 | 1020 | CGPG3730 | 70446 | SENSE |
| 218 | 1021 | CGPG3731 | 70613 | SENSE |
| 219 | 1022 | CGPG3734 | 70447 | SENSE |
| 220 | 1023 | CGPG3745 | 71725 | SENSE |
| 221 | 1024 | CGPG3764 | 70462 | SENSE |
| 222 | 1025 | CGPG3820 | 70545 | SENSE |
| 223 | 1026 | CGPG3851 | 70741 | SENSE |
| 224 | 1027 | CGPG3911 | 19702 | SENSE |
| 225 | 1028 | CGPG3948 | 19985 | SENSE |
| 226 | 1029 | CGPG3958 | 19775 | SENSE |
| 227 | 1030 | CGPG3981 | 19829 | SENSE |
| 228 | 1031 | CGPG3996 | 19982 | SENSE |
| 229 | 1032 | CGPG4006 | 19755 | SENSE |
| 230 | 1033 | CGPG4025 | 19732 | SENSE |
| 231 | 1034 | CGPG4028 | 70365 | SENSE |
| 232 | 1035 | CGPG403 | 10476 | SENSE |

TABLE 2-continued

| NUC SEQ ID NO | PEP SEQ ID NO | Gene ID | Construct ID | Orientation |
|---|---|---|---|---|
| 233 | 1036 | CGPG4041 | 19987 | SENSE |
| 234 | 1037 | CGPG4078 | 19893 | SENSE |
| 235 | 1038 | CGPG4079 | 19983 | SENSE |
| 236 | 1039 | CGPG4083 | 19825 | SENSE |
| 237 | 1040 | CGPG4092 | 19919 | SENSE |
| 238 | 1041 | CGPG4104 | 19979 | SENSE |
| 239 | 1042 | CGPG4127 | 19786 | SENSE |
| 240 | 1043 | CGPG4135 | 70903 | SENSE |
| 241 | 1044 | CGPG4161 | 70970 | SENSE |
| 242 | 1045 | CGPG4180 | 70980 | SENSE |
| 243 | 1046 | CGPG4191 | 70936 | SENSE |
| 244 | 1047 | CGPG4199 | 71425 | SENSE |
| 245 | 1048 | CGPG4241 | 78666 | SENSE |
| 246 | 1049 | CGPG427 | 71202 | SENSE |
| 247 | 1050 | CGPG4273 | 78973 | SENSE |
| 248 | 1051 | CGPG4301 | 76411 | SENSE |
| 249 | 1052 | CGPG4303 | 70635 | SENSE |
| 250 | 1053 | CGPG4313 | 73715 | SENSE |
| 251 | 1054 | CGPG4314 | 70638 | SENSE |
| 252 | 1055 | CGPG4329 | 70642 | SENSE |
| 253 | 1056 | CGPG4330 | 70643 | SENSE |
| 254 | 1057 | CGPG4338 | 71564 | SENSE |
| 255 | 1058 | CGPG4341 | 75039 | SENSE |
| 256 | 1059 | CGPG4347 | 70653 | SENSE |
| 257 | 1060 | CGPG4354 | 70655 | SENSE |
| 258 | 1061 | CGPG4386 | 78321 | SENSE |
| 259 | 1062 | CGPG4394 | 78307 | SENSE |
| 260 | 1063 | CGPG4396 | 71808 | SENSE |
| 261 | 1064 | CGPG4400 | 71810 | SENSE |
| 262 | 1065 | CGPG4401 | 71313 | SENSE |
| 263 | 1066 | CGPG441 | 72349 | SENSE |
| 264 | 1067 | CGPG4413 | 71318 | SENSE |
| 265 | 1068 | CGPG4427 | 71812 | SENSE |
| 266 | 1069 | CGPG4446 | 74060 | SENSE |
| 267 | 1070 | CGPG4448 | 71816 | SENSE |
| 268 | 1071 | CGPG4474 | 71569 | SENSE |
| 269 | 1072 | CGPG4482 | 70672 | SENSE |
| 270 | 1073 | CGPG4511 | 71336 | SENSE |
| 271 | 1074 | CGPG4517 | 71337 | SENSE |
| 272 | 1075 | CGPG4551 | 71339 | SENSE |
| 273 | 1076 | CGPG4559 | 71825 | SENSE |
| 274 | 1077 | CGPG4567 | 73696 | SENSE |
| 275 | 1078 | CGPG4586 | 70682 | SENSE |
| 276 | 1079 | CGPG4600 | 70686 | SENSE |
| 277 | 1080 | CGPG4631 | 78316 | SENSE |
| 278 | 1081 | CGPG4642 | 71667 | SENSE |
| 279 | 1082 | CGPG4645 | 71695 | SENSE |
| 280 | 1083 | CGPG4646 | 71696 | SENSE |
| 281 | 1084 | CGPG4649 | 72475 | SENSE |
| 282 | 1085 | CGPG4653 | 71677 | SENSE |
| 283 | 1086 | CGPG4656 | 71691 | SENSE |
| 284 | 1087 | CGPG4668 | 72476 | SENSE |
| 285 | 1088 | CGPG469 | 70803 | SENSE |
| 286 | 1089 | CGPG4708 | 71612 | SENSE |
| 287 | 1090 | CGPG4712 | 71637 | SENSE |
| 288 | 1091 | CGPG4714 | 71629 | SENSE |
| 289 | 1092 | CGPG4719 | 71622 | SENSE |
| 290 | 1093 | CGPG473 | 70810 | SENSE |
| 291 | 1094 | CGPG4734 | 72452 | SENSE |
| 292 | 1095 | CGPG4736 | 74071 | SENSE |
| 293 | 1096 | CGPG474 | 11042 | SENSE |
| 294 | 1097 | CGPG4802 | 72510 | SENSE |
| 295 | 1098 | CGPG4822 | 72537 | SENSE |
| 296 | 1099 | CGPG4826 | 72541 | SENSE |
| 297 | 1100 | CGPG4833 | 72617 | SENSE |
| 298 | 1101 | CGPG4841 | 73755 | SENSE |
| 299 | 1102 | CGPG4850 | 72630 | SENSE |
| 300 | 1103 | CGPG4868 | 72645 | SENSE |
| 301 | 1104 | CGPG4871 | 72647 | SENSE |
| 302 | 1105 | CGPG488 | 14316 | SENSE |
| 303 | 1106 | CGPG4908 | 73689 | SENSE |
| 304 | 1107 | CGPG4913 | 73345 | SENSE |
| 305 | 1108 | CGPG4921 | 73347 | SENSE |
| 306 | 1109 | CGPG4954 | 73231 | SENSE |
| 307 | 1110 | CGPG4956 | 78325 | SENSE |
| 308 | 1111 | CGPG4959 | 72658 | SENSE |
| 309 | 1112 | CGPG4965 | 72660 | SENSE |
| 310 | 1113 | CGPG4970 | 72662 | SENSE |
| 311 | 1114 | CGPG4980 | 73352 | SENSE |
| 312 | 1115 | CGPG4982 | 72814 | SENSE |
| 313 | 1116 | CGPG4985 | 72816 | SENSE |
| 314 | 1117 | CGPG4990 | 72820 | SENSE |
| 315 | 1118 | CGPG4991 | 73353 | SENSE |
| 316 | 1119 | CGPG5007 | 75066 | SENSE |
| 317 | 1120 | CGPG5015 | 78337 | SENSE |
| 318 | 1121 | CGPG5026 | 73317 | SENSE |
| 319 | 1122 | CGPG5029 | 73318 | SENSE |
| 320 | 1123 | CGPG5046 | 73749 | SENSE |
| 321 | 1124 | CGPG508 | 18704 | SENSE |
| 322 | 1125 | CGPG5103 | 73221 | SENSE |
| 323 | 1126 | CGPG511 | 71125 | SENSE |
| 324 | 1127 | CGPG5121 | 76203 | SENSE |
| 325 | 1128 | CGPG5126 | 75067 | SENSE |
| 326 | 1129 | CGPG5136 | 73729 | SENSE |
| 327 | 1130 | CGPG5146 | 75206 | SENSE |
| 328 | 1131 | CGPG5149 | 73248 | SENSE |
| 329 | 1132 | CGPG5181 | 73738 | SENSE |
| 330 | 1133 | CGPG52 | 73332 | SENSE |
| 331 | 1134 | CGPG5206 | 78335 | SENSE |
| 332 | 1135 | CGPG5208 | 75821 | SENSE |
| 333 | 1136 | CGPG5232 | 72038 | SENSE |
| 334 | 1137 | CGPG5239 | 72027 | SENSE |
| 335 | 1138 | CGPG5246 | 72016 | SENSE |
| 336 | 1139 | CGPG525 | 70835 | SENSE |
| 337 | 1140 | CGPG5268 | 72044 | SENSE |
| 338 | 1141 | CGPG5272 | 72092 | SENSE |
| 339 | 1142 | CGPG5333 | 72124 | SENSE |
| 340 | 1143 | CGPG5338 | 72110 | SENSE |
| 341 | 1144 | CGPG5341 | 73916 | SENSE |
| 342 | 1145 | CGPG5369 | 74268 | SENSE |
| 343 | 1146 | CGPG5372 | 74269 | SENSE |
| 344 | 1147 | CGPG5380 | 77902 | SENSE |
| 345 | 1148 | CGPG5386 | 74273 | SENSE |
| 346 | 1149 | CGPG5396 | 74280 | SENSE |
| 347 | 1150 | CGPG5397 | 74281 | SENSE |
| 348 | 1151 | CGPG5421 | 74287 | SENSE |
| 349 | 1152 | CGPG5433 | 73767 | SENSE |
| 350 | 1153 | CGPG5439 | 77304 | SENSE |
| 351 | 1154 | CGPG5453 | 73761 | SENSE |
| 352 | 1155 | CGPG5456 | 74721 | SENSE |
| 353 | 1156 | CGPG5483 | 74719 | SENSE |
| 354 | 1157 | CGPG5492 | 74257 | SENSE |
| 355 | 1158 | CGPG5508 | 72749 | SENSE |
| 356 | 1159 | CGPG5520 | 72703 | SENSE |
| 357 | 1160 | CGPG5525 | 72763 | SENSE |
| 358 | 1161 | CGPG5526 | 72775 | SENSE |
| 359 | 1162 | CGPG5530 | 72728 | SENSE |
| 360 | 1163 | CGPG5534 | 72776 | SENSE |
| 361 | 1164 | CGPG5537 | 72717 | SENSE |
| 362 | 1165 | CGPG5545 | 72718 | SENSE |
| 363 | 1166 | CGPG555 | 11715 | SENSE |
| 364 | 1167 | CGPG5558 | 72779 | SENSE |
| 365 | 1168 | CGPG5559 | 72791 | SENSE |
| 366 | 1169 | CGPG5562 | 72732 | SENSE |
| 367 | 1170 | CGPG5592 | 73027 | SENSE |
| 368 | 1171 | CGPG5625 | 73058 | SENSE |
| 369 | 1172 | CGPG5631 | 73126 | SENSE |
| 370 | 1173 | CGPG5632 | 73138 | SENSE |
| 371 | 1174 | CGPG5636 | 73174 | SENSE |
| 372 | 1175 | CGPG5637 | 73186 | SENSE |
| 373 | 1176 | CGPG564 | 11141 | SENSE |
| 374 | 1177 | CGPG5641 | 73139 | SENSE |
| 375 | 1178 | CGPG5650 | 73128 | SENSE |
| 376 | 1179 | CGPG5653 | 73164 | SENSE |
| 377 | 1180 | CGPG5657 | 73117 | SENSE |
| 378 | 1181 | CGPG5671 | 73142 | SENSE |
| 379 | 1182 | CGPG5672 | 73990 | SENSE |
| 380 | 1183 | CGPG5677 | 73166 | SENSE |
| 381 | 1184 | CGPG5678 | 73178 | SENSE |
| 382 | 1185 | CGPG5679 | 73190 | SENSE |
| 383 | 1186 | CGPG5682 | 73131 | SENSE |
| 384 | 1187 | CGPG5691 | 73108 | SENSE |

TABLE 2-continued

| NUC SEQ ID NO | PEP SEQ ID NO | Gene ID | Construct ID | Orientation |
|---|---|---|---|---|
| 385 | 1188 | CGPG5699 | 73074 | SENSE |
| 386 | 1189 | CGPG5705 | 73132 | SENSE |
| 387 | 1190 | CGPG5722 | 73146 | SENSE |
| 388 | 1191 | CGPG5734 | 73147 | SENSE |
| 389 | 1192 | CGPG5736 | 73080 | SENSE |
| 390 | 1193 | CGPG5744 | 73077 | SENSE |
| 391 | 1194 | CGPG5747 | 73183 | SENSE |
| 392 | 1195 | CGPG5748 | 73018 | SENSE |
| 393 | 1196 | CGPG5750 | 73112 | SENSE |
| 394 | 1197 | CGPG5751 | 73988 | SENSE |
| 395 | 1198 | CGPG577 | 10908 | ANTI-SENSE |
| 395 | 1198 | CGPG577 | 11147 | SENSE |
| 396 | 1199 | CGPG5780 | 72909 | SENSE |
| 397 | 1200 | CGPG5793 | 73987 | SENSE |
| 398 | 1201 | CGPG5795 | 72922 | SENSE |
| / | / | / | / | / |
| 399 | 1202 | CGPG5796 | 73036 | SENSE |
| 400 | 1203 | CGPG5800 | 72958 | SENSE |
| 401 | 1204 | CGPG5812 | 77006 | SENSE |
| 402 | 1205 | CGPG5815 | 74732 | SENSE |
| 403 | 1206 | CGPG5838 | 74333 | SENSE |
| 404 | 1207 | CGPG5844 | 74735 | SENSE |
| 405 | 1208 | CGPG5846 | 74736 | SENSE |
| 406 | 1209 | CGPG5851 | 74737 | SENSE |
| 407 | 1210 | CGPG5857 | 76657 | SENSE |
| 408 | 1211 | CGPG5862 | 76113 | SENSE |
| 409 | 1212 | CGPG5863 | 74747 | SENSE |
| 410 | 1213 | CGPG5867 | 77309 | SENSE |
| 411 | 1214 | CGPG5872 | 74322 | SENSE |
| 412 | 1215 | CGPG5913 | 76212 | SENSE |
| 413 | 1216 | CGPG5922 | 76514 | SENSE |
| 414 | 1217 | CGPG5961 | 75242 | SENSE |
| 415 | 1218 | CGPG5964 | 77324 | SENSE |
| 416 | 1219 | CGPG5968 | 74350 | SENSE |
| 417 | 1220 | CGPG5984 | 77606 | SENSE |
| 418 | 1221 | CGPG5991 | 76530 | SENSE |
| 419 | 1222 | CGPG6006 | 76716 | SENSE |
| 420 | 1223 | CGPG6015 | 77328 | SENSE |
| 421 | 1224 | CGPG603 | 12204 | SENSE |
| 422 | 1225 | CGPG6046 | 77011 | SENSE |
| 423 | 1226 | CGPG6063 | 77607 | SENSE |
| 424 | 1227 | CGPG6083 | 74612 | SENSE |
| 425 | 1228 | CGPG6092 | 76126 | SENSE |
| 426 | 1229 | CGPG6104 | 74376 | SENSE |
| 427 | 1230 | CGPG6106 | 74377 | SENSE |
| 428 | 1231 | CGPG6111 | 74381 | SENSE |
| 429 | 1232 | CGPG6113 | 78364 | SENSE |
| 430 | 1233 | CGPG6125 | 74623 | SENSE |
| 431 | 1234 | CGPG6132 | 74668 | SENSE |
| 432 | 1235 | CGPG6137 | 74629 | SENSE |
| 433 | 1236 | CGPG6147 | 74635 | SENSE |
| 434 | 1237 | CGPG6152 | 74638 | SENSE |
| 435 | 1238 | CGPG6154 | 76721 | SENSE |
| 436 | 1239 | CGPG6170 | 78365 | SENSE |
| 437 | 1240 | CGPG6171 | 74655 | SENSE |
| 438 | 1241 | CGPG6177 | 74660 | SENSE |
| 439 | 1242 | CGPG6181 | 74661 | SENSE |
| 440 | 1243 | CGPG6188 | 75259 | SENSE |
| 441 | 1244 | CGPG6202 | 75282 | SENSE |
| 442 | 1245 | CGPG6217 | 76724 | SENSE |
| 443 | 1246 | CGPG623 | 12350 | ANTI-SENSE |
| 444 | 1247 | CGPG6239 | 76522 | SENSE |
| 445 | 1248 | CGPG6244 | 77903 | SENSE |
| 446 | 1249 | CGPG6254 | 76653 | SENSE |
| 447 | 1250 | CGPG6266 | 76524 | SENSE |
| 448 | 1251 | CGPG627 | 11356 | SENSE |
| 449 | 1252 | CGPG6271 | 75275 | SENSE |
| 450 | 1253 | CGPG6278 | 76225 | SENSE |
| 451 | 1254 | CGPG6288 | 75281 | SENSE |
| 452 | 1255 | CGPG6309 | 74384 | SENSE |
| 453 | 1256 | CGPG633 | 71238 | SENSE |
| 454 | 1257 | CGPG635 | 12354 | ANTI-SENSE |
| 455 | 1258 | CGPG6350 | 76236 | SENSE |
| 456 | 1259 | CGPG6358 | 74682 | SENSE |
| 457 | 1260 | CGPG6365 | 73425 | SENSE |
| 458 | 1261 | CGPG6374 | 73438 | SENSE |
| 459 | 1262 | CGPG6377 | 73474 | SENSE |
| 460 | 1263 | CGPG638 | 70850 | SENSE |
| 461 | 1264 | CGPG6397 | 73429 | SENSE |
| 462 | 1265 | CGPG6398 | 73441 | SENSE |
| 463 | 1266 | CGPG6408 | 73466 | SENSE |
| 464 | 1267 | CGPG6415 | 73455 | SENSE |
| 465 | 1268 | CGPG6421 | 73432 | SENSE |
| 466 | 1269 | CGPG6442 | 73435 | SENSE |
| 467 | 1270 | CGPG6443 | 77726 | SENSE |
| 468 | 1271 | CGPG6446 | 73483 | SENSE |
| 469 | 1272 | CGPG6453 | 73472 | SENSE |
| 470 | 1273 | CGPG6466 | 73526 | SENSE |
| 471 | 1274 | CGPG6467 | 73538 | SENSE |
| 472 | 1275 | CGPG6470 | 73574 | SENSE |
| 473 | 1276 | CGPG6475 | 73539 | SENSE |
| 474 | 1277 | CGPG6477 | 73563 | SENSE |
| 475 | 1278 | CGPG6478 | 73575 | SENSE |
| 476 | 1279 | CGPG6493 | 73565 | SENSE |
| 477 | 1280 | CGPG6506 | 73531 | SENSE |
| 478 | 1281 | CGPG6518 | 73592 | SENSE |
| 479 | 1282 | CGPG6546 | 74149 | SENSE |
| 480 | 1283 | CGPG6556 | 74174 | SENSE |
| 481 | 1284 | CGPG6562 | 74151 | SENSE |
| 482 | 1285 | CGPG6566 | 74104 | SENSE |
| 483 | 1286 | CGPG6571 | 74164 | SENSE |
| 484 | 1287 | CGPG6576 | 74129 | SENSE |
| 485 | 1288 | CGPG659 | 72340 | SENSE |
| 486 | 1289 | CGPG6594 | 74155 | SENSE |
| 487 | 1290 | CGPG6603 | 74168 | SENSE |
| 488 | 1291 | CGPG6608 | 74133 | SENSE |
| 489 | 1292 | CGPG6634 | 74160 | SENSE |
| 490 | 1293 | CGPG6662 | 74485 | SENSE |
| 491 | 1294 | CGPG6667 | 74450 | SENSE |
| 492 | 1295 | CGPG6678 | 74487 | SENSE |
| 493 | 1296 | CGPG6695 | 74406 | SENSE |
| 494 | 1297 | CGPG6699 | 74454 | SENSE |
| 495 | 1298 | CGPG670 | 11361 | SENSE |
| 496 | 1299 | CGPG6705 | 74431 | SENSE |
| 497 | 1300 | CGPG6735 | 74411 | SENSE |
| 498 | 1301 | CGPG6744 | 74424 | SENSE |
| 499 | 1302 | CGPG6753 | 74525 | SENSE |
| 500 | 1303 | CGPG6757 | 74573 | SENSE |
| 501 | 1304 | CGPG6803 | 75827 | SENSE |
| 502 | 1305 | CGPG6806 | 77329 | SENSE |
| 503 | 1306 | CGPG6811 | 77330 | SENSE |
| 504 | 1307 | CGPG6812 | 75830 | SENSE |
| 505 | 1308 | CGPG6815 | 75832 | SENSE |
| 506 | 1309 | CGPG6827 | 75836 | SENSE |
| 507 | 1310 | CGPG6830 | 77034 | SENSE |
| 508 | 1311 | CGPG6839 | 76255 | SENSE |
| 509 | 1312 | CGPG6859 | 76542 | SENSE |
| 510 | 1313 | CGPG6864 | 77511 | SENSE |
| 511 | 1314 | CGPG6877 | 76261 | SENSE |
| 512 | 1315 | CGPG6878 | 78456 | SENSE |
| 513 | 1316 | CGPG6880 | 77041 | SENSE |
| 514 | 1317 | CGPG6886 | 76546 | SENSE |
| 515 | 1318 | CGPG6887 | 75848 | SENSE |
| 516 | 1319 | CGPG6895 | 77515 | SENSE |
| 517 | 1320 | CGPG6896 | 76266 | SENSE |
| 518 | 1321 | CGPG6903 | 75852 | SENSE |
| 519 | 1322 | CGPG6912 | 76556 | SENSE |
| 520 | 1323 | CGPG6933 | 77523 | SENSE |
| 521 | 1324 | CGPG6942 | 75863 | SENSE |
| 522 | 1325 | CGPG6944 | 77052 | SENSE |
| 523 | 1326 | CGPG6949 | 75865 | SENSE |
| 524 | 1327 | CGPG6969 | 76551 | SENSE |
| 525 | 1328 | CGPG6989 | 76280 | SENSE |
| 526 | 1329 | CGPG6991 | 75874 | SENSE |
| 527 | 1330 | CGPG7003 | 75879 | SENSE |
| 528 | 1331 | CGPG7009 | 75880 | SENSE |
| 529 | 1332 | CGPG7037 | 77519 | SENSE |
| 530 | 1333 | CGPG7051 | 76745 | SENSE |
| 531 | 1334 | CGPG7062 | 76554 | SENSE |

TABLE 2-continued

| NUC SEQ ID NO | PEP SEQ ID NO | Gene ID | Construct ID | Orientation |
|---|---|---|---|---|
| 532 | 1335 | CGPG7064 | 76746 | SENSE |
| 533 | 1336 | CGPG7086 | 76750 | SENSE |
| 534 | 1337 | CGPG7109 | 76621 | SENSE |
| 535 | 1338 | CGPG7123 | 76623 | SENSE |
| 536 | 1339 | CGPG7136 | 76461 | SENSE |
| 537 | 1340 | CGPG7147 | 76462 | SENSE |
| 538 | 1341 | CGPG7159 | 78987 | SENSE |
| 539 | 1342 | CGPG7186 | 76568 | SENSE |
| 540 | 1343 | CGPG7222 | 76176 | SENSE |
| 541 | 1344 | CGPG7224 | 76177 | SENSE |
| 542 | 1345 | CGPG7233 | 78380 | SENSE |
| 543 | 1346 | CGPG7238 | 76629 | SENSE |
| 544 | 1347 | CGPG7253 | 76189 | SENSE |
| 545 | 1348 | CGPG7255 | 76761 | SENSE |
| 546 | 1349 | CGPG7286 | 78608 | SENSE |
| 547 | 1350 | CGPG7292 | 78115 | SENSE |
| 548 | 1351 | CGPG7301 | 74873 | SENSE |
| 549 | 1352 | CGPG7305 | 74826 | SENSE |
| 550 | 1353 | CGPG7307 | 74850 | SENSE |
| 551 | 1354 | CGPG7318 | 74887 | SENSE |
| 552 | 1355 | CGPG7319 | 74804 | SENSE |
| 553 | 1356 | CGPG7345 | 74831 | SENSE |
| 554 | 1357 | CGPG7368 | 74822 | SENSE |
| 555 | 1358 | CGPG7385 | 74836 | SENSE |
| 556 | 1359 | CGPG7391 | 74901 | SENSE |
| 557 | 1360 | CGPG7405 | 74974 | SENSE |
| 558 | 1361 | CGPG7415 | 74904 | SENSE |
| 559 | 1362 | CGPG7416 | 74916 | SENSE |
| 560 | 1363 | CGPG7420 | 74964 | SENSE |
| 561 | 1364 | CGPG7432 | 74918 | SENSE |
| 562 | 1365 | CGPG7436 | 74966 | SENSE |
| 563 | 1366 | CGPG7445 | 74979 | SENSE |
| 564 | 1367 | CGPG7465 | 74934 | SENSE |
| 565 | 1368 | CGPG7473 | 77814 | SENSE |
| 566 | 1369 | CGPG7489 | 75387 | SENSE |
| 567 | 1370 | CGPG7492 | 75328 | SENSE |
| 568 | 1371 | CGPG7499 | 77808 | SENSE |
| 569 | 1372 | CGPG7505 | 75389 | SENSE |
| 570 | 1373 | CGPG7507 | 75318 | SENSE |
| 571 | 1374 | CGPG7508 | 75330 | SENSE |
| 572 | 1375 | CGPG7509 | 75342 | SENSE |
| 573 | 1376 | CGPG7511 | 75366 | SENSE |
| 574 | 1377 | CGPG7515 | 75319 | SENSE |
| 575 | 1378 | CGPG7521 | 75391 | SENSE |
| 576 | 1379 | CGPG7540 | 75334 | SENSE |
| 577 | 1380 | CGPG7547 | 75323 | SENSE |
| 578 | 1381 | CGPG7561 | 75396 | SENSE |
| 579 | 1382 | CGPG7562 | 75401 | SENSE |
| 580 | 1383 | CGPG7563 | 75413 | SENSE |
| 581 | 1384 | CGPG7567 | 75461 | SENSE |
| 582 | 1385 | CGPG7568 | 75473 | SENSE |
| 583 | 1386 | CGPG7571 | 77817 | SENSE |
| 584 | 1387 | CGPG7587 | 75416 | SENSE |
| 585 | 1388 | CGPG7591 | 75464 | SENSE |
| 586 | 1389 | CGPG7597 | 75441 | SENSE |
| 587 | 1390 | CGPG7606 | 75454 | SENSE |
| 588 | 1391 | CGPG7633 | 75493 | SENSE |
| 589 | 1392 | CGPG7637 | 75446 | SENSE |
| 590 | 1393 | CGPG7649 | 75495 | SENSE |
| 591 | 1394 | CGPG7658 | 75705 | SENSE |
| 592 | 1395 | CGPG7664 | 77818 | SENSE |
| 593 | 1396 | CGPG7666 | 75525 | SENSE |
| 594 | 1397 | CGPG7668 | 75549 | SENSE |
| 595 | 1398 | CGPG7742 | 75582 | SENSE |
| 596 | 1399 | CGPG7746 | 75535 | SENSE |
| 597 | 1400 | CGPG7747 | 75547 | SENSE |
| 598 | 1401 | CGPG7752 | 75512 | SENSE |
| 599 | 1402 | CGPG7766 | 75673 | SENSE |
| 600 | 1403 | CGPG7770 | 75626 | SENSE |
| 601 | 1404 | CGPG7774 | 75674 | SENSE |
| 602 | 1405 | CGPG7777 | 75615 | SENSE |
| 603 | 1406 | CGPG7778 | 75627 | SENSE |
| 604 | 1407 | CGPG7786 | 75628 | SENSE |
| 605 | 1408 | CGPG7788 | 75652 | SENSE |
| 606 | 1409 | CGPG7792 | 75605 | SENSE |
| 607 | 1410 | CGPG78 | 70228 | SENSE |
| 608 | 1411 | CGPG783 | 13302 | ANTI-SENSE |
| 609 | 1412 | CGPG7832 | 75610 | SENSE |
| 610 | 1413 | CGPG7841 | 75623 | SENSE |
| 611 | 1414 | CGPG7845 | 75671 | SENSE |
| 612 | 1415 | CGPG7847 | 75695 | SENSE |
| 613 | 1416 | CGPG7851 | 75648 | SENSE |
| 614 | 1417 | CGPG7853 | 75672 | SENSE |
| 615 | 1418 | CGPG7857 | 75713 | SENSE |
| 616 | 1419 | CGPG7865 | 75714 | SENSE |
| 617 | 1420 | CGPG7869 | 75762 | SENSE |
| 618 | 1421 | CGPG7891 | 77954 | SENSE |
| 619 | 1422 | CGPG7892 | 77955 | SENSE |
| 620 | 1423 | CGPG7906 | 77541 | SENSE |
| 621 | 1424 | CGPG7924 | 78131 | SENSE |
| 622 | 1425 | CGPG7934 | 78134 | SENSE |
| 623 | 1426 | CGPG7949 | 77554 | SENSE |
| 624 | 1427 | CGPG7954 | 78992 | SENSE |
| 625 | 1428 | CGPG7964 | 77557 | SENSE |
| 626 | 1429 | CGPG7968 | 78128 | SENSE |
| 627 | 1430 | CGPG7969 | 77560 | SENSE |
| 628 | 1431 | CGPG7972 | 77561 | SENSE |
| 629 | 1432 | CGPG7982 | 77958 | SENSE |
| 630 | 1433 | CGPG7985 | 77563 | SENSE |
| 631 | 1434 | CGPG7993 | 78994 | SENSE |
| 632 | 1435 | CGPG8 | 74508 | SENSE |
| 633 | 1436 | CGPG80 | 70229 | SENSE |
| 634 | 1437 | CGPG8001 | 77959 | SENSE |
| 635 | 1438 | CGPG8009 | 77567 | SENSE |
| 636 | 1439 | CGPG802 | 11749 | ANTI-SENSE |
| 637 | 1440 | CGPG8049 | 77578 | SENSE |
| 638 | 1441 | CGPG806 | 11751 | ANTI-SENSE |
| 639 | 1442 | CGPG8060 | 77963 | SENSE |
| 640 | 1443 | CGPG8068 | 77925 | SENSE |
| 641 | 1444 | CGPG8072 | 77927 | SENSE |
| 642 | 1445 | CGPG8075 | 77345 | SENSE |
| 643 | 1446 | CGPG81 | 70230 | SENSE |
| 644 | 1447 | CGPG8100 | 77353 | SENSE |
| 645 | 1448 | CGPG8101 | 77354 | SENSE |
| 646 | 1449 | CGPG8104 | 77355 | SENSE |
| 647 | 1450 | CGPG8108 | 77588 | SENSE |
| 648 | 1451 | CGPG8116 | 77591 | SENSE |
| 649 | 1452 | CGPG8125 | 77594 | SENSE |
| 650 | 1453 | CGPG8134 | 77595 | SENSE |
| 651 | 1454 | CGPG8138 | 77364 | SENSE |
| 652 | 1455 | CGPG8156 | 78904 | SENSE |
| 653 | 1456 | CGPG8159 | 77937 | SENSE |
| 654 | 1457 | CGPG8163 | 77369 | SENSE |
| 655 | 1458 | CGPG8179 | 77940 | SENSE |
| 656 | 1459 | CGPG8193 | 78746 | SENSE |
| 657 | 1460 | CGPG8197 | 77372 | SENSE |
| 658 | 1461 | CGPG8198 | 78126 | SENSE |
| 659 | 1462 | CGPG8204 | 77951 | SENSE |
| 660 | 1463 | CGPG8211 | 75901 | SENSE |
| 661 | 1464 | CGPG823 | 12123 | ANTI-SENSE |
| 662 | 1465 | CGPG8234 | 75987 | SENSE |
| 663 | 1466 | CGPG8238 | 75940 | SENSE |
| 664 | 1467 | CGPG8260 | 75919 | SENSE |
| 665 | 1468 | CGPG8267 | 75908 | SENSE |
| 666 | 1469 | CGPG8268 | 75920 | SENSE |
| 667 | 1470 | CGPG8274 | 75992 | SENSE |
| 668 | 1471 | CGPG8277 | 75933 | SENSE |
| 669 | 1472 | CGPG8279 | 77965 | SENSE |
| 670 | 1473 | CGPG8284 | 77966 | SENSE |
| 671 | 1474 | CGPG8345 | 77972 | SENSE |
| 672 | 1475 | CGPG8408 | 78522 | SENSE |
| 673 | 1476 | CGPG842 | 12194 | ANTI-SENSE |
| 674 | 1477 | CGPG8421 | 78525 | SENSE |
| 675 | 1478 | CGPG8435 | 78527 | SENSE |
| 676 | 1479 | CGPG8440 | 78917 | SENSE |
| 677 | 1480 | CGPG8453 | 78920 | SENSE |
| 678 | 1481 | CGPG8470 | 78535 | SENSE |

TABLE 2-continued

| NUC SEQ ID NO | PEP SEQ ID NO | Gene ID | Construct ID | Orientation |
|---|---|---|---|---|
| 679 | 1482 | CGPG8479 | 78538 | SENSE |
| 680 | 1483 | CGPG8489 | 78922 | SENSE |
| 681 | 1484 | CGPG8498 | 77984 | SENSE |
| 682 | 1485 | CGPG85 | 73938 | SENSE |
| 683 | 1486 | CGPG8501 | 78621 | SENSE |
| 684 | 1487 | CGPG8507 | 77990 | SENSE |
| 685 | 1488 | CGPG8509 | 78386 | SENSE |
| 686 | 1489 | CGPG8515 | 78001 | SENSE |
| 687 | 1490 | CGPG8517 | 78543 | SENSE |
| 688 | 1491 | CGPG8518 | 78002 | SENSE |
| 689 | 1492 | CGPG852 | 12259 | SENSE |
| 690 | 1493 | CGPG8523 | 78005 | SENSE |
| 691 | 1494 | CGPG8528 | 78008 | SENSE |
| 692 | 1495 | CGPG8552 | 78019 | SENSE |
| 693 | 1496 | CGPG8553 | 78020 | SENSE |
| 694 | 1497 | CGPG8562 | 78023 | SENSE |
| 695 | 1498 | CGPG8567 | 78548 | SENSE |
| 696 | 1499 | CGPG8580 | 78161 | SENSE |
| 697 | 1500 | CGPG8589 | 78162 | SENSE |
| 698 | 1501 | CGPG8590 | 78033 | SENSE |
| 699 | 1502 | CGPG8592 | 78622 | SENSE |
| 700 | 1503 | CGPG8594 | 78036 | SENSE |
| 701 | 1504 | CGPG8606 | 78043 | SENSE |
| 702 | 1505 | CGPG8628 | 78165 | SENSE |
| 703 | 1506 | CGPG8648 | 78066 | SENSE |
| 704 | 1507 | CGPG8654 | 78069 | SENSE |
| 705 | 1508 | CGPG8668 | 78183 | SENSE |
| 706 | 1509 | CGPG8678 | 78170 | SENSE |
| 707 | 1510 | CGPG8694 | 78953 | SENSE |
| 708 | 1511 | CGPG8702 | 78929 | SENSE |
| 709 | 1512 | CGPG8737 | 78564 | SENSE |
| 710 | 1513 | CGPG8745 | 78566 | SENSE |
| 711 | 1514 | CGPG8748 | 78591 | SENSE |
| 712 | 1515 | CGPG8749 | 78181 | SENSE |
| 713 | 1516 | CGPG8770 | 78190 | SENSE |
| 714 | 1517 | CGPG8777 | 78571 | SENSE |
| 715 | 1518 | CGPG8781 | 78933 | SENSE |
| 716 | 1519 | CGPG8786 | 78573 | SENSE |
| 717 | 1520 | CGPG8792 | 78632 | SENSE |
| 718 | 1521 | CGPG8801 | 78959 | SENSE |
| 719 | 1522 | CGPG8809 | 78191 | SENSE |
| 720 | 1523 | CGPG8840 | 78595 | SENSE |
| 721 | 1524 | CGPG8850 | 78646 | SENSE |
| 722 | 1525 | CGPG8870 | 76325 | SENSE |
| 723 | 1526 | CGPG8871 | 76337 | SENSE |
| 724 | 1527 | CGPG8872 | 76349 | SENSE |
| 725 | 1528 | CGPG8876 | 76302 | SENSE |
| 726 | 1529 | CGPG8902 | 76329 | SENSE |
| 727 | 1530 | CGPG8904 | 76353 | SENSE |
| 728 | 1531 | CGPG8907 | 76389 | SENSE |
| 729 | 1532 | CGPG8914 | 76378 | SENSE |
| 730 | 1533 | CGPG8931 | 76392 | SENSE |
| 731 | 1534 | CGPG8933 | 76321 | SENSE |
| 732 | 1535 | CGPG8935 | 76345 | SENSE |
| 733 | 1536 | CGPG8938 | 76381 | SENSE |
| 734 | 1537 | CGPG8944 | 76358 | SENSE |
| 735 | 1538 | CGPG895 | 12629 | SENSE |
| 736 | 1539 | CGPG8950 | 76335 | SENSE |
| 737 | 1540 | CGPG8961 | 76372 | SENSE |
| 738 | 1541 | CGPG8963 | 76396 | SENSE |
| 739 | 1542 | CGPG898 | 72314 | SENSE |
| 740 | 1543 | CGPG8993 | 77840 | SENSE |
| 741 | 1544 | CGPG8994 | 76886 | SENSE |
| 742 | 1545 | CGPG8995 | 76803 | SENSE |
| 743 | 1546 | CGPG90 | 10302 | ANTI-SENSE |
| 744 | 1547 | CGPG900 | 71107 | SENSE |
| 745 | 1548 | CGPG9002 | 76887 | SENSE |
| 746 | 1549 | CGPG9009 | 77842 | SENSE |
| 747 | 1550 | CGPG9011 | 76805 | SENSE |
| 748 | 1551 | CGPG9012 | 76817 | SENSE |
| 749 | 1552 | CGPG9017 | 77843 | SENSE |
| 750 | 1553 | CGPG9025 | 77844 | SENSE |
| 751 | 1554 | CGPG9026 | 76890 | SENSE |
| 752 | 1555 | CGPG9032 | 77839 | SENSE |
| 753 | 1556 | CGPG9040 | 76868 | SENSE |
| 754 | 1557 | CGPG9044 | 76821 | SENSE |
| 755 | 1558 | CGPG9048 | 76869 | SENSE |
| 756 | 1559 | CGPG9049 | 76881 | SENSE |
| 757 | 1560 | CGPG9058 | 76894 | SENSE |
| 758 | 1561 | CGPG906 | 11930 | ANTI-SENSE |
| 759 | 1562 | CGPG9070 | 76848 | SENSE |
| 760 | 1563 | CGPG9075 | 76901 | SENSE |
| 761 | 1564 | CGPG9084 | 76914 | SENSE |
| 762 | 1565 | CGPG9094 | 76939 | SENSE |
| 763 | 1566 | CGPG9098 | 76987 | SENSE |
| 764 | 1567 | CGPG9099 | 76904 | SENSE |
| 765 | 1568 | CGPG9110 | 76941 | SENSE |
| 766 | 1569 | CGPG9119 | 77113 | SENSE |
| 767 | 1570 | CGPG9125 | 77185 | SENSE |
| 768 | 1571 | CGPG913 | 12911 | SENSE |
| 769 | 1572 | CGPG9136 | 77127 | SENSE |
| 770 | 1573 | CGPG9156 | 77177 | SENSE |
| 771 | 1574 | CGPG9164 | 77178 | SENSE |
| 772 | 1575 | CGPG9172 | 77179 | SENSE |
| 773 | 1576 | CGPG9173 | 77191 | SENSE |
| 774 | 1577 | CGPG9185 | 77145 | SENSE |
| 775 | 1578 | CGPG9187 | 77169 | SENSE |
| 776 | 1579 | CGPG9190 | 77110 | SENSE |
| 777 | 1580 | CGPG9193 | 77146 | SENSE |
| 778 | 1581 | CGPG9195 | 77170 | SENSE |
| 779 | 1582 | CGPG9203 | 77171 | SENSE |
| 780 | 1583 | CGPG9209 | 77148 | SENSE |
| 781 | 1584 | CGPG921 | 11933 | ANTI-SENSE |
| 782 | 1585 | CGPG9210 | 77160 | SENSE |
| 783 | 1586 | CGPG9211 | 77172 | SENSE |
| 784 | 1587 | CGPG9212 | 77184 | SENSE |
| 785 | 1588 | CGPG9216 | 77225 | SENSE |
| 786 | 1589 | CGPG9226 | 77250 | SENSE |
| 787 | 1590 | CGPG9252 | 77277 | SENSE |
| 788 | 1591 | CGPG9281 | 77245 | SENSE |
| 789 | 1592 | CGPG9289 | 77246 | SENSE |
| 790 | 1593 | CGPG9298 | 77462 | SENSE |
| 791 | 1594 | CGPG9299 | 77414 | SENSE |
| 792 | 1595 | CGPG9304 | 77439 | SENSE |
| 793 | 1596 | CGPG9310 | 77463 | SENSE |
| 794 | 1597 | CGPG9316 | 77488 | SENSE |
| 795 | 1598 | CGPG9317 | 77441 | SENSE |
| 796 | 1599 | CGPG9318 | 77464 | SENSE |
| 797 | 1600 | CGPG9324 | 77442 | SENSE |
| 798 | 1601 | CGPG9357 | 77419 | SENSE |
| 799 | 1602 | CGPG965 | 12444 | SENSE |
| 800 | 1603 | CGPG970 | 11791 | ANTI-SENSE |
| 800 | 1603 | CGPG970 | 12445 | SENSE |
| 801 | 1604 | CGPG982 | 71249 | SENSE |
| 802 | 1605 | CGPG994 | 71237 | SENSE |
| 803 | 1606 | CGPG996 | 12315 | ANTI-SENSE |
| 803 | 1606 | CGPG996 | 12366 | SENSE |

Recombinant DNA

DNA for use in the present invention to improve traits in plants have a nucleotide sequence of SEQ ID NO:1 through SEQ ID NO:803, as well as the homologs of such DNA c molecules. A subset of the DNA for gene suppression aspects of the invention includes fragments of the disclosed full polynucleotides consisting of oligonucleotides of 21 or more consecutive nucleotides. In some embodiments, the nucleotides for gene suppression can be 18, 19, 20, 22, 23, 24, 25, 26, 27, 28, 29, 30 or more consecutive nucleotides. Oligonucleotides having a sequence selected from the group consisting of SEQ ID NO: 1 through SEQ ID NO: 803 can be as probes and primers for detection of the polynucleotides used in the invention. Other embodiments this invention are variants of the DNA. Such variants can be naturally occurring, including DNA from homologous genes from the same or a different species, or can be non-natural variants, for example DNA synthesized using chemical synthesis methods, or generated using recombinant DNA techniques. Degeneracy of the genetic code provides the possibility to substitute at least one base of the protein encoding sequence of a gene with a different base without causing the amino acid sequence of the polypeptide produced from the gene to be changed. Hence, a DNA in the present invention can have any base sequence that has been changed from the sequences provided herein by substitution in accordance with degeneracy of the genetic code.

Homologs of the genes providing DNA demonstrated uses in improving traits in model plants disclosed herein will generally have significant identity with the DNA disclosed herein. DNA is substantially identical to a reference DNA if, when the sequences of the polynucleotides are optimally aligned there is about 60% nucleotide equivalence; about 70% equivalence; about 80% equivalence; about 85% equivalence; about 90%; about 95%; about 98%, about 99% equivalence or about 99.5 equivalence over a comparison window. A comparison window can be at least 50-100 nucleotides or the entire length of the polynucleotide provided herein. Optimal alignment of sequences for aligning a comparison window can be conducted by algorithms; for example by computerized implementations of these algorithms (such as, the Wisconsin Genetics Software Package Release 7.0-10.0, Genetics Computer Group, 575 Science Dr., Madison, Wis.). The reference polynucleotide can be a full-length molecule or a portion of a longer molecule. In one embodiment, the window of comparison for determining polynucleotide identity of protein encoding sequences is the entire coding region.

Proteins used for imparting enhanced traits are entire proteins or at least a sufficient portion of the entire protein to impart the relevant biological activity of the protein. Proteins used for generation of transgenic plants having enhanced traits include the proteins with an amino acid sequence provided herein as SEQ ID NO: 804 through SD) ID NO: 1606, as well as homologs of such proteins.

Homologs of the proteins in the invention are identified by comparison of the amino acid sequence of the protein to amino acid sequences of proteins from the same or different plant sources, e.g., manually or by using known homology-based search algorithms such as those commonly known and referred to as BLAST, FASTA, and Smith-Waterman. As used herein, a homolog is a protein from the same or a different organism that performs the same biological function as the polypeptide to which it is compared. An orthologous relation between two organisms is not necessarily manifest as a one-to-one correspondence between two genes, because a gene can be duplicated or deleted after organism phylogenetic separation, such as speciation. For a given protein, there can be no ortholog or more than one ortholog. Other complicating factors include alternatively spliced transcripts from the same gene, limited gene identification, redundant copies of the same gene with different sequence lengths or corrected sequence. A local sequence alignment program, e.g., BLAST, can be used to search a database of sequences to find similar sequences, and the summary Expectation value (E-value) used to measure the sequence base similarity. As a protein hit with the best E-value for a particular organism could be an ortholog or the only ortholog, a reciprocal BLAST search is used in the present invention to filter hit sequences with significant E-values for ortholog identification. The reciprocal BLAST entails search of the significant hits against a database of amino acid sequences from the base organism that are similar to the sequence of the query protein. A hit is a likely ortholog, when the reciprocal BLAST's best hit is the query protein itself or a protein encoded by a duplicated gene after speciation. Thus, homolog is used herein to describe proteins that are assumed to have functional similarity by inference from sequence base similarity. The relationship of homologs with amino acid sequences of SEQ ID NO: 1607 to SEQ ID NO: 94613 to the proteins with amino acid sequences of SEQ ID NO: 804 to SEQ ID NO: 1606 are found in the listing of Table 19.

Other functional homolog proteins differ in one or more amino acids from those of a trait-improving protein disclosed herein as the result of one or more of the well-known conservative amino acid substitutions, e.g., valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2.) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention comprises proteins that differ in one or more amino acids from those of a described protein sequence as the result of deletion or insertion of one or more amino acids in a native sequence.

Homologs of the trait-improving proteins provided herein will generally demonstrate significant sequence identity. Of particular interest are proteins having at least about 50% sequence identity, at least about 70% sequence identity or higher, e.g., at least about 80% sequence identity with an amino acid sequence of SEQ ID NO: 804 to SEQ ID NO: 1606. Additional embodiments also include those with higher identity, e.g., about 90%, about 92.5%, about 95%, about 98%, about 99%, or to about 99.5% identity. Identity of protein homologs is determined by optimally aligning the amino acid sequence of a putative protein homolog with a defined amino acid sequence and by calculating the percentage of identical and conservatively substituted amino acids over the window of comparison. The window of comparison for determining identity can be the entire amino acid sequence disclosed herein, e.g., the full sequence of any of SEQ ID NO: 804 to SEQ ID NO: 1606.

Genes that are homologous to each other can be grouped into families and included in multiple sequence alignments. Then a consensus sequence for each group can be derived. This analysis enables the derivation of conserved and class-(family) specific residues or motifs that are functionally important. These conserved residues and motifs can be further validated with 3D protein structure if available. The consensus sequence can be used to define the full scope of the invention, e.g., to identify proteins with a homolog relationship. Thus, the present invention contemplates that protein homologs include proteins with an amino acid sequence that has at least 90% identity to such a consensus amino acid sequence sequences.

Discovery of Trait-Improving Recombinant DNA

To identify nuclei with recombinant DNA that confer enhanced traits to plants, Arabidopsis thaliana was transformed with a candidate recombinant DNA construct and screened for an enhanced trait.

Arabidopsis thaliana is used a model for genetics and metabolism in plants. Arabidopsis has a small genome, and well-documented studies are available. It is easy to grow in large numbers and mutants defining important genetically controlled mechanisms are either available, or can readily be obtained. Various methods to introduce and express isolated homologous genes are available (see Koncz, et al., Methods in Arabidopsis Research et al., (1992), World Scientific, New Jersey, New Jersey, in "Preface").

A two-step screening process was employed which comprised two passes of trait characterization to ensure that the trait modification was dependent on expression of the recombinant DNA, but not due to the chromosomal location of the integration of the transgene. Twelve independent transgenic lines for each recombinant DNA construct were established and assayed for the transgene expression levels. Five transgenic lines with high transgene expression levels were used in the first pass screen to evaluate the transgene's function in T2 transgenic plants. Subsequently, three transgenic events, which had been shown to have one or more enhanced traits, were further evaluated in the second pass screen to confirm the transgene's ability to impart an enhanced trait. The following Table 3 summarizes the enhanced traits that have been confirmed as provided by a recombinant DNA construct.

In particular, Table 3 reports:

"PEP SEQ ID" which is the amino acid sequence of the protein cognate to the DNA in the recombinant DNA construct corresponding to a protein sequence of a SEQ ID NO. in the Sequence Listing.

"construct_id" is an arbitrary name for the recombinant DNA describe more particularly in Table 1.

"annotation" refers to a description of the top hit protein obtained from an amino acid sequence query of each PEP SEQ ID NO to GenBank database of the National Center for Biotechnology Information (ncbi), More particularly, "gi" is the GenBank ID number for the top BLAST hit.

"description" refers to the description of the top BLAST hit.

"e-value" provides the expectation value for the BLAST hit.

"% id" refers to the percentage of identically matched amino acid residues along the length of the portion of the sequences which is aligned by BLAST between the sequence of interest provided herein and the hit sequence in GenBank.

"traits" identify by two letter codes the confirmed enhancement in a transgenic plant provided by the recombinant DNA. The codes for enhanced traits are:

"CK" which indicates cold tolerance enhancement identified under a cold shock tolerance screen;

"CS" which indicates cold tolerance enhancement identified by a cold germination tolerance screen;

"DS" which indicates drought tolerance enhancement identified by a soil drought stress tolerance screen;

"PEG" which indicates osmotic stress tolerance enhancement identified by a PEG induced osmotic stress tolerance screen;

"HS" which indicates heat stress tolerance enhancement identified by a heat stress tolerance screen;

"SS" which indicates high salinity stress tolerance enhancement identified by a salt stress tolerance screen;

"LN" which indicates nitrogen use efficiency enhancement identified by a limited nitrogen tolerance screen;

"LL" which indicates attenuated shade avoidance response identified by a shade tolerance screen under a low light condition;

"PP" which indicates enhanced growth and development at early stages identified by an early plant growth and development screen;

"SP" which indicates enhanced growth and development at late stages identified by a late plant growth and development screen provided herein,

TABLE 3

| PEP SEQ ID NO | Construct | Annotation | | | traits |
|---|---|---|---|---|---|
| | | E-value | % Id | Description | |
| 804 | 70244 | 0 | 95 | ref|NP_193113.1|CYP83A1 (CYTOCHROME P450 83A1); oxygen binding [Arabidopsis thaliana] | HS |
| 805 | 71108 | 3.00E−54 | 100 | gb|AAB61093.1|F20P5.4 gene product [Arabidopsis thaliana] | LL |
| 806 | 12816 | 0 | 79 | ref|NP_190754.2|CAX3 (cation exchanger 3); cation: cation antiporter [Arabidopsis thaliana] | LN |
| 807 | 12650 | 1.00E−159 | 89 | gb|AAC25513.1|AAC25513Strong similarity to hypothetical protein gb|Y09823 from A. thaliana. | LN |
| 808 | 12031 | 1.00E−56 | 88 | ref|NP_179413.1|unknown protein [Arabidopsis thaliana] | LN |
| 809 | 12217 | 1.00E−168 | 88 | ref|NP_194233.1|unknown protein [Arabidopsis thaliana] | LN |
| 810 | 12043 | 2.00E−46 | 100 | ref|NP_194730.1|unknown protein [Arabidopsis thaliana] | PP |
| 811 | 12147 | 2.00E−33 | 68 | ref|NP_190718.1|unknown protein [Arabidopsis thaliana] | LN |
| 812 | 13638 | 0 | 100 | ref|NP_189940.1|unknown protein [Arabidopsis thaliana] | DS |
| 813 | 11860 | 2.00E−81 | 93 | ref|NP_973419.1|unknown protein [Arabidopsis thaliana] | LN |

TABLE 3-continued

| PEP SEQ ID NO | Construct | E-value | % Id | Description | | traits | |
|---|---|---|---|---|---|---|---|
| 814 | 72361 | 1.00E−139 | 93 | ref|NP_178534.2|IBR5 (INDOLE-3-BUTYRIC ACID RESPONSE 5); protein tyrosine/serine/threonine phosphatase [*Arabidopsis thaliana*] | CK | | |
| 815 | 12230 | 1.00E−23 | 100 | ref|NP_564545.1|TOM6 (TRANSLOCASE OF THE OUTER MITOCHONDRIAL MEMBRANE 6) [*Arabidopsis thaliana*] sp|Q9XIA7|TOM6_ARATH Mitochondrial import receptor subunit TOM6 homolog (Translocase of outer membrane 6 kDa subunit homolog) | LN | | |
| 816 | 71626 | 1.00E−47 | 93 | ref|NP_177455.1|unknown protein [*Arabidopsis thaliana*] | CK | | |
| 817 | 13454 | 0 | 96 | ref|NP_566136.1|armadillo/beta-catenin repeat family protein [*Arabidopsis thaliana*] | LN | | |
| 818 | 12173 | 4.00E−49 | 100 | ref|NP_186751.1|ATISU2/ISU2 (IscU-like 2); structural molecule [*Arabidopsis thaliana*] | CK | | |
| 819 | 17806 | 1.00E−35 | 54 | ref|NP_188341.2|unknown protein [*Arabidopsis thaliana*] | LN | | |
| 820 | 12011 | 1.00E−144 | 99 | ref|NP_567393.1|ATP-binding family protein [*Arabidopsis thaliana*] | LN | | |
| 821 | 72915 | 1.00E−135 | 77 | sp|Q94A43|BEH2_ARATHBES1/BZR1 homolog protein 2 | SS | | |
| 822 | 13231 | 1.00E−161 | 96 | ref|NP_178361.2|nucleic acid binding [*Arabidopsis thaliana*] | HS | | |
| 823 | 13913 | 1.00E−147 | 88 | ref|NP_028242.1|PDV2 (PLASTID DIVISION2) [*Arabidopsis thaliana*] gb|AAD26950.1| expressed protein [*Arabidopsis thaliana*] | HS | | |
| 824 | 12749 | 1.00E−140 | 100 | ref|NP_196620.1|unknown protein [*Arabidopsis thaliana*] | LN | | |
| 825 | 78901 | 0 | 97 | ref|NP_565919.1|COI1 (CORONATINE INSENSITIVE 1); ubiquitin-protein ligase [*Arabidopsis thaliana*] | HS | PP | |
| 826 | 75969 | 0 | 100 | ref|NP_174005.1|ATCUL3/ATCUL3A/CUL3/CUL3A (Cullin 3A); protein binding/ubiquitin-protein ligase [*Arabidopsis thaliana*] | CS | HS | |
| 827 | 15606 | 0 | 96 | gb|AAA32781.1|cyclin emb|CAA44169.1| cyclin [*Arabidopsis thaliana*] | HS | | |
| 828 | 75946 | 0 | 96 | ref|NP_171797.2|CUL2 (cullin 2) [*Arabidopsis thaliana*] | LL | | |
| 829 | 13050 | 0 | 97 | ref|NP_175955.1|F-box family protein [*Arabidopsis thaliana*] | LN | | |
| 830 | 75958 | 0 | 94 | ref|NP_177170.1|lectin protein kinase, putative [*Arabidopsis thaliana*] | HS | LN | |
| 831 | 17333 | 0 | 93 | gb|AA.F02796.1|AF195115_16Similar to receptor-like protein kinase precursor; F5I10.19 [*Arabidopsis thaliana*] | PP | | |
| 832 | 76002 | 0 | 100 | ref|NP_193038.1|MHK; kinase [*Arabidopsis thaliana*] sp|P43294|MHK ARATH Serine/threonine-protein kinase MHK | HS | PEG | |
| 833 | 78735 | 0 | 94 | ref|NP_187132.1|protein kinase, putative [*Arabidopsis thaliana*] | LL | PEG | |
| 834 | 13914 | 0 | 100 | ref|NP_195033.1|pyruvate decarboxylase, putative [*Arabidopsis thaliana*] | HS | SS | |
| 835 | 14405 | 0 | 92 | ref|NP_187341.1|DIN3/LTA1 (DARK INDUCIBLE 3); alpha-ketoacid dehydrogenase [*Arabidopsis thaliana*] | LN | SP | |
| 836 | 75983 | 0 | 100 | ref|NP_171655.1|ACS2 (1-Amino-cyclopropane-1-carboxylate synthase 2) [*Arabidopsis thaliana*] | CK | | |
| 837 | 70721 | 0 | 94 | ref|NP_851005.1|LPD2 (LIPOAMIDE DEHYDROGENASE 2), FAD binding/dihydrolipoyl dehydrogenase/disulfide oxidoreductase/oxidoreductase [*Arabidopsis thaliana*] | HS | LN | |
| 838 | 13811 | 0 | 92 | ref|NP_178093.1|ATNADP-ME4 (NADP-MALIC ENZYME 4); malate dehydrogenase (oxaloacetate-decarboxylating) (NADP+)/malic enzyme/oxidoreductase, acting on NADH or NADPH, NAD or NADP as acceptor [*Arabidopsis thaliana*] | DS | | |
| 838 | 13828 | 0 | 92 | ref|NP_178093.1|ATNADP-ME4 (NADP-MALIC ENZYME 4): malate dehydrogenase (oxaloacetate-decarboxylating) (NADP+)/malic enzyme/oxidoreductase, acting on NADH or NADPH, NAD or NADP as acceptor [*Arabidopsis thaliana*] | LN | | |
| 839 | 13614 | 1.00E−122 | 96 | ref|NP_176518.1|ribulose-phosphate 3-epimerase, cytosolic, putative/pentose-5-phosphate 3-epimerase, putative [*Arabidopsis thaliana*] | LN | | |
| 840 | 76050 | 0 | 97 | ref|NP_567714.1|AMY1 (ALPHA-AMYLASE-LIKE); alpha-amylase [*Arabidopsis thaliana*] | CS | | |
| 841 | 13038 | 0 | 100 | ref|NP_194382.1|fructose-bisphosphate aldolase, cytoplasmic [*Arabidopsis thaliana*] | LN | | |
| 842 | 13040 | 1.00E−104 | 92 | gb|AAB66906.1|eukaryotic initiation factor (iso)-4F p28 subunit [*Arabidopsis thaliana*] | LN | | |
| 843 | 70716 | 1.00E−172 | 100 | ref|NP_974170.1|serine/threonine protein kinase, putative [*Arabidopsis thaliana*] | HS | | |
| 843 | 76039 | 0 | 99 | ref|NP_001078396.1|PPDK (PYRUVATE ORTHOPHOSPHATE DIKINASE) [*Arabidopsis thaliana*] | HS | | |

TABLE 3-continued

| PEP SEQ ID NO | Construct | E-value | % Id | Annotation Description | traits | |
|---|---|---|---|---|---|---|
| 844 | 71611 | 0 | 99 | ref|NP_001078396.1|PPDK (PYRUVATE ORTHOPHOSPHATE DIKINASE) [*Arabidopsis thaliana*] | CK | PP |
| 845 | 70253 | 0 | 100 | ref|NP_200694.1|CYP86A1 (cytochrome P450, family 86, subfamily A, polypeptide 1); oxygen binding [*Arabidopsis thaliana*] | HS | CK |
| 846 | 14415 | 0 | 96 | ref|NP_568054.1|SEC14 cytosolic factor, putative/ phosphoglyceride transfer protein, putative [*Arabidopsis thaliana*] | LN | |
| 847 | 13718 | 4.00E−56 | 100 | ref|NP_196413.1|unknown protein [*Arabidopsis thaliana*] sp|Q9SD88|U139_ARATH UPF0139 protein At5g07960 | LN | |
| 848 | 10706 | 0 | 88 | gb|AAA19118.1|glutamyl-tRNA reductase | CK | HS |
| 848 | 10709 | 0 | 88 | gb|AAA19118.1|glutamyl-tRNA reductase | LN | |
| 849 | 14340 | 1.00E−125 | 93 | ref|NP_175332.1|unknown protein [*Arabidopsis thaliana*] | LN | |
| 850 | 13471 | 1.00E−136 | 95 | ref|NP_565858.1|unknown protein [*Arabidopsis thaliana*] | LN | |
| 851 | 18304 | 1.00E−133 | 94 | ref|NP_189283.1|TIP2 (TONOPLAST INTRINSIC PROTEIN 2); water channel [*Arabidopsis thaliana*] | HS | |
| 852 | 13623 | 0 | 96 | ref|NP_176001.2|GTP-binding protein-related [*Arabidopsis thaliana*] | DS | |
| 853 | 18302 | 0 | 100 | ref|NP_194702.2|NFC5 (NUCLEOSOME/CHROMATIN ASSEMBLY FACTOR GROUP C 5) [*Arabidopsis thaliana*] sp|Q9SU78|MSI5_ARATH WD-40 repeat-containing protein MSI5 | HS | |
| 854 | 15053 | 0 | 97 | ref|NP_001031261.1|unknown protein [*Arabidopsis thaliana*] | LN | |
| 855 | 15624 | 0 | 93 | ref|NP_171975.2|RabGAP/TBC domain-containing protein [*Arabidopsis thaliana*] | LL | PP |
| 856 | 70412 | 0 | 81 | ref|NP_179257.1|nodulin family protein [*Arabidopsis thaliana*] | HS | |
| 857 | 17902 | 0 | 91 | ref|NP_564843.1|integral membrane transporter family protein [*Arabidopsis thaliana*] | PP | |
| 858 | 14272 | 0 | 90 | ref|NP_566584.1|YSL5 (YELLOW STRIPE LIKE 5); oligopeptide transporter [*Arabidopsis thaliana*] | LN | |
| 859 | 15122 | 0 | 95 | ref|NP_565817.2|glycogenin glucosyltransferase (glycogenin)-related [*Arabidopsis thaliana*] | LN | |
| 859 | 70723 | 0 | 95 | ref|NP_565817.2|glycogenin glucosyltransferase (glycogenin)-related [*Arabidopsis thaliana*] | HS | |
| 860 | 14248 | 1.00E−154 | 79 | ref|NP_176081.1|unknown protein [*Arabidopsis thaliana*] | DS | |
| 861 | 13965 | 0 | 100 | ref|NP_173104.1|Per1-like family protein [*Arabidopsis thaliana*] | CK | |
| 862 | 75912 | 1.00E−169 | 100 | ref|NP_199075.1|unknown protein [*Arabidopsis thaliana*] | CS | LL |
| 863 | 14344 | 1.00E−81 | 100 | ref|NP_566785.1|universal stress protein (USP) family protein [*Arabidopsis thaliana*] | CS | |
| 864 | 14807 | 0 | 89 | gb|AAD20391.1|hypothetical protein [*Arabidopsis thaliana*] | CS | |
| 865 | 17307 | 0 | 89 | dbj|BAE98505.1|hypothetical protein [*Arabidopsis thaliana*] | PP | |
| 866 | 16431 | 0 | 73 | ref|NP_201248.1|octicosapeptide/Phox/Bem1p (PB1) domain-containing protein [*Arabidopsis thaliana*] | LN | |
| 867 | 73075 | 0 | 96 | ref|NP_187459.2|protein binding/zinc ion binding [*Arabidopsis thaliana*] | CS | |
| 868 | 16323 | 9.00E−57 | 89 | ref|NP_171768.2|transcription initiation factor IID (TFIID) 18 kDa subunit (TAFII-18) family protein [*Arabidopsis thaliana*] | LN | |
| 869 | 14833 | 1.00E−141 | 90 | ref|NP_176342.1|CCR4-NOT transcription complex protein, putative [*Arabidopsis thaliana*] | SP | |
| 870 | 17030 | 0 | 95 | gb|AAG28899.1|AC008113_15F12A21.29 [*Arabidopsis thaliana*] | LL | |
| 871 | 76414 | 0 | 99 | ref|NP_180595.1|CIPK11 (SNF1-RELATED PROTEIN KINASE 3.22, SOS3-INTERACTING PROTEIN 4); kinase [*Arabidopsis thaliana*] | PEG | |
| 872 | 16021 | 0 | 82 | ref|NP_201301.1|CDKC; 2 (CYCLIN-DEPENDENT KINASE C; 2); kinase [*Arabidopsis thaliana*] | LN | |
| 873 | 78701 | 0 | 93 | ref|NP_564203.1|F-box family protein [*Arabidopsis thaliana*] | HS | |
| 874 | 78702 | 0 | 93 | ref|NP_565142.1|F-box family protein (FBX3) [*Arabidopsis thaliana*] | PEG | |
| 875 | 15220 | 0 | 89 | ref|NP_173623.1|kelch repeat-containing F-box family protein [*Arabidopsis thaliana*] sp|Q9LM55|FBK8_ARATH F-box/Kelch-repeat protein | LN | |
| 876 | 15623 | 0 | 88 | ref|NP_179623.1|transducin family protein/WD-40 repeat family protein [*Arabidopsis thaliana*] | HS | |
| 877 | 19402 | 0 | 96 | ref|NP_568408.1|F-box family protein/WD-40 repeat family protein [*Arabidopsis thaliana*] | PP | |
| 878 | 70559 | 0 | 98 | ref|NP_181061.1|SUVH5 (SU(VAR)3-9 HOMOLOG 5) [*Arabidopsis thaliana*] | LN | |

TABLE 3-continued

| PEP SEQ ID NO | Construct | E-value | % Id | Annotation Description | traits | |
|---|---|---|---|---|---|---|
| 879 | 15111 | 0 | 90 | ref|NP_197821.1|ATXR6 (*Arabidopsis thaliana* Trithorax-related protein 6); DNA binding sp|Q9FNE9|ATXR6_ARATH Histone-lysine N-methyltransferase ATXR6 (Trithorax-related protein 6) (TRX-related protein 6) | DS | |
| 880 | 70832 | 0 | 100 | ref|NP_172633.1|CYP51G1 (CYTOCHROME P450 51); oxygen binding [*Arabidopsis thaliana*] | HS | |
| 881 | 15129 | 4.00E−82 | 77 | ref|NP_188372.1|PHD finger family protein [*Arabidopsis thaliana*] | LN | |
| 882 | 76086 | 0 | 91 | ref|NP_192814.1|EMB1706 (EMBRYO DEFECTIVE 1706); S-adenosylmethionine-dependent methyltransferase [*Arabidopsis thaliana*] | PP | |
| 883 | 15203 | 1.00E−158 | 94 | gb|AAD30650.1|AC006085_23Similar to human CGI-33 protein [*Arabidopsis thaliana*] | CK | |
| 884 | 70216 | 0 | 95 | ref|NP_567665.2|CYP706A1 (cytochrome P450, family 706, subfamily A, polypeptide 1); oxygen binding [*Arabidopsis thaliana*] | HS | PP |
| 885 | 14910 | 0 | 100 | ref|NP_201191.1|UVR8 (UVB-RESISTANCE 8) [*Arabidopsis thaliana*] | DS | |
| 886 | 70318 | 0 | 92 | ref|NP_172325.2|ATCPNIFS/ATNFS2/ATSUFS/CPNIFS/SUFS (CHLOROPLASTIC NIFS-LIKE CYSTEINE DESULFURASE); cysteine desulfurase/selenocysteine lyase/transaminase [*Arabidopsis thaliana*] | HS | |
| 887 | 15207 | 1.00E−44 | 99 | gb|AAG51737.1|AC068667_16beta-1,3 glucanase, putative; 26636-27432 [*Arabidopsis thaliana*] | SP | |
| 888 | 14915 | 0 | 97 | ref|NP_199393.1|CIPK19 (CIPK19); kinase [*Arabidopsis thaliana*] | LN | |
| 889 | 15132 | 1.00E−152 | 80 | ref|NP_187881.1|ZIP1 (ZINC TRANSPORTER 1 PRECURSOR); zinc ion transporter [*Arabidopsis thaliana*] | LN | |
| 890 | 16229 | 0 | 100 | gb|ABG54330.1|double HA-tagged mitogen activated protein kinase 3 [synthetic construct] | SS | |
| 891 | 14932 | 0 | 100 | ref|NP_568748.1|nucleotide-binding family protein [*Arabidopsis thaliana*] | DS | |
| 892 | 76017 | 1.00E−180 | 100 | ref|NP_568235.1|unknown protein [*Arabidopsis thaliana*] | HS | PP |
| 893 | 15964 | 1.00E−44 | 100 | ref|NP_566894.1|unknown protein [*Arabidopsis thaliana*] | DS | |
| 894 | 17227 | 8.00E−83 | 73 | gb|AAD03429.1|similar to nascent polypeptide associated complex alpha chain [*Arabidopsis thaliana*] | CS | |
| 895 | 72952 | 0 | 96 | ref|NP_564480.1|unknown protein [*Arabidopsis thaliana*] | CS | |
| 896 | 73706 | 0 | 96 | ref|NP_568221.1|protein kinase, putative [*Arabidopsis thaliana*] | HS | SS |
| 897 | 18203 | 0 | 92 | ref|NP_568919.1|APRR3 (PSEUDO-RESPONSE REGULATOR 3); transcription regulator [*Arabidopsis thaliana*] | HS | |
| 898 | 16309 | 1.00E−163 | 88 | ref|NP_195558.1|GGR (GERANYLGERANYL REDUCTASE); farnesyltranstransferase [*Arabidopsis thaliana*] | LN | |
| 899 | 15986 | 3.00E−99 | 84 | dbj|BAF02216.1|hypothetical protein [*Arabidopsis thaliana*] | DS | |
| 900 | 15987 | 2.00E−54 | 79 | ref|NP_174170.1|glutaredoxin family protein [*Arabidopsis thaliana*] | DS | |
| 901 | 16204 | 2.00E−59 | 100 | ref|NP_566191.1|NADH-ubiquinone oxidoreductase-related [*Arabidopsis thaliana*] | LN | |
| 902 | 11133 | 1.00E−114 | 100 | ref|NP_563897.1|alanine racemase family protein [*Arabidopsis thaliana*] | LN | |
| 903 | 73977 | 9.00E−67 | 100 | ref|NP_194677.1|mitochondrial ATP synthase g subunit family protein [*Arabidopsis thaliana*] | HS | |
| 904 | 15995 | 1.00E−176 | 84 | ref|NP_564660.1|unknown protein [*Arabidopsis thaliana*] | DS | |
| 904 | 18201 | 1.00E−176 | 84 | ref|NP_564660.1|unknown protein [*Arabidopsis thaliana*] | PP | |
| 905 | 16887 | 1.00E−164 | 100 | ref|NP_171820.1|phenazine biosynthesis PhzC/PhzF family protein [*Arabidopsis thaliana*] | PP | |
| 906 | 16213 | 1.00E−140 | 82 | ref|NP_563991.1|unknown protein [*Arabidopsis thaliana*] | HS | |
| 907 | 15507 | 0 | 96 | ref|NP_172255.1|cupin family protein [*Arabidopsis thaliana*] | LN | |
| 908 | 15508 | 3.00E−86 | 100 | ref|NP_564937.1|unknown protein [*Arabidopsis thaliana*] | LN | |
| 909 | 15959 | 3.00E−56 | 74 | ref|NP_180097.1|unknown protein [*Arabidopsis thaliana*] | LN | |
| 910 | 72427 | 0 | 93 | ref|NP_568346.1|tubulin family protein [*Arabidopsis thaliana*] | HS | |
| 911 | 19041 | 2.00E−85 | 82 | ref|NP_565723.1|unknown protein [*Arabidopsis thaliana*] | HS | LN |
| 912 | 17802 | 1.00E−118 | 100 | ref|NP_187425.1|emp24/gp25L/p24 family protein [*Arabidopsis thaliana*] | HS | |
| 913 | 19042 | 0 | 94 | ref|NP_569048.1|ARA12; subtilase [*Arabidopsis thaliana*] | HS | |
| 914 | 76053 | 0 | 94 | ref|NP_172544.1|unknown protein [*Arabidopsis thaliana*] | HS | |
| 915 | 16120 | 1.00E−56 | 90 | ref|NP_192997.1|ribosomal protein L7Ae/L30e/S12e/Gadd45 family protein [*Arabidopsis thaliana*] | CK | |

TABLE 3-continued

| PEP SEQ ID NO | Construct | E-value | % Id | Annotation Description | traits | | |
|---|---|---|---|---|---|---|---|
| 916 | 15424 | 1.00E-103 | 94 | ref\|NP_196647.1\|CBS domain-containing protein [*Arabidopsis thaliana*] | HS | | |
| 917 | 16401 | 0 | 90 | ref\|NP_179995.1\|CYP71B6 (CYTOCHROME P450 71B6); oxygen binding [*Arabidopsis thaliana*] | PP | | |
| 918 | 72417 | 0 | 100 | gb\|AAK25868.1\|AF360158_1 unknown protein [*Arabidopsis thaliana*] | CK | | |
| 919 | 73702 | 0 | 90 | ref\|NP_564657.1\|spliceosome protein-related [*Arabidopsis thaliana*] | HS | SS | |
| 920 | 70706 | 0 | 100 | gb\|AAD17366.1\|similar to human phosphotyrosyl phosphatase activator PTPA (GB: X73478) [*Arabidopsis thaliana*] | HS | | |
| 921 | 71145 | 4.00E-57 | 86 | gb\|AAG40386.1\|AF325034_1AT5g02160 [*Arabidopsis thaliana*] | HS | | |
| 922 | 11609 | 0 | 97 | gb\|AAC34228.1\|putative cytochrome P450 [*Arabidopsis thaliana*] | LN | | |
| 923 | 71706 | 0 | 88 | gb\|AAF03464.1\|AC009327_3 hypothetical protein [*Arabidopsis thaliana*] | CK | | |
| 924 | 17325 | 1.00E-144 | 86 | ref\|NP_563896.1\|unknown protein [*Arabidopsis thaliana*] | PP | | |
| 925 | 70102 | 1.00E-166 | 100 | ref\|NP_353899.2\|hypothetical protein Atu0877 [*Agrobacterium tumefaciens* str. C58] | HS | | |
| 926 | 70106 | 1.00E-151 | 92 | ref\|NP_353321.1\|hypothetical protein Atu0291 [*Agrobacterium tumefaciens* str. C58] | HS | | |
| 927 | 70113 | 3.00E-94 | 94 | ref\|NP_013690.1\|Adenine phosphoribosyltransferase, catalyzes the formation of AMP from adenine and 5-phosphoribosylpyrophosphate; involved in the salvage pathway of purine nucleotide biosynthesis; Apt1p [*Saccharomyces cerevisiae*] | HS | | |
| 928 | 70115 | 0 | 100 | ref\|NP_116623.1\|Alanine: glyoxylate aminotransferase (AGT), catalyzes the synthesis of glycine from glyoxylate, which is one of three pathways for glycine biosynthesis in yeast; has similarity to mammalian and plant alanine: glyoxylate aminotransferases; Agx1p [*Saccharomyces cerevisiae*] | HS | | |
| 929 | 70118 | 0 | 94 | ref\|NP_012111.1\|Mitochondrial glycerol-3-phosphate dehydrogenase: expression is repressed by both glucose and cAMP and derepressed by non-fermentable carbon sources in a Snf1p, Rsf1p, Hap2/3/4/5 complex dependent manner; Gut2p [*Saccharomyces cerevisiae*] | SP | | |
| 930 | 70128 | 9.00E-85 | 70 | ref\|NP_638658.1\|membrane-bound proton-translocating pyrophosphatase [*Xanthomonas campestris* pv. *campestris* str. ATCC 33913] | HS | | |
| 931 | 70130 | 1.00E-161 | 99 | ref\|NP_639330.1\|a-type carbonic anhydrase [*Xanthomonas campestris* pv. *campestris* str. ATCC 33913] | HS | PEG | |
| 932 | 17103 | 0 | 88 | ref\|NP_173155.1\|CAT8 (CATIONIC AMINO ACID TRANSPORTER 8); cationic amino acid transporter [*Arabidopsis thaliana*] | SS | | |
| 933 | 72748 | 1.00E-33 | 74 | ref\|NP_568635.1\|unknown protein [*Arabidopsis thaliana*] | HS | | |
| 934 | 17502 | 3.00E-94 | 74 | ref\|NP_565588.1\|unknown protein [*Arabidopsis thaliana*] | HS | | |
| 935 | 17503 | 1.00E-130 | 100 | ref\|NP_176178.1\|ATGSTU16 (*Arabidopsis thaliana* Glutathione S-transferase (class tau) 16); glutathione transferase | HS | | |
| 936 | 78708 | 1.00E-168 | 95 | gb\|AAK43902.1\|AF370583_1Unknown protein [*Arabidopsis thaliana*] | LL | | |
| 937 | 17504 | 1.00E-139 | 95 | ref\|NP_565634.1\|harpin-induced protein-related/HIN1-related/harpin-responsive protein-related [*Arabidopsis thaliana*] | HS | LL | PP |
| 938 | 17132 | 1.00E-127 | 100 | ref\|NP_187978.1\|seven in absentia (SINA) family protein [*Arabidopsis thaliana*] | LN | | |
| 939 | 72965 | 0 | 91 | gb\|AAN60250.1\|unknown [*Arabidopsis thaliana*] | LL | | |
| 940 | 72796 | 3.00E-61 | 100 | ref\|NP_201508.1\|RALFL34 (RALF-LIKE 34) [*Arabidopsis thaliana*] | CS | | |
| 941 | 16617 | 5.00E-96 | 100 | ref\|NP_355193.2\|adenine phosphoribosyltransferase [*Agrobacterium tumefaciens* str. C58] | CS | HS | |
| 942 | 16640 | 0 | 100 | ref\|NP_355113.2\|alcohol dehydrogenase [*Agrobacterium tumefaciens* str. C58] | HS | | |
| 943 | 16603 | 1.00E-132 | 85 | ref\|NP_357530.1\|ribokinase [*Agrobacterium tumefaciens* str. C58] | HS | | |
| 944 | 16612 | 1.00E-137 | 100 | ref\|NP_010335.1\|Triose phosphate isomerase, abundant glycolytic enzyme; mRNA half-life is regulated by iron availability, transcription is controlled by activators Reb1p, Gcr1p, and Rap1p through binding sites in the 5' non-coding region; Tpi1p [*Saccharomyces cerevisiae*] | LN | SP | |

TABLE 3-continued

| PEP SEQ ID NO | Construct | E-value | % Id | Annotation Description | | traits | |
|---|---|---|---|---|---|---|---|
| 945 | 16614 | 1.00E−109 | 100 | ref|NP_010741.1|Stress inducible cytoplasmic thioredoxin peroxidase; cooperates with Tsa1p in the removal of reactive oxygen, nitrogen and sulfur species using thioredoxin as hydrogen donor; deletion enhances the mutator phenotype of tsa1 mutants; Tsa2p [*Saccharomyces cerevisiae*] | DS | | |
| 946 | 78354 | 7.00E−80 | 100 | ref|NP_192392.1|methionine sulfoxide reductase domain-containing protein/SeIR domain-containing protein [*Arabidopsis thaliana*] | SS | | |
| 947 | 17818 | 6.00E−19 | 60 | ref|NP_564780.1|TIM13 (TIM13); protein translocase [*Arabidopsis thaliana*] | PP | | |
| 948 | 78370 | 3.00E−64 | 91 | ref|NP_194900.1|TAFI|15 (SALT TOLERANCE DURING GERMINATION 1); transcription factor [*Arabidopsis thaliana*] | HS | | |
| 949 | 70411 | 0 | 90 | ref|NP_849806.1|UBP1A; mRNA 3'-UTR binding [*Arabidopsis thaliana*] | SP | | |
| 950 | 19154 | 1.00E−151 | 89 | ref|NP_197310.1|transcriptional factor B3 family protein [*Arabidopsis thaliana*] | HS | LN | PP |
| 951 | 19155 | 0 | 82 | ref|NP_200906.2|nuclear transport factor 2 (NTF2) family protein/RNA recognition motif (RRM)-containing protein [*Arabidopsis thaliana*] | HS | | |
| 952 | 18307 | 0 | 94 | ref|NP_194507.1|ACBP2 (ACYL-COA BINDING PROTEIN ACBP 2) [*Arabidopsis thaliana*] | HS | | |
| 953 | 72030 | 0 | 86 | ref|NP_177367.1|zinc finger (C3HC4-type RING finger) family protein [*Arabidopsis thaliana*] | LN | | |
| 954 | 17916 | 1.00E−173 | 95 | ref|NP_568839.1|CSN6A (COP9 signalosome subunit 6A) [*Arabidopsis thaliana*] | PP | | |
| 955 | 17917 | 0 | 96 | ref|NP_188478.1|aspartyl protease family protein [*Arabidopsis thaliana*] | SS | | |
| 956 | 17334 | 0 | 94 | ref|NP_178146.1|chloroplast ADP, ATP carrier protein 1/ADP, ATP translocase 1/adenine nucleotide translocase 1 (AATP1) [*Arabidopsis thaliana*] | PP | | |
| 957 | 71531 | 0 | 100 | ref|NP_565656.1|aldo/keto reductase family protein [*Arabidopsis thaliana*] | HS | | |
| 958 | 18441 | 7.00E−75 | 100 | ref|NP_973779.1|lactoylglutathione lyase family protein/glyoxalase I family protein [*Arabidopsis thaliana*] | HS | | |
| 959 | 19162 | 2.00E−73 | 85 | ref|NP_563687.1|photosystem II family protein [*Arabidopsis thaliana*] | DS | | |
| 960 | 73205 | 0 | 98 | ref|NP_190414.1|zinc finger (CCCH-type) family protein [*Arabidopsis thaliana*] | PEG | | |
| 961 | 18306 | 1.00E−172 | 100 | ref|NP_566769.1|LAG1 (Longevity assurance gene 1) [*Arabidopsis thaliana*] | SS | | |
| 962 | 70808 | 0 | 97 | ref|NP_196136.1|CESA3 (CELLULASE SYNTHASE 3); cellulose synthase/transferase, transferring glycosyl groups [*Arabidopsis thaliana*] | CS | CK | |
| 963 | 17653 | 1.00E−178 | 95 | ref|NP_199155.1|zinc finger (C3HC4-type RING finger) family protein [*Arabidopsis thaliana*] | LN | | |
| 964 | 19535 | 0 | 81 | ref|NP_567002.1|GCN5 (Histon acetyltransferase HAT1) [*Arabidopsis thaliana*] | HS | | |
| 965 | 71719 | 0 | 99 | ref|NP_192044.1|DC1 domain-containing protein [*Arabidopsis thaliana*] | HS | LL | PP |
| 966 | 18546 | 1.00E−102 | 92 | ref|NP_176285.1|AGL56 (AGAMOUS LIKE-56); DNA binding/transcription factor [*Arabidopsis thaliana*] | PP | | |
| 967 | 19534 | 0 | 78 | ref|NP_566721.1|binding [*Arabidopsis thaliana*] | HS | | |
| 968 | 18421 | 0 | 96 | gb|ABK06451.1|flag-tagged protein kinase domain of putative mitogen-activated protein kinase kinase kinase [synthetic construct] | HS | | |
| 969 | 18422 | 0 | 100 | ref|NP_194498.1|MSP1 protein, putative/intramitochondrial sorting protein, putative [*Arabidopsis thaliana*] | HS | | |
| 970 | 19539 | 0 | 95 | ref|NP_191747.1|CYP78A9 (CYTOCHROME P450 78A9); oxygen binding [*Arabidopsis thaliana*] | HS | PP | |
| 971 | 19244 | 3.00E−74 | 88 | ref|NP_565113.1|auxin-responsive family protein [*Arabidopsis thaliana*] | HS | | |
| 972 | 15803 | 1.00E−142 | 100 | ref|NP_199675.2|cyclin family protein [*Arabidopsis thaliana*] | HS | | |
| 973 | 19545 | 0 | 100 | ref|NP_568665.1|pentatricopeptide (PPR) repeat-containing protein [*Arabidopsis thaliana*] | HS | | |
| 974 | 10222 | 0 | 94 | ref|NP_190896.1|CYP71B5 (CYTOCHROME P450 71B5); oxygen binding [*Arabidopsis thaliana*] | LN | | |
| 974 | 72356 | 0 | 94 | ref|NP_190896.1|CYP71B5 (CYTOCHROME P450 71B5); oxygen binding [*Arabidopsis thaliana*] | CK | PEG | |

TABLE 3-continued

| PEP SEQ ID NO | Construct | E-value | % Id | Description | traits | | |
|---|---|---|---|---|---|---|---|
| 975 | 70425 | 0 | 98 | ref\|NP_200201.3\|unknown protein [*Arabidopsis thaliana*] | HS | | |
| 976 | 19237 | 1.00E−150 | 95 | ref\|NP_199836.1\|31 kDa ribonucleoprotein, chloroplast, putative/RNA-binding protein RNP-T, putative/RNA-binding protein 1/2/3, putative/RNA-binding protein cp31, putative [*Arabidopsis thaliana*] | HS | | |
| 977 | 71303 | 0 | 82 | ref\|NP_199431.1\|KH domain-containing protein [*Arabidopsis thaliana*] | HS | | |
| 978 | 19240 | 1.00E−180 | 100 | ref\|NP_566576.1\|meprin and TRAF homology domain-containing protein/MATH domain-containing protein [*Arabidopsis thaliana*] | LN | | |
| 979 | 18535 | 0 | 100 | ref\|NP_196179.1\|oxidoreductase, 2OG-Fe(II) oxygenase family protein [*Arabidopsis thaliana*] | HS | | |
| 980 | 19450 | 0 | 94 | ref\|NP_565422.1\|pentatricopeptide (PPR) repeat-containing protein [*Arabidopsis thaliana*] | LN | | |
| 981 | 18221 | 1.00E−66 | 100 | ref\|NP_193992.1\|protease inhibitor/seed storage/lipid transfer protein (LTP) family protein [*Arabidopsis thaliana*] | PP | | |
| 982 | 18233 | 1.00E−110 | 87 | ref\|NP_193179.1\|enoyl-CoA hydratase/isomerase family protein [*Arabidopsis thaliana*] | PP | | |
| 983 | 18236 | 1.00E−31 | 70 | ref\|NP_565410.1\|unknown protein [*Arabidopsis thaliana*] | PP | | |
| 984 | 18238 | 1.00E−129 | 88 | ref\|NP_197105.1\|3-oxo-5-alpha-steroid 4-dehydrogenase family protein/steroid 5-alpha-reductase family protein [*Arabidopsis thaliana*] | HS | | |
| 985 | 18309 | 1.00E−128 | 93 | gb\|AAM61596.1\|DNA-binding protein [*Arabidopsis thaliana*] | CS | PEG | |
| 986 | 70337 | 0 | 85 | gb\|AAP84710.2\|metacaspase 7 [*Arabidopsis thaliana*] | HS | | |
| 987 | 18319 | 1.00E−105 | 89 | ref\|NP_172721.1\|DDF1 (DWARF AND DELAYED FLOWERING 1); DNA binding/transcription factor [*Arabidopsis thaliana*] | LN | | |
| 988 | 70338 | 1.00E−172 | 85 | ref\|NP_200445.1\|zinc finger (C3HC4-type RING finger) family protein [*Arabidopsis thaliana*] | LL | | |
| 989 | 10471 | 1.00E−114 | 84 | dbj\|BAF00210.1\|hypothetical protein [*Arabidopsis thaliana*] | DS | | |
| 990 | 18331 | 1.00E−114 | 63 | ref\|NP_565124.1\|nucleic acid binding [*Arabidopsis thaliana*] | CS | | |
| 991 | 10228 | 0 | 97 | ref\|NP_563880.1\|TIF3H1 (eukaryotic translation initiation factor 3 subunit H1); translation initiation factor [*Arabidopsis thaliana*] | LN | | |
| 991 | 10473 | 0 | 97 | ref\|NP_563880.1\|TIF3H1 (eukaryotic translation initiation factor 3 subunit H1); translation initiation factor [*Arabidopsis thaliana*] | LN | | |
| 992 | 18261 | 1.00E−167 | 91 | ref\|NP_563732.1\|peroxidase, putative [*Arabidopsis thaliana*] | PP | | |
| 993 | 18848 | 0 | 94 | ref\|NP_177805.1\|O-methyltransferase family 2 protein [*Arabidopsis thaliana*] | LN | | |
| 994 | 18268 | 1.00E−130 | 92 | gb\|AAM62813.1\|unknown [*Arabidopsis thaliana*] | PP | | |
| 995 | 18345 | 0 | 92 | ref\|NP_182320.1\|SWA1 (SLOW WALKER1); nucleotide binding [*Arabidopsis thaliana*] | HS | | |
| 996 | 73607 | 0 | 92 | ref\|NP_851068.1\|WD-40 repeat family protein [*Arabidopsis thaliana*] | HS | | |
| 997 | 18352 | 1.00E−166 | 83 | ref\|NP_201275.1\|nodulin MtN21 family protein [*Arabidopsis thaliana*] | HS | SS | PEG |
| 998 | 18357 | 1.00E−171 | 100 | ref\|NP_172866.1\|mitochondrial substrate carrier family protein [*Arabidopsis thaliana*] | PP | | |
| 999 | 19423 | 0 | 100 | ref\|NP_177020.1\|CUT1 (CUTICULAR 1); acyltransferase [*Arabidopsis thaliana*] | DS | | |
| 1000 | 78373 | 0 | 94 | ref\|NP_179537.1\|CKL5 (Casein Kinase I-like 5); casein kinase 1/kinase [*Arabidopsis thaliana*] | CK | HS | |
| 1001 | 70603 | 0 | 100 | ref\|NP_175081.1\|ALDH3H1 (ALDEHYDE DEHYDROGENASE 4); 3-chloroallyl aldehyde dehydrogenase/aldehyde dehydrogenase (NAD) [*Arabidopsis thaliana*] | HS | LN | |
| 1002 | 19616 | 1.00E−159 | 100 | ref\|NP_563789.1\|SMO2-2 (sterol 4-alpha-methyl-oxidase 2); C-4 methylsterol oxidase [*Arabidopsis thaliana*] | HS | | |
| 1003 | 19425 | 1.00E−164 | 91 | ref\|NP_564407.1\|electron carrier/iron ion binding [*Arabidopsis thaliana*] | DS | | |
| 1004 | 19426 | 1.00E−152 | 89 | ref\|NP_564428.1\|unknown protein [*Arabidopsis thaliana*] | PP | | |
| 1005 | 18382 | 2.00E−51 | 87 | ref\|NP_564651.1\|unknown protein [*Arabidopsis thaliana*] | PP | | |
| 1006 | 71536 | 4.00E−86 | 86 | ref\|NP_564747.1\|ZCF37 [*Arabidopsis thaliana*] | HS | | |
| 1007 | 70419 | 6.00E−88 | 66 | ref\|NP_564888.1\|unknown protein [*Arabidopsis thaliana*] | LL | CK | DS |
| 1008 | 70827 | 6.00E−85 | 100 | ref\|NP_189667.1\|zinc finger (C3HC4-type RING finger) family protein [*Arabidopsis thaliana*] | HS | | |

TABLE 3-continued

| PEP SEQ ID NO | Construct | E-value | % Id | Description | traits | | | |
|---|---|---|---|---|---|---|---|---|
| 1009 | 19311 | 0 | 94 | ref|NP_010849.1|Ferrioxamine B transporter, member of the ARN family of transporters that specifically recognize siderophore-iron chelates; transcription is induced during iron deprivation and diauxic shift; potentially phosphorylated by Cdc28p; Sit1p [*Saccharomyces cerevisiae*] | LN | | | |
| 1010 | 19323 | 0 | 92 | ref|NP_354642.2|malic enzyme [*Agrobacterium tumefaciens* str. C58] | LL | | | |
| 1011 | 19320 | 0 | 100 | ref|NP_012542.1|Glyceraldehyde-3-phosphate dehydrogenase, isozyme 2, involved in glycolysis and gluconeogenesis; tetramer that catalyzes the reaction of glyceraldehyde-3-phosphate to 1,3 bis-phosphoglycerate; detected in the cytoplasm and cell-wall; Tdh2p [*Saccharomyces cerevisiae*] | HS | | | |
| 1012 | 73613 | 0 | 95 | ref|NP_197104.1|NIK1 (NSP-INTERACTING KINASE 1); kinase [*Arabidopsis thaliana*] | CK | | | |
| 1013 | 70432 | 1.00E-162 | 91 | ref|NP_196709.1|GTP binding [*Arabidopsis thaliana*] | SS | | | |
| 1014 | 70433 | 0 | 100 | ref|NP_196957.1|transducin family protein/WD-40 repeat family protein [*Arabidopsis thaliana*] | HS | | | |
| 1015 | 70434 | 1.00E-142 | 94 | ref|NP_180497.1|tropinone reductase, putative/tropine dehydrogenase, putative [*Arabidopsis thaliana*] | HS | | | |
| 1016 | 72614 | 1.00E-128 | 79 | ref|NP_197757.1|sterile alpha motif (SAM) domain-containing protein [*Arabidopsis thaliana*] | LL | | | |
| 1017 | 70436 | 7.00E-35 | 70 | ref|NP_197966.1|early nodulin-related [*Arabidopsis thaliana*] | CS | HS | | |
| 1018 | 74226 | 0 | 92 | dbj|BAB02016.1|MAP kinase [*Arabidopsis thaliana*] | PP | | | |
| 1019 | 70439 | 1.00E-123 | 91 | ref|NP_191247.1|VQ motif-containing protein [*Arabidopsis thaliana*] | HS | PEG | | |
| 1020 | 70446 | 1.00E-128 | 100 | ref|NP_568972.2|unknown protein [*Arabidopsis thaliana*] | CS | | | |
| 1021 | 70613 | 0 | 93 | ref|NP_174145.1|unknown protein [*Arabidopsis thaliana*] | PEG | | | |
| 1022 | 70447 | 0 | 97 | ref|NP_175977.1|uracil phosphoribosyltransferase, putative/UMP pyrophosphorylase, putative/UPRTase, putative [*Arabidopsis thaliana*] ref|NP_974037.1| uracil phosphoribosyltransferase, putative/UMP pyrophosphorylase, putative/UPRTase, putative [*Arabidopsis thaliana*] | CK | | | |
| 1023 | 71725 | 0 | 67 | gb|ABE65946.1| nucleolin [*Arabidopsis thaliana*] | CK | | | |
| 1024 | 70462 | 9.00E-73 | 92 | ref|NP_567037.1|ARR17 (response regulator 17), transcription regulator/two-component response regulator [*Arabidopsis thaliana*] | PEG | | | |
| 1025 | 70545 | 0 | 95 | ref|NP_176108.3|bZIP family transcription factor [*Arabidopsis thaliana*] | SP | | | |
| 1026 | 70741 | 0 | 100 | gb|AAM78097.1|AT4g18060/F15J5_30 [*Arabidopsis thaliana*] | HS | | | |
| 1027 | 19702 | 0 | 97 | ref|NP_011904.1|Protein of unknown function, green fluorescent protein (GFP)-fusion protein localizes to the endoplasmic reticulum; msc7 mutants are defective in directing meiotic recombination events to homologous chromatids; Msc7p [*Saccharomyces cerevisiae*] | HS | | | |
| 1028 | 19985 | 1.00E-140 | 86 | gb|AAA88792.1|nucleosome assembly protein 1 | HS | | | |
| 1029 | 19775 | 1.00E-80 | 54 | ref|NP_175779.1|unknown protein [*Arabidopsis thaliana*] | CK | HS | PP | LN |
| 1030 | 19829 | 3.00E-56 | 42 | ref|NP_565892.1|unknown protein [*Arabidopsis thaliana*] | CS | | | |
| 1031 | 19982 | 1.00E-123 | 79 | gb|AAV49506.1|L-galactose-1-phosphate phosphatase [*Actinidia deliciosa*] | HS | PEG | | |
| 1032 | 19755 | 1.00E-110 | 63 | emb|CAO23381.1|unnamed protein product [*Vitis vinifera*] | HS | | | |
| 1033 | 19732 | 0 | 96 | dbj|BAA22559.1|squalene synthase [*Glycine max*] | PP | | | |
| 1034 | 70365 | 0 | 91 | gb|AAQ84169.1|1-deoxy-D-xylulose 5-phosphate synthase [*Pueraria montana* var. lobata] | CS | | | |
| 1035 | 10476 | 1.00E-168 | 86 | ref|NP_194096.1|CDPK6 (CALCIUM-DEPENDENT PROTEIN KINASE 6); anion channel/calcium- and calmodulin-dependent protein kinase/kinase [*Arabidopsis thaliana*] | LN | | | |
| 1036 | 19987 | 0 | 83 | emb|CAO67062.1|unnamed protein product [*Vitis vinifera*] | HS | | | |
| 1037 | 19893 | 1.00E-166 | 85 | gb|ABC75353.2|Intracellular chloride channel [*Medicago truncatula*] | HS | | | |
| 1038 | 19983 | 6.00E-92 | 60 | emb|CAO39739.1|unnamed protein product [*Vitis vinifera*] | HS | LL | | |
| 1039 | 19825 | 1.00E-40 | 39 | emb|CAO18125.1|unnamed protein product [*Vitis vinifera*] | HS | | | |
| 1040 | 19919 | 1.00E-121 | 77 | emb|CAO61472.1|unnamed protein product [*Vitis vinifera*] | HS | | | |
| 1041 | 19979 | 0 | 67 | emb|CAO68238.1|unnamed protein product [*Vitis vinifera*] | HS | | | |
| 1042 | 19786 | 2.00E-80 | 75 | emb|CAO48404.1|unnamed protein product [*Vitis vinifera*] | HS | LN | | |
| 1043 | 70903 | 0 | 76 | emb|CAO66035.1|unnamed protein product [*Vitis vinifera*] | HS | PP | PEG | |
| 1044 | 70970 | 1.00E-102 | 67 | ref|NP_200538.1|unknown protein [*Arabidopsis thaliana*] | HS | | | |
| 1045 | 70980 | 0 | 89 | dbj|BAE71243.1|putative galactose kinase [*Trifolium pratense*] | CK | | | |

TABLE 3-continued

| PEP SEQ ID NO | Construct | E-value | % Id | Description | traits | |
|---|---|---|---|---|---|---|
| 1046 | 70936 | 1.00E−158 | 49 | emb\|CAO71465.1\|unnamed protein product [*Vitis vinifera*] | HS | |
| 1047 | 71425 | 1.00E−160 | 74 | emb\|CAO14679.1\|unnamed protein product [*Vitis vinifera*] | DS | |
| 1048 | 78666 | 3.00E−45 | 83 | ref\|NP_192698.1\|GASA3 (GAST1 PROTEIN HOMOLOG 3) [*Arabidopsis thaliana*] | LN | |
| 1049 | 71202 | 1.00E−163 | 95 | ref\|NP_194179.1\|serine/threonine protein kinase, putative [*Arabidopsis thaliana*] | LN | |
| 1050 | 78973 | 0 | 90 | ref\|NP_565672.1\|DRB2 (DSRNA-BINDING PROTEIN 2); double-stranded RNA binding [*Arabidopsis thaliana*] | LL | |
| 1051 | 76411 | 1.00E−179 | 99 | ref\|NP_172864.1\|2-oxoglutarate-dependent dioxygenase, putative [*Arabidopsis thaliana*] | PP | |
| 1052 | 70635 | 4.00E−64 | 100 | ref\|NP_851278.1\|senescence-associated family protein [*Arabidopsis thaliana*] | HS | |
| 1053 | 73715 | 0 | 92 | ref\|NP_198428.1\|G6PD1 (GLUCOSE-6-PHOSPHATE DEHYDROGENASE 1); glucose-6-phosphate 1-dehydrogenase [*Arabidopsis thaliana*] | PEG | |
| 1054 | 70638 | 6.00E−79 | 89 | ref\|NP_197398.1\|AWPM-19-like membrane family protein [*Arabidopsis thaliana*] | HS | LN |
| 1055 | 70642 | 1.00E−176 | 92 | ref\|NP_191315.1\|aspartate/glutamate/uridylate kinase family protein [*Arabidopsis thaliana*] | HS | |
| 1056 | 70643 | 0 | 96 | ref\|NP_191703.1\|ATCYSC1 (BETA-SUBSTITUTED ALA SYNTHASE 3; 1); L-3-cyanoalanine synthase/cysteine synthase [*Arabidopsis thaliana*] | HS | |
| 1057 | 71564 | 1.00E−121 | 95 | emb\|CAA47753.1\|proteasome subunit [*Arabidopsis thaliana*] | HS | SP |
| 1058 | 75039 | 1.00E−175 | 90 | ref\|NP_188659.1\|mitochondrial substrate carrier family protein [*Arabidopsis thaliana*] | LN | |
| 1059 | 70653 | 8.00E−82 | 100 | ref\|NP_566365.1\|unknown protein [*Arabidopsis thaliana*] | PEG | |
| 1060 | 70655 | 4.00E−87 | 82 | ref\|NP_566619.1\|unknown protein [*Arabidopsis thaliana*] | LL | PEG |
| 1061 | 78321 | 0 | 97 | ref\|NP_181404.1\|MVD1 (mevalonate diphosphate decarboxylase 1) [*Arabidopsis thaliana*] | DS | HS |
| 1062 | 78307 | 0 | 100 | ref\|NP_182079.1\|CYP76C4 (cytochrome P450, family 76, subfamily C, polypeptide 4); oxygen binding [*Arabidopsis thaliana*] | CK | |
| 1063 | 71808 | 0 | 91 | ref\|NP_182082.2\|CYP76C3 (cytochrome P450, family 76, subfamily C, polypeptide 3); oxygen binding [*Arabidopsis thaliana*] | HS | |
| 1064 | 71810 | 0 | 97 | gb\|AAF88087.1\|AC025417_15T12C24.27 [*Arabidopsis thaliana*] | LN | |
| 1065 | 71313 | 0 | 100 | ref\|NP_187667.1\|CYP77A7 (cytochrome P450, family 77, subfamily A, polypeptide 7, unfertilized embryo sac 9); oxygen binding [*Arabidopsis thaliana*] | CS | |
| 1066 | 72349 | 1.00E−134 | 100 | ref\|NP_191072.1\|TT5 (TRANSPARENT TESTA 5); chalcone isomerase [*Arabidopsis thaliana*] | SP | |
| 1067 | 71318 | 0 | 90 | ref\|NP_189261.1\|CYP71B34 (cytochrome P450, family 71, subfamily B, polypeptide 34); oxygen binding [*Arabidopsis thaliana*] | HS | |
| 1068 | 71812 | 0 | 92 | ref\|NP_195705.1\|CYP79B2 (cytochrome P450, family 79, subfamily B, polypeptide 2); oxygen binding [*Arabidopsis thaliana*] | LN | |
| 1069 | 74060 | 0 | 90 | ref\|NP_188731.1\|CYP705A32 (cytochrome P450, family 705, subfamily A, polypeptide 32); oxygen binding [*Arabidopsis thaliana*] | DS | |
| 1070 | 71816 | 0 | 93 | ref\|NP_568025.1\|CYP81F3 (cytochrome P450, family 81, subfamily F, polypeptide 3); oxygen binding [*Arabidopsis thaliana*] | LL | |
| 1071 | 71569 | 1.00E−142 | 95 | ref\|NP_189364.1\|ATPHB4 (PROHIBITIN 4) [*Arabidopsis thaliana*] | CS | |
| 1072 | 70672 | 0 | 100 | ref\|NP_567641.1\|PRXR1 (peroxidase 42); peroxidase [*Arabidopsis thaliana*] | PP | |
| 1073 | 71336 | 0 | 96 | ref\|NP_563762.1\|VHS domain-containing protein/GAT domain-containing protein [*Arabidopsis thaliana*] | DS | |
| 1074 | 71337 | 1.00E−179 | 100 | ref\|NP_179721.1\|mannose 6-phosphate reductase (NADPH-dependent), putative [*Arabidopsis thaliana*] | HS | |
| 1075 | 71339 | 0 | 93 | ref\|NP_200747.1\|XH/XS domain-containing protein [*Arabidopsis thaliana*] | CS | |
| 1076 | 71825 | 0 | 87 | ref\|NP_195998.2\|TRFL10 (TRF-LIKE 10); DNA binding [*Arabidopsis thaliana*] | LN | |
| 1077 | 73696 | 1.00E−166 | 86 | ref\|NP_192864.1\|MADS-box family protein [*Arabidopsis thaliana*] | SP | |
| 1078 | 70682 | 1.00E−129 | 94 | ref\|NP_001078595.1\|RNA recognition motif (RRM)-containing protein [*Arabidopsis thaliana*] | HS | |
| 1079 | 70686 | 1.00E−117 | 75 | ref\|NP_199096.1\|ATU2AF35B; RNA binding [*Arabidopsis thaliana*] | SP | LL |

TABLE 3-continued

| PEP SEQ ID NO | Construct | E-value | % Id | Description | | traits | |
|---|---|---|---|---|---|---|---|
| 1080 | 78316 | 0 | 100 | ref\|NP_192085.1\|DC1 domain-containing protein [*Arabidopsis thaliana*] | SS | | |
| 1081 | 71667 | 0 | 100 | ref\|NP_013976.1\|Glutamate decarboxylase, converts glutamate into gamma-aminobutyric acid (GABA) during glutamate catabolism; involved in response to oxidative stress; Gad1p [*Saccharomyces cerevisiae*] | DS | | |
| 1082 | 71695 | 0 | 77 | emb\|CAA75577.1\|L-ascorbate oxidase [*Medicago truncatula*] | CK | | |
| 1083 | 71696 | 0 | 96 | gb\|AAB03258.1\|phosphoinositide-specific phospholipase C P13 | HS | LN | |
| 1084 | 72475 | 1.00E−111 | 83 | gb\|AAF21310.1\|seed maturation protein PM24 [*Glycine max*] | HS | | |
| 1085 | 71677 | 1.00E−125 | 77 | gb\|ABD28522.1\|Cupin, RmlC-type [*Medicago truncatula*] | CK | | |
| 1086 | 71691 | 7.00E−34 | 35 | emb\|CAO44124.1\|unnamed protein product [*Vitis vinifera*] | CS | | |
| 1087 | 72476 | 1.00E−122 | 70 | emb\|CAO47395.1\|unnamed protein product [*Vitis vinifera*] | HS | | |
| 1088 | 70803 | 0 | 97 | ref\|NP_850874.1\|glutamate-tRNA ligase, putative/ glutamyl-tRNA synthetase, putative/GluRS, putative [*Arabidopsis thaliana*] | SP | LN | |
| 1089 | 71612 | 0 | 94 | ref\|NP_192179.1\|SULTR3; 2 (SULFATE TRANSPORTER 3; 2); sulfate transporter [*Arabidopsis thaliana*] | LL | | |
| 1090 | 71637 | 0 | 88 | gb\|AAD52696.1\|AF087819_1auxin transport protein [*Arabidopsis thaliana*] | LN | | |
| 1091 | 71629 | 0 | 97 | ref\|NP_565924.1\|unknown protein [*Arabidopsis thaliana*] | HS | PEG | |
| 1092 | 71622 | 0 | 97 | ref\|NP_566085.1\|APRR9 (PSEUDO-RESPONSE REGULATOR 9); transcription regulator [*Arabidopsis thaliana*] | LN | | |
| 1093 | 70810 | 0 | 91 | ref\|NP_175610.1\|mitochondrial processing peptidase alpha subunit, putative [*Arabidopsis thaliana*] | HS | SS | |
| 1094 | 72452 | 6.00E−76 | 77 | ref\|NP_199889.1\|auxin-responsive family protein [*Arabidopsis thaliana*] | LN | | |
| 1095 | 74071 | 0 | 93 | ref\|NP_174516.1\|ribose-phosphate pyrophosphokinase 2/ phosphoribosyl diphosphate synthetase 2 (PRS2) [*Arabidopsis thaliana*] | LL | | |
| 1096 | 11042 | 2.00E−89 | 93 | ref\|NP_179709.1\|peptidyl-prolyl cis-trans isomerase/ cyclophilin (CYP2)/rotamase [*Arabidopsis thaliana*] | LN | | |
| 1097 | 72510 | 0 | 89 | ref\|NP_196865.1\|unknown protein [*Arabidopsis thaliana*] | CK | | |
| 1098 | 72537 | 1.00E−124 | 82 | ref\|NP_851118.1\|unknown protein [*Arabidopsis thaliana*] | HS | LN | |
| 1099 | 72541 | 9.00E−57 | 88 | ref\|NP_568684.1\|unknown protein [*Arabidopsis thaliana*] | PP | | |
| 1100 | 72617 | 4.00E−88 | 100 | ref\|NP_568761.1\|unknown protein [*Arabidopsis thaliana*] | LL | | |
| 1101 | 73755 | 1.00E−132 | 100 | ref\|NP_200501.1\|cysteine protease inhibitor [*Arabidopsis thaliana*] | PP | SS | |
| 1102 | 72630 | 2.00E−86 | 93 | ref\|NP_201267.1\|C/VIF2 (CELL WALL/VACUOLAR INHIBITOR OF FRUCTOSIDASE 2); pectinesterase inhibitor [*Arabidopsis thaliana*] | SP | | |
| 1103 | 72645 | 5.00E−37 | 75 | ref\|NP_180615.1\|photosystem II reaction center W (PsbW) protein-related [*Arabidopsis thaliana*] | LN | | |
| 1104 | 72647 | 5.00E−43 | 100 | ref\|NP_566036.1\|protease inhibitor/seed storage/lipid transfer protein (LTP) family protein [*Arabidopsis thaliana*] | LN | | |
| 1105 | 14316 | 1.00E−55 | 86 | ref\|NP_188703.1\|histone H2A, putative [*Arabidopsis thaliana*] | DS | | |
| 1106 | 73689 | 6.00E−79 | 100 | ref\|NP_173037.1\|transducin family protein/WD-40 repeat family protein [*Arabidopsis thaliana*] | DS | SS | |
| 1107 | 73345 | 0 | 92 | ref\|NP_174226.1\|transducin family protein/WD-40 repeat family protein [*Arabidopsis thaliana*] | HS | LN | |
| 1108 | 73347 | 0 | 100 | ref\|NP_177513.2\|transducin family protein/WD-40 repeat family protein [*Arabidopsis thaliana*] | SP | | |
| 1109 | 73231 | 0 | 84 | ref\|NP_196332.1\|leucine-rich repeat family protein [*Arabidopsis thaliana*] | PP | | |
| 1110 | 78325 | 0 | 84 | ref\|NP_171637.1\|aspartyl protease family protein [*Arabidopsis thaliana*] | HS | | |
| 1111 | 72658 | 1.00E−138 | 93 | ref\|NP_172224.1\|tropinone reductase, putative/tropine dehydrogenase, putative [*Arabidopsis thaliana*] | PEG | | |
| 1112 | 72660 | 3.00E−78 | 82 | ref\|NP_564585.1\|zinc finger (AN1-like) family protein [*Arabidopsis thaliana*] | LN | | |
| 1113 | 72662 | 5.00E−49 | 100 | ref\|NP_179096.1\|gibberellin-regulated family protein [*Arabidopsis thaliana*] | LN | | |
| 1114 | 73352 | 0 | 97 | ref\|NP_566304.1\|armadillo/beta-catenin repeat family protein/U-box domain-containing protein [*Arabidopsis thaliana*] | LN | | |
| 1115 | 72814 | 0 | 100 | ref\|NP_566558.1\|F-box family protein [*Arabidopsis thaliana*] | PP | CS | PEG |
| 1116 | 72816 | 0 | 100 | ref\|NP_566824.1\|CARA (CARBAMOYL PHOSPHATE SYNTHETASE A); carbamoyl-phosphate synthase (glutamine-hydrolyzing) [*Arabidopsis thaliana*] | PP | | |

TABLE 3-continued

| PEP SEQ ID NO | Construct | E-value | % Id | Description | traits | | |
|---|---|---|---|---|---|---|---|
| 1117 | 72820 | 0 | 89 | ref|NP_194653.1|leucine-rich repeat family protein/ extensin family protein [*Arabidopsis thaliana*] | LL | | |
| 1118 | 73353 | 0 | 97 | ref|NP_194713.1|MTO2 (METHIONINE OVER-ACCUMULATOR); threonine synthase [*Arabidopsis thaliana*] | HS | PEG | |
| 1119 | 75066 | 1.00E−134 | 91 | ref|NP_175644.1|ABA2 (ABA DEFICIENT 2); oxidoreductase [*Arabidopsis thaliana*] | PEG | | |
| 1120 | 78337 | 2.00E−40 | 78 | dbj|BAD43663.1|unknown protein [*Arabidopsis thaliana*] | PEG | | |
| 1121 | 73317 | 0 | 96 | ref|NP_200121.4|oxidoreductase [*Arabidopsis thaliana*] | LN | | |
| 1122 | 73318 | 0 | 94 | ref|NP_568145.1|short-chain dehydrogenase/reductase (SDR) family protein [*Arabidopsis thaliana*] | CS | | |
| 1123 | 73749 | 0 | 97 | gb|AAG51266.1|[AC027135_7protein kinase, putative [*Arabidopsis thaliana*] | CS | | |
| 1124 | 18704 | 0 | 88 | ref|NP_201234.1|DCT/DIT2.1 (DICARBOXYLATE TRANSPORT); oxoglutarate: malate antiporter [*Arabidopsis thaliana*] | PEG | | |
| 1125 | 73221 | 1.00E−162 | 82 | ref|NP_563785.1|C2 domain-containing protein [*Arabidopsis thaliana*] | CK | LL | |
| 1126 | 71125 | 1.00E−117 | 94 | ref|NP_172671.1|Rho GDP-dissociation inhibitor family protein [*Arabidopsis thaliana*] | HS | | |
| 1127 | 76203 | 0 | 97 | ref|NP_200678.2|phosphoinositide-specific phospholipase C family protein [*Arabidopsis thaliana*] | PEG | | |
| 1128 | 75067 | 0 | 100 | ref|NP_566565.1|peroxidase, putative [*Arabidopsis thaliana*] | PEG | | |
| 1129 | 73729 | 0 | 100 | ref|NP_194944.1|CYP96A2 (cytochrome P450, family 96, subfamily A, polypeptide 2); oxygen binding [*Arabidopsis thaliana*] | LL | | |
| 1130 | 75206 | 0 | 95 | ref|NP_197962.1|GA3 (GA REQUIRING 3); oxygen binding [*Arabidopsis thaliana*] | HS | | |
| 1131 | 73248 | 0 | 100 | ref|NP_200532.1|CYP81F2 (cytochrome P450, family 81, subfamily F, polypeptide 2); oxygen binding [*Arabidopsis thaliana*] | HS | | |
| 1132 | 73738 | 0 | 93 | ref|NP_198641.1|serine/threonine protein kinase, putative [*Arabidopsis thaliana*] | DS | | |
| 1133 | 73332 | 0 | 97 | ref|NP_173685.1|SUC2 (SUCROSE-PROTON SYMPORTER 2); carbohydrate transporter/ sucrose: hydrogen symporter/sugar porter [*Arabidopsis thaliana*] | PP | | |
| 1134 | 78335 | 0 | 100 | ref|NP_189582.1|UDP-glucose 6-dehydrogenase, putative [*Arabidopsis thaliana*] | HS | LL | PP |
| 1135 | 75821 | 6.00E−76 | 90 | ref|NP_190424.1|unknown protein [*Arabidopsis thaliana*] | LL | | |
| 1136 | 72038 | 0 | 97 | emb|CAA18501.1|Calcium-dependent serine/threonine protein kinase [*Arabidopsis thaliana*] | HS | | |
| 1137 | 72027 | 0 | 91 | ref|NP_849857.1|copine-related [*Arabidopsis thaliana*] | DS | | |
| 1138 | 72016 | 0 | 97 | ref|NP_200887.1|ATGCN1 (*Arabidopsis thaliana* general control non-repressible 1) | CS | | |
| 1139 | 70835 | 1.00E−128 | 82 | ref|NP_181461.1|PGPS1 (PHOSPHATIDYLGLYCEROLPHOSPHATE + SYNTHASE + 1); CDP-alcohol phosphatidyltransferase [*Arabidopsis thaliana*] | SS | | |
| 1140 | 72044 | 0 | 99 | ref|NP_014446.1 protein proposed to interact with phospholipid translocases, shares similarity to Cdc50p; Ynr048wp [*Saccharomyces cerevisiae*] | CS | | |
| 1141 | 72092 | 0 | 92 | ref|NP_010796.1|High-affinity glutamine permease, also transports Leu, Ser, Thr, Cys, Met and Asn; expression is fully dependent on Grr1p and modulated by the Ssy1p-Ptr3p-Ssy5p (SPS) sensor of extracellular amino acids; Gnp1p [*Saccharomyces cerevisiae*] | CK | | |
| 1142 | 72124 | 1.00E−173 | 55 | emb|CAO64952.1|unnamed protein product [*Vitis vinifera*] | HS | | |
| 1143 | 72110 | 1.00E−172 | 63 | emb|CAN75218.1|hypothetical protein [*Vitis vinifera*] | HS | | |
| 1144 | 73916 | 1.00E−162 | 57 | ref|NP_569047.1|SKIP2 (SKP1 INTERACTING PARTNER 2); ubiquitin-protein ligase [*Arabidopsis thaliana*] | HS | | |
| 1145 | 74268 | 0 | 100 | ref|NP_186851.1|aspartate kinase, lysine-sensitive, putative [*Arabidopsis thaliana*] | HS | LL | |
| 1146 | 74269 | 0 | 94 | ref|NP_566764.1|bile acid: sodium symporter family protein [*Arabidopsis thaliana*] | DS | | |
| 1147 | 77902 | 0 | 96 | ref|NP_197021.2|tyrosyl-DNA phosphodiesterase-related [*Arabidopsis thaliana*] | SS | | |
| 1148 | 74273 | 1.00E−180 | 100 | ref|NP_199285.1|molybdenum cofactor sulfurase family protein [*Arabidopsis thaliana*] | HS | | |
| 1149 | 74280 | 1.00E−165 | 94 | emb|CAA58893.1|cysteine synthase [*Arabidopsis thaliana*] | HS | | |
| 1150 | 74281 | 0 | 94 | ref|NP_197655.1|prephenate dehydratase family protein [*Arabidopsis thaliana*] | LL | | |

TABLE 3-continued

| PEP SEQ ID NO | Construct | E-value | % Id | Description | traits | | |
|---|---|---|---|---|---|---|---|
| 1151 | 74287 | 0 | 100 | ref|NP_974217.1|SUVR4 [*Arabidopsis thaliana*] | CK | HS | |
| 1152 | 73767 | 1.00E−156 | 100 | ref|NP_194231.1|nodulin MtN3 family protein [*Arabidopsis thaliana*] | LN | | |
| 1153 | 77304 | 0 | 100 | ref|NP_175700.2|catalytic [*Arabidopsis thaliana*] | CK | HS | PEG |
| 1154 | 73761 | 0 | 95 | ref|NP_566683.1|mitochondrial substrate carrier family protein [*Arabidopsis thaliana*] | LL | | |
| 1155 | 74721 | 0 | 93 | ref|NP_194568.1|AAC3 (ADP/ATP CARRIER 3); ATP: ADP antiporter/binding [*Arabidopsis thaliana*] | LL | | |
| 1156 | 74719 | 0 | 91 | ref|NP_198474.1|protein phosphatase 2C, putative/PP2C, putative [*Arabidopsis thaliana*] | CK | | |
| 1157 | 74257 | 0 | 98 | ref|NP_179113.2|fatty acid elongase, putative [*Arabidopsis thaliana*] | DS | HS | |
| 1158 | 72749 | 0 | 95 | ref|NP_176767.1|regulator of chromosome condensation (RCC1) family protein/zinc finger protein-related [*Arabidopsis thaliana*] | HS | LL | |
| 1159 | 72703 | 2.00E−77 | 92 | ref|NP_013963.1|Subunit (17 kDa) of TFIID and SAGA complexes, involved in RNA polymerase II transcription initiation and in chromatin modification, similar to histone H3; Taf9p [*Saccharomyces cerevisiae*] | PEG | | |
| 1160 | 72763 | 0 | 98 | ref|NP_009691.1|Protein arginine N-methyltransferase that exhibits septin and Hsl1p-dependent bud neck localization and periodic Hsl1p-dependent phosphorylation; required along with Hsl1p for bud neck recruitment, phosphorylation, and degradation of Swe1p; Hsl7p [*Saccharomyces cerevisiae*] | SS | | |
| 1161 | 72775 | 1.00E−172 | 100 | ref|NP_009718.1|Catalytic subunit of the main cell cycle cyclin-dependent kinase (CDK); alternately associates with G1 cyclins (CLNs) and G2/M cyclins (CLBs) which direct the CDK to specific substrates; Cdc28p [*Saccharomyces cerevisiae*] | HS | | |
| 1162 | 72728 | 0 | 96 | ref|NP_013106.1|Cytoplasmic response regulator, part of a two-component signal transducer that mediates osmosensing via a phosphorelay mechanism; dephosphorylated form is degraded by the ubiquitin-proteasome system; potential Cdc28p substrate; Ssk1p [*Saccharomyces cerevisiae*] | CS | | |
| 1163 | 72776 | 1.00E−101 | 92 | gb|EDN62754.1|oxidant-induced cell cycle arrest [*Saccharomyces cerevisiae* YJM789] | HS | | |
| 1164 | 72717 | 1.00E−131 | 100 | ref|NP_011075.1|TATA-binding protein, general transcription factor that interacts with other factors to form the preinitiation complex at promoters, essential for viability, Spt15p [*Saccharomyces cerevisiae*] | DS | | |
| 1165 | 72718 | 1.00E−159 | 90 | ref|NP_011400.1|Activating gamma subunit of the AMP-activated Snf1p kinase complex (contains Snf1p and a Sip1p/Sip2p/Gal83p family member); activates glucose-repressed genes, represses glucose-induced genes; role in sporulation, and peroxisome biogenesis: Snf4p [*Saccharomyces cerevisiae*] | DS | | |
| 1166 | 11715 | 0 | 93 | ref|NP_187616.1|OMR1 (L-O-METHYLTHREONINE RESISTANT 1), threonine ammonia-lyase [*Arabidopsis thaliana*] | LN | | |
| 1167 | 72779 | 0 | 93 | ref|NP_011622.1|B-type cyclin involved in cell cycle progression; activates Cdc28p to promote the transition from G2 to M phase; accumulates during G2 and M, then targeted via a destruction box motif for ubiquitin-mediated degradation by the proteasome; Clb1p [*Saccharomyces cerevisiae*] | DS | | |
| 1168 | 72791 | 0 | 100 | ref|NP_009709.1|Protein of unknown function, required for normal localization of actin patches and for normal tolerance of sodium ions and hydrogen peroxide; localizes to both cytoplasm and nucleus; Apd1p [*Saccharomyces cerevisiae*] | DS | HS | |
| 1169 | 72732 | 0 | 100 | ref|NP_013662.1|Putative protein of unknown function; non-essential gene: null mutant displays increased frequency of mitochondrial genome loss (petite formation); Aim32p [*Saccharomyces cerevisiae*] | HS | | |
| 1170 | 73027 | 1.00E−125 | 93 | ref|NP_187445.1|Rho GDP-dissociation inhibitor family protein [*Arabidopsis thaliana*] | CS | | |
| 1171 | 73058 | 0 | 96 | ref|NP_175591.1|leucine-rich repeat protein kinase, putative [*Arabidopsis thaliana*] | CK | | |
| 1172 | 73126 | 0 | 95 | ref|NP_173076.1|protein kinase family protein [*Arabidopsis thaliana*] | PEG | | |
| 1173 | 73138 | 0 | 91 | ref|NP_356682.2|aldehyde dehydrogenase [*Agrobacterium tumefaciens* str. C58] | HS | | |

TABLE 3-continued

| PEP SEQ ID NO | Construct | E-value | % Id | Annotation Description | traits | |
|---|---|---|---|---|---|---|
| 1174 | 73174 | 0 | 94 | ref|NP_241069.1|glycine betaine aldehyde dehydrogenase [*Bacillus halodurans* C-125] | HS | |
| 1175 | 73186 | 0 | 99 | ref|NP_241405.1|NADP-dependent aldehyde dehydrogenase [*Bacillus halodurans* C-125] | HS | LN |
| 1176 | 11141 | 0 | 100 | ref|NP_568064.1|AGT2 (ALANINE: GLYOXYLATE AMINOTRANSFERASE 2); alanine-glyoxylate transaminase [*Arabidopsis thaliana*] | LN | |
| 1177 | 73139 | 0 | 89 | ref|NP_242876.1|aldehyde dehydrogenase [*Bacillus halodurans* C-125] | CS | |
| 1178 | 73128 | 0 | 97 | ref|NP_388272.1|4-aminobutyrate aminotransferase [*Bacillus subtilis* subsp. *subtilis* str. 168] | HS | |
| 1179 | 73164 | 0 | 93 | ref|NP_389241.1|transaminase [*Bacillus subtilis* subsp. *subtilis* str. 168] | PEG | |
| 1180 | 73117 | 0 | 97 | ref|NP_391762.1|aldehyde dehydrogenase [*Bacillus subtilis* subsp. *subtilis* str. 168] | CS | HS |
| 1181 | 73142 | 0 | 99 | ref|YP_585121.1|glyceraldehyde-3-phosphate dehydrogenase, type I [*Ralstonia metallidurans* CH34] | PP | SS |
| 1182 | 73990 | 1.00E−154 | 90 | ref|NP_949547.1|glutaminase [*Rhodopseudomonas palustris* CGA009] | HS | |
| 1183 | 73166 | 1.00E−117 | 100 | ref|NP_384268.1|phosphoglyceromutase [*Sinorhizobium meliloti* 1021] | SS | |
| 1184 | 73178 | 0 | 91 | ref|NP_385430.1|PUTATIVE AMINOTRANSFERASE PROTEIN [*Sinorhizobium meliloti* 1021] | LL | |
| 1185 | 73190 | 1.00E−142 | 99 | ref|NP_385544.1|PROBABLE TRIOSEPHOSPHATE ISOMERASE PROTEIN [*Sinorhizobium meliloti* 1021] | PEG | |
| 1186 | 73131 | 0 | 99 | ref|NP_386510.1|beta amino acid-pyruvate transaminase [*Sinorhizobium meliloti* 1021] | CK | |
| 1187 | 73108 | 0 | 92 | ref|NP_929378.1|pyruvate kinase [*Photorhabdus luminescens* subsp. *laumondii* TTO1] | CK | |
| 1188 | 73074 | 1.00E−171 | 87 | gb|AAO17215.1|Epd [*Photorhabdus luminescens*] | HS | |
| 1189 | 73132 | 1.00E−80 | 100 | ref|NP_390154.1|nucleoside diphosphate kinase [*Bacillus subtilis* subsp. *subtilis* str. 168] | CS | |
| 1190 | 73146 | 2.00E−94 | 93 | ref|NP_931715.1|inorganic pyrophosphatase [*Photorhabdus luminescens* subsp. *laumondii* TTO1] | DS | |
| 1191 | 73147 | 0 | 97 | ref|NP_015444.1|B-type cyclin involved in cell cycle progression; activates Cdc28p to promote the transition from G2 to M phase; accumulates during G2 and M, then targeted via a destruction box motif for ubiquitin-mediated degradation by the proteasome; Clb2p [*Saccharomyces cerevisiae*] | HS | |
| 1192 | 73080 | 0 | 92 | gb|AAB17351.1|protein phosphatase type 2C [*Saccharomyces cerevisiae*] | LN | |
| 1193 | 73077 | 0 | 97 | ref|NP_010018.1|Endosomal protein that regulates cell polarity, controls polarized growth; similar to Ynr048wp and Lem3p; Cdc50p [*Saccharomyces cerevisiae*] | HS | |
| 1194 | 73183 | 0 | 93 | ref|NP_011895.1|Serine/threonine MAP kinase involved in regulating the maintenance of cell wall integrity and progression through the cell cycle; regulated by the PKC1-mediated signaling pathway; Slt2p [*Saccharomyces cerevisiae*] | CS | HS |
| 1195 | 73018 | 0 | 100 | ref|NP_014582.1|NAD-dependent glycerol 3-phosphate dehydrogenase, homolog of Gpd1p, expression is controlled by an oxygen-independent signaling pathway required to regulate metabolism under anoxic conditions; located in cytosol and mitochondria; Gpd2p [*Saccharomyces cerevisiae*] | HS | |
| 1196 | 73112 | 0 | 97 | ref|NP_014271.1|Homolog of human tumor suppressor gene PTEN/MMAC1/TEP1 that has lipid phosphatase activity and is linked to the phosphatidylinositol signaling pathway; plays a role in normal sporulation; Tep1p [*Saccharomyces cerevisiae*] | HS | |
| 1197 | 73988 | 0 | 83 | ref|NP_013664.1|ER localized integral membrane protein that may promote secretion of certain hexose transporters, including Gal2p; involved in glucose-dependent repression; Gsf2p [*Saccharomyces cerevisiae*] | SS | PEG |
| 1198 | 10908 | 2.00E−61 | 100 | ref|NP_199112.1|ATTRX3 (thioredoxin H-type 3); thiol-disulfide exchange intermediate [*Arabidopsis thaliana*] | CK | |
| 1198 | 11147 | 2.00E−61 | 100 | ref|NP_199112.1|ATTRX3 (thioredoxin H-type 3); thiol-disulfide exchange intermediate [*Arabidopsis thaliana*] | LN | |
| 1199 | 72909 | 0 | 95 | ref|NP_011569.1|High affinity methionine permease, integral membrane protein with 13 putative membrane-spanning regions; also involved in cysteine uptake; Mup1p [*Saccharomyces cerevisiae*] | HS | |

TABLE 3-continued

| PEP SEQ ID NO | Construct | E-value | % Id | Annotation Description | traits | | |
|---|---|---|---|---|---|---|---|
| 1200 | 73987 | 0 | 94 | ref|NP_010444.1|Component of the SPS plasma membrane amino acid sensor system (Ssy1p-Ptr3p-Ssy5p), which senses external amino acid concentration and transmits intracellular signals that result in regulation of expression of amino acid permease genes; Ssy1p [*Saccharomyces cerevisiae*] | PP | SS | |
| 1201 | 72922 | 0 | 91 | ref|NP_010082.1|Putative transporter, member of the sugar porter family; Ydl199cp [*Saccharomyces cerevisiae*] | LL | | |
| 1202 | 73036 | 0 | 95 | ref|NP_010022.1|Plasma membrane permease, mediates uptake of glycerophosphoinositol and glycerophosphocholine as sources of the nutrients inositol and phosphate; expression and transport rate are regulated by phosphate and inositol availability; Git1p [*Saccharomyces cerevisiae*] | CS | HS | |
| 1203 | 72958 | 0 | 94 | ref|NP_014622.1|High affinity tryptophan and tyrosine permease, overexpression confers FK506 and FTY720 resistance; Tat2p [*Saccharomyces cerevisiae*] | HS | PP | |
| 1204 | 77006 | 1.00E−167 | 100 | ref|NP_182073.1|ATAUR3 (ATAURORA3); ATP binding/ histone serine kinase(H3-S10 specific)/protein kinase [*Arabidopsis thaliana*] | LL | LN | |
| 1205 | 74732 | 0 | 90 | ref|NP_177415.1|casein kinase, putative [*Arabidopsis thaliana*] | CK | | |
| 1206 | 74333 | 1.00E−158 | 100 | ref|NP_180976.1|protein kinase family protein [*Arabidopsis thaliana*] | HS | | |
| 1207 | 74735 | 0 | 100 | ref|NP_173489.2|protein kinase [*Arabidopsis thaliana*] | LN | | |
| 1208 | 74736 | 0 | 100 | ref|NP_176353.1|protein kinase, putative [*Arabidopsis thaliana*] | LL | | |
| 1209 | 74737 | 0 | 100 | gb|AAF16665.1|AC012394_14putative protein kinase; 59396-62219 [*Arabidopsis thaliana*] | HS | | |
| 1210 | 76657 | 0 | 95 | ref|NP_187827.1|protein kinase family protein [*Arabidopsis thaliana*] | SP | LL | |
| 1211 | 76113 | 0 | 94 | ref|NP_187165.2|protein kinase family protein [*Arabidopsis thaliana*] | CS | | |
| 1212 | 74747 | 0 | 92 | ref|NP_174161.1|protein kinase family protein [*Arabidopsis thaliana*] | HS | | |
| 1213 | 77309 | 0 | 87 | ref|NP_175879.2|protein kinase family protein [*Arabidopsis thaliana*] | PEG | | |
| 1214 | 74322 | 0 | 94 | gb|AAG52342.1|AC011663_21putative protein kinase; 29119-30743 [*Arabidopsis thaliana*] | LL | | |
| 1215 | 76212 | 1.00E−170 | 93 | ref|NP_200959.2|NADP-dependent oxidoreductase, putative [*Arabidopsis thaliana*] | HS | LN | |
| 1216 | 76514 | 1.00E−159 | 85 | ref|NP_568357.1|AAA-type ATPase family protein [*Arabidopsis thaliana*] | LL | DS | |
| 1217 | 75242 | 0 | 84 | ref|NP_200318.1|2-oxoacid dehydrogenase family protein [*Arabidopsis thaliana*] | LL | | |
| 1218 | 77324 | 0 | 97 | gb|AAF79717.1|AC020889_25T1N15.3 [*Arabidopsis thaliana*] | PEG | LN | |
| 1219 | 74350 | 3.00E−95 | 93 | ref|NP_178122.1|APT2 (ADENINE PHOSPHORIBOSYL TRANSFERASE 2); adenine phosphoribosyltransferase [*Arabidopsis thaliana*] | LN | | |
| 1220 | 77606 | 0 | 96 | ref|NP_190925.1|AFC1 (*ARABIDOPSIS* FUSS-COMPLEMENTING GENE 1); kinase [*Arabidopsis thaliana*] | HS | SS | |
| 1221 | 76530 | 0 | 92 | ref|NP_567069.1|F-box family protein-related [*Arabidopsis thaliana*] | HS | | |
| 1222 | 76716 | 1.00E−86 | 61 | ref|NP_565175.1|RNA recognition motif (RRM)-containing protein [*Arabidopsis thaliana*] | HS | | |
| 1223 | 77328 | 0 | 89 | ref|NP_567904.1|RNA recognition motif (RRM)-containing protein [*Arabidopsis thaliana*] | HS | | |
| 1224 | 12204 | 0 | 100 | ref|NP_189366.1|G6PD5 (GLUCOSE-6-PHOSPHATE. DEHYDROGENASE 5); glucose-6-phosphate 1-dehydrogenase [*Arabidopsis thaliana*] | DS | | |
| 1225 | 77011 | 0 | 96 | ref|NP_563818.1|strictosidine synthase family protein [*Arabidopsis thaliana*] | LL | | |
| 1226 | 77607 | 0 | 94 | ref|NP_175157.1|NRAMP2 (NRAMP metal ion transporter 2); metal ion transporter [*Arabidopsis thaliana*] | LL | PEG | |
| 1227 | 74612 | 1.00E−68 | 100 | ref|NP_177750.1|unknown protein [*Arabidopsis thaliana*] | HS | | |
| 1228 | 76126 | 1.00E−144 | 100 | ref|NP_179467.1|signal recognition particle binding [*Arabidopsis thaliana*] | HS | | |
| 1229 | 74376 | 1.00E−150 | 95 | ref|NP_181340.1|DET2 (DE-ETIOLATED 2) [*Arabidopsis thaliana*] | DS | | |
| 1230 | 74377 | 1.00E−46 | 100 | ref|NP_181546.1|ATEM6 (*ARABIDOPSIS* EARLY METHIONINE-LABELLED 6) [*Arabidopsis thaliana*] | DS | LL | PEG |

TABLE 3-continued

| PEP SEQ ID NO | Construct | E-value | % Id | Annotation Description | traits | | |
|---|---|---|---|---|---|---|---|
| 1231 | 74381 | 6.00E−63 | 100 | ref|NP_181990.1|mtACP-1 (MITOCHONDRIAL ACYL CARRIER PROTEIN T); acyl carrier [*Arabidopsis thaliana*] | CS | | |
| 1232 | 78364 | 6.00E−88 | 87 | ref|NP_566062.1|UBC6 (UBIQUITIN-CONJUGATING ENZYME 6), ubiquitin-protein ligase [*Arabidopsis thaliana*] | HS | | |
| 1233 | 74623 | 1.00E−115 | 75 | ref|NP_188379.1|late embryogenesis abundant domain-containing protein/LEA domain-containing protein [*Arabidopsis thaliana*] | HS | | |
| 1234 | 74668 | 1.00E−122 | 88 | ref|NP_188888.1|late embryogenesis abundant protein, putative/LEA protein, putative [*Arabidopsis thaliana*] | DS | | |
| 1235 | 74629 | 5.00E−83 | 90 | ref|NP_566782.1|unknown protein [*Arabidopsis thaliana*] | LL | | |
| 1236 | 74635 | 1.00E−113 | 92 | ref|NP_190864.1|peroxiredoxin type 2, putative [*Arabidopsis thaliana*] | CS | | |
| 1237 | 74638 | 1.00E−100 | 100 | ref|NP_191788.1|ATARFA1E (ADP-ribosylation factor A1E); GTP binding/phospholipase activator/protein binding [*Arabidopsis thaliana*] | HS | SS | |
| 1238 | 76721 | 1.00E−148 | 77 | ref|NP_192093.1|KCO5 (Ca2+ activated outward rectifying K+ channel 5); outward rectifier potassium channel [*Arabidopsis thaliana*] | PEG | | |
| 1239 | 78365 | 2.00E−83 | 90 | ref|NP_568004.1|UBC17 (UBIQUITIN-CONJUGATING ENZYME 17); ubiquitin-protein ligase [*Arabidopsis thaliana*] | CK | HS | |
| 1240 | 74655 | 1.00E−132 | 91 | ref|NP_195437.1|HCF164 (High chlorophyll fluorescence 164); thiol-disulfide exchange intermediate [*Arabidopsis thaliana*] | LN | | |
| 1241 | 74660 | 1.00E−160 | 92 | ref|NP_196119.1|ATTOC34/OEP34 (Translocase of chloroplast 34) [*Arabidopsis thaliana*] | CS | PEG | |
| 1242 | 74661 | 1.00E−180 | 96 | ref|NP_197135.1|ubiquitin carboxyl-terminal hydrolase family 1 protein [*Arabidopsis thaliana*] | HS | | |
| 1243 | 75259 | 1.00E−101 | 85 | ref|NP_198051.1|drought-responsive family protein [*Arabidopsis thaliana*] | HS | | |
| 1244 | 75282 | 3.00E−93 | 100 | ref|NP_201055.1|ATHVA22B (*Arabidopsis thaliana* HVA22 homologue B) | PEG | | |
| 1245 | 76724 | 0 | 93 | ref|NP_173089.1|organic cation transporter-related [*Arabidopsis thaliana*] | DS | | |
| 1246 | 12350 | 1.00E−131 | 78 | gb|AAM81424.1|serine O-acetyltransferase (EC 2.3.1.30) Sat-52 [*Arabidopsis thaliana*] | LN | | |
| 1247 | 76522 | 0 | 93 | ref|NP_001077495.1|unknown protein [*Arabidopsis thaliana*] | PP | | |
| 1248 | 77903 | 0 | 96 | ref|NP_194952.2|protein kinase family protein [*Arabidopsis thaliana*] | HS | LL | SS |
| 1249 | 76653 | 0 | 100 | ref|NP_568860.1|CIPK21 (CBL-INTERACTING PROTEIN KINASE 21); kinase [*Arabidopsis thaliana*] | CS | | |
| 1250 | 76524 | 0 | 100 | ref|NP_199469.1|protein kinase family protein [*Arabidopsis thaliana*] | CS | | |
| 1251 | 11356 | 1.00E−172 | 100 | ref|NP_181165.1|APG10 (ALBINO AND PALE GREEN 10); 1-(5-phosphoribosyl)-5-[(5-phosphoribosylamino)methylideneamino]imidazole-4-carboxamide isomerase [*Arabidopsis thaliana*] | LN | | |
| 1252 | 75275 | 0 | 94 | ref|NP_199586.1|protein kinase, putative [*Arabidopsis thaliana*] dbj|BAA01715.1| serine/threonine protein kinase [*Arabidopsis thaliana*] | LL | | |
| 1253 | 76225 | 0 | 94 | ref|NP_195285.3[CONNEXIN 32; kinase [*Arabidopsis thaliana*] | PEG | | |
| 1254 | 75281 | 0 | 94 | ref|NP_568893.1|protein kinase family protein [*Arabidopsis thaliana*] | HS | | |
| 1255 | 74384 | 1.00E−102 | 100 | ref|NP_175960.1|prenylated rab acceptor (PRA1) family protein [*Arabidopsis thaliana*] | LL | | |
| 1256 | 71238 | 1.00E−168 | 84 | ref|NP_563814.1|DCP1 (DECAPPING 1) [*Arabidopsis thaliana*] | LN | | |
| 1257 | 12354 | 0 | 100 | ref|NP_172738.1|UGE1 (UDP-D-glucose/UDP-D-galactose 4-epimerase 1); UDP-glucose 4-epimerase/protein dimerization [*Arabidopsis thaliana*] | DS | | |
| 1258 | 76236 | 1.00E−157 | 100 | ref|NP_201384.1|leucine-rich repeat family protein [*Arabidopsis thaliana*] | HS | | |
| 1259 | 74682 | 4.00E−83 | 100 | ref|NP_565581.1|unknown protein [*Arabidopsis thaliana*] | CS | | |
| 1260 | 73425 | 0 | 95 | ref|NP_391649.1|transaminase [*Bacillus subtilis* subsp. *subtilis* str. 168] | LL | | |
| 1261 | 73438 | 0 | 99 | ref|YP_351136.1|Glutamate-ammonia ligase [*Pseudomonas fluorescens* PfO-1] | SP | | |
| 1262 | 73474 | 0 | 92 | ref|NP_790236.1|phosphoglycerate kinase [*Pseudomonas syringae* pv. tomato str. DC3000] | HS | PP | |
| 1263 | 70850 | 0 | 97 | ref|NP_190853.1|ATELP1 (VACUOLAR SORTING RECEPTOR HOMOLOG) [*Arabidopsis thaliana*] | HS | | |

TABLE 3-continued

| PEP SEQ ID NO | Construct | E-value | % Id | Annotation Description | traits | | |
|---|---|---|---|---|---|---|---|
| 1264 | 73429 | 1.00E−144 | 100 | ref|ZP_01370194.1|pyrroline-5-carboxylate reductase [*Desulfitobacterium hafniense* DCB-2] | HS | SS | CS |
| 1265 | 73441 | 0 | 94 | ref|ZP_01370604.1|enolase [*Desulfitobacterium hafniense* DCB-2] | PEG | | |
| 1266 | 73466 | 0 | 97 | ref|ZP_00108577.1|COG1063: Threonine dehydrogenase and related Zn-dependent dehydrogenases [*Nostoc punctiforme* PCC 73102] | LN | | |
| 1267 | 73455 | 1.00E−159 | 100 | ref|NP_792905.1|UTP-glucose-1-phosphate uridylyltransferase [*Pseudomonas syringae* pv. tomato str. DC3000] | HS | | |
| 1268 | 73432 | 0 | 94 | ref|YP_582 700.1|Alcohol dehydrogenase, zinc-binding [*Ralstonia metallidurans* CH34] | CS | | |
| 1269 | 73435 | 0 | 97 | ref|NP_391271.1|phosphoglyceromutase [*Bacillus subtilis* subsp. *subtilis* str. 168] | LN | | |
| 1270 | 77726 | 0 | 99 | ref|NP_391273.1|phosphoglycerate kinase [*Bacillus subtilis* subsp. *subtilis* str. 168] | HS | | |
| 1271 | 73483 | 0 | 96 | ref|NP_009362.1|Pyruvate kinase, functions as a homotetramer in glycolysis to convert phosphoenolpyruvate to pyruvate, the input for aerobic (TCA cycle) or anaerobic (glucose fermentation) respiration; Cdc19p [*Saccharomyces cerevisiae*] | LL | | |
| 1272 | 73472 | 0 | 99 | ref|NP_387397.1|ASPARTATE AMINOTRANSFERASE B PROTEIN [*Sinorhizobium meliloti* 1021] | DS | | |
| 1273 | 73526 | 0 | 94 | ref|NP_242877.1|benzyl alcohol dehydrogenase [*Bacillus halodurans* C-125] | DS | | |
| 1274 | 73538 | 0 | 100 | ref|NP_243126.1|hypothetical protein BH2260 [*Bacillus halodurans* C-125] | HS | | |
| 1275 | 73574 | 1.00E−177 | 100 | ref|NP_244591.1|2-keto-3-deoxygluconate kinase [*Bacillus halodurans* C-125] | HS | | |
| 1276 | 73539 | 1.00E−170 | 100 | ref|NP_287481.1|UTP-glucose-1-phosphate uridylyltransferase subunit GalU [*Escherichia coli* O157: H7 EDL933] | CS | | |
| 1277 | 73563 | 3.00E−62 | 90 | ref|NP_743010.1|nucteoside diphosphate kinase [*Pseudomonas putida* KT2440] | CK | | |
| 1278 | 73575 | 1.00E−175 | 100 | ref|NP_792508.1|fructokinase [*Pseudomonas syringae* pv. tomato str. DC3000] | LL | | |
| 1279 | 73565 | 0 | 95 | ref|NP_011707.1|High-affinity histidine permease, also involved in the transport of manganese ions; Hip1p [*Saccharomyces cerevisiae*] | HS | | |
| 1280 | 73531 | 0 | 93 | ref|NP_388151.1|hypothetical protein BSU02690 [*Bacillus subtilis* subsp. *subtilis* str. 168] | DS | | |
| 1281 | 73592 | 0 | 96 | ref|NP_391888.1|6-phosphogluconate dehydrogenase [*Bacillus subtilis* subsp. *subtilis* str. 168] | LN | | |
| 1282 | 74149 | 0 | 100 | ref|NP_794093.1|pyruvate kinase [*Pseudomonas syringae* pv. tomato str. DC3000] | LL | | |
| 1283 | 74174 | 0 | 99 | ref|NP_416880.1|prediected aminotransferase, PLP-dependent [*Escherichia coli* K12] | LL | LN | |
| 1284 | 74151 | 0 | 100 | ref|NP_417148.1|4-aminobutyrate aminotransferase, PLP-dependent [*Escherichia coli* K12] | PP | | |
| 1285 | 74104 | 0 | 100 | ref|ZP_01369074.1|glucose-1-phosphate adenylyltransferase [*Desulfitobacterium hafniense* DCB-2] | CS | HS | |
| 1286 | 74164 | 0 | 89 | ref|NP_242876.1|aldehyde dehydrogenase [*Bacillus halodurans* C-125] | DS | | |
| 1287 | 74129 | 0 | 77 | ref|YP_001185919.1|methylmalonate-semialdehyde dehydrogenase [*Pseudomonas mendocina* ymp] | CK | | |
| 1288 | 72340 | 0 | 97 | ref|NP_195674.2|GGT1; gamma-glutamyltransferase/ glutathione gamma-glutamylcysteinyltransferase [*Arabidopsis thaliana*] | HS | | |
| 1289 | 74155 | 0 | 100 | ref|NP_385556.1|dihydrolipoamide dehydrogenase [*Sinorhizobium meliloti* 1021] | HS | LL | |
| 1290 | 74168 | 0 | 87 | ref|NP_927730.1|glutathione reductase [*Photorhabdus luminescens* subsp. *laumondii* TTO1] | LN | | |
| 1291 | 74133 | 0 | 96 | ref|ZP_00109554.2|COG1249: Pyruvate/2-oxoglutarate dehydrogenase complex, dihydrolipoamide dehydrogenase (E3) component, and related enzymes [*Nostoc punctiforme* PCC 73102] | HS | | |
| 1292 | 74160 | 4.00E−95 | 99 | ref|NP_441445.1|hypothetical protein slr0816 [*Synechocystis* sp. PCC 6803] dbj|BAA18125.1| slr0816 [*Synechocystis* sp. PCC 6803] | LL | | |
| 1293 | 74485 | 0 | 88 | ref|NP_439939.1|hypothetical protein slr1495 [*Synechocystis* sp. PCC 6803] | HS | | |
| 1294 | 74450 | 0 | 100 | ref|NP_442868.1|LIM17 protein [*Synechocystis* sp. PCC 6803] | CK | | |

TABLE 3-continued

| PEP SEQ ID NO | Construct | E-value | % Id | Annotation Description | traits | |
|---|---|---|---|---|---|---|
| 1295 | 74487 | 0 | 90 | ref|NP_357138.2|branched-chain alpha-keto acid dehydrogenase subunit E2 [*Agrobacterium tumefaciens* str. C58] | PP | |
| 1296 | 74406 | 0 | 96 | gb|AAN78639.1|AE016755_139Dihydrolipoamide dehydrogenase [*Escherichia coli* CFT073] | LN | |
| 1297 | 74454 | 1.00E−112 | 91 | ref|NP_927456.1|ribulose-phosphate 3-epimerase (pentose-5-phosphate 3-epimerase) (PPE) (R5P3E) [*Photorhabdus luminescens* subsp. *laumondii* TT01] | LL | |
| 1298 | 11361 | 6.00E−61 | 83 | ref|NP_176291.1|FED A (FERREDOXIN 2); electron carrier/iron ion binding [*Arabidopsis thaliana*] | LN | |
| 1299 | 74431 | 0 | 99 | ref|NP_390796.1|pyruvate kinase [*Bacillus subtilis* subsp. *subtilis* str. 168] | HS | |
| 1300 | 74411 | 0 | 94 | ref|NP_949979.1|fructose-1,6-bisphosphatase [*Rhodopseudomonas palustris* CGA009] | SS | |
| 1301 | 74424 | 1.00E−172 | 92 | ref|NP_386873.1|PROBABLE FRUCTOSE-BISPHOSPHATE ALDOLASE CLASS I PROTEIN [*Sinorhizobium meliloti* 1021] | PP | |
| 1302 | 74525 | 0 | 83 | ref|NP_931210.1|glutamate synthase subunit beta [*Photorhabdus luminescens* subsp. *laumondii* TT01] | HS | |
| 1303 | 74573 | 1.00E−75 | 38 | ref|YP_720246.1|aspartate aminotransferase [*Trichodesmium erythraeum* IMS101] | LN | |
| 1304 | 75827 | 2.00E−44 | 82 | ref|NP_565988.1|unknown protein [*Arabidopsis thaliana*] | LL | |
| 1305 | 77329 | 0 | 98 | ref|NP_566005.1|mitochondrial transcription termination factor-related/mTERF-related [*Arabidopsis thaliana*] | CK | |
| 1306 | 77330 | 0 | 97 | ref|NP_182296.1|auxin-responsive GH3 family protein [*Arabidopsis thaliana*] | PEG | |
| 1307 | 75830 | 6.00E−61 | 100 | ref|NP_186754.1|MUB1 (MEMBRANE-ANCHORED UBIQUITIN-FOLD PROTEIN 1 PRECURSOR) [*Arabidopsis thaliana*] | CK | |
| 1308 | 75832 | 2.00E−42 | 85 | ref|NP_186788.1|VMA10 (VACUOLAR MEMBRANE ATPASE 10) [*Arabidopsis thaliana*] | HS | |
| 1309 | 75836 | 7.00E−41 | 73 | ref|NP_187208.1|unknown protein [*Arabidopsis thaliana*] | CS | |
| 1310 | 77034 | 4.00E−28 | 95 | ref|NP_172702.1|unknown protein [*Arabidopsis thaliana*] | HS | PP |
| 1311 | 76255 | 0 | 92 | ref|NP_566390.1|unknown protein [*Arabidopsis thaliana*] | LL | |
| 1312 | 76542 | 1.00E−77 | 69 | ref|NP_188337.1|unknown protein [*Arabidopsis thaliana*] | CS | LL |
| 1313 | 77511 | 0 | 90 | ref|NP_566642.1|unknown protein [*Arabidopsis thaliana*] | SS | CK |
| 1314 | 76261 | 1.00E−127 | 86 | ref|NP_563649.1|unknown protein [*Arabidopsis thaliana*] | HS | |
| 1315 | 78456 | 0 | 97 | ref|NP_189202.1|MAP1B (METHIONINE AMINOPEPTIDASE 1C); metalloexopeptidase [*Arabidopsis thaliana*] | CK | |
| 1316 | 77041 | 1.00E−125 | 95 | ref|NP_189236.3|plastid-lipid associated protein PAP/fibrillin family protein [*Arabidopsis thaliana*] | LN | |
| 1317 | 76546 | 0 | 90 | gb|AAF79247.1|AC006917_32F10B6.11 [*Arabidopsis thaliana*] | LL | |
| 1318 | 75848 | 9.00E−96 | 100 | ref|NP_189535.1|AIG2 (AVRRPT2-INDUCED GENE 2) [*Arabidopsis thaliana*] | CK | HS |
| 1319 | 77515 | 0 | 80 | ref|NP_189945.1|zinc knuckle (CCHC-type) family protein [*Arabidopsis thaliana*] | HS | |
| 1320 | 76266 | 0 | 82 | emb|CAB83070.1|putative protein [*Arabidopsis thaliana*] | PEG | |
| 1321 | 75852 | 1.00E−26 | 100 | ref|NP_190227.1|unknown protein [*Arabidopsis thaliana*] | HS | |
| 1322 | 76556 | 0 | 86 | ref|NP_190445.2|zinc finger (DHHC type) family protein [*Arabidopsis thaliana*] | PEG | |
| 1323 | 77523 | 1.00E−174 | 96 | ref|NP_001078291.1|unknown protein [*Arabidopsis thaliana*] | HS | |
| 1324 | 75863 | 1.00E−120 | 100 | ref|NP_191267.1|eukaryotic rpb5 RNA polymerase subunit family protein [*Arabidopsis thaliana*] | CS | |
| 1325 | 77052 | 1.00E−171 | 96 | ref|NP_564000.2|unknown protein [*Arabidopsis thaliana*] | PP | |
| 1326 | 75865 | 1.00E−56 | 80 | ref|NP_173123.1|ribosomal protein-related [*Arabidopsis thaliana*] | CS | |
| 1327 | 76551 | 0 | 92 | ref|NP_173144.1|oxidoreductase, 2OG-Fe(II) oxygenase family protein [*Arabidopsis thaliana*] | PEG | |
| 1328 | 76280 | 0 | 86 | ref|NP_564064.1|phytochrome kinase substrate-related [*Arabidopsis thaliana*] | LL | |
| 1329 | 75874 | 7.00E−96 | 100 | ref|NP_193404.1|glycosyltransferase family protein 28 [*Arabidopsis thaliana*] | PP | |
| 1330 | 75879 | 9.00E−62 | 100 | ref|NP_194229.1|ATGP4 (*Arabidopsis thaliana* geranylgeranylated protein) | HS | |
| 1331 | 75880 | 7.00E−59 | 65 | ref|NP_173435.1|unknown protein [*Arabidopsis thaliana*] | HS | |
| 1332 | 77519 | 1.00E−176 | 90 | ref|NP_196118.1|sad1/unc-84 protein-related [*Arabidopsis thaliana*] | HS | CK |
| 1333 | 76745 | 1.00E−111 | 88 | dbj|BAB09403.1|unnamed protein product [*Arabidopsis thaliana*] | HS | |
| 1334 | 76554 | 1.00E−173 | 91 | ref|NP_197092.1|unknown protein [*Arabidopsis thaliana*] | DS | |
| 1335 | 76746 | 3.00E−93 | 75 | ref|NP_568333.1|unknown protein [*Arabidopsis thaliana*] | CK | |

TABLE 3-continued

| PEP SEQ ID NO | Construct | E-value | % Id | Description | traits | | |
|---|---|---|---|---|---|---|---|
| 1336 | 76750 | 1.00E−85 | 93 | ref|NP_197746.1|unknown protein [*Arabidopsis thaliana*] | LL | | |
| 1337 | 76621 | 3.00E−20 | 100 | ref|NP_198912.1|unknown protein [*Arabidopsis thaliana*] | HS | | |
| 1338 | 76623 | 1.00E−23 | 80 | ref|NP_568739.1|unknown protein [*Arabidopsis thaliana*] | LL | | |
| 1339 | 76461 | 1.00E−29 | 78 | gb|AAB86938.1|NOI protein [*Arabidopsis thaliana*] | CS | | |
| 1340 | 76462 | 5.00E−31 | 100 | ref|NP_564277.1|unknown protein [*Arabidopsis thaliana*] | HS | PP | |
| 1341 | 78987 | 1.00E−147 | 81 | ref|NP_201096.1|protein binding/zinc ion binding [*Arabidopsis thaliana*] | HS | | |
| 1342 | 76568 | 0 | 96 | ref|NP_564484.1|unknown protein [*Arabidopsis thaliana*] | HS | | |
| 1343 | 76176 | 0 | 95 | ref|NP_565009.1|glycosyltransferase family 14 protein/core-2/I-branching enzyme family protein [*Arabidopsis thaliana*] | CK | | |
| 1344 | 76177 | 1.00E−97 | 100 | ref|NP_177287.1|unknown protein [*Arabidopsis thaliana*] | LN | | |
| 1345 | 78380 | 0 | 100 | ref|NP_565058.1|eukaryotic translation initiation factor-related [*Arabidopsis thaliana*] | LN | | |
| 1346 | 76629 | 2.00E−46 | 100 | ref|NP_177894.1|unknown protein [*Arabidopsis thaliana*] | HS | | |
| 1347 | 76189 | 2.00E−58 | 100 | gb|AAD15467.2|unknown protein [*Arabidopsis thaliana*] | CS | | |
| 1348 | 76761 | 1.00E−106 | 94 | ref|NP_179133.1|ATARFB1A (ADP-ribosylation factor B1A), GTP binding [*Arabidopsis thaliana*] | LL | | |
| 1349 | 78608 | 0 | 100 | ref|NP_973624.1|ATORC2/ORC2 (ORIGIN RECOGNITION COMPLEX SECOND LARGEST SUBUNIT) [*Arabidopsis thaliana*] | PP | | |
| 1350 | 78115 | 1.00E−153 | 100 | ref|NP_181669.1|embryo-abundant protein-related [*Arabidopsis thaliana*] | CK | DS | |
| 1351 | 74873 | 0 | 100 | ref|NP_416275.1|glutamate dehydrogenase, NADP-specific [*Escherichia coli* K12] | DS | | |
| 1352 | 74826 | 0 | 99 | ref|NP_416651.1|predicted oxidoreductase [*Escherichia coli* K12] | HS | | |
| 1353 | 74850 | 0 | 99 | gb|AAN81953.1|AE016766_41D-erythrose 4-phosphate dehydrogenase [*Escherichia coli* CFT073] | HS | | |
| 1354 | 74887 | 4.00E−76 | 90 | gb|AAD25168.1| aquaporin [*Saccharomyces cerevisiae*] | PEG | | |
| 1355 | 74804 | 0 | 95 | gb|EDN59233.1|chromatin remodeling complex member, RSC [*Saccharomyces cerevisiae* YJM789] | HS | SS | PEG |
| 1356 | 74831 | 1.00E−167 | 81 | gb|EAY97794.1|hypothetical protein OsI_019027 [*Oryza sativa* (indica cultivar-group)] | LN | | |
| 1357 | 74822 | 0 | 69 | emb|CAO62934.1|unnamed protein product [*Vitis vinifera*] | PEG | | |
| 1358 | 74836 | 1.00E−121 | 70 | ref|NP_187378.1|transcriptional activator, putative [*Arabidopsis thaliana*] | LN | | |
| 1359 | 74901 | 3.00E−31 | 61 | ref|NP_001064928.1|Os10g0491900 [*Oryza sativa* (japonica cultivar-group)] | HS | | |
| 1360 | 74974 | 1.00E−112 | 87 | ref|NP_001063296.1|Os09g0443500 [*Oryza sativa* (japonica cultivar-group)] | HS | | |
| 1361 | 74904 | 1.00E−149 | 82 | ref|NP_001063966.1|Os09g0567900 [*Oryza sativa* (japonica cultivar-group)] | HS | | |
| 1362 | 74916 | 8.00E−92 | 76 | gb|EAZ28333.1|hypothetical protein OsJ_011816 [*Oryza sativa* (japonica cultivar-group)] | PEG | | |
| 1363 | 74964 | 1.00E−158 | 95 | ref|NP_417814.1|predicted phosphoribulokinase [*Escherichia coli* K12] | LL | | |
| 1364 | 74918 | 6.00E−82 | 82 | ref|NP_443015.1|hypothetical protein sll1109 [*Synechocystis* sp. PCC 6803] | LN | | |
| 1365 | 74966 | 0 | 99 | ref|NP_442146.1|hypothetical protein sll0209 [*Synechocystis* sp. PCC 6803] | HS | | |
| 1366 | 74979 | 1.00E−142 | 82 | ref|NP_440823.1|hypothetical protein slr1220 [*Synechocystis* sp. PCC 6803] | CK | LL | |
| 1367 | 74934 | 0 | 96 | ref|YP_350971.1|betaine aldehyde dehydrogenase [*Pseudomonas fluorescens* PfO-1] | PEG | | |
| 1368 | 77814 | 0 | 92 | ref|NP_116585.1|F-box protein required for G1/S and G2/M transition, associates with Skp1p and Cdc53p to form a complex, SCFCdc4, which acts as ubiquitin-protein ligase directing ubiquitination of the phosphorylated CDK inhibitor Sic1p; Cdc4p [*Saccharomyces cerevisiae*] | HS | | |
| 1369 | 75387 | 1.00E−148 | 53 | ref|NP_001067713.1|Os11g0293900 [*Oryza sativa* (japonica cultivar-group)] | CK | LL | |
| 1370 | 75328 | 0 | 93 | ref|NP_001050986.1|Os03g0699200 [*Oryza sativa* (japonica cultivar-group)] | PP | | |
| 1371 | 77808 | 0 | 74 | emb|CAO63310.1|unnamed protein product [*Vitis vinifera*] | CS | | |
| 1372 | 75389 | 0 | 69 | ref|NP_001045085.1|Os01g0897100 [*Oryza sativa* (japonica cultivar-group)] | HS | | |
| 1373 | 75318 | 1.00E−126 | 49 | emb|CAO40140.1|unnamed protein product [*Vitis vinifera*] | CK | | |
| 1374 | 75330 | 0 | 70 | emb|CAH66847.1|H0525C06.10 [*Oryza sativa* (indica cultivar-group)] | CS | HS | |
| 1375 | 75342 | 1.00E−75 | 69 | ref|NP_001056004.1|Os05g0509700 [*Oryza sativa* (japonica cultivar-group)] | CK | | |
| 1376 | 75366 | 4.00E−59 | 74 | ref|NP_001063106.1|Os09g0397700 [*Oryza sativa* (japonica cultivar-group)] | HS | | |

TABLE 3-continued

| PEP SEQ ID NO | Construct | E-value | % Id | Description | traits | | |
|---|---|---|---|---|---|---|---|
| 1377 | 75319 | 1.00E−121 | 73 | ref|NP_001050079.1|Os03g0343700 [*Oryza sativa* (japonica cultivar-group)] | HS | | |
| 1378 | 75391 | 0 | 96 | gb|ABU48662.1|G protein alpha subunit [*Sorghum bicolor*] | HS | | |
| 1379 | 75334 | 4.00E−45 | 92 | ref|NP_001049605.1|Os03g0257900 [*Oryza sativa* (japonica cultivar-group)] | HS | | |
| 1380 | 75323 | 0 | 82 | ref|NP_001053032.1|Os04g0466600 [*Oryza sativa* (japonica cultivar-group)] | HS | | |
| 1381 | 75396 | 5.00E−84 | 77 | ref|NP_001068537.1|Os11g0703400 [*Oryza sativa* (japonica cultivar-group)] | PEG | | |
| 1382 | 75401 | 2.00E−72 | 93 | ref|NP_001059557.1|Os07g0454700 [*Oryza sativa* (japonica cultivar-group)] | HS | | |
| 1383 | 75413 | 1.00E−139 | 90 | ref|NP_001050848.1|Os03g0666700 [*Oryza sativa* (japonica cultivar-group)] | LL | | |
| 1384 | 75461 | 0 | 92 | ref|NP_001066463.1|Os12g0236500 [*Oryza sativa* (japonica cultivar-group)] | HS | SS | PP |
| 1385 | 75473 | 6.00E−50 | 71 | ref|NP_001043914.1|Os01g0687600 [*Oryza sativa* (japonica cultivar-group)] | DS | | |
| 1386 | 77817 | 8.00E−26 | 93 | ref|NP_001045143.1|Os01g0908400 [*Oryza sativa* (japonica cultivar-group)] | LL | | |
| 1387 | 75416 | 1.00E−165 | 81 | gb|EAY92384.1|hypothetical protein OsI_013617 [*Oryza sativa* (indica cultivar-group)] | CK | | |
| 1388 | 75464 | 0 | 68 | gb|EAZ22667.1|hypothetical protein OsJ_006150 [*Oryza sativa* (japonica cultivar-group)] | HS | | |
| 1389 | 75441 | 5.00E−46 | 68 | gb|AAA33773.1|PVPR3 | LN | | |
| 1390 | 75454 | 2.00E−82 | 73 | ref|NP_001064989.1|Os10g0502000 [*Oryza saliva* (japonica cultivar-group)] | HS | | |
| 1391 | 75493 | 4.00E−31 | 51 | emb|CAO48835.1|unnamed protein product [*Vitis vinifera*] | HS | PP | PEG |
| 1392 | 75446 | 2.00E−29 | 55 | gb|ABU54835.1|defender against apoptotic death [*Penaeus monodon*] | CS | HS | |
| 1393 | 75495 | 2.00E−86 | 82 | gb|ABG23395.1|2C-methyl-D-erythritol 2,4-cyclodiphosphate synthase [*Stevia rebaudiana*] | SS | | |
| 1394 | 75705 | 1.00E−102 | 71 | ref|NP_001046126.1|Os02g0187100 [*Oryza sativa* (japonica cultivar-group)] | SP | | |
| 1395 | 77818 | 0 | 100 | ref|NP_241861.1|succinate-semialdehyde dehydrogenase [*Bacillus halodurans* C-125] | HS | PEG | |
| 1396 | 75525 | 0 | 99 | ref|NP_415448.1|aspartate aminotransferase, PLP-dependent [*Escherichia coli* K12] | LN | | |
| 1397 | 75549 | 1.00E−115 | 37 | dbj|BAC10067.1|hypothetical protein [*Oryza sativa* Japonica Group] | SS | | |
| 1398 | 75582 | 0 | 68 | emb|CAO16731.1|unnamed protein product [*Vitis vinifera*] | CS | PEG | |
| 1399 | 75535 | 6.00E−53 | 62 | emb|CAO18074.1|unnamed protein product [*Vitis vinifera*] | PEG | | |
| 1400 | 75547 | 1.00E−164 | 74 | emb|CAO42486.1|unnamed protein product [*Vitis vinifera*] | LL | LN | |
| 1401 | 75512 | 1.00E−141 | 63 | emb|CAO40060.1|unnamed protein product [*Vitis vinifera*] | CS | HS | |
| 1402 | 75673 | 1.00E−158 | 55 | ref|NP_001050262.1|Os03g0387900 [*Oryza sativa* (japonica cultivar-group)] | CK | | |
| 1403 | 75626 | 0 | 78 | gb|EAZ07965.1|hypothetical protein OsI_029197 [*Oryza sativa* (indica cultivar-group)] | HS | | |
| 1404 | 75674 | 4.00E−53 | 66 | gb[EAY98259.1|hypothetical protein OsI_019492 [*Oryza sativa* (indica cultivar-group)] | HS | LN | |
| 1405 | 75615 | 2.00E−46 | 59 | gb[EAY75762.1|hypothetical protein OsI_003609 [*Oryza sativa* (indica cultivar-group)] | CK | | |
| 1406 | 75627 | 1.00E−135 | 92 | gb|EAZ15023.1|hypothetical protein OsJ_004848 [*Oryza sativa* (japonica cultivar-group)] | SS | | |
| 1407 | 75628 | 1.00E−103 | 88 | gb|AAQ24835.1|partner of Nob1 [*Sorghum bicolor*] | PEG | | |
| 1408 | 75652 | 1.00E−139 | 85 | gb|EAY93006.1|hypothetical protein OsI_014239 [*Oryza sativa* (indica cultivar-group)] | CK | | |
| 1409 | 75605 | 1.00E−121 | 55 | ref|NP_001047861.1|Os02g0704600 [*Oryza sativa* (japonica cultivar-group)] | CK | HS | LN |
| 1410 | 70228 | 1.00E−83 | 100 | ref|NP_189581.1|AHP2 (HISTIDINE-CONTAINING PHOSPHOTRANSMITTER 2); histidine phosphotransfer kinase/signal transducer [*Arabidopsis thaliana*] | CK | | |
| 1411 | 13302 | 0 | 95 | gb|AAF21885.1|AF101056_1MEI2 [*Arabidopsis thaliana*] | LN | | |
| 1412 | 75610 | 0 | 86 | ref|NP_001054248.1|Os04g0675500 [*Oryza sativa* (japonica cultivar-group)] | CK | | |
| 1413 | 75623 | 0 | 95 | ref|NP_194630.1|AIM1 (ABNORMAL INFLORESCENCE MERISTEM); enoyl-CoA hydratase [*Arabidopsis thaliana*] | HS | | |
| 1414 | 75671 | 0 | 88 | ref|NP_176918.1|leucine-rich repeat family protein [*Arabidopsis thaliana*] | PP | | |
| 1415 | 75695 | 4.00E−78 | 63 | emb|CAO21783.1|unnamed protein product [*Vitis vinifera*] | HS | | |
| 1416 | 75648 | 2.00E−32 | 46 | ref|NP_001054395.1|Os05g0103500 [*Oryza sativa* (japonica cultivar-group)] dbj|BAF16309.1| Os05g0103500 [*Oryza sativa* (japonica cultivar-group)] | SS | | |

TABLE 3-continued

| PEP SEQ ID NO | Construct | E-value | % Id | Description | | traits | |
|---|---|---|---|---|---|---|---|
| | | | | Annotation | | | |
| 1417 | 75672 | 0 | 84 | ref|NP_196925.1|leucine-rich repeat transmembrane protein kinase, putative [*Arabidopsis thaliana*] dbj|BAB08300.1|receptor protein kinase-like protein [*Arabidopsis thaliana*] | PP | | |
| 1418 | 75713 | 1.00E−141 | 43 | emb|CAO21763.1|unnamed protein product [*Vitis vinifera*] | CK | | |
| 1419 | 75714 | 7.00E−35 | 36 | gb|ABK93511.1|unknown [*Populus trichocarpa*] | HS | PP | |
| 1420 | 75762 | 1.00E−171 | 65 | emb|CAN68895.1|hypothetical protein [*Vitis vinifera*] | CK | | |
| 1421 | 77954 | 0 | 94 | ref|NP_172684.1|flavin-containing monooxygenase family protein/FMO family protein [*Arabidopsis thaliana*] | HS | | |
| 1422 | 77955 | 0 | 95 | ref|NP_172680.1|flavin-containing monooxygenase family protein/FMO family protein [*Arabidopsis thaliana*] | HS | | |
| 1423 | 77541 | 7.00E−85 | 100 | gb|ABK28567.1|unknown [*Arabidopsis thaliana*] | LN | | |
| 1424 | 78131 | 0 | 93 | emb|CAB42923.1|putative mitochondrial protein [*Arabidopsis thaliana*] | HS | | |
| 1425 | 78134 | 6.00E−95 | 91 | ref|NP_192051.2|CBL5 (CALCINEURIN B-LIKE PROTEIN 5) [*Arabidopsis thaliana*] | LN | SS | |
| 1426 | 77554 | 1.00E−138 | 75 | tpg|DAA00869.1|TPA_exp: PDR2 ABC transporter [*Arabidopsis thaliana*] | HS | | |
| 1427 | 78992 | 1.00E−170 | 90 | ref|NP_194508.1|calcium-binding EF hand family protein [*Arabidopsis thaliana*] | CK | | |
| 1428 | 77557 | 0 | 84 | ref|NP_196016.1|IQD12 (IQ-domain 12); calmodulin binding [*Arabidopsis thaliana*] | LL | LN | |
| 1429 | 78128 | 0 | 96 | ref|NP_196397.1|flavin-containing monooxygenase family protein/FMO family protein [*Arabidopsis thaliana*] | HS | | |
| 1430 | 77560 | 0 | 94 | ref|NP_568202.1|calcium-binding EF hand family protein [*Arabidopsis thaliana*] | CK | HS | |
| 1431 | 77561 | 0 | 100 | ref|NP_196694.1|monooxygenase family protein [*Arabidopsis thaliana*] | CS | CK | |
| 1432 | 77958 | 1.00E−108 | 74 | ref|NP_197694.1|TET12 (TETRASPANIN12) [*Arabidopsis thaliana*] | PP | | |
| 1433 | 77563 | 0 | 92 | ref|NP_197887.1|integral membrane transporter family protein [*Arabidopsis thaliana*] | CS | CK | |
| 1434 | 78994 | 0 | 91 | ref|NP_001032056.1|F-box family protein [*Arabidopsis thaliana*] | HS | | |
| 1435 | 74508 | 0 | 90 | ref|NP_850439.1|CYP76C1 (cytochrome P450, family 76, subfamily C, polypeptide 1); heme binding/iron ion binding/monooxygenase [*Arabidopsis thaliana*] | CS | HS | |
| 1436 | 70229 | 0 | 100 | ref|NP_194337.1|MEK1 (mitogen-activated protein kinase kinase 1); MAP kinase kinase/kinase [*Arabidopsis thaliana*] | HS | | |
| 1437 | 77959 | 0 | 90 | ref|NP_200937.1|flavin-containing monooxygenase family protein/FMO family protein [*Arabidopsis thaliana*] | HS | | |
| 1438 | 77567 | 0 | 88 | ref|NP_171951.2|integral membrane transporter family protein [*Arabidopsis thaliana*] | HS | LN | |
| 1439 | 11749 | 2.00E−52 | 74 | ref|NP_181812.1|PDF1 (PROTODERMAL FACTOR 1) [*Arabidopsis thaliana*] | CK | | |
| 1440 | 77578 | 0 | 90 | ref|NP_180886.1|integral membrane transporter family protein [*Arabidopsis thaliana*] | HS | | |
| 1441 | 11751 | 1.00E−110 | 90 | ref|NP_180871.1|SAR1 (SYNAPTOBREVIN-RELATED PROTEIN 1) [*Arabidopsis thaliana*] | LN | | |
| 1442 | 77963 | 0 | 86 | ref|NP_566652.1|unknown protein [*Arabidopsis thaliana*] | LN | | |
| 1443 | 77925 | 1.00E−149 | 94 | ref|NP_190985.1|ATFIP37 (*ARABIDOPSIS THALIANA* FKBP12 INTERACTING PROTEIN 37) [*Arabidopsis thaliana*] | HS | PP | |
| 1444 | 77927 | 0 | 90 | ref|NP_564083.1|unknown protein [*Arabidopsis thaliana*] | HS | | |
| 1445 | 77345 | 2.00E−57 | 100 | ref|NP_564113.1|unknown protein [*Arabidopsis thaliana*] | HS | | |
| 1446 | 70230 | 0 | 96 | gb|ABF55662.1|double MYC-tagged mitogen activated protein kinase kinase 2 [synthetic construct] | HS | | |
| 1447 | 77353 | 1.00E−65 | 100 | ref|NP_564301.1|unknown protein [*Arabidopsis thaliana*] | HS | | |
| 1448 | 77354 | 6.00E−42 | 81 | ref|NP_564312.1|unknown protein [*Arabidopsis thaliana*] | LL | | |
| 1449 | 77355 | 1.00E−41 | 90 | ref|NP_564515.1|unknown protein [*Arabidopsis thaliana*] | PP | | |
| 1450 | 77588 | 1.00E−152 | 100 | ref|NP_176415.1|unknown protein [*Arabidopsis thaliana*] | CS | | |
| 1451 | 77591 | 1.00E−164 | 92 | ref|NP_565628.1|unknown protein [*Arabidopsis thaliana*] | LL | | |
| 1452 | 77594 | 1.00E−143 | 72 | emb[CAB46003.1|RING-H2 finger protein RHF1a [*Arabidopsis thaliana*] | DS | | |
| 1453 | 77595 | 1.00E−144 | 71 | ref|NP_567661.1|SWIB complex BAF60b domain-containing protein [*Arabidopsis thaliana*] | LL | | |
| 1454 | 77364 | 5.00E−76 | 84 | ref|NP_194770.1|transcription factor [*Arabidopsis thaliana*] | LN | | |
| 1455 | 78904 | 0 | 100 | emb|CAB87764.1|putative protein [*Arabidopsis thaliana*] | HS | | |
| 1456 | 77937 | 0 | 100 | ref|NP_197133.1|acetolactate synthase small subunit, putative [*Arabidopsis thaliana*] | HS | | |
| 1457 | 77369 | 1.00E−103 | 86 | ref|NP_197494.1|plastid-lipid associated protein PAP-related/fibrillin-related [*Arabidopsis thaliana*] | DS | | |

TABLE 3-continued

| PEP SEQ ID NO | Construct | E-value | % Id | Description | Annotation traits | | |
|---|---|---|---|---|---|---|---|
| 1458 | 77940 | 0 | 89 | ref|NP_568648.1|transducin family protein/WD-40 repeat family protein [*Arabidopsis thaliana*] | CK | HS | |
| 1459 | 78746 | 0 | 100 | ref|NP_201387.2|ankyrin repeat family protein [*Arabidopsis thaliana*] | HS | | |
| 1460 | 77372 | 1.00E−119 | 94 | ref|NP_201515.1|F-box family protein [*Arabidopsis thaliana*] | DS | | |
| 1461 | 78126 | 0 | 86 | gb|AAF24593.1|AC007654_9T19E23.14 [*Arabidopsis thaliana*] | CK | | |
| 1462 | 77951 | 0 | 100 | ref|NP_565803.1|ATEYA (*ARABIDOPSIS THALIANA* EYES ABSENT HOMOLOG); protein tyrosine phosphatase, metal-dependent [*Arabidopsis thaliana*] | LL | PEG | |
| 1463 | 75901 | 0 | 97 | gb|EDN61448.1|F-box protein [*Saccharomyces cerevisiae* YJM789] | CS | | |
| 1464 | 12123 | 1.00E−115 | 86 | ref|NP_196598.1|EMB3010 (EMBRYO DEFECTIVE 3010); structural constituent of ribosome [*Arabidopsis thaliana*] | LN | | |
| 1465 | 75987 | 9.00E−84 | 80 | ref|NP_001105929.1|high affinity nitrate transporter [*Zea mays*] | CS | | |
| 1466 | 75940 | 0 | 100 | ref|NP_842265.1|Phosphoglucose isomerase (PGI) [*Nitrosomonas europaea* ATCC 19718] | HS | PP | |
| 1467 | 75919 | 1.00E−175 | 95 | ref|NP_780153.1|isocitrate dehydrogenase [*Xylella fastidiosa* Temecula1] | HS | LL | SS |
| 1468 | 75908 | 0 | 99 | ref|NP_440384.1|glutamate decarboxylase [*Synechocystis* sp. PCC 6803] | HS | | |
| 1469 | 75920 | 0 | 100 | ref|NP_440189.1|ferredoxin-sulfite reductase [*Synechocystis* sp. PCC 6803] | HS | | |
| 1470 | 75992 | 0 | 94 | ref|YP_001636715.1|pyruvate kinase [*Chloroflexus aurantiacus* J-10-fl] | HS | | |
| 1471 | 75933 | 1.00E−116 | 94 | ref|NP_442343.1|ribose-5-phosphate isomerase A [*Synechocystis* sp. PCC 6803] | HS | PP | |
| 1472 | 77965 | 0 | 92 | ref|NP_181991.1|kelch repeat-containing F-box family protein [*Arabidopsis thaliana*] | DS | | |
| 1473 | 77966 | 0 | 89 | ref|NP_186818.1|unknown protein [*Arabidopsis thaliana*] | LN | | |
| 1474 | 77972 | 0 | 90 | ref|NP_189657.1|unknown protein [*Arabidopsis thaliana*] | HS | | |
| 1475 | 78522 | 0 | 96 | ref|NP_175744.1|unknown protein [*Arabidopsis thaliana*] | SP | | |
| 1476 | 12194 | 3.00E−78 | 91 | ref|NP_176772.1|TPX2 (THIOREDOXIN-DEPENDENT PEROXIDASE 2); antioxidant [*Arabidopsis thaliana*] | CK | | |
| 1477 | 78525 | 0 | 87 | gb|AAC24050.1|Similar to *S. cerevisiae* SIK1P protein | LN | | |
| 1478 | 78527 | 0 | 87 | gb|AAC18814.1|Contains homology to serine/threonine protein kinase gb|X99618 from *Mycobacterium tuberculosis*. | PEG | | |
| 1479 | 78917 | 0 | 95 | ref|NP_177258.3|armadillo/beta-catenin repeat family protein/U-box domain-containing protein [*Arabidopsis thaliana*] | LN | | |
| 1480 | 78920 | 0 | 100 | ref|NP_565146.1|ACR3 (ACT Domain Repeat 3) [*Arabidopsis thaliana*] | PP | | |
| 1481 | 78535 | 0 | 96 | ref|NP_179324.2|pantothenate kinase-related [*Arabidopsis thaliana*] | CK | | |
| 1482 | 78538 | 0 | 98 | ref|NP_180538.1|kelch repeat-containing F-box family protein [*Arabidopsis thaliana*] | HS | | |
| 1483 | 78922 | 0 | 95 | ref|NP_181393.1|F-box family protein [*Arabidopsis thaliana*] | HS | PP | CS |
| 1484 | 77984 | 1.00E−109 | 100 | ref|NP_566068.1|unknown protein [*Arabidopsis thaliana*] | LN | CK | |
| 1485 | 73938 | 0 | 100 | ref|NP_201190.1|AAP4 (amino acid permease 4); amino acid permease [*Arabidopsis thaliana*] | DS | CS | |
| 1486 | 78621 | 0 | 100 | gb|AAD13704.1|hypothetical protein [*Arabidopsis thaliana*] | HS | | |
| 1487 | 77990 | 1.00E−74 | 85 | ref|NP_187290.1|integral membrane family protein [*Arabidopsis thaliana*] | DS | | |
| 1488 | 78386 | 1.00E−132 | 100 | ref|NP_187319.1|peptidyl-prolyl cis-trans isomerase cyclophilin-type family protein [*Arabidopsis thaliana*] | SP | | |
| 1489 | 78001 | 1.00E−70 | 100 | gb|AAF23196.1|AC016795_9unknown protein [*Arabidopsis thaliana*] | HS | | |
| 1490 | 78543 | 0 | 90 | ref|NP_187807.1|S-locus related protein SLR1, putative (S1) [*Arabidopsis thaliana*] | HS | | |
| 1491 | 78002 | 1.00E−136 | 100 | ref|NP_187847.1|unknown protein [*Arabidopsis thaliana*] | LL | | |
| 1492 | 12259 | 1.00E−134 | 100 | gb|AAM67061.1|ribosomal protein S2, putative [*Arabidopsis thaliana*] | LN | | |
| 1493 | 78005 | 3.00E−93 | 96 | ref|NP_172796.1|unknown protein [*Arabidopsis thaliana*] | LL | | |
| 1494 | 78008 | 1.00E−135 | 88 | ref|NP_188459.1|unknown protein [*Arabidopsis thaliana*] | PEG | | |
| 1495 | 78019 | 1.00E−176 | 94 | ref|NP_001031574.1|unknown protein [*Arabidopsis thaliana*] | CK | HS | |
| 1496 | 78020 | 2.00E−74 | 89 | gb|ABK28619.1|unknown [*Arabidopsis thaliana*] | SS | | |
| 1497 | 78023 | 1.00E−121 | 94 | ref|NP_173373.2|unknown protein [*Arabidopsis thaliana*] | DS | | |
| 1498 | 78548 | 1.00E−146 | 86 | ref|NP_564100.1|abscisic acid-responsive HVA22 family protein [*Arabidopsis thaliana*] | LN | PP | |

TABLE 3-continued

| PEP SEQ ID NO | Construct | E-value | % Id | Description | traits | | | |
|---|---|---|---|---|---|---|---|---|
| 1499 | 78161 | 1.00E−103 | 94 | ref|NP_173738.2|caleosin-related family protein [*Arabidopsis thaliana*] | HS | PEG | | |
| 1500 | 78162 | 1.00E−179 | 100 | ref|NP_564270.1|unknown protein [*Arabidopsis thaliana*] | CK | LN | PP | PEG |
| 1501 | 78033 | 1.00E−148 | 90 | ref|NP_564297.1|unknown protein [*Arabidopsis thaliana*] | LL | | | |
| 1502 | 78622 | 0 | 95 | ref|NP_564315.1|unknown protein [*Arabidopsis thaliana*] | CK | | | |
| 1503 | 78036 | 1.00E−67 | 100 | ref|NP_174257.1|unknown protein [*Arabidopsis thaliana*] | DS | | | |
| 1504 | 78043 | 0 | 96 | ref|NP_175182.2|endonuclease/exonuclease/phosphatase family protein [*Arabidopsis thaliana*] | CS | | | |
| 1505 | 78165 | 2.00E−92 | 84 | ref|NP_564788.1|unknown protein [*Arabidopsis thaliana*] | LL | | | |
| 1506 | 78066 | 1.00E−116 | 86 | gb|AAF68106.1|AC010793_1F20B17.2 [*Arabidopsis thaliana*] | PP | | | |
| 1507 | 78069 | 1.00E−124 | 64 | ref|NP_178248.2|pentatricopeptide (PPR) repeat-containing protein [*Arabidopsis thaliana*] | PP | | | |
| 1508 | 78183 | 1.00E−115 | 100 | ref|NP_180390.2|unknown protein [*Arabidopsis thaliana*] | PP | | | |
| 1509 | 78170 | 2.00E−37 | 100 | gb|AAS47599.1|At2g33690 [*Arabidopsis thaliana*] | PP | | | |
| 1510 | 78953 | 1.00E−125 | 88 | ref|NP_565921.1|unknown protein [*Arabidopsis thaliana*] | PP | | | |
| 1511 | 78929 | 0 | 97 | ref|NP_182026.1|CCD7 (more axillary growth 3) [*Arabidopsis thaliana*] | LN | | | |
| 1512 | 78564 | 1.00E−63 | 100 | ref|NP_188669.1|unknown protein [*Arabidopsis thaliana*] | PEG | | | |
| 1513 | 78566 | 0 | 100 | ref|NP_566813.1|unknown protein [*Arabidopsis thaliana*] | HS | | | |
| 1514 | 78591 | 0 | 96 | gb|AAG12668.1|AC027033_3hypothetical protein; 23726-25026 [*Arabidopsis thaliana*] | SS | | | |
| 1515 | 78181 | 3.00E−99 | 100 | ref|NP_563968.1|unknown protein [*Arabidopsis thaliana*] | LN | | | |
| 1516 | 78190 | 2.00E−30 | 71 | ref|NP_564173.1|unknown protein [*Arabidopsis thaliana*] | LL | | | |
| 1517 | 78571 | 0 | 93 | gb|AAF79874.1|AC000348_27T7N9.16 [*Arabidopsis thaliana*] | CK | | | |
| 1518 | 78933 | 1.00E−107 | 84 | gb|AAG51731.1|AC068667_10hypothetical protein; 69078-67980 [*Arabidopsis thaliana*] | LN | | | |
| 1519 | 78573 | 8.00E−73 | 80 | ref|NP_174417.1|LOB domain protein 4/lateral organ boundaries domain protein 4 (LBD4) [*Arabidopsis thaliana*] | CK | | | |
| 1520 | 78632 | 0 | 100 | ref|NP_564507.1|unknown protein [*Arabidopsis thaliana*] | HS | LL | PP | |
| 1521 | 78959 | 0 | 100 | ref|NP_175985.1|pentatricopeptide (PPR) repeat-containing protein [*Arabidopsis thaliana*] | LN | | | |
| 1522 | 78191 | 3.00E−51 | 63 | ref|NP_564986.1|ribosomal protein L12 family protein [*Arabidopsis thaliana*] | HS | LN | | |
| 1523 | 78595 | 1.00E−150 | 92 | gb|AAB70396.1|Similar to ATP-dependent Clp protease (gb|D90915). | HS | PEG | | |
| 1524 | 78646 | 0 | 100 | ref|NP_172453.1|pentatricopeptide (PPR) repeat-containing protein [*Arabidopsis thaliana*] | HS | | | |
| 1525 | 76325 | 1.00E−143 | 82 | gb|EAY88291.1|hypothetical protein OsI_009524 [*Oryza sativa* (indica cultivar-group)] | CS | | | |
| 1526 | 76337 | 6.00E−76 | 87 | ref|NP_001053732.1|Os04g0595200 [*Oryza sativa* (japonica cultivar-group)] | HS | | | |
| 1527 | 76349 | 1.00E−139 | 56 | ref|NP_001066102.1|Os12g0136200 [*Oryza sativa* (japonica cultivar-group)] | PP | | | |
| 1528 | 76302 | 4.00E−75 | 82 | ref|NP_001047161.1|Os02g0564500 [*Oryza sativa* (japonica cultivar-group)] | LL | | | |
| 1529 | 76329 | 0 | 92 | ref|NP_014151.1|RNA polymerase I subunit A.49; Rpa49p [*Saccharomyces cerevisiae*] | PEG | PP | | |
| 1530 | 76353 | 0 | 97 | ref|NP_010937.1|Nucleotide binding alpha subunit of the heterotrimeric G protein that interacts with the receptor Gpr1p, has signaling role in response to nutrients; green fluorescent protein (GFP)-fusion protein localizes to the cell periphery; Gpa2p [*Saccharomyces cerevisiae*] | SS | | | |
| 1531 | 76389 | 0 | 83 | ref|NP_014172.1|Co-chaperone that stimulates the ATPase activity of Ssa1p, required for a late step of ribosome biogenesis, associated with the cytosolic large ribosomal subunit; contains a J-domain: mutation causes defects in fluid-phase endocytosis; Jjj1p [*Saccharomyces cerevisiae*] | CK | | | |
| 1532 | 76378 | 1.00E−119 | 79 | ref|NP_014726.1|Repressor of G1 transcription that binds to SCB binding factor (SBF) at SCB target promoters in early G1; phosphorylation of Whi5p by the CDK, Cln3p/Cdc28p relieves repression and promoter binding by Whi5; periodically expressed in G1; Whi5p [*Saccharomyces cerevisiae*] | HS | PEG | | |
| 1533 | 76392 | 1.00E−59 | 55 | ref|NP_001045725.1|Os02g0122300 [*Oryza sativa* (japonica cultivar-group)] | LL | | | |
| 1534 | 76321 | 0 | 76 | ref|NP_001058970.1|Os07g0166100 [*Oryza sativa* (japonica cultivar-group)] | LN | | | |
| 1535 | 76345 | 0 | 86 | ref|NP_001043794.1|Os01g0665200 [*Oryza sativa* (japonica cultivar-group)] | DS | | | |
| 1536 | 76381 | 0 | 88 | ref|NP_001058289.1|Os06g0663200 [*Oryza sativa* (japonica cultivar-group)] | HS | | | |

TABLE 3-continued

| PEP SEQ ID NO | Construct | E-value | % Id | Description | traits | | | |
|---|---|---|---|---|---|---|---|---|
| 1537 | 76358 | 0 | 76 | ref|NP_001050845.1|Os03g0666200 [*Oryza sativa* (japonica cultivar-group)] | LN | | | |
| 1538 | 12629 | 0 | 97 | ref|NP_194110.2|unknown protein [*Arabidopsis thaliana*] | HS | | | |
| 1539 | 76335 | 1.00E−101 | 66 | ref|NP_001065630.1|Os11g0127700 [*Oryza sativa* (japonica cultivar-group)] | LL | | | |
| 1540 | 76372 | 0 | 82 | gb|EAY93387.1|hypothetical protein OsI_014620 [*Oryza sativa* (indica cultivar-group)] | PP | | | |
| 1541 | 76396 | 0 | 57 | ref|NP_001047355.1|Os02g0602100 [*Oryza sativa* (japonica cultivar-group)] | DS | | | |
| 1542 | 72314 | 0 | 92 | ref|NP_187714.1|steroid hormone receptor/transcription factor [*Arabidopsis thaliana*] | HS | | | |
| 1543 | 77840 | 1.00E−166 | 87 | ref|NP_001066296.1|Os12g0176500 [*Oryza sativa* (japonica cultivar-group)] | CS | CK | | |
| 1544 | 76886 | 1.00E−143 | 85 | dbj|BAC99390.1|putative U3 snoRNP_protein IMP4 [*Oryza sativa* Japonica Group] | PP | PEG | | |
| 1545 | 76803 | 1.00E−163 | 90 | gb|EAY89818.1|hypothetical protein OsI_011051|*Oryza sativa* (indica cultivar-group)] | LL | | | |
| 1546 | 10302 | 0 | 97 | ref|NP_172288.1|ATNRT2: 1 (*Arabidopsis thaliana* high affinity nitrate transporter 2.1); nitrate transporter | HS | | | |
| 1547 | 71107 | 0 | 96 | ref|NP_030560.1|unknown protein [*Arabidopsis thaliana*] | HS | | | |
| 1548 | 76887 | 0 | 86 | ref|NP_001044302.1|Os01g0758400 [*Oryza sativa* (japonica cultivar-group)] | HS | PP | PEG | |
| 1549 | 77842 | 0 | 76 | ref|NP_001047779.1|Os02g0688500 [*Oryza sativa* (japonica cultivar-group)] | LN | | | |
| 1550 | 76805 | 1.00E−165 | 85 | dbj|BAD08085.1|putative ornithine carbamoyltransferase [*Oryza sativa* Japonica Group] | HS | | | |
| 1551 | 76817 | 2.00E−51 | 78 | ref|NP_001063927.1|Os09g0560500 [*Oryza sativa* (japonica cultivar-group)] | HS | | | |
| 1552 | 77843 | 1.00E−68 | 66 | ref|NP_001053206.1|Os04g0497400 [*Oryza sativa* (japonica cultivar-group)] | CS | | | |
| 1553 | 77844 | 0 | 94 | ref|NP_001105843.1|sialyltransferase like protein [*Zea mays*] | PP | | | |
| 1554 | 76890 | 0 | 98 | ref|NP_001044001.1|Os01g0703600 [*Oryza sativa* (japonica cultivar-group)] | HS | | | |
| 1555 | 77839 | 1.00E−155 | 74 | ref|NP_001047096.1|Os02g0550700 [*Oryza sativa* (japonica cultivar-group)] | DS | PP | | |
| 1556 | 76868 | 0 | 83 | ref|NP_001052270.1|Os04g0223000 [*Oryza sativa* (japonica cultivar-group)] | HS | PP | PEG | CS |
| 1557 | 76821 | 1.00E−144 | 80 | ref|NP_001042197.1|Os01g0179200 [*Oryza sativa* (japonica cultivar-group)] | LN | | | |
| 1558 | 76869 | 3.00E−98 | 73 | gb|EAZ29350.1|hypothetical protein OsJ_012833 [*Oryza sativa* (japonica cultivar-group)] | HS | PP | | |
| 1559 | 76881 | 0 | 88 | ref|NP_001049165.1|Os03g0180700 [*Oryza sativa* (japonica cultivar-group)] | PP | | | |
| 1560 | 76894 | 4.00E−33 | 94 | ref|NP_001066312.1|Os12g0180400 [*Oryza sativa* (japonica cultivar-group)] | LN | | | |
| 1561 | 11930 | 0 | 100 | dbj|BAF01049.1|hypothetical protein [*Arabidopsis thaliana*] | SS | | | |
| 1562 | 76848 | 2.00E−80 | 90 | ref|NP_001043542.1|Os01g0610100 [*Oryza sativa* (japonica cultivar-group)] | HS | | | |
| 1563 | 76901 | 2.00E−44 | 85 | gb|EAY92619.1|hypothetical protein OsI_013852 [*Oryza sativa* (indica cultivar-group)] | LN | | | |
| 1564 | 76914 | 1.00E−139 | 78 | gb|EAY79090.1|hypothetical protein OsI_033049 [*Oryza sativa* (indica cultivar-group)] | PP | | | |
| 1565 | 76939 | 1.00E−137 | 71 | gb|EAY98958.1|hypothetical protein OsI_020191|*Oryza sativa* (indica cultivar-group)] | CK | | | |
| 1566 | 76987 | 1.00E−150 | 72 | gb[ABF93996.1|Integral membrane protein DUF6 containing protein, expressed [*Oryza sativa* (japonica cultivar-group)] | CK | | | |
| 1567 | 76904 | 4.00E−58 | 76 | gb|EAZ05371.1|hypothetical protein OsI_026603 [*Oryza sativa* (indica cultivar-group)] | HS | LN | | |
| 1568 | 76941 | 4.00E−26 | 69 | gb|EAY83408.1|hypothetical protein OsI_037367 [*Oryza sativa* (indica cultivar-group)] | HS | | | |
| 1569 | 77113 | 0 | 58 | ref|NP_001064033.1|Os10g0110600 [*Oryza sativa* (japonica cultivar-group)] | PEG | | | |
| 1570 | 77185 | 0 | 80 | dbj|BAD45738.1|thiF family protein-like [*Oryza sativa* Japonica Group] | DS | | | |
| 1571 | 12911 | 0 | 100 | ref|NP_001078414.1|binding [*Arabidopsis thaliana*] | LN | HS | | |
| 1572 | 77127 | 0 | 89 | ref|NP_001062585.1|Os09g0115600 [*Oryza sativa* (japonica cultivar-group)] | HS | PEG | | |
| 1573 | 77177 | 0 | 85 | gb|EAY84671.1|hypothetical protein OsI_005904 [*Oryza sativa* (indica cultivar-group)] | PEG | | | |

TABLE 3-continued

| PEP SEQ ID NO | Construct | E-value | % Id | Annotation Description | traits | |
|---|---|---|---|---|---|---|
| 1574 | 77178 | 0 | 100 | ref|NP_441510.1|bifunctional 3,4-dihydroxy-2-butanone 4-phosphate synthase/GTP cyclohydrolase II protein [*Synechocystis* sp. PCC 6803] | HS | |
| 1575 | 77179 | 2.00E−15 | 60 | gb|EAY74575.1|hypothetical protein OsI_002422 [*Oryza sativa* (indica cultivar-group)] | HS | |
| 1576 | 77191 | 8.00E−61 | 81 | ref|NP_001046564.1|Os02g0282100 [*Oryza sativa* (japonica cultivar-group)] | PP | |
| 1577 | 77145 | 2.00E−48 | 81 | ref|NP_001051289.1|Os03g0751000 [*Oryza sativa* (japonica cultivar-group)] | CK | PP |
| 1578 | 77169 | 1.00E−137 | 87 | gb|AAP50960.1|putative aurora-related kinase [*Oryza sativa* (japonica cultivar-group)] | PP | |
| 1579 | 77110 | 5.00E−30 | 56 | ref|NP_001042508.1|Os01g0233000 [*Oryza sativa* (japonica cultivar-group)] | LL | LN |
| 1580 | 77146 | 0 | 100 | ref|NP_353311.1|bifunctional GMP synthase/glutamine amidotransferase protein [*Agrobacterium tumefaciens* str. C58] | PP | |
| 1581 | 77170 | 7.00E−59 | 82 | emb|CAH67592.1|OSIGBa0092M08.4 [*Oryza sativa* (indica cultivar-group)] | DS | |
| 1582 | 77171 | 0 | 95 | ref|NP_244906.1|potassium/proton antiporter [*Bacillus halodurans* C-125] | HS | |
| 1583 | 77148 | 0 | 100 | ref|NP_661081.1|bifunctional GMP synthase/glutamine amidotransferase protein [*Chlorobium tepidum* TLS] | CK | |
| 1584 | 11933 | 1.00E−149 | 94 | ref|NP_849952.1|GONST1 (GOLGI NUCLEOTIDE SUGAR TRANSPORTER 1) [*Arabidopsis thaliana*] | LN | |
| 1585 | 77160 | 0 | 87 | ref|NP_414589.1|potassium: proton antiporter [*Escherichia coli* K12] | DS | |
| 1586 | 77172 | 0 | 92 | gb|AAC77846.1|mannose-1-P guanosyltransferase [*Escherichia coli*] | LL | |
| 1587 | 77184 | 0 | 92 | ref|NP_243321.1|flagellum-specific ATP synthase [*Bacillus halodurans* C-125] | HS | |
| 1588 | 77225 | 0 | 94 | ref|NP_662474.1|3,4-dihydroxy-2-butanone 4-phosphate synthase/GTP cyclohydrolase II [*Chlorobium tepidum* TLS] | LL | |
| 1589 | 77250 | 0 | 97 | ref|NP_599940.1|detergent sensitivity rescuer dtsR1 [*Corynebacterium glutamicum* ATCC 13032] | LN | |
| 1590 | 77277 | 0 | 95 | ref|NP_001048987.1|Os03g0151800 [*Oryza sativa* (japonica cultivar-group)] ica cultivar-group)] | DS | |
| 1591 | 77245 | 7.00E−45 | 64 | gb|EAY86480.1|hypothetical protein OsI_007713 [*Oryza sativa* (indica cultivar-group)] | SS | |
| 1592 | 77246 | 4.00E−49 | 98 | gb|EAZ21400.1|hypothetical protein OsJ_004883 [*Oryza sativa* (japonica cultivar-group)] | HS | |
| 1593 | 77462 | 0 | 75 | ref|NP_001065111.1|Os10g0525000 [*Oryza sativa* (japonica cultivar-group)] | CK | |
| 1594 | 77414 | 0 | 82 | ref|NP_001046919.1|Os02g0506500 [*Oryza sativa* (japonica cultivar-group)] | HS | |
| 1595 | 77439 | 0 | 82 | ref|NP_001045101.1|Os01g0899500 [*Oryza sativa* (japonica cultivar-group)] | PEG | |
| 1596 | 77463 | 1.00E−106 | 89 | ref|NP_001048776.1|Os03g0119000 [*Oryza sativa* (japonica cultivar-group)] | HS | |
| 1597 | 77488 | 0 | 80 | gb|EAT84267.1|hypothetical protein SNOG_07991 [*Phaeosphaeria nodorum* SN15] | DS | |
| 1598 | 77441 | 5.00E−87 | 82 | ref|NP_001053804.1|Os04g0606900 [*Oryza sativa* (japonica cultivar-group)] | SS | PEG |
| 1599 | 77464 | 1.00E−164 | 90 | gb|EAT77502.1|hypothetical protein SNOG_14959 [*Phaeosphaeria nodorum* SN15] | PEG | |
| 1600 | 77442 | 0 | 83 | ref|NP_013943.1|SR protein kinase (SRPK) involved in regulating proteins involved in mRNA metabolism and cation homeostasis, similar to human SRPK1; Sky1p [*Saccharomyces cerevisiae*] | HS | |
| 1601 | 77419 | 0 | 100 | ref|NP_191311.1|ATSIP2 (*ARABIDOPSIS THALIANA* SEED IMBIBITION 2); hydrolase, hydrolyzing O-glycosyl compounds [*Arabidopsis thaliana*] | CK | HS |
| 1602 | 12444 | 1.00E−146 | 100 | ref|NP_569036.1|GAMMA CAS (GAMMA CARBONIC ANHYDRASE 3); carbonate dehydratase [*Arabidopsis thaliana*] | LN | |
| 1603 | 11791 | 0 | 87 | ref|NP_188619.2|phototropic-responsive NPH3 family protein [*Arabidopsis thaliana*] | LN | |
| 1603 | 12445 | 0 | 87 | ref|NP_188619.2|phototropic-responsive NPH3 family protein [*Arabidopsis thaliana*] | HS | |
| 1604 | 71249 | 0 | 96 | ref|NP_189251.1|CYP71B22 (cytochrome P450, family 71, subfamily B, polypeptide 22); oxygen binding [*Arabidopsis thaliana*] | HS | |
| 1605 | 71237 | 0 | 95 | ref|NP_192740.1|short-chain dehydrogenase/reductase (SDR) family protein [*Arabidopsis thaliana*] | CK | |

TABLE 3-continued

| PEP SEQ ID NO | Construct | E-value | % Id | Annotation Description | traits |
|---|---|---|---|---|---|
| 1606 | 12315 | 1.00E−97 | 100 | ref|NP_567911.1|unknown protein [*Arabidopsis thaliana*] gb|AA.M66960.1| unknown [*Arabidopsis thaliana*] | DS |
| 1606 | 12366 | 1.00E−97 | 100 | ref|NP_567911.1|unknown protein [*Arabidopsis thaliana*] gb|AAM66960.1| unknown [*Arabidopsis thaliana*] | DS |

Trait Enhancement Screens

Enhancement of drought tolerance identified by a soil drought stress tolerance screen: Drought or water deficit conditions impose mainly osmotic stress on plants. Plants are particularly vulnerable to drought during the flowering stage. The drought condition in the screening process disclosed in Example 1B started from the flowering time and was sustained to the end of harvesting. The present invention provides recombinant DNA that can improve the plant survival rate under such sustained drought condition. Exemplary, recombinant DNA for conferring such drought tolerance are identified as such in Table 3. Such recombinant DNA can find particular use in generating transgenic plants that are tolerant to the drought condition imposed during flowering time and in other stages of the plant life cycle. As demonstrated from the model plant screen, in some embodiments of transgenic plants with trait-improving recombinant DNA grown under such sustained drought condition can also have increased total seed weight per plant in addition to the increased survival rate within a transgenic population, providing a higher yield potential as compared to control plants.

PEG-Enhancement of drought tolerance identified by PEG induced osmotic stress tolerance screen: Various drought levels can be artificially induced by using various concentrations of polyethylene glycol (PEG) to produce different osmotic potentials (Pilon-Smits et al., (1995) Plant Physiol. 107:125-130). Several physiological characteristics have been reported as being reliable indications for selection of plants possessing drought tolerance. These characteristics include the rate of seed germination and seedling growth. The traits can be assayed relatively easily by measuring the growth rate of seedling in PEG solution. Thus, a PEG-induced osmotic stress tolerance screen can be a surrogate for drought tolerance screen. As demonstrated from the model plant screen, embodiments of transgenic plants with trait-improving recombinant DNA identified in the PEG-induced osmotic stress tolerance screen can survive better drought conditions providing a higher yield potential as compared to control plants.

SS-Enhancement of drought tolerance identified by high salinity stress tolerance screen: Three different factors are responsible for salt damages: (1) osmotic effects, (2) disturbances in the mineralization process, and (3) toxic effects caused by the salt ions, e.g., inactivation of enzymes. While the first factor of salt stress results in the wilting of the plants that is similar to drought effect, the ionic aspect of salt stress is clearly distinct from drought. The present invention provides genes that help plants maintain biomass, root growth, and/or plant development in high salinity conditions, which are identified as such in Table 3. Since osmotic effect is one of the major components of salt stress, which is common to the drought stress, trait-improving recombinant DNA identified in a high salinity stress tolerance screen can also provide transgenic crops with enhanced drought tolerance. As demonstrated from the model plant screen, embodiments of transgenic plants with trait-improving recombinant DNA identified in a high salinity stress tolerance screen can survive better drought conditions and/or high salinity conditions providing a higher yield potential as compared to control plants.

HS-Enhancement of drought tolerance identified by heat stress tolerance screen: Heat and drought stress often occur simultaneously, limiting plant growth. Heat stress can cause the reduction in photosynthesis rate, inhibition of leaf growth and osmotic potential in plants. Thus, genes identified by the present invention as heat stress tolerance conferring genes can also impart enhanced drought tolerance to plants. As demonstrated from the model plant screen, embodiments of transgenic plants with trait-improving recombinant DNA identified in a heat stress tolerance screen can survive better heat stress conditions and/or drought conditions providing a higher yield potential as compared to control plants.

CK and CS-Enhancement of tolerance to cold stress: Low temperature can immediately result in mechanical constraints, changes in activities of macromolecules, and reduced osmotic potential. In the present invention, two screening conditions, e.g., cold shock tolerance screen (CK) and cold germination tolerance screen (CS), were set up to look for transgenic plants that display visual growth advantage at lower temperature. In cold germination tolerance screen, the transgenic *Arabidopsis* plants were exposed to a constant temperature of 8° C. from planting until day 28 post plating. The trait-improving recombinant DNA identified by such screen can be used for the production of transgenic plant that can germinate more robustly in a cold temperature as compared to the wild type plants. In cold shock tolerance screen, the transgenic plants were first grown under the normal growth temperature of 22° C. until day 8 post plating, and subsequently were placed under 8° C. until day 28 post plating. As demonstrated from the model plant screen, embodiments of transgenic plants with trait-improving recombinant DNA identified in a cold shock stress tolerance screen and/or a cold germination stress tolerance screen can survive better cold conditions providing a higher yield potential as compared to control plants.

Enhancement of tolerance to multiple stresses: Different kinds of stresses often lead to identical or similar reaction in the plants. Genes that are activated or inactivated as a reaction to stress can either act directly in a way the genetic product reduces a specific stress, or they can act indirectly by activating other specific stress genes. By manipulating the activity of such regulatory genes, e.g., multiple stress tolerance genes, the plant can be enabled to react to different kinds of stresses. For examples, PEP SEQ ID NO: 1000 can be used to enhance both salt stress tolerance and heat stress tolerance in plants. Of particular interest, plants transformed with PEP SEQ ID NO: 1495 can resist salt and heat stress, Plants transformed with PEP SEQ ID NO: 1483 can also improve growth in early stage and under heat stress. In addition to these multiple stress tolerance genes, the stress tolerance conferring genes provided by the present invention can be used in combinations to generate transgenic plants that can resist multiple stress conditions.

PP-Enhancement of early plant growth and development: It has been known in the art that to minimize the impact of disease on crop profitability, it is important to start the season with healthy and vigorous plants. This means avoiding seed and seedling diseases, leading to increased nutrient uptake and increased yield potential. Traditionally early planting and applying fertilizer are the methods used for promoting early seedling vigor. In early development stage, plant embryos establish only the basic root-shoot axis, a cotyledon storage organ(s), and stem cell populations, called the root and shoot apical meristems that continuously generate new organs throughout post-embryonic development. "Early growth and development" used herein encompasses the stages of seed imbibition through the early vegetative phase. The present invention provides genes that can be used to produce transgenic plants that have advantages in one or more processes including, but not limited to, germination, seedling vigor, root growth and root morphology under non-stressed conditions. The transgenic plants starting from a more robust seedling are less susceptible to the fungal and bacterial pathogens that attach germinating seeds and seedling. Furthermore, seedlings with advantage in root growth are more resistant to drought stress due to extensive and deeper root architecture. Therefore, it can be recognized by those skilled in the art that genes conferring the growth advantage in early stages to plants can also be used to generate transgenic plants that are more resistant to various stress conditions due to enhanced early plant development. The present invention provides such exemplary recombinant DNA that confer both the stress tolerance and growth advantages to plants, identified as such in Table 3, e.g., PEP SEQ ID NO: 1043 which can improve the plant early growth and development, and impart heat stress tolerance to plants. As demonstrated from the model plant screen, embodiments of transgenic plants with trait-improving recombinant DNA identified in the early plant development screen can grow better under non-stress conditions and/or stress conditions providing a higher yield potential as compared to control plants.

SP-Enhancement of late plant growth and development: "Late growth and development" used herein encompasses the stages of leaf development, flower production, and seed maturity. In certain embodiments, transgenic plants produced using genes that confer growth advantages to plants provided by the present invention, identified as such in Table 3, exhibit at least one phenotypic characteristics including, but not limited to, increased rosette radius, increased rosette dry weight, seed dry weight, silique dry weight, and silique length. On one hand, the rosette radius and rosette dry weight are used as the indexes of photosynthesis capacity, and thereby plant source strength and yield potential of a plant. On the other hand, the seed dry weight, silique dry weight and silique length are used as the indexes for plant sink strength, which are considered as the direct determinants of yield. As demonstrated from the model plant screen, embodiments of transgenic plants with trait-improving recombinant DNA identified in the late development screen can grow better and/or have enhanced development during leaf development and seed maturation providing a higher yield potential as compared to control plants.

LL-Enhancement of tolerance to shade stress identified in a low light screen: The effects of light on plant development are especially prominent at the seedling stage. Under normal light conditions with unobstructed direct light, a plant seedling develops according to a characteristic photomorphogenic pattern, in which plants have open and expanded cotyledons and short hypocotyls. Then the plant's energy is devoted to cotyledon and leaf development while longitudinal extension growth is minimized. Under low light condition where light quality and intensity are reduced by shading, obstruction or high population density, a seedling displays a shade-avoidance pattern, in which the seedling displays a reduced cotyledon expansion, and hypocotyls extension is greatly increased. As the result, a plant under low light condition increases significantly its stem length at the expanse of leaf, seed or fruit and storage organ development, thereby adversely affecting of yield. The present invention provides recombinant DNA that enable plants to have an attenuated shade avoidance response so that the source of plant can be contributed to reproductive growth efficiently, resulting higher yield as compared to the wild type plants. As demonstrated from the model plant screen, embodiments of transgenic plants with trait-improving recombinant DNA identified in a shade stress tolerance screen can have attenuated shade response under shade conditions providing a higher yield potential as compared to control plants. The transgenic plants generated by the present invention can be suitable for a higher density planting, thereby resulting increased yield per unit area.

LN-Enhancement of Tolerance to Low Nitrogen Availability Stress

Nitrogen is a key factor in plant growth and crop yield. The metabolism, growth and development of plants are profoundly affected by their nitrogen supply. Restricted nitrogen supply alters shoot to root ratio, root development, activity of enzymes of primary metabolism and the rate of senescence (death) of older leaves. All field crops have a fundamental dependence on inorganic nitrogenous fertilizer. Since fertilizer is rapidly depleted from most soil types, it must be supplied to growing crops two or three times during the growing season. Enhanced nitrogen use efficiency by plants should enable crops cultivated under low nitrogen availability stress condition resulted from low fertilizer input or poor soil quality.

According to the present invention, transgenic plants generated using the recombinant nucleotides, which confer enhanced nitrogen use efficiency, identified as such in Table 3, exhibit one or more desirable traits including, but not limited to, increased seedling weight, greener leaves, increased number of rosette leaves, increased or decreased root length, One skilled in the art can recognize that the transgenic plants provided by the present invention with enhanced nitrogen use efficiency can also have altered amino acid or protein compositions, increased yield and/or better seed quality. The transgenic plants of the present invention can be productively cultivated under low nitrogen growth conditions, e.g., nitrogen-poor soils and low nitrogen fertilizer inputs, which would cause the growth of wild type plants to cease or to be so diminished as to make the wild type plants practically, useless. The transgenic plants also can be advantageously used to achieve earlier maturing, faster growing, and/or higher yielding crops and/or produce more nutritious foods and animal feedstocks when cultivated using nitrogen non-limiting growth conditions.

Stacked Traits: The present invention also encompasses transgenic plants with stacked engineered traits, e.g., a crop having an enhanced phenotype resulting from expression of a trait-improving recombinant DNA, in combination with herbicide and/or pest resistance traits. For example, genes of the current invention can be stacked with other traits of agronomic interest, such as a trait providing herbicide resistance, for example a RoundUp Ready® trait, or insect resistance, such as using a gene from *Bacillus thuringensis* to provide resistance against lepidopteran, coliopteran, homopteran, hemiopteran, and other insects. Explementary herbicides include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and gluphosinate herbicides. To illustrate that the production of transgenic plants with herbicide resistance is a capability of those of ordinary skill in the art, reference is made to U.S. patent application publications 2003/0106096A1 and 2002/0112260A1 and U.S. Pat. Nos. 5,034,322; 5,776,760, 6,107,549 and 6,376,754, all of which are incorporated herein by reference. To illustrate that the production of transgenic plants with pest resistance is a capability of those of ordinary skill in the art reference is made to U.S. Pat. Nos. 5,250,515 and 5,880,275 which disclose plants expressing an endotoxin of Bacillus thuringiensis bacteria, to U.S. Pat. No. 6,506,599 which discloses control of invertebrates which feed on transgenic plants which express dsRNA for suppressing a target gene in the invertebrate, to U.S. Pat. No. 5,986,175 which discloses the control of viral pests by transgenic plants which express viral replicase, and to U.S. Patent Application Publication 2003/0150017 A1 which discloses control of pests by a transgenic plant which express a dsRNA targeted to suppressing a gene in the pest, all of which are incorporated herein by, reference.

Once one recombinant DNA has been identified as conferring an enhanced trait of interest in transgenic *Arabidopsis* plants, several methods are available for using the sequence of that recombinant DNA and knowledge about the protein it encodes to identify homologs of that sequence from the same plant or different plant species or other organisms, e.g., bacteria and yeast. Thus, in one aspect, the invention provides methods for identifying a homologous gene with a DNA sequence homologous to any of SEQ ID NO: 1 through SEQ ID NO: 803, or a homologous protein with an amino acid sequence homologous to any of SEQ ID NO: 804 to SEQ ID NO: 1606. In another aspect, the present invention provides the protein sequences of identified homologs for a sequence listed as SEQ ID NO: 1607 through SEQ ID NO: 94613. In yet another aspect, the present invention also includes linking or associating one or more desired traits, or gene function with a homolog sequence provided herein.

The trait-improving recombinant DNA and methods of using such trait-improving recombinant DNA for generating transgenic plants with enhanced traits provided by the present invention are not limited to any particular plant species. Indeed, the plants according to the present invention can be of any plant species, e.g., can be monocotyledonous or dicotyledonous. In one embodiment, they are agricultural plants, e.g., plants cultivated by man for purposes of food production or technical, particularly industrial applications. Of particular interest in the present invention are corn and soybean plants. The recombinant DNA constructs optimized for soybean transformation and recombinant DNA constructs optimized for corn transformation are provided by the present invention. Other plants of interest in the present invention for production of transgenic plants having enhanced traits include, without limitation, cotton, canola, wheat, sunflower, sorghum, alfalfa, barley, millet, rice, tobacco, fruit and vegetable crops, and turfgrass.

In certain embodiments, the present invention contemplates to use an orthologous gene in generating the transgenic plants with similarly enhanced traits as the transgenic *Arabidopsis* counterpart. Enhanced physiological properties in transgenic plants of the present invention can be confirmed in responses to stress conditions, for example in assays using imposed stress conditions to detect enhanced responses to drought stress, nitrogen deficiency, cold growing conditions, or alternatively, under naturally present stress conditions, for example under field conditions. Biomass measures can be made on greenhouse or field grown plants and can include such measurements as plant height, stem diameter, root and shoot dry weights, and, for corn plants, ear length and diameter.

Trait data on morphological changes can be collected by visual observation during the process of plant regeneration as well as in regenerated plants transferred to soil. Such trait data includes characteristics such as normal plants, bushy plants, taller plants, thicker stalks, narrow leaves, striped leaves, knotted phenotype, chlorosis, albino, anthocyanin production, or altered tassels, ears or roots. Other enhanced traits can be identified by measurements taken under field conditions, such as days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, trait characteristics of harvested grain can be confirmed, including number of kernels per row on the ear, number of rows of kernels on the ear, kernel abortion, kernel weight, kernel size, kernel density and physical grain quality.

To confirm hybrid yield in transgenic corn plants expressing genes of the present invention, it can be desirable to test hybrids over multiple years at multiple locations in a geographical location where maize is conventionally grown, e.g., in Iowa, Illinois or other locations in the midwestern United States, under "normal" field conditions as well as under stress conditions, e.g., under drought or population density stress.

Transgenic plants can be used to provide plant parts according to the invention for regeneration or tissue culture of cells or tissues containing the constructs described herein. Plant parts for these purposes can include leaves, stems, roots, flowers, tissues, epicotyl, meristems, hypocotyls, cotyledons, pollen, ovaries, cells and protoplasts, or any other portion of the plant which can be used to regenerate additional transgenic plants, cells, protoplasts or tissue culture. Seeds of transgenic plants are provided by this invention can be used to propagate more plants containing the trait-improving recombinant DNA constructs of this invention. These descendants are intended to be included in the scope of this invention if they contain a trait-improving recombinant DNA construct of this invention, whether or not these plants are selfed or crossed with different varieties of plants.

The various aspects of the invention are illustrated by means of the following examples which are in no way intended to limit the full breath and scope of claims.

EXAMPLES

Example 1. Identification of Recombinant DNA that Confers Enhanced Trait to Plants A. Plant Expression Constructs for *Arabidopsis* Transformation Each gene of interest was amplified from a genomic or cDNA library using primers specific to sequences upstream and downstream of the coding region. Transformation vectors were prepared to constitutively transcribe DNA in either sense orientation (for enhanced protein expression) or antisense orientation (for endogenous gene suppression) under the control of an enhanced Cauliflower Mosaic Virus 35S promoter (U.S. Pat. No. 5,359,142) directly or indirectly (Moore, et al., PNAS 95:376-381, 1998; Guyer, e.g., Genetics 149: 633-639, 1998; International patent application NO. PCT/EP98/07577). The transformation vectors also contain a bar gene as a selectable marker for resistance to glufosinate herbicide. The transformation of *Arabidopsis* plants was carried out using the vacuum infiltration method known in the art (Bethtold, et al., Methods Mol. Biol. 82:259-66, 1998). Seeds harvested from the plants, named as T1 seeds, were subsequently grown in a glufosinate-containing selective medium to select for plants which were actually transformed and which produced T2 transgenic seed.

B. Soil Drought Tolerance Screen

This example describes a soil drought tolerance screen to identify *Arabidopsis* plants transformed with recombinant DNA that wilt less rapidly and/or produce higher seed yield when grown in soil under drought conditions T2 seeds were sown in flats filled with Metro/Mix® 200 (The Scotts® Company, USA). Humidity domes were added to each flat and flats were assigned locations and placed in climate-controlled growth chambers. Plants were grown under a temperature regime of 22° C. at day and 20° C. at night, with a photoperiod of 16 hours and average light intensity of 170 µmol/m$^2$/s. After the first true leaves appeared, humidity domes were removed. The plants were sprayed with glufosinate herbicide and put back in the growth chamber for 3 additional days. Flats were watered for 1 hour the week following the herbicide treatment, Watering was continued every seven days until the flower bud primordia became apparent, at which time plants were watered for the last time.

To identify drought tolerant plants, plants were evaluated for wilting response and seed yield. Beginning ten days after the last watering, plants were examined daily until 4 plants/line had wilted. In the next six days, plants were monitored for wilting response. Five drought scores were assigned according to the visual inspection of the phenotypes: 1 for healthy, 2 for dark green, 3 for wilting, 4 severe wilting, and 5 for dead. A score of 3 or higher was considered as wilted.

At the end of this assay, seed yield measured as seed weight per plant under the drought condition was characterized for the transgenic plants and their controls and analyzed as a quantitative response according to example 1M.

Two approaches were used for statistical analysis on the wilting response. First, the risk score was analyzed for wilting phenotype and treated as a qualitative response according to the example 1L. Alternatively, the survival analysis was carried out in which the proportions of wilted and non-wilted transgenic and control plants were compared over each of the six days under scoring and an overall log rank test was performed to compare the two survival curves using S-PLUS statistical software (S-PLUS 6, Guide to statistics, Insightful, Seattle, Wash., USA). A list of recombinant DNA constructs which improve drought tolerance in transgenic plants is illustrated in Table 4

TABLE 4

| PEP SEQ ID | Construct ID | Orientation | Drought score Delta mean | P-value | Seed yield Delta mean | P-value |
|---|---|---|---|---|---|---|
| 989 | 10471 | SENSE | 0.069 | 0.285 | 0.368 | 0.021 |
| 1224 | 12204 | SENSE | 0.152 | 0.018 | −0.519 | 0.041 |
| 1606 | 12315 | ANTI-SENSE | 0.067 | 0.029 | −0.126 | 0.210 |
| 1257 | 12354 | ANTI-SENSE | 0.118 | 0.334 | −0.663 | 0.001 |

TABLE 4-continued

| PEP SEQ ID | Construct ID | Orientation | Drought score Delta mean | P-value | Seed yield Delta mean | P-value |
|---|---|---|---|---|---|---|
| 1606 | 12366 | SENSE | −0.105 | 0.735 | −0.072 | 0.403 |
| 852 | 13623 | SENSE | 0.309 | 0.005 | −0.202 | 0.403 |
| 812 | 13638 | ANTI-SENSE | 0.195 | 0.047 | −0.930 | 0.045 |
| 838 | 13811 | SENSE | −0.037 | 0.729 | −0.578 | 0.032 |
| 860 | 14248 | SENSE | 0.205 | 0.013 | −0.484 | 0.066 |
| 885 | 14910 | ANTI-SENSE | −0.087 | 0.305 | −0.261 | 0.220 |
| 891 | 14932 | ANTI-SENSE | 0.222 | 0.011 | −0.019 | 0.957 |
| 879 | 15111 | ANTI-SENSE | 0.082 | 0.241 | 0.624 | 0.019 |
| 893 | 15964 | ANTI-SENSE | 0.003 | 0.023 | −0.396 | 0.028 |
| 899 | 15986 | ANTI-SENSE | 0.199 | 0.128 | −0.022 | 0.773 |
| 900 | 15987 | ANTI-SENSE | 0.223 | 0.416 | −0.156 | 0.576 |
| 904 | 15995 | ANTI-SENSE | 0.281 | 0.196 | −0.362 | 0.157 |
| 945 | 16614 | SENSE | 0.136 | 0.001 | 0.059 | 0.440 |
| 959 | 19162 | SENSE | 0.007 | 0.887 | 0.348 | 0.019 |
| 999 | 19423 | SENSE | 0.222 | 0.024 | −0.460 | 0.069 |
| 1003 | 19425 | SENSE | 0.002 | 0.556 | 0.099 | 0.019 |
| 1081 | 71667 | SENSE | 0.064 | 0.790 | −0.314 | 0.101 |
| 1164 | 72717 | SENSE | 0.043 | 0.031 | −0.173 | 0.221 |
| 1165 | 72718 | SENSE | 0.119 | 0.037 | −0.272 | 0.359 |
| 1167 | 72779 | SENSE | −0.026 | 0.491 | 0.395 | 0.006 |
| 1168 | 72791 | SENSE | 0.284 | 0.046 | −1.867 | 0.009 |
| 1272 | 73472 | SENSE | 0.159 | 0.036 | −0.223 | 0.511 |
| 1273 | 73526 | SENSE | −0.219 | 0.141 | −0.250 | 0.145 |
| 1280 | 73531 | SENSE | −0.277 | 0.022 | −0.097 | 0.740 |
| 1132 | 73738 | SENSE | 0.386 | 0.022 | −1.025 | 0.018 |
| 1485 | 73938 | SENSE | 0.117 | 0.050 | 0.309 | 0.052 |
| 1069 | 74060 | SENSE | 0.116 | 0.016 | 0.195 | 0.200 |
| 1286 | 74164 | SENSE | 0.602 | 0.031 | 0.287 | 0.137 |
| 1157 | 74257 | SENSE | −0.139 | 0.622 | −0.366 | 0.059 |
| 1146 | 74269 | SENSE | 0.176 | 0.057 | −0.101 | 0.273 |
| 1229 | 74376 | SENSE | −0.023 | 0.583 | −0.747 | 0.053 |
| 1234 | 74668 | SENSE | 0.112 | 0.018 | −0.931 | 0.063 |
| 1351 | 74873 | SENSE | 0.256 | 0.006 | 0.110 | 0.627 |
| 1385 | 75473 | SENSE | 0.108 | 0.031 | −1.469 | 0.015 |
| 1535 | 76345 | SENSE | −0.024 | 0.476 | 0.318 | 0.017 |
| 1541 | 76396 | SENSE | −0.146 | 0.218 | −0.137 | 0.518 |
| 1245 | 76724 | SENSE | 0.514 | 0.029 | −1.467 | 0.021 |
| 1581 | 77170 | SENSE | 0.258 | 0.020 | −0.436 | 0.026 |
| 1570 | 77185 | SENSE | 0.180 | 0.037 | −0.602 | 0.086 |
| 1457 | 77369 | SENSE | −0.117 | 0.194 | −0.324 | 0.096 |
| 1460 | 77372 | SENSE | 0.623 | 0.017 | −0.108 | 0.028 |
| 1597 | 77488 | SENSE | 0.001 | 0.973 | −0.252 | 0.075 |
| 1452 | 77594 | SENSE | 0.200 | 0.032 | −0.334 | 0.096 |
| 1555 | 77839 | SENSE | 0.082 | 0.021 | −0.242 | 0.298 |
| 1472 | 77965 | SENSE | 0.643 | 0.003 | −0.157 | 0.456 |
| 1487 | 77990 | SENSE | 0.246 | 0.022 | −0.303 | 0.458 |
| 1497 | 78023 | SENSE | 0.364 | 0.004 | −3.072 | 0.012 |
| 1503 | 78036 | SENSE | 0.651 | 0.010 | −0.959 | 0.095 |
| 1350 | 78115 | SENSE | 0.412 | 0.027 | −0.024 | 0.880 |
| 1061 | 78321 | SENSE | 0.254 | 0.044 | −0.941 | 0.014 |
| 1230 | 74377 | SENSE | 0.327 | 0.028 | / | / |
| 1007 | 70419 | SENSE | 0.007 | 0.047 | −0.599 | 0.012 |

Transgenic plants comprising recombinant DNA expressing protein as set forth in SEQ ID NO: 1047, 1073, 1105, 1106, 1137, 1190, 1216, 1334, 1585, or 1590 showed enhanced drought tolerance by the second criteria as illustrated in Example 1L.

C. Heat Stress Tolerance Screen

Under high temperatures, *Arabidopsis* seedlings become chlorotic and root growth is inhibited. This example sets forth the heat stress tolerance screen to identify *Arabidopsis* plants transformed with the gene of interest that are more resistant to heat stress based on primarily their seedling weight and root growth under high temperature.

T2 seeds were plated on ½×MS salts, 1/% phytagel, with 10 µg/ml BASTA (7 per plate with 2 control seeds; 9 seeds total per plate). Plates were placed at 4° C. for 3 days to stratify seeds. Plates were then incubated at room temperature for 3 hours and then held vertically for 11 additional days at temperature of 34° C. at day and 20° C. at night.

Photoperiod was 16 h. Average light intensity was ~140 µmol/m²/s. After 14 days of growth, plants were scored for glufosinate resistance, root length, final growth stage, visual color, and seedling fresh weight. A photograph of the whole plate was taken on day 14.

The seedling weight and root length were analyzed as quantitative responses according to example 1M. The final grow stage at day 14 was scored as success if 50% of the plants had reached 3 rosette leaves and size of leaves are greater than 1 mm (Boyes, et al., (2001) The Plant Cell 13, 1499-1510). The growth stage data was analyzed as a qualitative response according to example 1L. A list of recombinant DNA constructs that improve heat tolerance in transgenic plants illustrated in Table 5.

TABLE 5

| PEP SEQ ID | Construct ID | Orientation | Root length day 14 Delta mean | Root length day 14 P-value | Growth stage at day 14 Risk score mean | Growth stage at day 14 P-value | Seedling weight Delta mean | Seedling weight P-value |
|---|---|---|---|---|---|---|---|---|
| 848 | 10706 | ANTI-SENSE | −0.080 | 0.577 | −0.056 | 0.371 | 0.423 | 0.023 |
| 822 | 13231 | SENSE | 0.267 | 0.037 | 1.633 | 0.010 | 1.492 | 0.000 |
| 834 | 13914 | SENSE | 0.283 | 0.096 | 0.466 | 0.230 | 1.497 | 0.016 |
| 827 | 15606 | SENSE | −0.107 | 0.459 | 0.032 | 0.889 | 0.658 | 0.049 |
| 876 | 15623 | SENSE | 0.265 | 0.088 | 0.150 | 0.371 | 1.064 | 0.012 |
| 906 | 16213 | SENSE | 0.020 | 0.917 | 0.048 | 0.579 | 0.681 | 0.013 |
| 943 | 16603 | SENSE | 0.171 | 0.300 | 0.783 | 0.192 | 0.994 | 0.035 |
| 941 | 16617 | SENSE | 0.327 | 0.055 | 0.179 | 0.312 | 1.362 | 0.007 |
| 934 | 17502 | SENSE | −0.082 | 0.580 | 0.989 | 0.402 | 0.519 | 0.026 |
| 935 | 17503 | SENSE | 0.149 | 0.052 | 0.015 | 0.828 | 0.697 | 0.003 |
| 897 | 18203 | SENSE | −0.078 | 0.640 | −0.221 | 0.300 | 0.728 | 0.041 |
| 984 | 18238 | SENSE | 0.031 | 0.845 | −0.077 | 0.457 | 0.820 | 0.047 |
| 853 | 18302 | SENSE | 0.315 | 0.074 | 1.298 | 0.269 | 1.271 | 0.011 |
| 851 | 18304 | SENSE | 0.346 | 0.222 | 0.374 | 0.381 | 1.111 | 0.043 |
| 952 | 18307 | SENSE | 0.394 | 0.183 | 1.676 | 0.287 | 1.088 | 0.013 |
| 997 | 18352 | SENSE | 0.239 | 0.055 | 0.036 | 0.894 | 0.924 | 0.019 |
| 968 | 18421 | SENSE | 0.069 | 0.684 | 0.941 | 0.213 | 0.918 | 0.012 |
| 969 | 18422 | SENSE | 0.236 | 0.243 | / | / | 1.127 | 0.033 |
| 958 | 18441 | SENSE | 0.175 | 0.289 | 0.832 | 0.497 | 0.907 | 0.043 |
| 979 | 18535 | SENSE | −0.007 | 0.946 | −0.100 | 0.496 | 0.853 | 0.015 |
| 911 | 19041 | ANTI-SENSE | 0.160 | 0.012 | −0.063 | 0.102 | 0.932 | 0.003 |
| 913 | 19042 | ANTI-SENSE | 0.068 | 0.618 | 0.024 | 0.725 | 0.767 | 0.030 |
| 950 | 19154 | SENSE | 0.109 | 0.609 | 1.642 | 0.111 | 0.877 | 0.041 |
| 951 | 19155 | SENSE | 0.244 | 0.237 | 0.085 | 0.434 | 0.905 | 0.018 |
| 976 | 19237 | SENSE | 0.094 | 0.296 | 0.492 | 0.362 | 0.663 | 0.047 |
| 971 | 19244 | SENSE | 0.473 | 0.104 | 1.137 | 0.259 | 1.324 | 0.020 |
| 1011 | 19320 | SENSE | −0.265 | 0.212 | / | / | 0.329 | 0.043 |
| 967 | 19534 | SENSE | 0.064 | 0.756 | 0.920 | 0.315 | 0.630 | 0.039 |
| 964 | 19535 | SENSE | 0.190 | 0.158 | −0.025 | 0.750 | 0.961 | 0.013 |
| 970 | 19539 | SENSE | 0.083 | 0.373 | 0.521 | 0.256 | 0.466 | 0.031 |
| 973 | 19545 | SENSE | −0.083 | 0.150 | / | / | 0.609 | 0.038 |
| 1002 | 19616 | SENSE | 0.288 | 0.094 | −0.068 | 0.565 | 0.689 | 0.003 |
| 1027 | 19702 | SENSE | −0.017 | 0.915 | −0.033 | 0.798 | 0.783 | 0.043 |
| 1032 | 19755 | SENSE | 0.312 | 0.129 | 1.611 | 0.029 | 1.285 | 0.008 |
| 1029 | 19775 | SENSE | 0.126 | 0.362 | 2.093 | 0.172 | 0.775 | 0.004 |
| 1042 | 19786 | SENSE | 0.226 | 0.265 | 0.580 | 0.372 | 1.083 | 0.040 |
| 1039 | 19825 | SENSE | 0.053 | 0.662 | −0.055 | 0.759 | 0.872 | 0.022 |
| 1037 | 19893 | SENSE | −0.089 | 0.168 | −0.130 | 0.249 | 0.787 | 0.023 |
| 1040 | 19919 | SENSE | −0.214 | 0.277 | 0.198 | 0.435 | 0.814 | 0.050 |
| 1041 | 19979 | SENSE | 0.202 | 0.080 | 0.738 | 0.222 | 1.048 | 0.047 |
| 1031 | 19982 | SENSE | 0.241 | 0.111 | 0.933 | 0.263 | 1.127 | 0.025 |
| 1038 | 19983 | SENSE | 0.238 | 0.218 | 0.834 | 0.367 | 0.876 | 0.002 |
| 1028 | 19985 | SENSE | 0.216 | 0.057 | 0.414 | 0.306 | 0.860 | 0.001 |
| 1036 | 19987 | SENSE | 0.052 | 0.568 | 0.584 | 0.442 | 0.834 | 0.028 |
| 925 | 70102 | SENSE | −0.013 | 0.877 | −0.115 | 0.461 | 0.779 | 0.012 |
| 926 | 70106 | SENSE | 0.038 | 0.667 | −0.016 | 0.692 | 0.869 | 0.028 |
| 927 | 70113 | SENSE | 0.163 | 0.289 | 1.098 | 0.222 | 1.005 | 0.012 |
| 930 | 70128 | SENSE | 0.025 | 0.785 | 0.347 | 0.302 | 0.920 | 0.016 |
| 931 | 70130 | SENSE | 0.238 | 0.111 | −0.041 | 0.447 | 1.275 | 0.000 |
| 884 | 70216 | SENSE | 0.012 | 0.932 | 0.165 | 0.689 | 0.708 | 0.007 |
| 1436 | 70229 | SENSE | −0.074 | 0.761 | 0.228 | 0.259 | 0.494 | 0.034 |
| 1446 | 70230 | SENSE | 0.068 | 0.053 | −0.005 | 0.908 | 0.554 | 0.008 |
| 804 | 70244 | SENSE | 0.019 | 0.894 | / | / | 0.468 | 0.036 |
| 845 | 70253 | SENSE | −0.080 | 0.196 | −0.189 | 0.436 | 1.085 | 0.004 |
| 856 | 70412 | SENSE | 0.151 | 0.185 | 1.151 | 0.374 | 0.757 | 0.023 |
| 975 | 70425 | SENSE | −0.050 | 0.712 | / | / | 0.815 | 0.011 |
| 1014 | 70433 | SENSE | 0.196 | 0.242 | / | / | 0.737 | 0.021 |
| 1015 | 70434 | SENSE | 0.136 | 0.106 | / | / | 0.814 | 0.000 |
| 1017 | 70436 | SENSE | 0.199 | 0.196 | 0.008 | 0.918 | 0.969 | 0.017 |
| 1019 | 70439 | SENSE | 0.188 | 0.127 | 0.846 | 0.311 | 1.250 | 0.012 |
| 1001 | 70603 | SENSE | 0.430 | 0.028 | 0.301 | 0.281 | 1.573 | 0.004 |
| 1052 | 70635 | SENSE | −0.199 | 0.020 | −0.185 | 0.234 | 0.381 | 0.045 |
| 1054 | 70638 | SENSE | 0.004 | 0.943 | −0.069 | 0.197 | 0.788 | 0.036 |
| 1055 | 70642 | SENSE | −0.100 | 0.336 | −0.278 | 0.049 | 0.385 | 0.003 |
| 1056 | 70643 | SENSE | 0.160 | 0.445 | −0.001 | 0.423 | 0.947 | 0.021 |
| 1078 | 70682 | SENSE | −0.203 | 0.156 | −0.278 | 0.057 | 0.404 | 0.024 |
| 920 | 70706 | ANTI-SENSE | −0.354 | 0.066 | −0.162 | 0.208 | 0.517 | 0.010 |
| 843 | 70716 | ANTI-SENSE | 0.098 | 0.240 | 0.013 | 0.970 | 0.858 | 0.001 |
| 837 | 70721 | ANTI-SENSE | 0.254 | 0.047 | 0.346 | 0.068 | 0.859 | 0.008 |
| 859 | 70723 | ANTI-SENSE | 0.180 | 0.341 | 1.110 | 0.253 | 0.990 | 0.016 |
| 1026 | 70741 | SENSE | 0.046 | 0.693 | 0.469 | 0.265 | 0.927 | 0.008 |
| 1093 | 70810 | SENSE | 0.168 | 0.053 | −0.072 | 0.275 | 0.897 | 0.013 |
| 1008 | 70827 | SENSE | −0.106 | 0.519 | 0.878 | 0.158 | 0.646 | 0.045 |
| 880 | 70832 | SENSE | 0.224 | 0.152 | 1.398 | 0.318 | 0.912 | 0.008 |
| 1263 | 70850 | SENSE | −0.002 | 0.986 | 0.312 | 0.296 | 0.887 | 0.035 |
| 1043 | 70903 | SENSE | 0.065 | 0.734 | 0.623 | 0.454 | 0.776 | 0.002 |
| 1046 | 70936 | SENSE | 0.393 | 0.063 | 0.889 | 0.020 | 1.352 | 0.008 |
| 1044 | 70970 | SENSE | 0.335 | 0.231 | 0.520 | 0.444 | 1.429 | 0.031 |
| 1547 | 71107 | SENSE | −0.257 | 0.177 | 0.027 | 0.685 | 0.528 | 0.045 |
| 1126 | 71125 | SENSE | 0.236 | 0.091 | 1.197 | 0.112 | 1.308 | 0.029 |
| 921 | 71145 | SENSE | 0.093 | 0.534 | / | / | 0.535 | 0.030 |
| 1604 | 71249 | SENSE | −0.150 | 0.372 | 0.056 | 0.768 | 0.866 | 0.035 |
| 977 | 71303 | SENSE | 0.103 | 0.377 | / | / | 0.858 | 0.025 |
| 1067 | 71318 | SENSE | 0.100 | 0.212 | 0.498 | 0.324 | 1.190 | 0.004 |
| 957 | 71531 | SENSE | −0.087 | 0.696 | −0.085 | 0.224 | 0.718 | 0.048 |
| 1006 | 71536 | SENSE | 0.021 | 0.831 | −0.134 | 0.725 | 0.922 | 0.047 |
| 1057 | 71564 | SENSE | 0.305 | 0.153 | 0.033 | 0.795 | 0.793 | 0.013 |
| 1091 | 71629 | SENSE | 0.084 | 0.202 | 1.387 | 0.044 | 1.001 | 0.019 |
| 1083 | 71696 | SENSE | 0.222 | 0.304 | 0.850 | 0.296 | 0.885 | 0.043 |
| 965 | 71719 | SENSE | 0.113 | 0.605 | 0.088 | 0.689 | 0.989 | 0.046 |
| 1063 | 71808 | SENSE | 0.158 | 0.043 | 0.589 | 0.172 | 0.956 | 0.011 |
| 1143 | 72110 | SENSE | −0.031 | 0.607 | −0.114 | 0.565 | 0.329 | 0.041 |
| 1142 | 72124 | SENSE | −0.211 | 0.255 | −0.100 | 0.411 | 0.568 | 0.049 |
| 1542 | 72314 | SENSE | 0.127 | 0.271 | 1.270 | 0.224 | 0.943 | 0.002 |
| 1288 | 72340 | SENSE | 0.089 | 0.574 | 0.893 | 0.258 | 0.864 | 0.032 |
| 910 | 72427 | ANTI-SENSE | −0.024 | 0.813 | −0.019 | 0.423 | 0.658 | 0.006 |
| 1084 | 72475 | SENSE | −0.129 | 0.192 | 0.024 | 0.896 | 0.697 | 0.013 |
| 1087 | 72476 | SENSE | −0.136 | 0.228 | −0.168 | 0.134 | 0.729 | 0.007 |
| 1098 | 72537 | SENSE | −0.124 | 0.341 | −0.254 | 0.011 | 0.352 | 0.025 |
| 1169 | 72732 | SENSE | 0.191 | 0.165 | 0.090 | 0.641 | 0.700 | 0.020 |
| 933 | 72748 | SENSE | 0.125 | 0.369 | 1.403 | 0.138 | 1.010 | 0.000 |
| 1158 | 72749 | SENSE | 0.053 | 0.642 | 0.625 | 0.250 | 0.881 | 0.027 |
| 1161 | 72775 | SENSE | −0.050 | 0.707 | −0.157 | 0.333 | 0.861 | 0.049 |
| 1163 | 72776 | SENSE | 0.091 | 0.358 | 1.128 | 0.239 | 1.244 | 0.006 |
| 1168 | 72791 | SENSE | −0.095 | 0.672 | / | / | 0.763 | 0.034 |
| 1199 | 72909 | SENSE | 0.254 | 0.065 | −0.033 | 0.348 | 0.818 | 0.048 |
| 1203 | 72958 | SENSE | −0.030 | 0.774 | −0.052 | 0.358 | 0.840 | 0.034 |
| 1195 | 73018 | SENSE | 0.053 | 0.638 | 0.057 | 0.895 | 0.856 | 0.042 |
| 1202 | 73036 | SENSE | −0.005 | 0.957 | 0.282 | 0.386 | 0.783 | 0.007 |
| 1188 | 73074 | SENSE | −0.146 | 0.202 | −0.081 | 0.319 | 0.667 | 0.028 |
| 1193 | 73077 | SENSE | 0.028 | 0.770 | 0.495 | 0.459 | 0.944 | 0.001 |
| 1196 | 73112 | SENSE | 0.021 | 0.846 | / | / | 0.886 | 0.019 |
| 1180 | 73117 | SENSE | −0.060 | 0.537 | 0.124 | 0.759 | 0.996 | 0.018 |
| 1178 | 73128 | SENSE | 0.149 | 0.075 | 0.248 | 0.598 | 0.934 | 0.038 |
| 1191 | 73147 | SENSE | 0.689 | 0.024 | 0.822 | 0.293 | 1.572 | 0.010 |
| 1174 | 73174 | SENSE | 0.305 | 0.027 | 0.532 | 0.480 | 0.779 | 0.046 |
| 1194 | 73183 | SENSE | 0.113 | 0.617 | 0.180 | 0.573 | 0.969 | 0.004 |

TABLE 5-continued

| PEP SEQ ID | Construct ID | Orientation | Root length day 14 Delta mean | P-value | Growth stage at day 14 Risk score mean | P-value | Seedling weight Delta mean | P-value |
|---|---|---|---|---|---|---|---|---|
| 1175 | 73186 | SENSE | 0.101 | 0.628 | 1.230 | 0.130 | 0.714 | 0.014 |
| 1131 | 73248 | SENSE | 0.289 | 0.103 | 0.455 | 0.104 | 1.034 | 0.018 |
| 1118 | 73353 | SENSE | 0.108 | 0.504 | 0.947 | 0.218 | 0.864 | 0.024 |
| 1264 | 73429 | SENSE | 0.305 | 0.067 | 0.867 | 0.057 | 1.190 | 0.003 |
| 1267 | 73455 | SENSE | 0.133 | 0.064 | 0.299 | 0.033 | 0.559 | 0.018 |
| 1262 | 73474 | SENSE | −0.433 | 0.105 | −0.164 | 0.092 | 0.433 | 0.024 |
| 1274 | 73538 | SENSE | −0.003 | 0.962 | 0.241 | 0.339 | 0.741 | 0.003 |
| 1279 | 73565 | SENSE | 0.182 | 0.325 | 0.650 | 0.525 | 1.279 | 0.021 |
| 1275 | 73574 | SENSE | 0.067 | 0.721 | 0.363 | 0.636 | 0.758 | 0.043 |
| 996 | 73607 | SENSE | −0.070 | 0.388 | 0.401 | 0.673 | 0.636 | 0.024 |
| 896 | 73706 | SENSE | 0.064 | 0.744 | 0.294 | 0.124 | 1.082 | 0.012 |
| 1144 | 73916 | SENSE | −0.004 | 0.980 | 0.495 | 0.265 | 1.060 | 0.024 |
| 903 | 73977 | SENSE | 0.230 | 0.065 | 0.096 | 0.370 | 0.596 | 0.014 |
| 1182 | 73990 | SENSE | 0.133 | 0.346 | / | / | 1.140 | 0.025 |
| 1291 | 74133 | SENSE | −0.170 | 0.121 | −0.027 | 0.729 | 0.635 | 0.013 |
| 1289 | 74155 | SENSE | 0.211 | 0.210 | 0.458 | 0.420 | 0.945 | 0.017 |
| 1148 | 74273 | SENSE | 0.050 | 0.756 | 0.694 | 0.467 | 0.837 | 0.026 |
| 1149 | 74280 | SENSE | 0.117 | 0.251 | −0.103 | 0.271 | 0.785 | 0.002 |
| 1151 | 74287 | SENSE | 0.044 | 0.644 | −0.148 | 0.027 | 0.928 | 0.000 |
| 1206 | 74333 | SENSE | 0.144 | 0.114 | 0.144 | 0.521 | 0.748 | 0.023 |
| 1299 | 74431 | SENSE | 0.002 | 0.987 | −0.190 | 0.282 | 0.674 | 0.012 |
| 1293 | 74485 | SENSE | −0.007 | 0.920 | −0.098 | 0.273 | 0.923 | 0.007 |
| 1435 | 74508 | SENSE | 0.409 | 0.104 | 0.221 | 0.394 | 0.825 | 0.001 |
| 1302 | 74525 | SENSE | 0.110 | 0.261 | 0.080 | 0.467 | 0.967 | 0.004 |
| 1227 | 74612 | SENSE | −0.319 | 0.220 | −0.591 | 0.063 | 0.563 | 0.017 |
| 1233 | 74623 | SENSE | −0.167 | 0.140 | / | / | 0.521 | 0.000 |
| 1237 | 74638 | SENSE | 0.036 | 0.848 | 0.418 | 0.399 | 0.828 | 0.049 |
| 1209 | 74737 | SENSE | 0.004 | 0.959 | 0.877 | 0.414 | 0.972 | 0.008 |
| 1212 | 74747 | SENSE | 0.254 | 0.074 | 1.728 | 0.157 | 0.961 | 0.027 |
| 1355 | 74804 | SENSE | 0.615 | 0.095 | 1.179 | 0.314 | 1.685 | 0.019 |
| 1352 | 74826 | SENSE | −0.062 | 0.460 | / | / | 0.655 | 0.009 |
| 1353 | 74850 | SENSE | 0.167 | 0.271 | 0.910 | 0.352 | 0.950 | 0.040 |
| 1359 | 74901 | SENSE | 0.117 | 0.664 | 0.258 | 0.353 | 0.897 | 0.041 |
| 1361 | 74904 | SENSE | −0.030 | 0.814 | −0.030 | 0.791 | 0.866 | 0.016 |
| 1365 | 74966 | SENSE | −0.041 | 0.658 | 0.114 | 0.770 | 0.671 | 0.015 |
| 1360 | 74974 | SENSE | 0.142 | 0.382 | −0.117 | 0.116 | 0.793 | 0.047 |
| 1130 | 75206 | SENSE | 0.044 | 0.484 | −0.217 | 0.093 | 0.671 | 0.010 |
| 1254 | 75281 | SENSE | 0.207 | 0.020 | 0.046 | 0.795 | 0.827 | 0.009 |
| 1380 | 75323 | SENSE | 0.041 | 0.684 | −0.202 | 0.074 | 0.473 | 0.006 |
| 1374 | 75330 | SENSE | −0.005 | 0.712 | −0.001 | 0.998 | 0.753 | 0.001 |
| 1379 | 75334 | SENSE | 0.427 | 0.107 | 0.050 | 0.599 | 1.040 | 0.004 |
| 1376 | 75366 | SENSE | −0.013 | 0.883 | / | / | 0.832 | 0.008 |
| 1372 | 75389 | SENSE | 0.304 | 0.038 | 0.181 | 0.377 | 0.923 | 0.005 |
| 1378 | 75391 | SENSE | 0.076 | 0.434 | 0.109 | 0.434 | 0.918 | 0.020 |
| 1382 | 75401 | SENSE | 0.020 | 0.910 | / | / | 0.854 | 0.005 |
| 1392 | 75446 | SENSE | 0.431 | 0.174 | 0.231 | 0.269 | 0.967 | 0.021 |
| 1390 | 75454 | SENSE | 0.055 | 0.585 | 0.288 | 0.378 | 0.770 | 0.022 |
| 1384 | 75461 | SENSE | 0.032 | 0.434 | 0.020 | 0.936 | 0.931 | 0.034 |
| 1388 | 75464 | SENSE | −0.117 | 0.288 | 0.085 | 0.651 | 0.717 | 0.014 |
| 1391 | 75493 | SENSE | 0.007 | 0.891 | −0.021 | 0.738 | 1.080 | 0.013 |
| 1401 | 75512 | SENSE | 0.089 | 0.652 | 0.860 | 0.279 | 0.806 | 0.032 |
| 1409 | 75605 | SENSE | 0.153 | 0.136 | −0.016 | 0.721 | 1.065 | 0.014 |
| 1413 | 75623 | SENSE | 0.151 | 0.321 | −0.030 | 0.721 | 0.751 | 0.000 |
| 1403 | 75626 | SENSE | 0.364 | 0.001 | 0.619 | 0.475 | 1.127 | 0.014 |
| 1404 | 75674 | SENSE | −0.028 | 0.530 | / | / | 0.893 | 0.021 |
| 1415 | 75695 | SENSE | 0.132 | 0.300 | 0.072 | 0.640 | 1.108 | 0.010 |
| 1419 | 75714 | SENSE | −0.049 | 0.701 | 0.169 | 0.588 | 0.853 | 0.025 |
| 1308 | 75832 | SENSE | 0.043 | 0.229 | −0.006 | 0.944 | 0.691 | 0.013 |
| 1318 | 75848 | SENSE | 0.117 | 0.485 | 0.324 | 0.491 | 0.953 | 0.035 |
| 1321 | 75852 | SENSE | −0.218 | 0.196 | −0.017 | 0.895 | 0.468 | 0.039 |
| 1330 | 75879 | SENSE | 0.126 | 0.570 | −0.007 | 0.937 | 0.863 | 0.042 |
| 1331 | 75880 | SENSE | 0.198 | 0.119 | 0.331 | 0.249 | 0.842 | 0.011 |
| 1468 | 75908 | SENSE | 0.057 | 0.686 | −0.064 | 0.759 | 0.916 | 0.015 |
| 1467 | 75919 | SENSE | −0.063 | 0.562 | −0.056 | 0.586 | 0.640 | 0.036 |
| 1471 | 75933 | SENSE | 0.126 | 0.099 | 0.431 | 0.238 | 0.905 | 0.004 |
| 1466 | 75940 | SENSE | 0.147 | 0.429 | 1.316 | 0.343 | 0.872 | 0.049 |
| 830 | 75958 | SENSE | 0.036 | 0.515 | −0.144 | 0.102 | 1.048 | 0.001 |
| 826 | 75969 | SENSE | 0.164 | 0.316 | 0.002 | 0.990 | 0.696 | 0.025 |
| 1470 | 75992 | SENSE | 0.103 | 0.525 | 0.101 | 0.605 | 0.853 | 0.005 |
| 832 | 76002 | SENSE | −0.016 | 0.860 | 0.032 | 0.815 | 0.868 | 0.023 |
| 892 | 76017 | SENSE | 0.107 | 0.424 | 0.359 | 0.280 | 0.978 | 0.022 |
| 843 | 76039 | SENSE | 0.226 | 0.299 | 0.039 | 0.656 | 1.072 | 0.008 |
| 914 | 76053 | SENSE | 0.293 | 0.058 | 0.940 | 0.022 | 1.142 | 0.004 |
| 1215 | 76212 | SENSE | 0.006 | 0.732 | 0.105 | 0.829 | 0.808 | 0.012 |
| 1258 | 76236 | SENSE | −0.062 | 0.693 | 0.941 | 0.453 | 0.871 | 0.031 |
| 1314 | 76261 | SENSE | 0.065 | 0.490 | 0.699 | 0.344 | 0.901 | 0.039 |
| 1526 | 76337 | SENSE | 0.121 | 0.439 | 0.454 | 0.199 | 0.924 | 0.010 |
| 1532 | 76378 | SENSE | −0.077 | 0.500 | 0.220 | 0.481 | 0.829 | 0.034 |
| 1536 | 76381 | SENSE | −0.011 | 0.954 | 0.712 | 0.324 | 0.806 | 0.004 |
| 1340 | 76462 | SENSE | −0.019 | 0.861 | −0.004 | 0.959 | 0.716 | 0.038 |
| 1221 | 76530 | SENSE | 0.260 | 0.305 | −0.053 | 0.801 | 1.088 | 0.004 |
| 1342 | 76568 | SENSE | −0.008 | 0.748 | 0.059 | 0.677 | 0.610 | 0.016 |
| 1337 | 76621 | SENSE | −0.098 | 0.270 | 0.001 | 0.995 | 0.622 | 0.006 |
| 1346 | 76629 | SENSE | 0.154 | 0.603 | 0.550 | 0.509 | 0.982 | 0.049 |
| 1222 | 76716 | SENSE | −0.007 | 0.945 | / | / | 0.792 | 0.024 |
| 1333 | 76745 | SENSE | 0.044 | 0.738 | −0.010 | 0.927 | 0.695 | 0.021 |
| 1550 | 76805 | SENSE | 0.369 | 0.113 | 0.041 | 0.519 | 0.950 | 0.018 |
| 1551 | 76817 | SENSE | 0.126 | 0.645 | 0.007 | 0.790 | 0.861 | 0.024 |
| 1562 | 76848 | SENSE | −0.080 | 0.699 | −0.112 | 0.185 | 0.804 | 0.006 |
| 1558 | 76869 | SENSE | 0.345 | 0.160 | 1.378 | 0.130 | 1.205 | 0.030 |
| 1548 | 76887 | SENSE | 0.319 | 0.292 | / | / | 0.812 | 0.036 |
| 1554 | 76890 | SENSE | 0.226 | 0.007 | −0.032 | 0.300 | 0.659 | 0.027 |
| 1567 | 76904 | SENSE | 0.178 | 0.268 | / | / | 0.917 | 0.004 |
| 1310 | 77034 | SENSE | −0.033 | 0.843 | 0.479 | 0.109 | 0.953 | 0.001 |
| 1572 | 77127 | SENSE | 0.061 | 0.705 | −0.026 | 0.704 | 0.769 | 0.043 |
| 1582 | 77171 | SENSE | 0.054 | 0.519 | −0.133 | 0.026 | 0.698 | 0.000 |
| 1575 | 77179 | SENSE | 0.146 | 0.392 | 0.039 | 0.517 | 1.072 | 0.010 |
| 1587 | 77184 | SENSE | 0.025 | 0.782 | / | / | 0.979 | 0.012 |
| 1153 | 77304 | SENSE | 0.174 | 0.297 | 1.437 | 0.321 | 1.010 | 0.047 |
| 1223 | 77328 | SENSE | 0.116 | 0.253 | / | / | 1.016 | 0.024 |
| 1445 | 77345 | SENSE | 0.222 | 0.005 | 0.215 | 0.529 | 0.833 | 0.010 |
| 1447 | 77353 | SENSE | 0.124 | 0.184 | 0.043 | 0.702 | 0.830 | 0.007 |
| 1594 | 77414 | SENSE | 0.115 | 0.229 | / | / | 0.965 | 0.002 |
| 1601 | 77419 | SENSE | 0.309 | 0.205 | 0.762 | 0.199 | 1.166 | 0.013 |
| 1600 | 77442 | SENSE | 0.112 | 0.214 | 0.779 | 0.067 | 0.825 | 0.019 |
| 1596 | 77463 | SENSE | −0.027 | 0.865 | −0.143 | 0.007 | 0.674 | 0.045 |
| 1319 | 77515 | SENSE | 0.242 | 0.195 | 0.088 | 0.276 | 1.411 | 0.014 |
| 1332 | 77519 | SENSE | 0.667 | 0.043 | 1.824 | 0.173 | 1.142 | 0.021 |
| 1323 | 77523 | SENSE | 0.190 | 0.379 | 1.044 | 0.059 | 1.312 | 0.014 |
| 1426 | 77554 | SENSE | 0.358 | 0.257 | 1.126 | 0.108 | 0.949 | 0.034 |
| 1430 | 77560 | SENSE | −0.047 | 0.095 | 0.786 | 0.380 | 0.583 | 0.012 |
| 1438 | 77567 | SENSE | −0.178 | 0.220 | / | / | 0.437 | 0.020 |
| 1440 | 77578 | SENSE | 0.213 | 0.119 | 1.089 | 0.387 | 0.931 | 0.013 |
| 1270 | 77726 | SENSE | −0.060 | 0.338 | / | / | 0.990 | 0.007 |
| 1368 | 77814 | SENSE | −0.032 | 0.843 | −0.117 | 0.556 | 0.885 | 0.025 |
| 1395 | 77818 | SENSE | 0.094 | 0.220 | 0.336 | 0.311 | 0.879 | 0.004 |
| 1248 | 77903 | SENSE | 0.014 | 0.798 | 0.015 | 0.874 | 0.675 | 0.017 |
| 1443 | 77925 | SENSE | 0.005 | 0.960 | 0.085 | 0.472 | 0.911 | 0.001 |
| 1444 | 77927 | SENSE | −0.167 | 0.181 | −0.114 | 0.590 | 0.638 | 0.002 |
| 1456 | 77937 | SENSE | 0.231 | 0.151 | 0.815 | 0.062 | 1.368 | 0.001 |
| 1458 | 77940 | SENSE | −0.017 | 0.859 | / | / | 0.706 | 0.004 |
| 1421 | 77954 | SENSE | 0.326 | 0.111 | 1.981 | 0.208 | 1.139 | 0.014 |
| 1422 | 77955 | SENSE | −0.078 | 0.652 | −0.062 | 0.104 | 0.529 | 0.029 |
| 1437 | 77959 | SENSE | 0.345 | 0.055 | 0.505 | 0.429 | 1.016 | 0.038 |
| 1474 | 77972 | SENSE | 0.101 | 0.481 | 0.125 | 0.606 | 1.030 | 0.008 |
| 1495 | 78019 | SENSE | 0.030 | 0.321 | 0.320 | 0.481 | 0.931 | 0.034 |
| 1429 | 78128 | SENSE | 0.341 | 0.052 | 0.016 | 0.764 | 1.007 | 0.021 |
| 1424 | 78131 | SENSE | 0.042 | 0.138 | 0.018 | 0.829 | 0.687 | 0.005 |
| 1499 | 78161 | SENSE | 0.156 | 0.202 | 0.170 | 0.418 | 0.898 | 0.000 |
| 1522 | 78191 | SENSE | 0.177 | 0.313 | 0.964 | 0.512 | 0.854 | 0.020 |
| 1061 | 78321 | SENSE | 0.196 | 0.245 | −0.007 | 0.773 | 1.013 | 0.048 |
| 1110 | 78325 | SENSE | 0.046 | 0.345 | 0.123 | 0.609 | 0.643 | 0.007 |
| 1232 | 78364 | SENSE | 0.054 | 0.615 | 0.837 | 0.243 | 0.475 | 0.038 |
| 1239 | 78365 | SENSE | 0.083 | 0.384 | / | / | 1.153 | 0.030 |
| 948 | 78370 | SENSE | 0.016 | 0.854 | 0.310 | 0.456 | 0.826 | 0.036 |
| 1000 | 78373 | SENSE | 0.018 | 0.774 | 0.595 | 0.263 | 1.046 | 0.009 |
| 1482 | 78538 | SENSE | 0.123 | 0.332 | 1.152 | 0.342 | 0.921 | 0.024 |
| 1490 | 78543 | SENSE | −0.003 | 0.979 | / | / | 0.934 | 0.008 |
| 1513 | 78566 | SENSE | 0.131 | 0.429 | 0.479 | 0.532 | 0.820 | 0.017 |
| 1523 | 78595 | SENSE | 0.182 | 0.295 | 0.005 | 0.938 | 0.766 | 0.014 |
| 1520 | 78632 | SENSE | 0.394 | 0.058 | 0.997 | 0.314 | 1.143 | 0.017 |
| 1459 | 78746 | SENSE | 0.192 | 0.256 | 1.115 | 0.346 | 1.025 | 0.013 |
| 1455 | 78904 | SENSE | 0.150 | 0.222 | 0.970 | 0.084 | 0.946 | 0.030 |
| 1483 | 78922 | SENSE | 0.162 | 0.307 | 2.327 | 0.024 | 1.156 | 0.007 |

TABLE 5-continued

| PEP SEQ ID | Construct ID | Orientation | Root length day 14 Delta mean | Root length day 14 P-value | Growth stage at day 14 Risk score mean | Growth stage at day 14 P-value | Seedling weight Delta mean | Seedling weight P-value |
|---|---|---|---|---|---|---|---|---|
| 1341 | 78987 | SENSE | −0.034 | 0.626 | 0.689 | 0.246 | 0.828 | 0.005 |
| 1434 | 78994 | SENSE | 0.282 | 0.000 | 2.384 | 0.009 | 0.940 | 0.002 |

Transgenic plants comprising recombinant DNA expressing protein as set forth in SEQ ID NO: 823, 825, 873, 886, 912, 916, 919, 928, 937, 942, 972, 986, 995, 1074, 1107, 1134, 1136, 1145, 1157, 1173, 1220, 1228, 1242, 1243, 1285, 1377, 1469, 1486, 1489, 1524, 1538, 1546, 1556, 1568, 1571, 1574, 1592, or 1603 showed enhanced heat stress tolerance by the second criteria as illustrated in Example 1L and 1M.

D. Salt Stress Tolerance Screen

This example sets forth the high salinity stress screen to identify *Arabidopsis* plants transformed with the gene of interest that are tolerant to high levels of salt based on their rate of development, root growth and chlorophyll accumulation under high salt conditions.

T2 seeds were plated on glufosinate selection plates containing 90 mM NaCl and grown under standard light and temperature conditions. All seedlings used in the experiment were grown at a temperature of 22° C. at day and 20° C. at night, a 16-hour photoperiod, an average light intensity of approximately 120 umol/m². On day 11, plants were measured for primary root length. After 3 more days of growth (day 14), plants were scored for transgenic status, primary root length, growth stage, visual color, and the seedlings were pooled for fresh weight measurement. A photograph of the whole plate was also taken on day 14.

The seedling weight and root length were analyzed as quantitative responses according to example 1M. The final growth stage at day 14 was scored as success if 50% of the plants reached 3 rosette leaves and size of leaves are greater than 1 mm (Boyes, D. C., et al., (2001), The Plant Cell 13, 1499/1510). The growth stage data was analyzed as a qualitative response according to example 1L. A list of recombinant DNA constructs that improve high salinity tolerance in transgenic plants illustrated in Table 6.

Transgenic plants comprising recombinant DNA expressing protein as set forth in SEQ ID NO: 821, 834, 890, 919, 946, 961, 997, 1013, 1080, 1101, 1147, 1160, 1181, 1197, 1200, 1220, 1237, 1248, 1264, 1300, 1313, 1355, 1393, 1397, 1406, 1467, 1496, 1514, 1530 or 1561 showed enhanced salt stress tolerance by the second criteria as illustrated in Example 1L and 1M.

E. Polyethylene Glycol (PEG) Induced Osmotic Stress Tolerance Screen

There are numerous factors, which can influence seed germination and subsequent seedling growth, one being the availability of water. Genes, which can directly affect the success rate of germination and early seedling growth, are usable agronomic traits for improving the germination and growth of crop plants under drought stress. In this assay, PEG was used to induce osmotic stress on germinating transgenic lines of *Arabidopsis thaliana* seeds in order to screen for osmotically resistant seed lines.

T2 seeds were plated on BASTA selection plates containing 3% PEG and grown under standard light and temperature conditions. Seeds were plated on each plate containing 3% PEG, ½×MS salts, 1% phytagel, and 10 µg/ml glufosinate. Plates were placed at 4° C. for 3 days to stratify seeds. On day 11, plants were measured for primary root length. After 3 more days of growth, e.g., at day 14, plants were scored for transgenic status, primary root length, growth stage, visual color, and the seedlings were pooled for fresh weight measurement. A photograph of the whole plate was taken on day 14.

Seedling weight and root length were analyzed as quantitative responses according to example 1M. The final growth stage at day 14 was scored as success or failure based on whether the plants reached 3 rosette leaves and size of leaves are greater than 1 mm. The growth stage data was analyzed as a qualitative response according to example 1L. A list of recombinant DNA constructs that improve osmotic stress tolerance in transgenic plants illustrated in Table 7.

TABLE 6

| PEP SEQ ID | Orientation | Root length at day 11 Delta mean | Root length at day 11 P-value | Root length at day 14 Delta mean | Root length at day 14 P-value | Growth stage at day 14 Delta mean | Growth stage at day 14 P-value | Seedling weight at day 14 Delta mean | Seedling weight at day 14 P-value |
|---|---|---|---|---|---|---|---|---|---|
| 932 | ANTI-SENSE | 0.305 | 0.019 | 0.360 | 0.093 | 0.583 | 0.428 | 0.835 | 0.050 |
| 955 | SENSE | 0.028 | 0.336 | 0.085 | 0.047 | −0.038 | 0.866 | 0.060 | 0.036 |
| 1093 | SENSE | 0.097 | 0.010 | 0.046 | 0.488 | 0.605 | 0.172 | 0.166 | 0.016 |
| 1139 | SENSE | 0.187 | 0.011 | 0.092 | 0.015 | −0.038 | 0.923 | −0.002 | 0.987 |
| 1183 | SENSE | 0.251 | 0.118 | 0.328 | 0.016 | / | / | 0.404 | 0.148 |
| 1106 | SENSE | 0.093 | 0.383 | 0.169 | 0.030 | 0.370 | 0.357 | 0.215 | 0.053 |
| 896 | SENSE | 0.349 | 0.000 | 0.270 | 0.069 | 0.057 | 0.797 | 0.421 | 0.047 |
| 1416 | SENSE | 0.062 | 0.516 | 0.081 | 0.035 | −0.159 | 0.513 | −0.076 | 0.670 |
| 1591 | SENSE | 0.034 | 0.592 | 0.051 | 0.003 | 0.255 | 0.623 | 0.194 | 0.052 |
| 1598 | SENSE | 0.227 | 0.004 | 0.224 | 0.002 | 1.203 | 0.316 | 0.281 | 0.258 |
| 1425 | SENSE | −0.107 | 0.327 | −0.028 | 0.724 | −0.215 | 0.425 | 0.384 | 0.029 |
| 1384 | SENSE | −0.088 | 0.195 | −0.0557 | 0.531 | −0.009 | 0.980 | 0.101 | 0.025 |

TABLE 7

| PEP Seq ID | Orientation | Root length at day 11 | | Root length at day 14 | | Growth stage at day 14 | | Seedling weight at day 14 | |
|---|---|---|---|---|---|---|---|---|---|
| | | Delta mean | P-value | Delta mean | P-value | Delta mean | P-value | Delta mean | P-value |
| 1019 | SENSE | 0.003 | 0.883 | 0.068 | 0.022 | 0.113 | 0.715 | −0.139 | 0.215 |
| 960 | SENSE | 0.139 | 0.278 | 0.065 | 0.010 | 2.264 | 0.322 | 0.197 | 0.256 |
| 1241 | SENSE | 0.061 | 0.690 | 0.096 | 0.044 | 1.011 | 0.569 | −0.095 | 0.666 |
| 1119 | SENSE | 0.002 | 0.978 | −0.107 | 0.415 | 2.760 | 0.156 | 0.156 | 0.000 |
| 1391 | SENSE | 0.602 | 0.012 | 0.533 | 0.044 | / | / | 0.866 | 0.005 |
| 1322 | SENSE | 0.062 | 0.041 | 0.150 | 0.020 | / | / | −0.132 | 0.218 |
| 1238 | SENSE | 0.099 | 0.387 | 0.118 | 0.004 | 2.693 | 0.175 | −0.187 | 0.005 |
| 1556 | SENSE | 0.153 | 0.116 | 0.271 | 0.081 | / | / | 0.331 | 0.019 |
| 1153 | SENSE | 0.063 | 0.067 | 0.081 | 0.134 | 2.964 | 0.104 | 0.280 | 0.020 |
| 1218 | SENSE | 0.040 | 0.067 | −0.089 | 0.170 | 0.492 | 0.806 | 0.198 | 0.030 |
| 1599 | SENSE | 0.099 | 0.168 | 0.103 | 0.237 | / | / | 0.292 | 0.031 |
| 1478 | SENSE | 0.216 | 0.115 | 0.197 | 0.041 | 1.353 | 0.414 | 0.234 | 0.388 |
| 1512 | SENSE | −0.167 | 0.071 | −0.230 | 0.141 | −1.066 | 0.090 | 0.085 | 0.012 |
| 1572 | SENSE | 0.447 | 0.005 | 0.352 | 0.025 | 4 | / | 0.656 | 0.046 |

Transgenic plants comprising recombinant DNA expressing protein as set forth in SEQ ID NO: 832, 833, 871, 874, 931, 974, 985, 997, 1021, 1024, 1031, 1043, 1053, 1059, 1060, 1091, 1111, 1115, 1118, 1120, 1124, 1127, 1128, 1159, 1172, 1179, 1185, 1197, 1213, 1226, 1230, 1244, 1253, 1265, 1306, 1320, 1327, 1354, 1355, 1357, 1362, 1367, 1381, 1395, 1398, 1399, 1407, 1462, 1494, 1499, 1500, 1523, 1529, 1532, 1544, 1548, 1569, 1572, 1573, 1595, or 1598 showed enhanced PEG osmotic stress tolerance by the second criteria as illustrated in Example 1L and 1M.

F. Cold Shock Tolerance Screen

This example set forth a screen to identify *Arabidopsis* plants transformed with the genes of interest that are more tolerant to cold stress subjected during day 8 to day 28 after seed planting. During these crucial early stages, seedling growth and leaf area increase were measured to assess tolerance when *Arabidopsis* seedlings were exposed to low temperatures. Using this screen, genetic alterations can be found that enable plants to germinate and grow better than wild type plants under sudden exposure to low temperatures.

Eleven seedlings from T2 seeds of each transgenic line plus one control line were plated together on a plate containing ½× Gamborg Salts with 0.8 Phytagel™, 1% Phytagel, and 0.3% Sucrose, Plates were then oriented horizontally and stratified for three days at 4° C. At day three, plates were removed from stratification and exposed to standard conditions (16 hr photoperiod, 22° C. at day and 20° C. at night) until day 8. At day eight, plates were removed from standard conditions and exposed to cold shock conditions (4 hr photoperiod, 8° C. at both day and night) until the final day of the assay, e.g., day 28. Rosette areas were measured at day 8 and day 28, which were analyzed as quantitative responses according to example 1M. A list of recombinant nucleotides that improve cold shock stress tolerance in plants illustrated in Table 8.

TABLE 8

| PEP SEQ ID | Construct ID | Orientation | Rosette area at day 8 | | Rosette area at day 28 Risk score | | Rosette area difference | |
|---|---|---|---|---|---|---|---|---|
| | | | Delta mean | P-value | mean | P-value | Delta mean | P-value |
| 814 | 72361 | SENSE | 0.172 | 0.712 | 0.657 | 0.000 | 0.757 | 0.001 |
| 816 | 71626 | SENSE | 0.634 | 0.013 | 0.456 | 0.032 | 0.513 | 0.003 |
| 861 | 13965 | ANTI-SENSE | 0.414 | 0.077 | 0.248 | 0.117 | 0.274 | 0.012 |
| 915 | 16120 | SENSE | 0.494 | 0.247 | 0.758 | 0.042 | 0.722 | 0.077 |
| 918 | 72417 | SENSE | 0.984 | 0.041 | 0.125 | 0.023 | 0.114 | 0.051 |
| 923 | 71706 | SENSE | 0.010 | 0.943 | 0.231 | 0.064 | 0.459 | 0.019 |
| 962 | 70808 | SENSE | 0.394 | 0.285 | 0.290 | 0.014 | 0.362 | 0.072 |
| 974 | 72356 | SENSE | 0.570 | 0.057 | 0.823 | 0.044 | 0.888 | 0.096 |
| 1000 | 78373 | SENSE | −0.020 | 0.948 | 0.846 | 0.006 | 0.923 | 0.005 |
| 1012 | 73613 | SENSE | 0.574 | 0.024 | 0.579 | 0.010 | 0.570 | 0.012 |
| 1022 | 70447 | SENSE | 0.294 | 0.369 | 0.195 | 0.015 | 0.106 | 0.089 |
| 1023 | 71725 | SENSE | 0.201 | 0.492 | 0.199 | 0.026 | 0.225 | 0.055 |
| 1085 | 71677 | SENSE | 0.596 | 0.003 | 0.741 | 0.021 | 0.425 | 0.226 |
| 1097 | 72510 | SENSE | 0.813 | 0.250 | 0.891 | 0.009 | 1.105 | 0.015 |
| 1125 | 73221 | SENSE | 0.582 | 0.016 | 0.412 | 0.027 | 0.425 | 0.117 |
| 1141 | 72092 | SENSE | 0.092 | 0.750 | 0.568 | 0.006 | 0.480 | 0.027 |
| 1151 | 74287 | SENSE | 0.692 | 0.065 | 0.795 | 0.017 | 0.774 | 0.015 |
| 1153 | 77304 | SENSE | 0.664 | 0.194 | 1.164 | 0.014 | 1.479 | 0.014 |
| 1156 | 74719 | SENSE | 0.350 | 0.133 | 0.393 | 0.083 | 0.449 | 0.013 |
| 1171 | 73058 | SENSE | 0.500 | 0.180 | 0.322 | 0.027 | 0.329 | 0.049 |
| 1186 | 73131 | SENSE | 0.369 | 0.286 | 0.725 | 0.031 | 0.907 | 0.052 |
| 1187 | 73108 | SENSE | 0.579 | 0.065 | 0.725 | 0.018 | 0.644 | 0.025 |
| 1198 | 10908 | ANTI-SENSE | −0.549 | 0.086 | 0.112 | 0.095 | 0.136 | 0.050 |
| 1205 | 74732 | SENSE | 0.348 | 0.082 | 0.457 | 0.059 | 0.513 | 0.019 |
| 1239 | 78365 | SENSE | 0.430 | 0.141 | 0.621 | 0.035 | 0.600 | 0.043 |
| 1307 | 75830 | SENSE | 0.865 | 0.113 | 1.430 | 0.003 | 1.558 | 0.002 |
| 1315 | 78456 | SENSE | −0.352 | 0.118 | 0.534 | 0.077 | 0.650 | 0.049 |
| 1335 | 76746 | SENSE | 0.552 | 0.112 | 0.508 | 0.071 | 0.734 | 0.041 |
| 1343 | 76176 | SENSE | 0.435 | 0.095 | 1.337 | 0.018 | 1.472 | 0.018 |
| 1350 | 78115 | SENSE | 0.136 | 0.464 | 0.413 | 0.016 | 0.421 | 0.018 |
| 1375 | 75342 | SENSE | 1.019 | 0.029 | 1.486 | 0.039 | 1.752 | 0.046 |
| 1408 | 75652 | SENSE | −0.425 | 0.454 | 0.388 | 0.005 | 0.415 | 0.009 |
| 1409 | 75605 | SENSE | 0.424 | 0.100 | 0.703 | 0.041 | 0.808 | 0.010 |
| 1420 | 75762 | SENSE | 1.078 | 0.039 | 0.558 | 0.037 | 0.480 | 0.011 |
| 1430 | 77560 | SENSE | 0.378 | 0.128 | 0.261 | 0.028 | 0.288 | 0.041 |
| 1431 | 77561 | SENSE | −0.191 | 0.296 | 0.446 | 0.054 | 0.511 | 0.047 |
| 1439 | 11749 | ANTI-SENSE | −0.458 | 0.494 | 0.622 | 0.028 | 0.710 | 0.008 |
| 1458 | 77940 | SENSE | 0.498 | 0.200 | 0.305 | 0.167 | 0.573 | 0.009 |
| 1461 | 78126 | SENSE | −0.708 | 0.080 | 0.426 | 0.046 | 0.485 | 0.071 |
| 1500 | 78162 | SENSE | 1.502 | 0.000 | 1.496 | 0.025 | 1.778 | 0.024 |
| 1502 | 78622 | SENSE | 0.550 | 0.221 | 0.722 | 0.018 | 0.752 | 0.016 |
| 1517 | 78571 | SENSE | 1.529 | 0.033 | 1.204 | 0.001 | 1.303 | 0.001 |
| 1519 | 78573 | SENSE | 0.292 | 0.457 | 0.603 | 0.007 | 0.542 | 0.038 |
| 1543 | 77840 | SENSE | −0.182 | 0.173 | 0.232 | 0.030 | 0.299 | 0.020 |
| 1565 | 76939 | SENSE | 0.598 | 0.154 | 0.520 | 0.037 | 0.597 | 0.035 |
| 1566 | 76987 | SENSE | 0.953 | 0.052 | 0.845 | 0.010 | 0.936 | 0.007 |
| 1577 | 77145 | SENSE | 0.408 | 0.180 | 0.403 | 0.041 | 0.368 | 0.140 |
| 1593 | 77462 | SENSE | 1.157 | 0.052 | 1.077 | 0.012 | 0.969 | 0.003 |
| 1601 | 77419 | SENSE | 0.156 | 0.513 | 0.763 | 0.010 | 0.844 | 0.031 |

TABLE 8-continued

| PEP SEQ ID | Construct ID | Orientation | Rosette area at day 8 Delta mean | P-value | Rosette area at day 28 Risk score mean | P-value | Rosette area difference Delta mean | P-value |
|---|---|---|---|---|---|---|---|---|
| 1605 | 71237 | SENSE | 0.836 | 0.009 | 0.825 | 0.005 | 1.041 | 0.007 |
| 845 | 70253 | SENSE | 0.578 | 0.007 | 0.571 | 0.064 | 0.459 | 0.007 |
| 1007 | 70419 | SENSE | −0.079 | 0.646 | 0.197 | 0.126 | 0.266 | 0.012 |
| 1313 | 77511 | SENSE | 0.822 | 0.011 | 0.131 | 0.013 | 0.063 | 0.189 |
| 1332 | 77519 | SENSE | 0.275 | 0.286 | 0.911 | 0.034 | 1.020 | 0.031 |
| 1484 | 77984 | SENSE | −0.104 | 0.724 | 0.255 | 0.055 | 0.274 | 0.048 |

Transgenic plants comprising recombinant DNA expressing protein as set forth in SEQ ID NO: 818, 836, 844, 848, 883, 1029, 1045, 1062, 1082, 1277, 1287, 1294, 1305, 1318, 1366, 1369, 1373, 1387, 1402, 1405, 1410, 1412, 1418, 1427, 1433, 1476, 1481, 1495, 1531, or 1583 showed enhanced cold stress tolerance by the second criterial as illustrated in Example 1L and 1M.

G. Cold Germination Tolerance Screen

This example sets forth a screen to identify *Arabidopsis* plants transformed with the genes of interests are resistant to cold stress based on their rate of development, root growth and chlorophyll accumulation under low temperature conditions.

T2 seeds were plated and all seedlings used in the experiment were grown at 8° C. Seeds were first surface disinfested using chlorine gas and then seeded on assay plates containing an aqueous solution of ½× Gamborg's B/5 Basal Salt Mixture (Sigma/Aldrich Corp., St. Louis, Mo., USA G/5788), 1% Phytagel™ (Sigma-Aldrich, P-8169), and 10 ug/ml glufosinate with the final pH adjusted to 5.8 using KOH. Test plates were held vertically for 28 days at a constant temperature of 8° C., a photoperiod of 16 hr, and average light intensity of approximately 100 umol/m²/s. At 28 days post plating, root length was measured, growth stage was observed, the visual color was assessed, and a whole plate photograph was taken.

The root length at day 28 was analyzed as a quantitative response according to example 1M. The growth stage at day 7 was analyzed as a qualitative response according to example 1L. A list of recombinant DNA constructs that improve cold stress tolerance in transgenic plants illustrated in Table 9.

TABLE 9

| NUC Seq ID NO | PEP SEQ ID NO | Construct ID | Nomination ID | Orientation | Root length at day 28 Delta mean | P-value | Growth stage at day 28 Delta mean | P-value |
|---|---|---|---|---|---|---|---|---|
| 187 | 990 | 18331 | CGPG3338 | SENSE | / | / | / | / |
| 227 | 1030 | 19829 | CGPG3981 | SENSE | −0.021 | 0.389 | 0.597 | 0.031 |
| 231 | 1034 | 70365 | CGPG4028 | SENSE | −0.088 | 0.312 | 0.725 | 0.013 |
| 214 | 1017 | 70436 | CGPG3703 | SENSE | 0.051 | 0.747 | 1.952 | 0.005 |
| 217 | 1020 | 70446 | CGPG3730 | SENSE | −0.064 | 0.784 | 1.572 | 0.009 |
| 159 | 962 | 70808 | CGPG289 | SENSE | 0.090 | 0.637 | 2.318 | 0.003 |
| 262 | 1065 | 71313 | CGPG4401 | SENSE | 0.160 | 0.542 | 1.654 | 0.001 |
| 272 | 1075 | 71339 | CGPG4551 | SENSE | / | / | / | / |
| 283 | 1086 | 71691 | CGPG4656 | SENSE | −0.048 | 0.305 | 1.121 | 0.003 |
| 335 | 1138 | 72016 | CGPG5246 | SENSE | 0.385 | 0.012 | 1.855 | 0.161 |
| 337 | 1140 | 72044 | CGPG5268 | SENSE | 0.442 | 0.044 | 1.908 | 0.003 |
| 359 | 1162 | 72728 | CGPG5530 | SENSE | 0.243 | 0.300 | 2.142 | 0.002 |
| 137 | 940 | 72796 | CGPG2451 | SENSE | 0.187 | 0.063 | 0.775 | 0.014 |
| 92 | 895 | 72952 | CGPG2095 | SENSE | / | / | / | / |
| 399 | 1202 | 73036 | CGPG5796 | SENSE | 0.246 | 0.127 | 2.235 | 0.001 |
| 64 | 867 | 73075 | CGPG1797 | SENSE | 0.046 | 0.788 | 1.242 | 0.007 |
| 377 | 1180 | 73117 | CGPG5657 | SENSE | 0.384 | 0.033 | 1.764 | 0.001 |
| 386 | 1189 | 73132 | CGPG5705 | SENSE | 0.208 | 0.283 | 2.646 | 0.003 |
| 374 | 1177 | 73139 | CGPG5641 | SENSE | 0.040 | 0.536 | 1.183 | 0.002 |
| 473 | 1276 | 73539 | CGPG6475 | SENSE | 0.004 | 0.967 | 1.052 | 0.002 |
| 482 | 1285 | 74104 | CGPG6566 | SENSE | 0.107 | 0.490 | 1.060 | 0.003 |
| 428 | 1231 | 74381 | CGPG6111 | SENSE | 0.060 | 0.631 | 0.457 | 0.049 |
| 632 | 1435 | 74508 | CGPG8 | SENSE | 0.323 | 0.009 | 1.197 | 0.387 |
| 433 | 1236 | 74635 | CGPG6147 | SENSE | 0.165 | 0.172 | 1.596 | 0.006 |
| 438 | 1241 | 74660 | CGPG6177 | SENSE | 0.358 | 0.007 | 1.518 | 0.001 |
| 571 | 1374 | 75330 | CGPG7508 | SENSE | 0.019 | 0.906 | 0.570 | 0.026 |
| 589 | 1392 | 75446 | CGPG7637 | SENSE | / | / | / | / |
| 598 | 1401 | 75512 | CGPG7752 | SENSE | 0.057 | 0.576 | 1.652 | 0.001 |
| 595 | 1398 | 75582 | CGPG7742 | SENSE | 0.213 | 0.374 | 1.883 | 0.003 |
| 506 | 1309 | 75836 | CGPG6827 | SENSE | 0.228 | 0.076 | 1.314 | 0.041 |
| 521 | 1324 | 75863 | CGPG6942 | SENSE | 0.162 | 0.132 | 1.468 | 0.002 |
| 523 | 1326 | 75865 | CGPG6949 | SENSE | 0.046 | 0.615 | 1.742 | 0.006 |
| 660 | 1463 | 75901 | CGPG8211 | SENSE | 0.437 | 0.015 | 1.733 | 0.070 |
| 59 | 862 | 75912 | CGPG1726 | SENSE | −0.035 | 0.550 | 0.265 | 0.000 |
| 37 | 840 | 76050 | CGPG1463 | SENSE | −0.146 | 0.404 | 0.213 | 0.043 |
| 408 | 1211 | 76113 | CGPG5862 | SENSE | 0.135 | 0.014 | 0.615 | 0.453 |
| 544 | 1347 | 76189 | CGPG7253 | SENSE | 0.015 | 0.018 | 0.333 | 0.645 |
| 722 | 1525 | 76325 | CGPG8870 | SENSE | −0.141 | 0.553 | 0.557 | 0.026 |
| 447 | 1250 | 76524 | CGPG6266 | SENSE | 0.099 | 0.300 | 1.123 | 0.015 |
| 446 | 1249 | 76653 | CGPG6254 | SENSE | 0.507 | 0.101 | 3.257 | 0.004 |
| 628 | 1431 | 77561 | CGPG7972 | SENSE | 0.278 | 0.061 | 1.265 | 0.009 |
| 647 | 1450 | 77588 | CGPG8108 | SENSE | 0.063 | 0.677 | 1.028 | 0.032 |
| 749 | 1552 | 77843 | CGPG9017 | SENSE | 0.382 | 0.011 | 1.325 | 0.006 |
| 701 | 1504 | 78043 | CGPG8606 | SENSE | 0.237 | 0.204 | 0.859 | 0.003 |

TABLE 9-continued

| | | | | | Root length at day 28 | | Growth stage at day 28 | |
|---|---|---|---|---|---|---|---|---|
| NUC Seq ID NO | PEP SEQ ID NO | Construct ID | Nomination ID | Orientation | Delta mean | P-value | Delta mean | P-value |
| 91 | 894 | 17227 | CGPG2077 | SENSE | 0.071 | 0.621 | 0.820 | 0.006 |
| 319 | 1122 | 73318 | CGPG5029 | SENSE | 0.004 | 0.989 | 0.532 | 0.011 |
| 465 | 1268 | 73432 | CGPG6421 | SENSE | −0.038 | 0.743 | 0.532 | 0.011 |
| 568 | 1371 | 77808 | CGPG7499 | SENSE | 0.170 | 0.037 | 1.138 | 0.023 |
| 312 | 1115 | 72814 | CGPG4982 | SENSE | 0.080 | 0.592 | 1.467 | 0.013 |
| 461 | 1264 | 73429 | CGPG6397 | SENSE | 0.320 | 0.206 | 1.589 | 0.017 |
| 682 | 1485 | 73938 | CGPG85 | SENSE | 0.029 | 0.927 | 1.140 | 0.005 |
| 680 | 1483 | 78922 | CGPG8489 | SENSE | 0.260 | 0.123 | 1.326 | 0.004 |

Transgenic plants comprising recombinant DNA expressing protein as set forth in 863, 864, 941, 985, 1071, 1123, 1170, 1194, 1259, 1312, 1339, 1433, 1465, 1543, 1556 showed enhanced cold stress tolerance by the second criterial as illustrated in Example 1L and 1M.

H. Shade Tolerance Screen

Plants undergo a characteristic morphological response in shade that includes the elongation of the petiole, a change in the leaf angle, and a reduction in chlorophyll content. While these changes can confer a competitive advantage to individuals, in a monoculture the shade avoidance response is thought to reduce the overall biomass of the population. Thus, genetic alterations that prevent the shade avoidance response can be associated with higher yields. Genes that favor growth under low light conditions can also promote yield, as inadequate light levels frequently limit yield. This protocol describes a screen to look for *Arabidopsis* plants that show an attenuated shade avoidance response and/or grow better than control plants under low light intensity. Of particular interest, we were looking for plants that didn't extend their petiole length, had an increase in seedling weight relative to the reference and had leaves that were more close to parallel with the plate surface.

T2 seeds were plated on glufosinate selection plates with ½ MS medium. Seeds were sown on ½×MS salts, 1% Phytagel, 10 ug/ml BASTA. Plants were grown on vertical plates at a temperature of 22° C. at day, 20° C. at night and under low light (approximately 30 uE/m$^2$/s, far/red ratio (655/665/725/735) ~0.35 using PLAQ lights with GAM color filter #680). Twenty-three days after seedlings were sown, measurements were recorded including seedling status, number of rosette leaves, status of flower bud, petiole leaf angle, petiole length, and pooled fresh weights. A digital image of the whole plate was taken on the measurement day. Seedling weight and petiole length were analyzed as quantitative responses according to example 1M. The number of rosette leaves, flowering bud formation and leaf angel were analyzed as qualitative responses according to example 1L.

A list of recombinant DNA constructs that improve shade tolerance in plants illustrated in Table 10.

TABLE 10

| NUC | PEP | Con- | | Seedling weight at day 23 | | Petiole length at day 23 | |
|---|---|---|---|---|---|---|---|
| Seq ID | SEQ ID | struct ID | Orientation | Delta mean | P-value | Delta mean | P-value |
| 52 | 855 | 15624 | SENSE | 0.327 | 0.041 | 0.141 | 0.189 |
| 398 | 1201 | 72922 | SENSE | 0.421 | 0.049 | 0.339 | 0.070 |
| 427 | 1230 | 74377 | SENSE | 0.411 | 0.039 | 0.374 | 0.067 |
| 405 | 1208 | 74736 | SENSE | 0.268 | 0.024 | 0.147 | 0.141 |
| 566 | 1369 | 75387 | SENSE | 0.329 | 0.008 | 0.342 | 0.010 |
| 59 | 862 | 75912 | SENSE | 0.470 | 0.035 | 0.572 | 0.058 |
| 664 | 1467 | 75919 | SENSE | 0.453 | 0.007 | 0.114 | 0.063 |
| 736 | 1539 | 76335 | SENSE | −1.012 | 0.081 | −0.594 | 0.007 |
| 783 | 1586 | 77172 | SENSE | 0.426 | 0.044 | 0.218 | 0.164 |
| 698 | 1501 | 78033 | SENSE | 0.060 | 0.033 | −0.129 | 0.612 |

For "seeding weight", if p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference with p<0.2.

"petiole length", if p<0.05 and delta <0, the transgenic plants showed statistically significant trait enhancement as compared to the reference. If p<0.2 and delta <0, the transgenic plants showed a trend of trait enhancement as compared to the reference.

Transgenic plants comprising recombinant DNA expressing protein as set forth in SEQ ID NO: 805, 828, 833, 870, 936, 937, 939, 965, 988, 1007, 1010, 1016, 1038, 1050, 1060, 1070, 1079, 1089, 1095, 1100, 1117, 1125, 1129, 1134, 1135, 1145, 1150, 1154, 1155, 1158, 1184, 1204, 1210, 1214, 1216, 1217, 1225, 1226, 1235, 1248, 1252, 1255, 1260, 1271, 1278, 1282, 1283, 1289, 1292, 1297, 1304, 1311, 1312, 1317, 1328, 1336, 1338, 1348, 1363, 1366, 1383, 1386, 1400, 1428, 1448, 1451, 1453, 1462, 1491, 1493, 1505, 1516, 1520, 1528, 1533, 1545, 1579, or 1588 showed enhanced tolerance to shade or low light condition by the second criteria as illustrated in Example 1L and 1M.

I. Early Plant Growth and Development Screen

This example sets forth a plate based phenotypic analysis platform for the rapid detection of phenotypes that are evident during the first two weeks of growth. In this screen, we were looking for genes that confer advantages in the processes of germination, seedling vigor, root growth and root morphology under non-stressed growth conditions to plants. The transgenic plants with advantages in seedling growth and development were determined by, the seedling weight and root length at day 14 after seed planting.

T2 seeds were plated on glufosinate selection plates and grown under standard conditions (~100 uE/m$^2$/s, 16 h photoperiod, 22° C. at day, 20° C. at night). Seeds were stratified for 3 days at 4° C. Seedlings were grown vertically (at a temperature of 22° C. at day 20° C. at night). Observations were taken on day 10 and day 14. Both seedling weight and root length at day 14 were analyzed as quantitative responses according to example 1M.

A list recombinant DNA constructs that improve early plant growth and development illustrated in Table 11.

TABLE 11

| NUC SEQ ID | PEP SEQ ID | Orientation | Root length at day 10 Delta mean | Root length at day 10 P-value | Root length at day 14 Delta mean | Root length at day 14 P-value | Seedling weight at day 14 Delta mean | Seedling weight at day 14 P-value |
|---|---|---|---|---|---|---|---|---|
| 52 | 855 | SENSE | 0.091 | 0.027 | 0.071 | 0.018 | 0.037 | 0.744 |
| 102 | 905 | SENSE | 0.188 | 0.210 | 0.104 | 0.247 | 0.308 | 0.021 |
| 121 | 924 | SENSE | 0.242 | 0.015 | 0.128 | 0.063 | 0.203 | 0.078 |
| 153 | 956 | SENSE | 0.153 | 0.027 | 0.122 | 0.197 | 0.256 | 0.010 |
| 134 | 937 | SENSE | 0.329 | 0.048 | 0.250 | 0.085 | 0.712 | 0.020 |
| 144 | 947 | SENSE | 0.127 | 0.146 | 0.045 | 0.566 | 0.371 | 0.023 |
| 101 | 904 | SENSE | 0.537 | 0.026 | 0.356 | 0.004 | 0.634 | 0.021 |
| 178 | 981 | SENSE | 0.372 | 0.136 | 0.273 | 0.033 | 0.346 | 0.082 |
| 179 | 982 | SENSE | 0.404 | 0.001 | 0.222 | 0.051 | 0.288 | 0.111 |
| 191 | 994 | SENSE | 0.282 | 0.008 | 0.285 | 0.009 | 0.445 | 0.012 |
| 163 | 966 | SENSE | 0.132 | 0.219 | 0.121 | 0.035 | 0.135 | 0.439 |
| 74 | 877 | SENSE | 0.282 | 0.033 | 0.166 | 0.015 | 0.143 | 0.363 |
| 162 | 965 | SENSE | 0.320 | 0.119 | 0.253 | 0.035 | 0.458 | 0.109 |
| 296 | 1099 | SENSE | 0.047 | 0.653 | 0.057 | 0.369 | 0.141 | 0.013 |
| 313 | 1116 | SENSE | 0.222 | 0.124 | 0.166 | 0.039 | 0.187 | 0.202 |
| 400 | 1203 | SENSE | 0.103 | 0.336 | 0.171 | 0.067 | 0.263 | 0.049 |
| 459 | 1262 | SENSE | 0.278 | 0.081 | 0.273 | 0.027 | 0.308 | 0.121 |
| 215 | 1018 | SENSE | 0.138 | 0.023 | 0.088 | 0.068 | 0.167 | 0.092 |
| 498 | 1301 | SENSE | 0.248 | 0.245 | 0.203 | 0.100 | 0.435 | 0.002 |
| 492 | 1295 | SENSE | 0.066 | 0.018 | −0.052 | 0.334 | 0.215 | 0.171 |
| 567 | 1370 | SENSE | −0.134 | 0.218 | 0.030 | 0.770 | −0.132 | 0.305 |
| 611 | 1414 | SENSE | 0.232 | 0.220 | 0.168 | 0.035 | 0.165 | 0.319 |
| 614 | 1417 | SENSE | 0.142 | 0.277 | 0.147 | 0.174 | 0.167 | 0.562 |
| 616 | 1419 | SENSE | 0.038 | 0.549 | 0.046 | 0.130 | −0.028 | 0.873 |
| 526 | 1329 | SENSE | −0.044 | 0.135 | 0.070 | 0.044 | −0.026 | 0.085 |
| 663 | 1466 | SENSE | 0.075 | 0.043 | −0.065 | 0.418 | 0.047 | 0.639 |
| 79 | 882 | SENSE | 0.127 | 0.094 | 0.117 | 0.041 | 0.111 | 0.266 |
| 724 | 1527 | SENSE | 0.512 | 0.024 | 0.437 | 0.010 | 0.634 | 0.001 |
| 737 | 1540 | SENSE | −0.011 | 0.931 | 0.120 | 0.151 | −0.090 | 0.487 |
| 248 | 1051 | SENSE | 0.197 | 0.003 | 0.145 | 0.007 | 0.020 | 0.783 |
| 444 | 1247 | SENSE | 0.369 | 0.009 | 0.279 | 0.012 | 0.255 | 0.004 |
| 741 | 1544 | SENSE | 0.205 | 0.011 | 0.129 | 0.350 | 0.168 | 0.158 |
| 522 | 1325 | SENSE | 0.134 | 0.354 | 0.160 | 0.069 | 0.085 | 0.653 |
| 777 | 1580 | SENSE | 0.218 | 0.022 | 0.064 | 0.601 | 0.067 | 0.770 |
| 775 | 1578 | SENSE | −0.192 | 0.322 | 0.019 | 0.780 | −0.333 | 0.091 |
| 629 | 1432 | SENSE | −0.042 | 0.151 | 0.075 | 0.016 | −0.184 | 0.176 |
| 704 | 1507 | SENSE | −0.074 | 0.546 | 0.123 | 0.058 | 0.113 | 0.433 |
| 697 | 1500 | SENSE | 0.173 | 0.049 | 0.078 | 0.546 | 0.109 | 0.054 |
| 706 | 1509 | SENSE | 0.074 | 0.018 | 0.076 | 0.301 | 0.059 | 0.664 |
| 331 | 1134 | SENSE | 0.107 | 0.013 | 0.050 | 0.569 | 0.202 | 0.178 |
| 546 | 1349 | SENSE | −0.182 | 0.037 | −0.050 | 0.104 | −0.150 | 0.613 |
| 717 | 1520 | SENSE | 0.297 | 0.085 | 0.223 | 0.029 | 0.292 | 0.213 |
| 22 | 825 | SENSE | / | / | / | / | 0.444 | 0.025 |
| 581 | 1384 | SENSE | 0.116 | 0.126 | 0.193 | 0.013 | 0.181 | 0.175 |
| 726 | 1529 | SENSE | 0.375 | 0.012 | 0.088 | 0.188 | 0.353 | 0.015 |
| 755 | 1558 | SENSE | 0.409 | 0.031 | 0.203 | 0.091 | 0.346 | 0.198 |

Transgenic plants comprising recombinant DNA expressing a protein as set forth in 810, 831, 844, 857, 865, 884, 892, 917, 950, 954, 970, 983, 992, 998, 1004, 1005, 1029, 1033, 1043, 1072, 1101, 1109, 1115, 1133, 1181, 1200, 1284, 1310, 1340, 1384, 1391, 1443, 1449, 1471, 1480, 1483, 1498, 1506, 1508, 1510, 1529, 1548, 1553, 1555, 1556, 1558, 1559, 1564, 1576, or 1577 showed enhanced tolerance to shade or low light condition by the second criterial as illustrated in Example 1L and 1M.

J. Late Plant Growth and Development Screen

This example sets forth a soil based phenotypic platform to identify genes that confer advantages in the processes of leaf development, flowering production and seed maturity to plants.

*Arabidopsis* plants were grown on a commercial potting mixture (Metro Mix 360, Scotts Co., Marysville, Ohio) consisting of 30-40% medium grade horticultural vermiculite, 35-55% sphagnum peat moss, 10-20% processed bark ash, 1-15% pine bark and a starter nutrient charge. Soil was supplemented with Osmocote time-release fertilizer at a rate of 30 mg/W. T2 seeds were imbibed in 1% agarose solution for 3 days at 4° C. and then sown at a density of ~5 per 2½" pot. Thirty-two pots were ordered in a 4 by 8 grid in standard greenhouse flat. Plants were grown in environmentally controlled rooms under a 16 h day length with an average light intensity of ~200 μmoles/m$^2$/s. Day and night temperature set points were 22° C. and 20° C., respectively. Humidity was maintained at 65?/. Plants were watered by sub-irrigation every two days on average until mid-flowering, at which point the plants were watered daily until flowering was complete.

Application of the herbicide glufosinate was performed to select T2 individuals containing the target transgene. A single application of glufosinate was applied when the first true leaves were visible. Each pot was thinned to leave a single glufosinate-resistant seedling ~3 days after the selection was applied.

The rosette radius was measured at day 25. The silique length was measured at day 40. The plant parts were harvested at day 49 for dry weight measurements if flowering production was stopped. Otherwise, the dry weights of rosette and silique were carried out at day 53. The seeds were harvested at day 58. All measurements were analyzed as quantitative responses according to example 1M. A list of recombinant DNA constructs that improve late plant growth and development illustrated in Table 12.

TABLE 12

| PEP SEQ ID | Construct ID | Rosette dry weight at day 53 Delta mean | Rosette dry weight at day 53 P-value | Rosette radius at day 25 Delta mean | Rosette radius at day 25 P-value | Seed net dry weight at day 62 Delta mean | Seed net dry weight at day 62 P-value | Silique dry weight at day 53 Delta mean | Silique dry weight at day 53 P-value | Silique length at day 40 Delta mean | Silique length at day 40 P-value |
|---|---|---|---|---|---|---|---|---|---|---|---|
| 835 | 14405 | 0.110 | 0.430 | / | / | 0.557 | 0.001 | 0.200 | 0.214 | 0.043 | 0.252 |
| 869 | 14833 | 0.247 | 0.382 | / | / | 1.126 | 0.021 | 0.587 | 0.044 | 0.075 | 0.340 |
| 887 | 15207 | 0.238 | 0.023 | −0.407 | 0.087 | 0.047 | 0.785 | 0.343 | 0.046 | −0.015 | 0.540 |
| 949 | 70411 | 0.181 | 0.008 | / | / | −0.268 | 0.192 | 0.061 | 0.025 | −0.039 | 0.240 |
| 1057 | 71564 | 0.397 | 0.049 | 0.190 | 0.205 | 0.440 | 0.005 | 0.342 | 0.035 | 0.070 | 0.043 |
| 1066 | 72349 | 0.174 | 0.011 | / | / | −0.526 | 0.049 | −0.292 | 0.131 | 0.041 | 0.265 |
| 1102 | 72630 | 0.200 | 0.022 | / | / | 0.537 | 0.030 | −0.257 | 0.034 | −0.297 | 0.015 |
| 1108 | 73347 | 0.063 | 0.559 | −0.046 | 0.475 | 0.848 | 0.035 | 0.243 | 0.188 | −0.005 | 0.706 |
| 944 | 16612 | −0.438 | 0.116 | −0.280 | 0.026 | 0.493 | 0.023 | −0.746 | 0.034 | −0.023 | 0.289 |

TABLE 12-continued

| PEP SEQ ID | Construct ID | Rosette dry weight at day 53 | | Rosette radius at day 25 | | Seed net dry weight at day 62 | | Silique dry weight at day 53 | | Silique length at day 40 | |
|---|---|---|---|---|---|---|---|---|---|---|---|
| | | Delta mean | P-value | Delta mean | P-value | Delta mean | P-value | Delta mean | P-value | Delta mean | P-value |
| 929 | 70118 | −0.186 | 0.237 | −0.004 | 0.944 | 1.043 | 0.042 | / | / | 0.040 | 0.279 |
| 1025 | 70545 | 0.057 | 0.434 | 0.111 | 0.355 | 1.228 | 0.021 | / | / | −0.060 | 0.418 |
| 1079 | 70686 | −0.071 | 0.644 | 0.136 | 0.109 | 0.700 | 0.004 | / | / | 0.014 | 0.571 |
| 1088 | 70803 | 0.173 | 0.197 | −0.207 | 0.053 | 0.691 | 0.008 | / | / | 0.067 | 0.094 |
| 1261 | 73438 | 0.397 | 0.057 | −0.251 | 0.005 | 0.733 | 0.014 | −0.056 | 0.542 | −0.012 | 0.809 |
| 1077 | 73696 | −0.384 | 0.425 | −0.284 | 0.129 | 0.666 | 0.020 | / | / | −0.097 | 0.154 |
| 1394 | 75705 | 0.570 | 0.049 | 0.019 | 0.797 | 0.477 | 0.165 | 0.213 | 0.337 | −0.164 | 0.018 |
| 1210 | 76657 | 0.091 | 0.481 | −0.370 | 0.031 | 0.744 | 0.019 | −0.016 | 0.927 | −0.038 | 0.395 |
| 1488 | 78386 | 0.092 | 0.010 | −0.118 | 0.227 | −0.578 | 0.034 | / | / | 0.017 | 0.502 |
| 1475 | 78522 | 0.386 | 0.003 | 0.728 | 0.001 | 1.532 | 0.007 | / | / | 0.170 | 0.038 |

If p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference.

K. Limited Nitrogen Tolerance Screen

Under low nitrogen conditions, *Arabidopsis* seedlings become chlorotic and have less biomass. This example sets forth the limited nitrogen tolerance screen to identify *Arabidopsis* plants transformed with the gene of interest that are altered in their ability to accumulate biomass and/or retain chlorophyll under low nitrogen condition.

T2 seeds were plated on glufosinate selection plates containing 0.5×N-Free Hoagland's T 0.1 mM $NH_4NO_3$ T 0.1% sucrose T 1% phytagel media and grown under standard light and temperature conditions. At 12 days of growth, plants were scored for seedling status (e.g., viable or non-viable) and root length. After 21 days of growth, plants were scored for BASTA resistance, visual color, seedling weight, number of green leaves, number of rosette leaves, root length and formation of flowering buds. A photograph of each plant was also taken at this time point.

The seedling weight and root length were analyzed as quantitative responses according to example 1M. The number green leaves, the number of rosette leaves and the flowerbud formation were analyzed as qualitative responses according to example 1L. The leaf color raw data were collected on each plant as the percentages of five color elements (Green, DarkGreen, LightGreen, RedPurple, YellowChlorotic) using a computer imaging system. A statistical logistic regression model was developed to predict an overall value based on five colors for each plant.

A list of recombinant DNA constructs that improve low nitrogen availability tolerance in plants illustrated in Table 13.

TABLE 13

| NUC SEQ ID | PEP SEQ ID | Construct ID | Orientation | Leaf color at day 21 | | Rosette weight at day 21 | |
|---|---|---|---|---|---|---|---|
| | | | | Risk score mean | P-value | Delta mean | P-value |
| 188 | 991 | 10473 | SENSE | 4.078 | 0.017 | −0.181 | 0.023 |
| 373 | 1176 | 11141 | SENSE | 4.800 | 0.027 | −0.059 | 0.513 |
| 395 | 1198 | 11147 | SENSE | 3.499 | 0.012 | −0.157 | 0.323 |
| 10 | 813 | 11860 | ANTI-SENSE | −3.108 | 0.157 | 0.345 | 0.017 |
| 781 | 1584 | 11933 | ANTI-SENSE | 0.412 | 0.024 | 0.004 | 0.902 |
| 661 | 1464 | 12123 | ANTI-SENSE | 4.867 | 0.025 | 0.036 | 0.750 |
| 8 | 811 | 12147 | ANTI-SENSE | 2.164 | 0.134 | 0.074 | 0.007 |
| 6 | 809 | 12217 | SENSE | 3.494 | 0.047 | 0.086 | 0.245 |
| 12 | 815 | 12230 | SENSE | 1.878 | 0.077 | 0.111 | 0.015 |
| 799 | 1602 | 12444 | SENSE | 0.144 | 0.926 | 0.014 | 0.010 |
| 21 | 824 | 12749 | ANTI-SENSE | 0.315 | 0.022 | 0.109 | 0.325 |
| 3 | 806 | 12816 | SENSE | −0.989 | 0.012 | 0.098 | 0.002 |
| 38 | 841 | 13038 | ANTI-SENSE | 2.207 | 0.450 | 0.074 | 0.040 |
| 39 | 842 | 13040 | ANTI-SENSE | 3.223 | 0.039 | 0.137 | 0.241 |
| 608 | 1411 | 13302 | ANTI-SENSE | 2.956 | 0.013 | 0.040 | 0.100 |
| 35 | 838 | 13828 | ANTI-SENSE | 3.733 | 0.002 | −0.043 | 0.188 |
| 46 | 849 | 14340 | ANTI-SENSE | 3.417 | 0.023 | −0.113 | 0.049 |
| 32 | 835 | 14405 | SENSE | 2.350 | 0.158 | 0.097 | 0.031 |
| 43 | 846 | 14415 | SENSE | 3.195 | 0.006 | −0.131 | 0.066 |
| 85 | 888 | 14915 | ANTI-SENSE | 3.923 | 0.005 | −0.081 | 0.079 |
| 78 | 881 | 15129 | SENSE | 3.751 | 0.002 | 0.096 | 0.164 |
| 104 | 907 | 15507 | ANTI-SENSE | 8.130 | 0.013 | −0.086 | 0.312 |
| 106 | 909 | 15959 | ANTI-SENSE | 5.694 | 0.032 | −0.165 | 0.121 |
| 98 | 901 | 16204 | SENSE | 7.476 | 0.013 | −0.012 | 0.416 |
| 95 | 898 | 16309 | SENSE | 0.678 | 0.046 | 0.072 | 0.436 |
| 65 | 868 | 16323 | SENSE | 2.085 | 0.019 | −0.008 | 0.779 |
| 16 | 819 | 17806 | ANTI-SENSE | 3.639 | 0.036 | −0.087 | 0.208 |
| 184 | 987 | 18319 | SENSE | 1.043 | 0.023 | −0.100 | 0.061 |
| 147 | 950 | 19154 | SENSE | −1.213 | 0.201 | 0.146 | 0.033 |
| 175 | 978 | 19240 | SENSE | 0.175 | 0.828 | 0.098 | 0.002 |
| 289 | 1092 | 71622 | SENSE | 0.222 | 0.357 | 0.082 | 0.003 |
| 287 | 1090 | 71637 | SENSE | 0.074 | 0.772 | 0.061 | 0.001 |
| 261 | 1064 | 71810 | SENSE | 2.561 | 0.010 | −0.038 | 0.111 |
| 416 | 1219 | 74350 | SENSE | 8.315 | 0.006 | 0.020 | 0.504 |
| 500 | 1303 | 74573 | SENSE | 4.232 | 0.015 | 0.093 | 0.207 |
| 555 | 1358 | 74836 | SENSE | 1.278 | 0.002 | −0.133 | 0.018 |
| 561 | 1364 | 74918 | SENSE | 5.122 | 0.022 | 0.414 | 0.346 |
| 27 | 830 | 75958 | SENSE | 1.827 | 0.046 | −0.078 | 0.101 |
| 731 | 1534 | 76321 | SENSE | 5.099 | 0.004 | −0.120 | 0.313 |
| 754 | 1557 | 76821 | SENSE | 4.293 | 0.011 | −0.157 | 0.044 |
| 757 | 1560 | 76894 | SENSE | 3.806 | 0.048 | 0.123 | 0.102 |
| 513 | 1316 | 77041 | SENSE | 1.772 | 0.042 | −0.186 | 0.098 |
| 786 | 1589 | 77250 | SENSE | 7.658 | 0.015 | 0.035 | 0.664 |
| 620 | 1423 | 77541 | SENSE | 1.896 | 0.045 | −0.189 | 0.081 |
| 746 | 1549 | 77842 | SENSE | 4.863 | 0.048 | −0.184 | 0.037 |
| 670 | 1473 | 77966 | SENSE | 1.716 | 0.120 | 0.218 | 0.022 |
| 719 | 1522 | 78191 | SENSE | 2.686 | 0.037 | 0.121 | 0.113 |
| 695 | 1498 | 78548 | SENSE | 1.766 | 0.191 | 0.116 | 0.027 |
| 226 | 1029 | 19775 | SENSE | 0.037 | 0.858 | 0.240 | 0.042 |
| 34 | 837 | 70721 | ANTI-SENSE | 1.858 | 0.012 | 0.052 | 0.047 |
| 280 | 1083 | 71696 | SENSE | −0.133 | 0.002 | 0.085 | 0.049 |

For rosette weight, if p<0.05 and delta or risk score mean >0, the transgenic plants showed statistically significant trait enhancement as compared to the reference. If p<0.2 and delta or risk score mean >0, the transgenic plants showed a trend of trait enhancement as compared to the reference with p<0.2. For root length, if p<0.05, the transgenic plants showed statistically significant trait enhancement as compared to the reference. If p<0.2, the transgenic plants showed a trend of trait enhancement as compared to the reference.

Transgenic plants comprising recombinant DNA expressing a protein as set forth in 807, 808, 817, 820, 829, 839, 847, 848, 850, 854, 858, 859, 866, 872, 875, 878, 889, 902, 908, 911, 922, 938, 944, 953, 963, 974, 980, 993, 1001, 1009, 1035, 1042, 1048, 1049, 1054, 1058, 1068, 1076, 1088, 1094, 1096, 1098, 1103, 1104, 1107, 1112, 1113, 1114, 1121, 1152, 1166, 1175, 1192, 1204, 1207, 1215, 1218, 1240, 1246, 1251, 1256, 1266, 1269, 1281, 1283, 1290, 1296, 1298, 1344, 1345, 1356, 1389, 1396, 1400, 1404, 1409, 1425, 1428, 1438, 1441, 1442, 1454, 1477, 1479, 1484, 1492, 1500, 1511, 1515, 1518, 1521, 1537, 1563, 1567, 1571, 1579, or 1603 showed enhanced tolerance to shade or low light condition by the second criterial as illustrated in Example 1L and 1M.

L. Statistic Analysis for Qualitative Responses

A list of responses that were analyzed as qualitative responses illustrated in Table 14.

TABLE 14

| response | Screen | categories (success vs. failure) |
|---|---|---|
| Wilting response Risk Score | Soil drought tolerance screen | non-wilted vs. wilted |
| growth stage at day 14 | heat stress tolerance screen | 50% of plants reach stage 1.03 vs. not |
| growth stage at day 14 | salt stress tolerance screen | 50% of plants reach stage 1.03 vs. not |
| growth stage at day 14 | PEG induced osmotic stress tolerance screen | 50% of plants reach stage 1.03 vs. not |
| growth stage at day 7 | cold germination tolerance screen | 50% of plants reach stage 0.5 vs. not |
| number of rosette leaves at day 23 | Shade tolerance screen | 5 leaves appeared vs. not |
| Flower bud formation at day 23 | Shade tolerance screen | flower buds appear vs. not |
| leaf angle at day 23 | Shade tolerance screen | >60 degree vs. <60 degree |
| number of green leaves at day 21 | limited nitrogen tolerance screen | 6 or 7 leaves appeared vs. not |
| number of rosette leaves at day 21 | limited nitrogen tolerance screen | 6 or 7 leaves appeared vs. not |
| Flower bud formation at day 21 | limited nitrogen tolerance screen | flower buds appear vs. not |

Plants were grouped into transgenic and reference groups and were scored as success or failure according to Table 14. First, the risk (R) was calculated, which is the proportion of plants that were scored as of failure plants within the group. Then the relative risk (RR) was calculated as the ratio of R (transgenic) to R (reference). Risk score (RS) was calculated as $-\log_2^{RR}$. Two criteria were used to determine a transgenic with enhanced trait(s). Transgenic plants comprising recombinant DNA disclosed herein showed trait enhancement according to either or both of the two criteria.

For the first criteria, the risk scores from multiple events of the transgene of interest were evaluated for statistical significance by t-test using SAS statistical software (SAS 9, SAS/STAT User's Guide, SAS institute Inc, Cary, N.C., USA). RS with a value greater than 0 indicates that the transgenic plants perform better than the reference. RS with a value less than 0 indicates that the transgenic plants perform worse than the reference. The RS with a value equal to 0 indicates that the performance of the transgenic plants and the reference don't show any difference. If p<0.05 and risk score mean >0, the transgenic plants showed statistically significant trait enhancement as compared to the reference. If p<0.2 and risk score mean >0, the transgenic plants showed a trend of trait enhancement as compared to the reference.

For the second criteria, the RS from each event was evaluated for statistical significance by t-test using SAS statistical software (SAS 9, SAS/STAT User's Guide, SAS Institute Inc, Cary, N.C., USA). The RS with a value greater than 0 indicates that the transgenic plants from this event \ perform better than the reference. The RS with a value less than 0 indicates that the transgenic plants from this event perform worse than the reference. The RS with a value equal to 0 indicates that the performance of the transgenic plants from this event and the reference don't show any difference. If p<0.05 and risk score mean >0, the transgenic plants from this event showed statistically significant trait enhancement as compared to the reference. If p<0.2 and risk score mean >0, the transgenic plants showed a trend of trait enhancement as compared to the reference. If two or more events of the transgene of interest showed improvement in the same response, the transgene was deemed to show trait enhancement.

M. Statistic Analysis for Quantitative Responses

A list of responses that were analyzed as quantitative responses illustrated in Table 15.

TABLE 15

| response | screen |
|---|---|
| seed yield | Soil drought stress tolerance screen |
| seedling weight at day 14 | heat stress tolerance screen |
| root length at day 14 | heat stress tolerance screen |
| seedling weight at day 14 | salt stress tolerance screen |
| root length at day 14 | salt stress tolerance screen |
| root length at day 11 | salt stress tolerance screen |
| seedling weight at day 14 | PEG induced osmotic stress tolerance screen |
| root length at day 11 | PEG induced osmotic stress tolerance screen |
| root length at day 14 | PEG induced osmotic stress tolerance screen |
| rosette area at day 8 | cold shock tolerance screen |
| rosette area at day 28 | cold shock tolerance screen |
| difference in rosette area from day 8 to day 28 | cold shock tolerance screen |
| root length at day 28 | cold germination tolerance screen |
| seedling weight at day 23 | Shade tolerance screen |
| petiole length at day 23 | Shade tolerance screen |
| root length at day 14 | Early plant growth and development screen |
| Seedling weight at day 14 | Early plant growth and development screen |
| Rosette dry weight at day 53 | Late plant growth and development screen |
| rosette radius at day 25 | Late plant growth and development screen |
| seed dry weight at day 58 | Late plant growth and development screen |
| silique dry weight at day 53 | Late plant growth and development screen |
| silique length at day 40 | Late plant growth and development screen |
| Seedling weight at day 21 | Limited nitrogen tolerance screen |
| Root length at day 21 | Limited nitrogen tolerance screen |

The measurements (M) of each plant were transformed by $\log_2$ calculation. The Delta was calculated as $\log_2 M$(transgenic)$-\log_2 M$(reference). Two criteria were used to determine trait enhancement. A transgene of interest could show trait enhancement according to either or both of the two criteria. The measurements (M) of each plant were transformed by $\log_2$ calculation. The Delta was calculated as $\log_2 M$(transgenic)$-\log_2 M$(reference). If the measured response was Petiole Length for the Low Light assay, Delta was subsequently multiplied by −1, to account for the fact that a shorter petiole length is considered an indication of trait enhancement.

For the first criteria, the Deltas from multiple events of the transgene of interest were evaluated for statistical significance by t-test using SAS statistical software (SAS 9, SAS/STAT User's Guide, SAS institute Inc, Cary, N.C., USA). Delta with a value greater than 0 indicates that the transgenic plants perform better than the reference. Delta with a value less than 0 indicates that the transgenic plants perform worse than the reference. The Delta with a value equal to 0 indicates that the performance of the transgenic plants and the reference don't show any difference. If $p<0.05$ and risk score mean >0, the transgenic plants showed statistically significant trait enhancement as compared to the reference. If $p<0.2$ and risk score mean >0, the transgenic plants showed a trend of trait enhancement as compared to the reference.

For the second criteria, the delta from each event was evaluated for statistical significance by t-test using SAS statistical software (SAS 9, SAS/STAT User's Guide, SAS Institute Inc, Cary, N.C., USA). The Delta with a value greater than 0 indicates that the transgenic plants from this event perform better than the reference. The Delta with a value less than 0 indicates that the transgenic plants from this event perform worse than the reference. The Delta with a value equal to 0 indicates that the performance of the transgenic plants from this event and the reference don't show any difference. If $p<0.05$ and delta mean >0, the transgenic plants from this event showed statistically significant trait improvement as compared to the reference. If $p<0.2$ and delta mean >0, the transgenic plants showed a trend of trait enhancement as compared to the reference. If two or more events of the transgene of interest showed enhancement in the same response, the transgene was deemed to show trait improvement.

Example 2. Plant Expression Constructs

This example illustrates the construction of plasmids for transferring recombinant DNA into a plant cell nucleus that can be regenerated into transgenic plants.

Plant Expression Constructs for Corn Transformation

A base corn transformation vector pMON93039, as set forth in SEQ ID NO: 94614, illustrated in Table 16 and FIG. 1, is made for use in preparing recombinant DNA for *Agrobacterium*-mediated transformation into corn tissue.

TABLE 16

| Function | Name | Annotation | Coordinates of SEQ ID NO: 94614 |
|---|---|---|---|
| *Agrobacterium* T-DNA transfer | B-AGRtu.right border | Agro right border sequence, essential for transfer of T-DNA. | 11364-11720 |
| Gene of interest expression cassette | E-Os.Act1 | Upstream promoter region of the rice actin 1 gene | 19-775 |
| | E-CaMV.35S.2xA1-B3 | Duplicated35S A1-B3 domain without TATA box | 788-1120 |
| | P-Os.Act1 | Promoter region of the rice actin 1 gene | 1125-1204 |
| | L-Ta.Lhcb1 | 5' untranslated leader of wheat major chlorophyll a/b binding protein | 1210-1270 |
| | I-Os.Act1 | First intron and flanking UTR exon sequences from the rice actin 1 gene | 1287-1766 |
| | T-St.Pis4 | 3' non-translated region of the potato proteinase inhibitor II gene which functions to direct polyadenylation of the mRNA | 1838-2780 |
| Plant selectable marker expression cassette | P-Os.Act1 | Promoter from the rice actin 1 gene | 2830-3670 |
| | L-Os.Act1 | First exon of the rice actin 1 gene | 3671-3750 |
| | I-Os.Act1 | First intron and flanking UTR exon sequences from the rice actin 1 gene | 3751-4228 |
| | TS-At.ShkG-CTP2 | Transit peptide region of *Arabidopsis* EPSPS | 4238-4465 |
| | CR-AGRtu.aroA-CP4.nat | Coding region for bacterial strain CP4 native aroA gene. | 4466-5833 |
| | T-AGRtu.nos | A 3' non-translated region of the nopaline synthase gene of *Agrobacterium tumefaciens* Ti plasmid which functions to direct polyadenylation of the mRNA. | 5849-6101 |
| *Agrobacterium* T-DNA transfer | B-AGRtu.left border | Agro left border sequence, essential for transfer of T-DNA. | 6168-6609 |

TABLE 16-continued

| Function | Name | Annotation | Coordinates of SEQ ID NO: 94614 |
|---|---|---|---|
| Maintenance in E. coli | OR-Ec.oriV-RK2 | The vegetative origin of replication from plasmid RK2. | 6696-7092 |
| | CR-Ec.rop | Coding region for repressor of primer from the ColE1 plasmid. Expression of this gene product interferes with primer binding at the origin of replication, keeping plasmid copy number low. | 8601-8792 |
| | OR-Ec.ori-ColE1 | The minimal origin of replication from the E. coli plasmid ColE1. | 9220-9808 |
| | P-Ec.aadA-SPC/STR | Promoter for Tn7 adenylyltransferase (AAD(3")) | 10339-10380 |
| | CR-Ec.aadA-SPC/STR | Coding region for Tn7 adenylyltransferase (AAD(3")) conferring spectinomycin and streptomycin resistance. | 10381-11169 |
| | T-Ec.aadA-SPC/STR | 3' UTR from the Tn7 adenylyltransferase (AAD(3")) gene of E. coli. | 11170-11227 |

Primers for PCR amplification of protein coding nucleotides of recombinant DNA are designed at or near the start and stop codons of the coding sequence in order to eliminate most of the 5' and 3' untranslated regions. Each recombinant DNA coding for or suppressing a protein identified in Table 2 is amplified by PCR prior to insertion into the insertion site within the gene of interest expression cassette of the base vector.

B. Plant Expression Constructs for Soy and Canola Transformation

Figure 2:
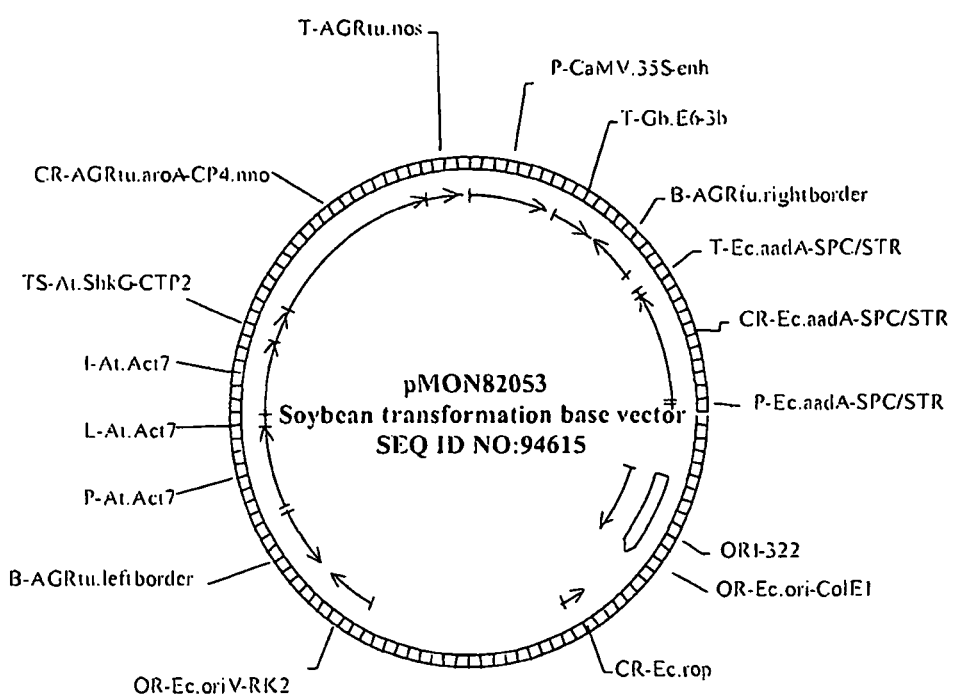

Vectors for use in transformation of soybean and canola can also be prepared. Elements of an exemplary common expression vector pMON82053 (SEQ ID NO: 94615) are shown in Table 17 below and FIG. 2.

TABLE 17

| Function | Name | Annotation | Coordinates of SEQ ID NO: 94615 |
|---|---|---|---|
| Agrobacterium T-DNA transfer | B-AGRtu.left border | Agro left border sequence, essential for transfer of T-DNA. | 6144-6585 |
| Plant selectable marker expression cassette | P-At.Act7 | Promoter from the Arabidopsis actin 7 gene | 6624-7861 |
| | L-At.Act7 | 5'UTR of Arabidopsis Act 7 gene | |
| | I-At.Act7 | Intron from the Arabidopsis actin7 gene | |
| | TS-At.ShkG-CTP2 | Transit peptide region of Arabidopsis EPSPS | 7864-8091 |
| | CR-AGRtu.aroA-CP4.nno_At | Synthetic CP4 coding region with dicot preferred codon usage. | 8092-9459 |
| | T-AGRtu.nos | A 3' non-translated region of the nopaline synthase gene of Agrobacterium tumefaciens Ti plasmid which functions to direct polyadenylation of the mRNA. | 9466-9718 |
| Gene of interest expression cassette | P-CaMV.35S-enh | Promoter for 35S RNA from CaMV containing a duplication of the −90 to −350 region. | 1-613 |
| | T-Gb.E6-3b | 3' untranslated region from the fiber protein E6 gene of sea-island cotton. | 688-1002 |
| Agrobacterium T-DNA transfer | B-AGRtu.right border | Agro right border sequence, essential for transfer of T-DNA. | 1033-1389 |
| Maintenance in E. coli | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the origin of replication, keeping plasmid copy number low. | 3961-4152 |
| | OR-Ec.ori-ColE1 | The minimal origin of replication from the E. coli plasmid ColE1. | 2945-3533 |

TABLE 17-continued

| Function | Name | Annotation | Coordinates of SEQ ID NO: 94615 |
|---|---|---|---|
| | P-Ec.aadA-SPC/STR | Promoter for Tn7 adenylyl transferase (AAD(3")) | 2373-2414 |
| | CR-Ec.aadA-SPC/STR | Coding region for Tn7 adenylyl transferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of E. coli. | 1526-1583 |

Primers for PCR amplification of protein coding nucleotides of recombinant DNA are designed at or near the start and stop codons of the coding sequence in order to eliminate most of the 5' and 3' untranslated regions. Each recombinant DNA coding for or suppressing a protein identified in Table 2 is amplified by PCR prior to insertion into the insertion site within the gene of interest expression cassette of the base vector.

C. Cotton Transformation Vector

Figure 3:
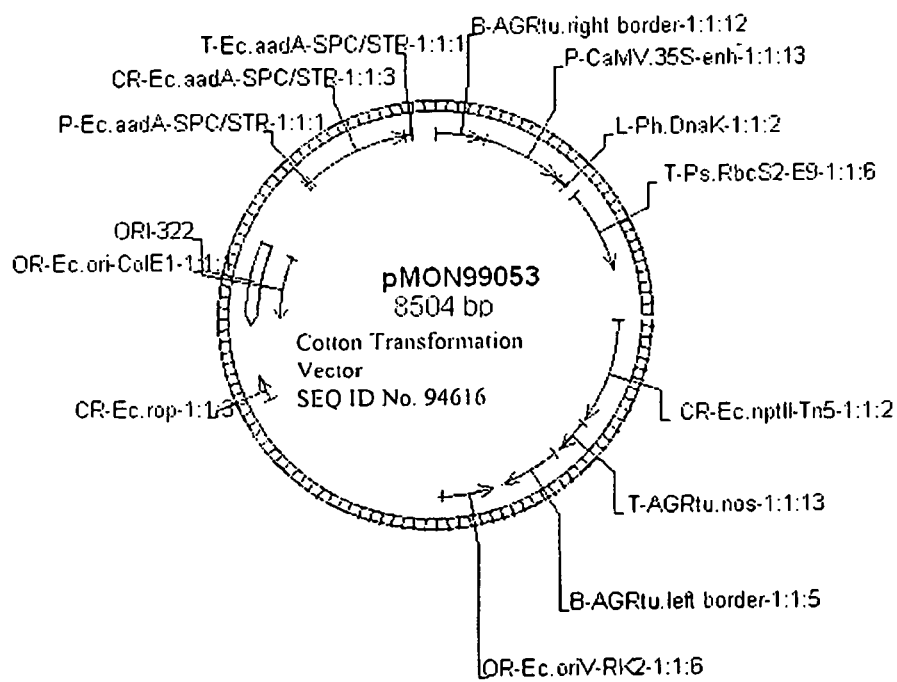

Plasmids for use in transformation of cotton tissue are prepared with elements of expression vector pMON99053 (SEQ ID NO: 94616) are shown in Table 18 below and FIG. 3, Primers for PCR amplification of protein coding nucleotides of recombinant DNA are designed at or near the start and stop codons of the coding sequence in order to eliminate most of the 5' and 3' untranslated regions. Each recombinant DNA coding for or suppressing a protein identified in Table 2 is amplified by PCR prior to insertion into the insertion site within the gene of interest expression cassette of the base vector.

TABLE 18

| Function | Name | Annotation | Coordinates of SEQ ID NO: 94616 |
|---|---|---|---|
| Agrobacterium T-DNA transfer | B-AGRtu.right border | Agro right border sequence, essential for transfer of T-DNA. | 1-357 |
| Gene of interest expression cassette | Exp-CaMV.35S-enh + Ph.DnaK | Enhanced version of the 35S RNA promoter from CaMV plus the petunia hsp70 5' untranslated region | 388-1091 |
| | T-Ps.RbcS2-E9 | The 3' non-translated region of the pea RbcS2 gene which functions to direct polyadenylation of the mRNA. | 1165-1797 |
| Plant selectable marker expression cassette | Exp-CaMV.35S | Promoter and 5' untranslated region from the 35S RNA of CaMV | 1828-2151 |
| | CR-Ec.nptII-Tn5 | Coding region for neomycin phosphotransferase gene from transposon Tn5 which confers resistance to neomycin and kanamycin. | 2185-2979 |
| | T-AGRtu.nos | A 3' non-translated region of the nopaline synthase gene of Agrobacterium tumefaciens Ti plasmid which functions to direct polyadenylation of the mRNA. | 3011-3263 |
| Agrobacterium T-DNA transfer | B-AGRtu.left border | Agro left border sequence, essential for transfer of T-DNA. | 3309-3750 |
| Maintenance in E. coli | OR-Ec.oriV-RK2 | The vegetative origin of replication from plasmid RK2. | 3837-4233 |
| | CR-Ec.rop | Coding region for repressor of primer from the ColE1 plasmid. Expression of this gene product interferes with primer binding at the origin of replication, keeping plasmid copy number low. | 5742-5933 |
| | OR-Ec.ori-ColE1 | The minimal origin of replication from the E. coli plasmid ColE1. | 6363-6949 |

TABLE 18-continued

| Function | Name | Annotation | Coordinates of SEQ ID NO: 94616 |
|---|---|---|---|
| | P-Ec.aadA-SPC/STR | Promoter for Tn7 adenylyltransferase (AAD(3")) | 7480-7521 |
| | CR-Ec.aadA-SPC/STR | Coding region for Tn7 adenylyltransferase (AAD(3")) conferring spectinomycin and streptomycin resistance. | 7522-8310 |
| | T-Ec.aadA-SPC/STR | 3' UTR from the Tn7 adenylyltransferase (AAD(3")) gene of E. coli. | 8311-8368 |

Example 3. Corn Transformation

This example illustrates transformation methods in producing a transgenic nucleus in a corn plant cell and the plants, seeds and pollen produced from a transgenic cell with such a nucleus having an enhanced trait, e.g. enhanced water use efficiency, enhanced cold tolerance, increased yield, enhanced nitrogen use efficiency, enhanced seed protein and enhanced seed oil. Plasmid vectors are prepared by cloning DNA identified in Table 2 in the base vector for use in corn transformation of corn tissue.

For Agrobacterium-mediated transformation of corn embryo cells corn plants of a readily transformable line are grown in the greenhouse and ears are harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, Agrobacterium cells are grown overnight at room temperature. Immature maize embryo cells are inoculated with Agrobacterium shortly after excision, and incubated at room temperature with Agrobacterium for 5-20 minutes. Immature embryo plant cells are then co-cultured with Agrobacterium for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformed plant cells are recovered 6 to 8 weeks after initiation of selection.

For Agrobacterium-mediated transformation of maize callus immature embryos are cultured for approximately 8-21 days after excision to allow callus to develop. Callus is then incubated for about 30 minutes at room temperature with the Agrobacterium suspension, followed by removal of the liquid by aspiration. The callus and Agrobacterium are co-cultured without selection for 3-6 days followed by selection on paromomycin for approximately 6 weeks, with biweekly transfers to fresh media. Paromomycin resistant calli are identified about 6-8 weeks after initiation of selection.

For transformation by microprojectile bombardment maize immature embryos are isolated and cultured 3-4 days prior to bombardment. Prior to microprojectile bombardment, a suspension of gold particles is prepared onto which the desired recombinant DNA expression cassettes are precipitated. DNA is introduced into maize cells as described in U.S. Pat. Nos. 5,550,318 and 6,399,861 using the electric discharge particle acceleration gene delivery device. Following microprojectile bombardment, tissue is cultured in the dark at 27° C. Additional transformation methods and materials for making transgenic plants of this invention, for example, various media and recipient target cells, transformation of immature embryos and subsequence regeneration of fertile transgenic plants are disclosed in U.S. Pat. Nos. 6,194,636, 6,232,526 and 7,151,204, which are incorporated herein by reference.

To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

Transgenic corn plant cells are transformed with recombinant DNA from each of the genes identified in Table 2. Progeny transgenic plants and seed of the transformed plant cells are screened for enhanced water use efficiency, enhanced cold tolerance, increased yield, enhanced nitrogen use efficiency, enhanced seed protein and enhanced seed oil as obtained in Example 7.

Example 4. Soybean Transformation

This example illustrates plant transformation in producing the transgenic soybean plants of this invention and the production and identification of transgenic seed for transgenic soybean having enhanced water use efficiency, enhanced cold tolerance, increased yield, enhanced nitrogen use efficiency, enhanced seed protein and enhanced seed oil.

For Agrobacterium mediated transformation, soybean seeds are imbided overnight and the meristem explants excised. The explants are placed in a wounding vessel. Soybean explants and induced Agrobacterium cells from a strain containing plasmid DNA with the gene of interest cassette and a plant selectable marker cassette are mixed no later than 14 hours from the time of initiation of seed imbibition, and wounded using sonication. Following wounding, explants are placed in co-culture for 2-5 days at which point they are transferred to selection media for 6-8 weeks to allow selection and growth of transgenic shoots. Resistant shoots are harvested approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil. Additionally, a DNA construct can be transferred into the genome of a soybean cell by particle bombardment and the cell regenerated into a fertile soybean plant as described in U.S. Pat. No. 5,015,580, herein incorporated by reference.

Transgenic soybean plant cells are transformed with recombinant DNA from each of the genes identified in Table 2. Transgenic progeny plants and seed of the transformed plant cells are screened for enhanced water use efficiency, enhanced cold tolerance, increased yield, enhanced nitrogen use efficiency, enhanced seed protein and enhanced seed oil as obtained in Example 10.

Example 5. Cotton Transgenic Plants with Enhanced Agronomic Traits

Cotton transformation is performed as generally described in WO0036911 and in U.S. Pat. No. 5,846,797. Transgenic cotton plants containing each recombinant DNA having a sequence of SEQ ID NO: 1 through SEQ ID NO: 803 are obtained by transforming with recombinant DNA from each of the genes identified in Table 2, Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, e.g. cotton variety ST474, cotton variety FM 958, and cotton variety Siokra L-23, are used to compare the relative performance of the transgenic cotton plants containing the recombinant DNA. The specified culture conditions are growing a first set of transgenic and control plants under "wet" conditions, e.g. irrigated in the range of 85 to 100 percent of evapotranspiration to provide leaf water potential of −14 to −18 bars, and growing a second set of transgenic and control plants under "dry" conditions, e.g. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area, Enhanced water use efficiency is indicated by increased yield, improved relative water content, enhanced leaf water potential, increased biomass, enhanced leaf extension rates, and improved fiber parameters.

The transgenic cotton plants of this invention are identified from among the transgenic cotton plants by agronomic trait screening as having increased yield and enhanced water use efficiency.

Example 6. Canola Transformation

This example illustrates plant transformation in producing the transgenic canola plants of this invention and the production and identification of transgenic seed for transgenic canola having enhanced water use efficiency, enhanced cold tolerance, increased yield, enhanced nitrogen use efficiency, enhanced seed protein and enhanced seed oil.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterization is performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant Transgenic canola plant cells are transformed with recombinant DNA from each of the genes identified in Table 1. Transgenic progeny plants and seed of the transformed plant cells are screened for enhanced water use efficiency, enhanced cold tolerance, increased yield, enhanced nitrogen use efficiency, enhanced seed protein and enhanced seed oil as obtained in Example 7.

Example 7. Identification of Homologs

This example illustrates the identification of homologs of proteins encoded by the DNA identified in Table 1 which is used to provide transgenic seed and plants having enhanced agronomic traits. From the sequence of the homologs, homologous DNA sequence can be identified for preparing additional transgenic seeds and plants of this invention with enhanced agronomic traits.

An "All Protein Database" is constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" is constructed of known protein sequences of the organism; it is a subset of the All Protein Database based on the NCBI taxonomy ID for the organism.

The All Protein Database is queried using amino acid sequences provided herein as SEQ ID NO: 804 through SEQ ID NO: 1606 using NCBI "blastp" program with E-value cutoff of 1e-8. Up to 1000 top hits are kept, and separated by organism names. For each organism other than that of the query sequence, a list is kept for hits from the query, organism itself with a more significant E-value than the best hit of the organism. The list contains likely duplicated genes of the polynucleotides provided herein, and is referred to as the Core List. Another list is kept for all the hits from each organism, sorted by E-value, and referred to as the 1-lit List.

The Organism Protein Database is queried using polypeptide sequences provided herein as SEQ ID NO: 804 through SEQ ID NO: 1606 using NCBI "blastp" program with E-value cutoff of 1e$^{-4}$. Up to 1000 top hits are kept. A BLAST searchable database is constructed based on these hits, and is referred to as "SubDB". SubDB is queried with each sequence in the Hit List using NCBI "blastp" program with E-value cutoff of 1e$^{-8}$. The hit with the best E-value is compared with the Core List from the corresponding organism. The hit is deemed a likely ortholog if it belongs to the Core List, otherwise it is deemed not a likely ortholog and there is no further search of sequences in the Hit List for the same organism. Likely orthologs from a large number of distinct organisms were identified and are reported by amino acid sequences of SEQ ID NO: 1607 to SEQ ID NO: 94613. These orthologs are reported in Tables 19 as homologs to the proteins cognate to genes used in trait-improving recombinant DNA Example 8. Consensus Sequence Build ClustalW program is selected for multiple sequence alignments of an amino acid sequence of SEQ ID NO: 804 and its homologs, through SEQ ID NO: 1606 and its homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested. On the basis of the test results, Blosum weight matrix, gap open penalty of 10 and gap extension penalty of 1 were chosen for multiple sequence alignment. The consensus sequence of SEQ ID NO: 1325 and its 30 homologs were derived according to the procedure described above and is displayed in FIG. 4.

Example 9. Pfam Module Annotation

This example illustrates the identification of domain and domain module by Pfam analysis.

The amino acid sequence of the expressed proteins that were shown to be associated with an enhanced trait were analyzed for Pfam protein family against the current Pfam collection of multiple sequence alignments and hidden Markov models using the HMMER software in the appended computer listing. The Pfam domain modules and individual protein domain for the proteins of SEQ ID NO: 804 through 1606 are shown in Table 20 and Table 21 respectively. The Hidden Markov model databases for the identified patent families are also in the appended computer listing allowing identification of other homologous proteins and their cognate encoding DNA to enable the full breadth of the invention for a person of ordinary skill in the art. Certain proteins are identified by a single Pfam domain and others by multiple Pfam domains. For instance, the protein with amino acids of SEQ ID NO: 830 is characterized by two Pfam domains, e.g. "Lectin_legB" and "Pkinase". See also the protein with amino acids of SEQ ID NO: 817 which is characterized by four copies of the Pfam domain "Arm". In Table 21 "score" is the gathering score for the Hidden Markov Model of the domain which exceeds the gathering cutoff reported in Table 22.

TABLE 20

| PEP Seq ID No. | Construct ID | Pfam_module | Position |
|---|---|---|---|
| 804 | CGPG10.pep | p450 | 31-495 |
| 805 | CGPG1008.pep | Tryp_alpha_amyl | 23-95 |
| 806 | CGPG1023.pep | Na_Ca_ex::Na_Ca_ex | 104-255::299-432 |
| 807 | CGPG1038.pep | DUF1475 | 1-256 |
| 812 | CGPG1113.pep | DUF1350 | 49-370 |
| 814 | CGPG1163.pep | DSPc | 49-182 |
| 817 | CGPG1205.pep | Arm::Arm::Arm::Arm | 94-134::135-175::176-216::258-298 |
| 818 | CGPG1207.pep | NifU_N | 26-105 |
| 820 | CGPG1223.pep | ATP_bind_1 | 7-250 |
| 821 | CGPG1250.pep | DUF822 | 12-160 |
| 824 | CGPG1319.pep | DUF599 | 10-233 |
| 826 | CGGPG1329.pep | Cullin | 29-631 |
| 827 | CGPG133.pep | Cyclin_N::Cyclin_C | 168-293::295-422 |
| 828 | CGPG1332.pep | Cullin | 12-646 |
| 829 | CGPG1343.pep | LRR_1 | 389-412 |
| 830 | CGPG1348.pep | Lectin_legB::Pkinase | 27-248::334-604 |
| 831 | CGPG1349.pep | B_lectin::S_locus_glycop::PAN_1::Pkinase | 65-171::180-312::327-404::484-731 |
| 832 | CGPG1373.pep | Pkinase | 12-291 |
| 833 | CGPG1377.pep | Pkinase | 4-258 |
| 834 | CGPG1412.pep | TPP_enzyme_N::TPP_enzyme_M::TPP_enzyme_C | 45-221::243-376::431-578 |
| 835 | CGPG1421.pep | Biotin_lipoyl::E3_binding::2-oxoacid_dh | 76-149::180-218::249-480 |
| 836 | CGPG1426.pep | Aminotran_1_2 | 48-432 |
| 837 | CGPG1433.pep | Pyr_redox_2::Pyr_redox_dim | 45-359::388-497 |
| 838 | CGPG1453.pep | malic::Malic_M | 171-360::362-615 |
| 839 | CGPG1454.pep | Ribul_P_3_epim | 7-207 |
| 840 | CGPG1463.pep | Alpha-amylase::Alpha-amyl_C2 | 26-361::362-422 |
| 841 | CGPG1464.pep | Glycolytic | 11-358 |
| 842 | CGPG1471.pep | IF4E | 1-198 |
| 843 | CGPG1481.pep | Pkinase | 4-260 |
| 844 | CGPG1499.pep | PPDK_N::PEP-utilizers::PEP-utilizers_C | 85-445::496-586::598-955 |
| 845 | CGPG150.pep | p450 | 30-507 |
| 846 | CGPG1536.pep | CRAL_TRIO_N::CRAL_TRIO | 73-142::159-345 |
| 847 | CGPG1539.pep | UPF0139 | 8-107 |

TABLE 20-continued

| PEP Seq ID No. | Construct ID | Pfam_module | Position |
|---|---|---|---|
| 848 | CGPG155.pep | GlutR_N::Shikimate_DH::GlutR_dimer | 100-251::255-407::420-526 |
| 849 | CGPG1583.pep | PLAC8 | 88-187 |
| 850 | CGPG1588.pep | PLAC8 | 75-214 |
| 851 | CGPG16.pep | MIP | 14-235 |
| 852 | CGPG1609.pep | MMR_HSR1::DUF933 | 54-190::337-420 |
| 853 | CGPG1629.pep | WD40::WD40::WD40 | 262-301::307-346::356-395 |
| 854 | CGPG1637.pep | DUF220 | 163-262 |
| 855 | CGPG1653.pep | TBC | 200-415 |
| 856 | CGPG1658.pep | Nodulin-like | 14-260 |
| 857 | CGPG1663.pep | BT1 | 30-441 |
| 858 | CGPG1682.pep | OPT | 62-685 |
| 859 | CGPG1701.pep | Glyco_transf_8 | 76-299 |
| 861 | CGPG1724.pep | Per1 | 63-334 |
| 862 | CGPG1726.pep | DUF607 | 111-291 |
| 863 | CGPG1736.pep | Usp | 1-148 |
| 864 | CGPG1741.pep | mTERF | 279-627 |
| 865 | CGPG1783.pep | PB1 | 42-132 |
| 866 | CGPG1790.pep | PB1 | 59-153 |
| 868 | CGPG1845.pep | TFIID-18kDa | 29-119 |
| 869 | CGPG1855.pep | CAF1 | 3-227 |
| 870 | CGPG1870.pep | Pkinase | 406-572 |
| 871 | CGPG1879.pep | Pkinase::NAF | 21-277::303-364 |
| 872 | CGPG1886.pep | Pkinase | 26-325 |
| 873 | CGPG1903.pep | F-box | 320-367 |
| 874 | CGPG1905.pep | F-box::Kelch_2::Kelch_2 | 4-51::104-150::255-306 |
| 875 | CGPG1914.pep | F-box::Kelch_1::Kelch_1 | 42-89::170-215::217-266 |
| 876 | CGPG193.pep | WD40::WD40::WD40::WD40 | 167-205::268-307::318-355::363-401 |
| 877 | CGPG1939.pep | F-box::WD40::WD40::WD40 | 66-113::152-190::247-283::325-364 |
| 878 | CGPG1949.pep | YDG_SRA::Pre-SET::SET | 360-519::543-639::641-771 |
| 879 | CGPG1959.pep | PHD::SET | 34-82::208-344 |
| 880 | CGPG197.pep | p450 | 40-481 |
| 882 | CGPG1981.pep | MT-A70 | 476-636 |
| 883 | CGPG1999.pep | Nfu_N::NifU | 78-193::221-291 |
| 884 | CGPG2.pep | p450 | 71-531 |
| 885 | CGPG2006.pep | RCC1::RCC1::RCC1::RCC1 | 32-82::438-187::190-239::294-343 |
| 886 | CGPG2010.pep | Aminotran_5 | 74-448 |
| 887 | CGPG2011.pep | X8 | 128-209 |
| 888 | CGPG2014.pep | Pkinase::NAF | 28-282::341-398 |
| 889 | CGPG2023.pep | Zip | 48-352 |
| 890 | CGPG2026.pep | Pkinase | 38-324 |
| 892 | CGPG2064.pep | Cenp-O | 123-201 |
| 894 | CGPG2077.pep | NAC::UBA | 88-147::195-232 |
| 895 | CGPG2095.pep | AARP2CN::DUF663 | 228-309::483-780 |
| 896 | CGPG2105.pep | Pkinase::Pkinase_C | 102-404::422-471 |
| 897 | CGPG2108.pep | Response_reg::CCT | 64-180::442-484 |
| 898 | CGPG2111.pep | polyprenyl_synt | 74-324 |
| 899 | CGPG2124.pep | UIM::efhand | 139-156::220-248 |
| 900 | CGPG2125.pep | Glutaredoxin | 44-110 |
| 903 | CGPG2134.pep | ATP-synt_G | 8-122 |
| 904 | CGPG2139.pep | DUF1517 | 94-391 |
| 905 | CGPG2140.pep | PhzC-PbzF | 6-282 |
| 907 | CGPG2163.pep | Cupin_1::Cupin_1 | 5-157::190-339 |
| 908 | CGPG2165.pep | ClpS | 76-152 |
| 910 | CGPG2218.pep | Spc97_Spc98 | 67-555 |
| 912 | CGPG2225.pep | EMP24_GP25L | 52-116 |
| 913 | CGPG2229.pep | Subtilisin_N::PA | 30-106::362-461 |
| 915 | CGPG2254.pep | Ribosomal_L7Ae | 20-114 |
| 916 | CGPG2268.pep | CBS | 66-188 |
| 917 | CGPG227.pep | p450 | 37-494 |
| 918 | CGPG2312.pep | UPF0061 | 75-571 |
| 919 | CGPG2315.pep | SIP1 | 286-514 |
| 920 | CGPG2316.pep | PTPA | 98-396 |
| 922 | CGPG235.pep | p450 | 74-510 |
| 923 | CGPG2358.pep | Branch | 54-278 |
| 925 | CGPG2361.pep | Metallophos | 9-231 |
| 926 | CGPG2365.pep | Epimerase | 3-211 |
| 927 | CGPG2372.pep | Pribosyltran | 29-169 |
| 928 | CGPG2374.pep | Aminotran_5 | 8-370 |
| 929 | CGPG2377.pep | DAO | 69-466 |

TABLE 20-continued

| PEP Seq ID No. | Construct ID | Pfam_module | Position |
|---|---|---|---|
| 930 | CGPG2387.pep | H_PPase | 1-239 |
| 931 | CGPG2389.pep | Carb_anhydrase | 52-275 |
| 932 | CGPG2395.pep | AA_permease | 89-526 |
| 934 | CGPG2409.pep | DUF862 | 17-154 |
| 935 | CGPG2410.pep | GST_N::GST_C | 5-79::101-204 |
| 937 | CGPG2416.pep | Hin1 | 97-235 |
| 938 | CGPG12441.pep | Sina | 5-205 |
| 939 | CGPG2450.pep | Epimerase | 114-371 |
| 940 | CGPG2451.pep | RALF | 57-129 |
| 941 | CGPG2492.pep | Pribosyltran | 80-216 |
| 942 | CGPG2495.pep | ADH_N::ADH_zinc_N | 25-134::165-307 |
| 943 | CGPG2506.pep | PfkB | 5-289 |
| 944 | CGPG2515.pep | TIM | 5-244 |
| 945 | CGPG2531.pep | AhpC-TSA | 5-138 |
| 946 | CGPG2581.pep | SelR | 12-133 |
| 947 | CGPG2584.pep | zf-Tim10_DDP | 22-86 |
| 948 | CGPG2592.pep | TFIID_30kDa | 30-80 |
| 949 | CGPG2612.pep | RRM_1::RRM_1::RRM_1 | 65-132::150-225::275-343 |
| 950 | CGPG2660.pep | B3::B3 | 17-115::211-301 |
| 951 | CGPG2663.pep | NTF2::RRM_1 | 15-131::295-365 |
| 952 | CGPG2679.pep | ACBP::Ank::Ank | 104-190::265-297::298-330 |
| 953 | CGPG2696.pep | zf-C3HC4 | 177-218 |
| 954 | CGPG2772.pep | Mov34 | 6-136 |
| 955 | CGPG2773.pep | Asp | 161-498 |
| 956 | CGPG281.pep | TLC | 91-574 |
| 957 | CGPG2846.pep | Aldo_ket_red | 49-365 |
| 958 | CGPG2852.pep | Glyoxalase | 9-132 |
| 960 | CGPG2870.pep | zf-CCCH::zf-CCCH::zf-CCCH::zf-CCCH::zf-CCCH | 111-137::159-185::205-231::347-373::393-419 |
| 961 | CGPG2877.pep | LAG1 | 96-307 |
| 962 | CGPG289.pep | Cellulose_synt | 243-1060 |
| 963 | CGPG2924.pep | zf-C3HC4 | 138-179 |
| 964 | CGPG2947.pep | Acetyltransf_1::Bromodomain | 265-343::460-548 |
| 965 | CGPG2963.pep | C1_2::C1_3::C1_3::C1_2::C1_3::C1_3::C1_2 | 81-108::136-164::194-223::305-335::391-420::494-522::552-581 |
| 966 | CGPG2987.pep | SRF-TF | Nov-66 |
| 968 | CGPG3045.pep | Pkinase_Tyr | 82-356 |
| 969 | CGPG3046.pep | AAA | 121-305 |
| 970 | CGPG3060.pep | p450 | 67-528 |
| 971 | CGPG3075.pep | Auxin_inducible | 7-106 |
| 972 | CGPG310.pep | Cyclin_N | 18-143 |
| 973 | CGPG3103.pep | PPR::PPR::PPR::PPR::PPR::PPR::PPR::PPR::PPR::PPR::PPR | 14-48::49-83::84-118::119-153::155-188::189-223::224-258::259-293::295-329::330-364::365-398 |
| 974 | CGPG315.pep | p450 | 29-491 |
| 976 | CGPG3189.pep | RRM_1::RRM_1 | 115-186::209-280 |
| 977 | CGPG3204.pep | KH_1::KH_1::KH_1::KH_1::KH_1 | 45-104::151-221::318-381::400-467::575-637 |
| 978 | CGPG3208.pep | MATH::MATH | 26-153::180-302 |
| 979 | CGPG3219.pep | 2OG-FeII_Oxy | 220-320 |
| 980 | CGPG3233.pep | PPR::PPR::PPR::PPR::PPR::PPR::PPR::PPR | 160-194::195-229::231-265::266-300::301-335::336-370::371-405::406-440 |
| 981 | CGPG3263.pep | Tryp_alpha_amyl | 28-104 |
| 982 | CGPG3276.pep | ECH | 11-186 |
| 984 | CGPG3282.pep | Steroid_dh | 117-268 |
| 985 | CGPG3300.pep | zf-CCHC::zf-CCHC::zf-CCHC::zf-CCHC::zf-CCHC::zf-CCHC::zf-CCHC | 55-72::74-91::93-110::112-129::138-155::157-174::229-246 |
| 986 | CGPG3318.pep | Peptidase_C14 | 3-416 |
| 987 | CGPG3319.pep | AP2 | 28-79 |
| 988 | CGPG3326.pep | zf-C3HC4 | 259-299 |
| 989 | CGPG333.pep | PTS_2-RNA | 48-239 |
| 990 | CGPG3338.pep | Alba | 17-87 |
| 991 | CGPG3334.pep | Mov34 | 20-128 |
| 992 | CGPG3374.pep | peroxidase | 42-286 |
| 993 | CGPG3402.pep | Dimerisation::Methyltransf_2 | 30-89::99-342 |
| 995 | CGPG3413.pep | WD40::U3_snoRNA_C | 168-207::377-523 |
| 996 | CGPG3422.pep | WD40::WD40::WD40 | 241-279::387-425::519-559 |
| 997 | CGPG3436.pep | DUF6::DUF6 | 17-144::198-327 |
| 998 | CGPG3539.pep | Mito_carr::Mito_carr::Mito_carr | 11-105::113-209::214-303 |
| 999 | CGPG3550.pep | FAE1_CUT1_RppA::ACP_syn_III_C | 81-370::384-468 |

TABLE 20-continued

| PEP Seq ID No. | Construct ID | Pfam_module | Position |
|---|---|---|---|
| 1000 | CGPG3551.pep | Pkinase | 9-273 |
| 1001 | CGPG3552.pep | Aldedh | 23-441 |
| 1002 | CGPG3572.pep | FA_hydroxylase | 112-225 |
| 1004 | CGPG3599.pep | DUF579 | 51-289 |
| 1008 | CGPG364.pep | zf-C3HC4 | 97-137 |
| 1010 | CGPG3679.pep | malic::Malic_M::PTA_PTB | 36-179::181-418::446-768 |
| 1011 | CGPG3686.pep | Gp_dh_N::Gp_dh_C | 2-150::155-312 |
| 1012 | CGPG3694.pep | LRRNT_2::LRR_1::LRR_1::LRR_1::LRR_1::Pkinase_Tyr | 38-78::106-128::130-152::154-176::178-201::312-583 |
| 1013 | CGPG3696.pep | MMR_HSR1 | 136-257 |
| 1014 | CGPG3698.pep | WD40::WD40 | 104-142::234-272 |
| 1015 | CGPG3699.pep | adh_short | 19-187 |
| 1016 | CGPG3702.pep | SAM_1 | 228-291 |
| 1017 | CGPG3703.pep | ENOD93 | 25-103 |
| 1018 | CGPG3707.pep | Pkinase | 42-333 |
| 1019 | CGPG3710.pep | VQ | 118-148 |
| 1020 | CGPG3730.pep | DUF167 | 140-216 |
| 1021 | CGPG3731.pep | DUF616 | 194-508 |
| 1022 | CGPG3734.pep | PRK::Pribosyltran | 46-233::280-425 |
| 1023 | CGPG3745.pep | RRM_1::RRM_1 | 386-455::481-553 |
| 1024 | CGPG3764.pep | Response_reg | 20-145 |
| 1026 | CGPG3851.pep | SH3_1 | 284-338 |
| 1027 | CGPG3911.pep | Aldedh | 104-587 |
| 1028 | CGPG3948.pep | NAP | 50-295 |
| 1031 | CGPG3996.pep | Inositol_P | 6-267 |
| 1032 | CGPG4006.pep | ENT | 1-74 |
| 1033 | CGPG4025.pep | SQS_PSY | 44-331 |
| 1034 | CGPG4028.pep | Transket_pyr::Transketolase_C | 398-565::579-702 |
| 1035 | CGPG403.pep | Pkinase | 78-336 |
| 1036 | CGPG4041.pep | DEAD::Helicase_C | 141-315::386-462 |
| 1037 | CGPG4078.pep | GST_C | 180-283 |
| 1038 | CGPG4079.pep | RRS1 | 1-178 |
| 1041 | CGPG4104.pep | LRRNT_2::LRR_1::LRR_1::LRR_1::LRR_1::Pkinase | 30-67::95-117::119-141::143-165::167-188::367-633 |
| 1042 | CGPG4127.pep | Hydrolase | 43-239 |
| 1043 | CGPG4135.pep | Pkinase::efhand::efhand::efhand::efhand | 118-376::423-451::459-487::495-523::529-557 |
| 1044 | CGPG4161.pep | Methyltransf_11 | 56-159 |
| 1045 | CGPG4180.pep | GHMP_kinases_N::GHMP_kinases_C | 152-219::382-466 |
| 1046 | CGPG4191.pep | Bombesin | 163-176 |
| 1047 | CGPG4199.pep | Copine::zf-C3HC4 | 117-265::385-417 |
| 1048 | CGPG4241.pep | GASA | 3-99 |
| 1049 | CGPG427.pep | Pkinase_Tyr | 8-262 |
| 1050 | CGPG4273.pep | dsrm::dsrm | 2-68::88-153 |
| 1051 | CGPG4301.pep | 2OG-FeII_Oxy | 151-253 |
| 1052 | CGPG4303.pep | Rhodanese | 13-114 |
| 1053 | CGPG4313.pep | G6PD_N::G6PD_C | 94-273::276-573 |
| 1054 | CGPG4314.pep | AWPM-19 | 15-156 |
| 1055 | CGPG4329.pep | AA_kinase | 86-324 |
| 1056 | CGPG4330.pep | PALP | 53-341 |
| 1057 | CGPG4338.pep | Proteasome | 21-217 |
| 1058 | CGPG4341.pep | Mito_carr::Mito_carr::Mito_carr | 51-134::158-246::252-343 |
| 1061 | CGPG4386.pep | GHMP_kinases_N::GHMP_kinases_C | 113-171::245-338 |
| 1062 | CGPG4394.pep | p450 | 39-503 |
| 1063 | CGPG4396.pep | p450 | 39-504 |
| 1064 | CGPG4400.pep | p450 | 32-474 |
| 1065 | CGPG4401.pep | p450 | 47-511 |
| 1066 | CGPG441.pep | Chalcone | 14-225 |
| 1067 | CGPG4413.pep | p450 | 32-547 |
| 1068 | CGPG4427.pep | p450 | 57-530 |
| 1069 | CGPG4446.pep | p450 | 43-504 |
| 1070 | CGPG4448.pep | p450 | 32-486 |
| 1071 | CGPG4474.pep | Band_7 | 33-212 |
| 1072 | CGPG4482.pep | peroxidase | 47-291 |
| 1073 | CGPG4511.pep | VHS::GAT | 36-166::227-315 |
| 1074 | CGPG4517.pep | Aldo_ket_red | 5-292 |
| 1075 | CGPG4551.pep | XS::XH | 30-148::418-557 |
| 1077 | CGPG4567.pep | SRF-TF | 3-53 |
| 1078 | CGPG4586.pep | RRM_1 | 8-73 |
| 1079 | CGPG4600.pep | zf-CCCH::zf-CCCH | 13-39::149-174 |
| 1080 | CGPG4631.pep | C1_2::C1_2::C1_3::C1_2::C1_3::C1_2 | 88-115::209-237::264-292::319-349::404-433::566-595 |
| 1081 | CGPG4642.pep | Pyridoxal_deC | 63-412 |
| 1082 | CGPG4645.pep | Cu-oxidase_3::Cu-oxidase::Cu-oxidase_2 | 31-148::157-325::414-551 |

TABLE 20-continued

| PEP Seq ID No. | Construct ID | Pfam_module | Position |
|---|---|---|---|
| 1083 | CGPG4646.pep | efhand_like::PI-PLC-X::PI-PLC-Y::C2 | 27-105::108-251::332-450::471-563 |
| 1084 | CGPG4649.pep | SMP::SMP::SMP | 14-72::130-191::195-256 |
| 1085 | CGPG4653.pep | DUF1637 | 47-280 |
| 1087 | CGPG4668.pep | SYF2 | 140-306 |
| 1088 | CGPG469.pep | tRNA-synt_1c::tRNA-synt_1c_C | 213-518::520-697 |
| 1089 | CGPG4708.pep | Sulfate_transp::STAS | 172-482::505-623 |
| 1090 | CGPG4712.pep | Mem_trans | 9-565 |
| 1091 | CGPG4714.pep | DUF231 | 248-423 |
| 1092 | CGPG4719.pep | Response_reg::CCT | 37-153::417-461 |
| 1093 | CGPG473.pep | Peptidase_M16::Peptidase_M16_C | 88-234::239-423 |
| 1094 | CGPG4734.pep | Auxin_inducible | 19-119 |
| 1095 | CGPG4736.pep | Pribosyltran | 225-358 |
| 1096 | CGPG474.pep | Pro_isomerase | 6-172 |
| 1102 | CGPG4850.pep | PMEI | 25-174 |
| 1103 | CGPG4868.pep | PsbW | 1-133 |
| 1104 | CGPG4871.pep | Tryp_alpha_amyl | 52-133 |
| 1105 | CGPG488.pep | Histone | 19-92 |
| 1106 | CGPG4908.pep | WD40::WD40 | 16-54::63-101 |
| 1108 | CGPG4921.pep | WD40::WD40::WD40::WD40::WD40 | 202-241::253-291::295-333::337-375::472-510 |
| 1109 | CGPG4954.pep | LRRNT_2::LRR_1::LRR_1::LRR_1 | 33-72::76-98::100-122::124-145 |
| 1110 | CGPG4956.pep | Asp | 141-482 |
| 1111 | CGPG4959.pep | adh_short | 15-183 |
| 1112 | CGPG4965.pep | zf-A20::zf-AN1 | 15-39::114-154 |
| 1113 | CGPG4970.pep | GASA | 1-108 |
| 1114 | CGPG4980.pep | U-box::Arm::Arm | 73-147::246-287::288-328 |
| 1115 | CGPG4982.pep | F-box::FBA_1 | 2-49::209-387 |
| 1116 | CGPG4985.pep | CPSase_sm_chain::GATase | 56-203::245-422 |
| 1117 | CGPG4990.pep | LRRNT_2::LRR_1::LRR_1::LRR_1::LRR_1::LRR_1 | 73-112::139-161::163-183::187-206::210-232::306-328 |
| 1118 | CGPG4991.pep | PALP | 164-473 |
| 1119 | CGPG5007.pep | adh_short | 21-192 |
| 1120 | CGPG5015.pep | adh_short | 13-126 |
| 1121 | CGPG5026.pep | adh_short | 46-221 |
| 1122 | CGPG5029.pep | adh_short | 80-252 |
| 1123 | CGPG5046.pep | LRRNT_2::LRR_1::LRR_1::LRR_1::Pkinase | 30-70::99-121::123-145::147-169::306-573 |
| 1124 | CGPG508.pep | Na_sulph_symp | 93-563 |
| 1125 | CGPG5103.pep | C2 | 9-95 |
| 1126 | CGPG511.pep | Rho_GDI | 22-222 |
| 1127 | CGPG5121.pep | efhand_like::PI-PLC-X::PI-PLC-Y::C2 | 30-113::116-258::331-449::470-562 |
| 1128 | CGPG5126.pep | peroxidase | 54-303 |
| 1129 | CGPG5136.pep | p450 | 35-500 |
| 1130 | CGPG5146.pep | p450 | 45-501 |
| 1131 | CGPG5149.pep | p450 | 31-478 |
| 1132 | CGPG5181.pep | Pkinase | 278-540 |
| 1133 | CGPG52.pep | Sugar_tr | 32-472 |
| 1134 | CGPG5206.pep | UDPG_MGDP_dh_N::UDPG_MGDP_dh::UDPG_MGDP_dh_C | 2-200::209-306::328-452 |
| 1136 | CGPG5232.pep | Pkinase | 71-328 |
| 1137 | CGPG5239.pep | Copine | 136-284 |
| 1138 | CGPG5246.pep | ABC_tran::ABC_tran | 94-285::406-571 |
| 1139 | CGPG525.pep | CDP-OH_P_transf | 138-277 |
| 1140 | CGPG5268.pep | CDC50 | 65-368 |
| 1141 | CGPG5272.pep | AA_permease | 153-621 |
| 1142 | CGPG5333.pep | MBS_1 | 55-468 |
| 1143 | CGPG5338.pep | RRM_1::RRM_1 | 8-77::108-178 |
| 1144 | CGPG5341.pep | F-box | 33-79 |
| 1145 | CGPG5369.pep | AA_kinase::ACT::ACT | 83-366::400-469::477-539 |
| 1146 | CGPG5372.pep | SBF | 142-322 |
| 1147 | CGPG5380.pep | Tyr-DNA_phospho | 137-581 |
| 1148 | CGPG5386.pep | MOSC_N::MOSC | 4-132::138-296 |
| 1149 | CGPG5396.pep | PALP | 9-297 |
| 1150 | CGPG5397.pep | PDT | 128-307 |
| 1151 | CGPG5421.pep | Pre-SET::SET | 119-267::269-414 |
| 1152 | CGPG5433.pep | MtN3_slv::MtN3_slv | 10-98::132-218 |
| 1153 | CGPG5439.pep | LANC_like | 69-410 |
| 1154 | CGPG5453.pep | Mito_carr::Mito_carr::Mito_carr | 14-116::125-215::233-334 |
| 1155 | CGPG5456.pep | Mito_carr::Mito_carr::Mito_carr | 78-175::183-279::283-373 |

TABLE 20-continued

| PEP Seq ID No. | Construct ID | Pfam_module | Position |
|---|---|---|---|
| 1156 | CGPG5483.pep | PP2C | 66-369 |
| 1157 | CGPG5492.pep | FAE1_CUT1_RppA::ACP_syn_III_C | 61-358::372-456 |
| 1158 | CGPG5508.pep | RCC1::RCC_1::RCC_1::RCC_1::FYVE::DZC | 310-359::413-462::478-526::582-630::633-701::967-1002 |
| 1159 | CGPG5520.pep | TFIID-31kDa | 19-152 |
| 1160 | CGPG5525.pep | PRMT5 | 187-679 |
| 1161 | CGPG5526.pep | Pkinase | 8-295 |
| 1162 | CGPG5530.pep | Response_reg | 504-644 |
| 1163 | CGPG5534.pep | Y_phosphatase2 | 3-169 |
| 1164 | CGPG5537.pep | TBP::TBP | 62-147::152-238 |
| 1165 | CGPG5545.pep | CBS::CBS | 35-175::193-318 |
| 1166 | CGPG555.pep | PALP::Thr_dehydrat_C::Thr_dehydrat_C | 104-396::409-498::504-591 |
| 1167 | CGPG5558.pep | Cyclin_N::Cyclin_C | 212-337::339-458 |
| 1168 | CGPG5559.pep | Suc_Fer-like | 69-311 |
| 1169 | CGPG5562.pep | Suc_Fer-like | 59-308 |
| 1170 | CGPG5592.pep | Rho_GDI | 35-239 |
| 1171 | CGPG5625.pep | LRR_1::LRR_1::Pkinase | 433-455::457-476::586-854 |
| 1172 | CGPG5631.pep | WAK::Pkinase | 171-270::390-658 |
| 1173 | CGPG5632.pep | Aldedh | 29-491 |
| 1174 | CGPG5636.pep | Aldedh | 15-476 |
| 1175 | CGPG5637.pep | Aldedh | 32-493 |
| 1176 | CGPG564.pep | Aminotran_3 | 80-413 |
| 1177 | CGPG5641.pep | Aldedh | 14-472 |
| 1178 | CGPG5650.pep | Aminotran_3 | 32-374 |
| 1179 | CGPG5653.pep | Aminotran_1_2 | 32-383 |
| 1180 | CGPG5657.pep | Aldedh | 15-474 |
| 1181 | CGPG5671.pep | Gp_dh_N::Gp_dh_C | 3-151::156-313 |
| 1182 | CGPG5672.pep | Glutaminase | 24-309 |
| 1183 | CGPG5677.pep | PGAM | 4-165 |
| 1184 | CGPG5678.pep | Aminotran_1_2 | 35-385 |
| 1185 | CGPG5679.pep | TIM | 7-248 |
| 1186 | CGPG5682.pep | Aminotran_3 | 31-384 |
| 1187 | CGPG5691.pep | PK::PK_C | 5-350::362-478 |
| 1188 | CGPG5699.pep | Gp_dh_N::Gp_dh_C | 3-155::160-316 |
| 1189 | CGPG5705.pep | NDK | 3-137 |
| 1190 | CGPG5722.pep | Pyrophosphatase | 17-175 |
| 1191 | CGPG5734.pep | Cyclin_N::Cyclin_C | 232-357::359-478 |
| 1192 | CGPG5736.pep | PP2C | 22-280 |
| 1193 | CGPG5744.pep | CDC50 | 63-365 |
| 1194 | CGPG5747.pep | Pkinase | 23-318 |
| 1195 | CGPG5748.pep | NAD_Gly3P_dh_N::NAD_Gly3P_dh_C | 84-259::282-432 |
| 1198 | CGPG577.pep | Thioredoxin | 7-111 |
| 1199 | CGPG5780.pep | AA_permease | 68-517 |
| 1200 | CGPG5793.pep | AA_permease | 285-815 |
| 1201 | CGPG5795.pep | Sugar_tr | 123-565 |
| 1202 | CGPG5796.pep | Sugar_tr | 43-466 |
| 1203 | CGPG5800.pep | AA_permease | 86-546 |
| 1204 | CGPG5812.pep | Pkinase | 22-273 |
| 1205 | CGPG5815.pep | Pkinase | 9-272 |
| 1206 | CGPG5838.pep | Pkinase | 1-264 |
| 1207 | CGPG5844.pep | Pkinase | 78-351 |
| 1208 | CGPG5846.pep | Pkinase | 99-376 |
| 1209 | CGPG5851.pep | Pkinase | 121-401 |
| 1210 | CGPG5857.pep | Pkinase | 19-273 |
| 1211 | CGPG5862.pep | Pkinase | 181-447 |
| 1212 | CGPG5863.pep | Pkinase | 52-330 |
| 1213 | CGPG5867.pep | Pkinase | 142-423 |
| 1214 | CGPG5872.pep | Pkinase | 18-288 |
| 1215 | CGPG5913.pep | ADH_N::ADH_zinc_N | 28-109::140-284 |
| 1217 | CGPG5961.pep | Biotin_lipoyl::2-oxoacid_dh | 94-167::232-462 |
| 1219 | CGPG5968.pep | Pribosyltran | 36-172 |
| 1220 | CGPG5984.pep | Pkinase | 115-443 |
| 1221 | CGPG5991.pep | LRR_1 | 266-293 |
| 1222 | CGPG6006.pep | RRM_1 | 19-89 |
| 1223 | CGPG6015.pep | La::RRM_1::RRM_3 | 14-85::118-188::302-404 |
| 1224 | CGPG603.pep | G6PD_N::G6PD_C | 35-222::224-508 |
| 1225 | CGPG6046.pep | Str_synth | 179-266 |
| 1226 | CGPG6063.pep | Nramp | 88-451 |
| 1228 | CGPG6092.pep | SRPRB | 53-235 |
| 1229 | CGPG6104.pep | Steroid_dh | 111-262 |
| 1230 | CGPG6106.pep | LEA_5 | 1-92 |
| 1231 | CGPG6111.pep | PP-binding | 48-115 |
| 1232 | CGPG6113.pep | UQ_con | 7-143 |

TABLE 20-continued

| PEP Seq ID No. | Construct ID | Pfam_module | Position |
|---|---|---|---|
| 1234 | CGPG6132.pep | SMP::SMP::SMP | 13-71::135-196::200-262 |
| 1236 | CGPG6147.pep | Redoxin | 74-234 |
| 1237 | CGPG6152.pep | Arf | 5-177 |
| 1238 | CGPG6154.pep | Ion_trans_2::Ion_trans_2 | 122-204::253-328 |
| 1239 | CGPG6170.pep | UQ_con | 19-158 |
| 1240 | CGPG6171.pep | Thioredoxin | 120-227 |
| 1241 | CGPG6177.pep | AIG1 | 39-236 |
| 1242 | CGPG6181.pep | Peptidase_C12 | 2-214 |
| 1243 | CGPG6188.pep | Di19 | 10-217 |
| 1244 | CGPG6202.pep | TB2_DP1_HVA22 | 9-106 |
| 1245 | CGPG6217.pep | MFS_1::Sugar_tr | 40-460::90-507 |
| 1246 | CGPG623.pep | SATase_N::Hexapep::Hexapep::Hexapep | 45-149::203-220::229-246::247-264 |
| 1247 | CGPG6239.pep | Sugar_tr | 27-458 |
| 1248 | CGPG6244.pep | Pkinase | 39-303 |
| 1249 | CGPG6254.pep | Pkinase::NAF | 12-264::292-352 |
| 1251 | CGPG627.pep | His_biosynth | 48-289 |
| 1252 | CGPG6271.pep | Pkinase | 191-527 |
| 1253 | CGPG6278.pep | Pkinase | 86-368 |
| 1254 | CGPG6288.pep | Pkinase_Tyr | 207-463 |
| 1255 | CGPG6309.pep | PRA1 | 29-181 |
| 1256 | CGPG633.pep | DCP1 | 12-134 |
| 1257 | CGPG635.pep | Epimerase | 9-273 |
| 1258 | CGPG6350.pep | LRRNT_2::LRR_1::LRR_1::LRR_1::LRR_1 | 32-78::105-127::129-151::153-175::177-196 |
| 1260 | CGPG6365.pep | Aminotran_1_2 | 32-384 |
| 1261 | CGPG6374.pep | Gln-synt_C | 120-380 |
| 1262 | CGPG6377.pep | PGK | 2-383 |
| 1263 | CGPG638.pep | PA | 51-163 |
| 1264 | CGPG6397.pep | F420_oxidored | 3-246 |
| 1265 | CGPG6398.pep | Enolase_N::Enolase_C | 5-135::140-430 |
| 1266 | CGPG6408.pep | ADH_N::ADH_zinc_N | 25-155::185-350 |
| 1267 | CGPG6415.pep | NTP_transferase | 4-271 |
| 1268 | CGPG6421.pep | ADH_N::ADH_zinc_N | 25-148::179-318 |
| 1269 | CGPG6442.pep | iPGM_N::Metalloenzyme | 2-363::373-488 |
| 1270 | CGPG6443.pep | PGK | 1-391 |
| 1271 | CGPG6446.pep | PK::PK_C | 106-453::467-587 |
| 1272 | CGPG6453.pep | Aminotran_1_2 | 41-402 |
| 1273 | CGPG6466.pep | ADH_N::ADH_zinc_N | 27-153::184-322 |
| 1274 | CGPG6467.pep | Aminotran_3 | 19-366 |
| 1275 | CGPG6470.pep | PfkB | 1-302 |
| 1276 | CGPG6475.pep | NTP_transferase | 10-282 |
| 1277 | CGPG6477.pep | NDK | 4-138 |
| 1278 | CGPG6478.pep | PfkB | 1-308 |
| 1279 | CGPG6493.pep | AA_permease | 94-561 |
| 1280 | CGPG6506.pep | Asparaginase | 140-457 |
| 1281 | CGPG6518.pep | NAD_binding_2::6PGD | 2-173::177-467 |
| 1282 | CGPG6546.pep | PK::PK_C | 3-348::360-477 |
| 1283 | CGPG6556.pep | Aminotran_1_2 | 124-475 |
| 1284 | CGPG6562.pep | Aminotran_3 | 116-451 |
| 1285 | CGPG6566.pep | NTP_transferase::Hexapep::Hexapep::Hexapep | 95-350::398-415::432-449::460-477 |
| 1286 | CGPG6571.pep | Aldedh | 102-560 |
| 1287 | CGPG6576.pep | Aldedh | 99-565 |
| 1288 | CGPG659.pep | G_glu_transpept | 48-567 |
| 1289 | CGPG6594.pep | Pyr_redox_2::Pyr_redox_dim | 94-419::450-559 |
| 1290 | CGPG6603.pep | Pyr_redox_2::Pyr_redox_dim | 94-397::427-538 |
| 1291 | CGPG6608.pep | Pyr_redox_2::Pyr_redox_dim | 93-394::423-532 |
| 1292 | CGPG6634.pep | DUF177 | 100-252 |
| 1294 | CGPG6667.pep | Invertase_neut | 89-577 |
| 1295 | CGPG6678.pep | Biotin_lipoyl::E3_binding::2-oxoacid_dh | 92-165::225-263::281-512 |
| 1296 | CGPG6695.pep | Pyr_redox_2::Pyr_redox_dim | 97-408::436-545 |
| 1297 | CGPG6699.pep | Ribul_P_3_epim | 94-295 |
| 1298 | CGPG670.pep | Fer2 | 60-135 |
| 1299 | CGPG6705.pep | PK::PK_C::PEP-utilizers | 89-433::445-559::584-663 |
| 1300 | CGPG6735.pep | FBPase | 93-413 |
| 1301 | CGPG6744.pep | Glycolytic | 92-429 |
| 1302 | CGPG6753.pep | Pyr_redox_2 | 236-538 |
| 1303 | CGPG6757.pep | Aminotran_1_2 | 127-473 |
| 1305 | CGPG6806.pep | mTERF | 110-457 |
| 1306 | CGPG6811.pep | GH3 | 10-567 |
| 1308 | CGPG6815.pep | V-ATPase_G | 5-109 |
| 1310 | CGPG6830.pep | Tbf5 | 13-76 |
| 1313 | CGPG6864.pep | DUF620 | 190-438 |

TABLE 20-continued

| PEP Seq ID No. | Construct ID | Pfam_module | Position |
|---|---|---|---|
| 1314 | CGPG6877.pep | Hep_59 | 101-194 |
| 1315 | CGPG6878.pep | Peptidase_M24 | 107-343 |
| 1316 | CGPG6880.pep | PAP_fibrillin | 72-232 |
| 1318 | CGPG6887.pep | AIG2 | 12-111 |
| 1319 | CGPG6895.pep | zf-CCHC::zf-CCHC::zf-CCHC::zf-CCHC | 166-183::208-225::325-342::356-373 |
| 1322 | CGPG6912.pep | zf-DHHC | 149-213 |
| 1324 | CGPG6942.pep | RNA_pol_Rpb5_N::RNA_pol_Rpb5_C | 18-108::149-222 |
| 1327 | CGPG6969.pep | 2OG-FeII_Oxy | 223-323 |
| 1329 | CGPG6991.pep | Glyco_tran_28_C | 11-170 |
| 1332 | CGPG7037.pep | Sad1_UNC | 313-416 |
| 1333 | CGPG7051.pep | PAP_fibrillin | 84-236 |
| 1336 | CGPG7086.pep | SFT2 | 44-163 |
| 1339 | CGPG7136.pep | NOT | 1-72 |
| 1340 | CGPG7147.pep | RAMP4 | 1-64 |
| 1343 | CGPG7222.pep | Branch | 49-274 |
| 1345 | CGPG7233.pep | eIF2A | 214-407 |
| 1346 | CGPG7238.pep | UPF0185 | 5-80 |
| 1347 | CGPG7253.pep | ArfGap | 15-117 |
| 1348 | CGPG7255.pep | Arf | 5-177 |
| 1349 | CGPG7286.pep | ORC2 | 20-345 |
| 1350 | CGPG7292.pep | Methyltransf_11 | 38-135 |
| 1351 | CGPG7301.pep | ELFV_dehydrog_N::ELFV_dehydrog | 57-187::202-445 |
| 1352 | CGPG7305.pep | Pyr_redox_2 | 126-386 |
| 1353 | CGPG7307.pep | Gp_dh_N::Gp_dh_C | 11-163::168-324 |
| 1354 | CGPG7318.pep | M1P | 1-142 |
| 1355 | CGPG7319.pep | SNF5 | 172-400 |
| 1356 | CGPG7345.pep | Lipase_3 | 97-237 |
| 1357 | CGPG7368.pep | MT-A70 | 516-676 |
| 1358 | CGPG7385.pep | FHA | 32-107 |
| 1359 | CGPG7391.pep | G-patch | 6-50 |
| 1360 | CGPG7405.pep | TATA_RF | 1-216 |
| 1361 | CGPG7415.pep | IU_nuc_hydro | 1-312 |
| 1362 | CGPG7416.pep | GLTP | 52-233 |
| 1363 | CGPG7420.pep | PRK | 95-302 |
| 1366 | CGPG7445.pep | PRC::PRC | 92-169::171-252 |
| 1367 | CGPG7465.pep | Aldedh | 103-567 |
| 1368 | CGPG7473.pep | F-box::WD40::WD40::WD40::WD40 | 273-320::412-449::453-493::520-556::560-598 |
| 1369 | CGPG7489.pep | UBX | 295-376 |
| 1370 | CGPG7492.pep | Pescadillo_N::BRCT | 8-291::337-414 |
| 1371 | CGPG7499.pep | G-alpha | 423-839 |
| 1374 | CGPG7508.pep | Smg4_LTPF3 | 1-170 |
| 1375 | CGPG7509.pep | SSB | 76-187 |
| 1376 | CGPG7511.pep | GFA | 31-125 |
| 1377 | CGPG7515.pep | Brix | 45-297 |
| 1378 | CGPG7521.pep | G-alpha | 23-386 |
| 1380 | CGPG7547.pep | PAD_porph | 14-368 |
| 1381 | CGPG7561.pep | Snf7 | 17-187 |
| 1382 | CGPG7562.pep | Sybindin | 6-136 |
| 1383 | CGPG7563.pep | DUF887 | 40-279 |
| 1384 | CGPG7567.pep | Peptidase_M18 | 14-461 |
| 1389 | CGPG7597.pep | zf-AN1 | 76-116 |
| 1390 | CGPG7606.pep | Pentapeptide::Pentapeptide | 127-166::172-211 |
| 1392 | CGPG7637.pep | DAD | 2-112 |
| 1393 | CGPG7649.pep | YgbB | 71-227 |
| 1394 | CGPG7658.pep | Cyclase | 56-256 |
| 1395 | CGPG7664.pep | Aldedh | 9-463 |
| 1396 | CGPG7666.pep | Aminotran_1_2 | 26-392 |
| 1397 | CGPG7668.pep | DUF594 | 660-719 |
| 1399 | CGPG7746.pep | UPF0153 | 49-139 |
| 1400 | CGPG7747.pep | Copine | 113-261 |
| 1401 | CGPG7752.pep | zf-MYND::PDCD2_C | 176-214::241-403 |
| 1403 | CGPG7770.pep | YTH | 263-353 |
| 1406 | CGPG7778.pep | Ubie_methyltran | 51-304 |
| 1407 | CGPG7786.pep | KH_1 | 141-193 |
| 1408 | CGPG7788.pep | YIF1 | 34-263 |
| 1410 | CGPG78.pep | Hpt | 46-132 |
| 1411 | CGPG783.pep | RRM_1::RRM_2 | 288-354::682-778 |
| 1412 | CGPG7832.pep | STT3 | 26-670 |
| 1413 | CGPG7841.pep | ECH::3HCDH_N::3HCDH | 17-186::311-490::492-585 |
| 1414 | CGPG7845.pep | LRRNT_2:LRR_1::LRR_1::LRR_1::LRR_1::LRR_1 | 23-64::97-119::121-143::145-167::169-192::194-216 |
| 1415 | CGPG7847.pep | Peptidase_C48 | 30-225 |

TABLE 20-continued

| PEP Seq ID No. | Construct ID | Pfam_module | Position |
|---|---|---|---|
| 1417 | CGPG7853.pep | LRR_1::LRR_1::LRR_1::LRR_1::LRR_1::LRR_1::LRR_1 | 142-164::166-188::190-212::214-235::258-280::282-304::306-325 |
| 1418 | CGPG7857.pep | Response_reg::CCT | 79-195::689-736 |
| 1420 | CGPG7869.pep | Acyltransferase | 117-264 |
| 1421 | CGPG7891.pep | FMO-like | 11-427 |
| 1422 | CGPG7892.pep | FMO-like | 9-416 |
| 1423 | CGPG7906.pep | Skp1_POZ::Skp1 | 4-65::76-153 |
| 1424 | CGPG7924.pep | AAA | 249-462 |
| 1428 | CGPG7964.pep | IQ::IQ | 108-128::130-150 |
| 1429 | CGPG7968.pep | FMO-like | 13-427 |
| 1431 | CGPG7972.pep | FAD_binding_3 | 5-372 |
| 1432 | CGPG7982.pep | Tetraspannin | 4-241 |
| 1433 | CGPG7985.pep | BT1 | 57-469 |
| 1434 | CGPG7993.pep | F-box::LRR_2 | 27-73::278-304 |
| 1435 | CGPG8.pep | p450 | 39-503 |
| 1436 | CGPG80.pep | Pkinase | 68-328 |
| 1437 | CGPG8001.pep | FMO-like | 13-433 |
| 1438 | CGPG8009.pep | BT1 | 41-511 |
| 1440 | CGPG8049.pep | BT1 | 1-436 |
| 1441 | CGPG806.pep | Synaptobrevin | 127-215 |
| 1442 | CGPG8060.pep | DUF829 | 161-425 |
| 1446 | CGPG81.pep | Pkinase | 70-330 |
| 1452 | CGPG8125.pep | zf-C3HC4 | 46-86 |
| 1453 | CGPG8134.pep | DEK_C::SWIB::SWIB | 3-57::197-272::305-382 |
| 1455 | CGPG8156.pep | PCI | 258-362 |
| 1456 | CGPG8159.pep | ACT::ACT | 77-141::308-374 |
| 1458 | CGPG8179.pep | WD40::WD40 | 138-177::264-305 |
| 1459 | CGPG8193.pep | Ank::Ank | 22-54::55-87 |
| 1460 | CGPG8197.pep | F-box | 5-53 |
| 1461 | CGPG8198.pep | F-box::Kelch_2::Kelch_1::Kelch_2 | 74-119::174-221::223-278::329-369 |
| 1463 | CGPG8211.pep | F-box::WD40::WD40::WD40::WD40::WD40::WD40 | 182-229::292-328::332-368::372-408::411-449::453-538::542-578 |
| 1464 | CGPG823.pep | Ribosomal_S6e | 1-129 |
| 1466 | CGPG8238.pep | PGI | 49-537 |
| 1467 | CGPG8260.pep | Iso_dh | 4-331 |
| 1468 | CGPG8267.pep | Pyridoxal_deC | 34-383 |
| 1469 | CGPG8268.pep | NIR_SIR_ferr::NIR_SIR_::NIR_SIR_ferr | 62-131::164-345::360-432 |
| 1470 | CGPG8274.pep | PK::PK_C | 5-347::363-476 |
| 1471 | CGPG8277.pep | Rib_5-P_isom_A | 55-229 |
| 1472 | CGPG8279.pep | F-box::Kelch_1::Kelch_1 | 22-69::124-168::170-213 |
| 1475 | CGPG8408.pep | DUF641 | 60-192 |
| 1476 | CGPG842.pep | Redoxin | 5-162 |
| 1477 | CGPG8421.pep | NOSIC::Nop | 121-173::213-361 |
| 1478 | CGPG8435.pep | NHL::NHL | 55-82::115-142 |
| 1479 | CGPG8440.pep | U-box::Arm::Arm::Arm::Arm | 242-316::372-413::455-495::496-537::538-578 |
| 1480 | CGPG8453.pep | ACT::ACT::ACT::ACT | 36-99::129-201::265-332::343-406 |
| 1481 | CGPG8470.pep | DUF89 | 18-357 |
| 1482 | CGPG8479.pep | F-box::Kelch_1::Kelch_1 | 31-78::124-170::172-216 |
| 1483 | CGPG8489.pep | F-box::FBA_1 | 3-50::219-384 |
| 1484 | CGPG8498.pep | Fcf1 | 87-185 |
| 1485 | CGPG85.pep | Aa_trans | 19-454 |
| 1486 | CGPG8501.pep | PPR::PPR::PPR::PPR::PPR::PPR | 149-183::189-223::224-258::259-292::330-364::401-435 |
| 1487 | CGPG8507.pep | DUF588 | 31-185 |
| 1488 | CGPG8509.pep | Pro_isomerase | 80-233 |
| 1490 | CGPG8517.pep | B_lectin::S_locus_glycop::PAN_2 | 84-197::211-339::356-422 |
| 1492 | CGPG852.pep | Ribosomal_S5::Ribosomal_S5_C | 94-160::177-250 |
| 1498 | CGPG8567.pep | TB2_DP1_HVA22 | 3-98 |
| 1499 | CGPG8580.pep | Caleosin | 22-195 |
| 1501 | CGPG8590.pep | DUF579 | 42-289 |
| 1503 | CGPG8594.pep | DUF584 | 1-139 |
| 1504 | CGPG8606.pep | Exo_endo_phos | 56-327 |
| 1505 | CGPG8628.pep | DUF584 | 32-203 |
| 1507 | CGPG8654.pep | PPR::PPR | 73-107::141-175 |
| 1508 | CGPG8668.pep | TATA_RF | 1-200 |
| 1511 | CGPG8702.pep | RPE65 | 50-622 |
| 1514 | CGPG8748.pep | AAA | 201-357 |

TABLE 20-continued

| PEP Seq ID No. | Construct ID | Pfam_module | Position |
|---|---|---|---|
| 1516 | CGPG8770.pep | DUF543 | 1-73 |
| 1517 | CGPG8777.pep | DUF569::DUF569 | 1-144::227-368 |
| 1519 | CGPG8786.pep | DUF260 | 13-113 |
| 1520 | CGPG8792.pep | Abhydrolase_3 | 75-290 |
| 1521 | CGPG8801.pep | PPR::PPR::PPR::PPR::PPR::PPR::PPR | 110-144::145-179::181-215::216-250::251-285::286-320::321-355 |
| 1522 | CGPG8809.pep | Ribosomal_L12 | 141-208 |
| 1523 | CGPG8840.pep | CEP_protease | 115-289 |
| 1524 | CGPG8850.pep | PPR::PPR::PPR::PPR::PPR::PPR::PPR::PPR:PPR | 189-223::224-258::297-331::332-366::367-401::402-436::437-470::471-505::506-540::542-576 |
| 1525 | CGPG8870.pep | Fructosamin_kin | 54-339 |
| 1526 | CGPG8871.pep | DUF59 | 36-115 |
| 1527 | CGPG8872.pep | RRM_1::RRM_1::RRM_1 | 138-205::214-288::308-378 |
| 1528 | CGPG8876.pep | SFT2 | 43-162 |
| 1529 | CGPG8902.pep | RNA_pol_I_A49 | 31-415 |
| 1530 | CGPG8904.pep | G-alpha | 103-447 |
| 1531 | CGPG8907.pep | DnaJ::zf-C2H2 | 4-67::338-362 |
| 1532 | CGPG8914.pep | Whi5 | 181-205 |
| 1533 | CGPG8931.pep | eIF3_subunit | 1-231 |
| 1534 | CGPG8933.pep | MACPF | 126-322 |
| 1535 | CGPG8935.pep | Pkinase | 33-324 |
| 1536 | CGPG8938.pep | Pkinase | 71-348 |
| 1537 | CGPG8944.pep | PH | 31-134 |
| 1538 | CGPG895.pep | DUF231 | 251-427 |
| 1540 | CGPG8961.pep | Dus | 59-392 |
| 1541 | CGPG8963.pep | Pkinase | 319-612 |
| 1542 | CGPG898.pep | DUF231 | 276-448 |
| 1543 | CGPG8993.pep | AAA::Rep_fac_C | 44-226::237-326 |
| 1544 | CGPG8994.pep | Brix | 86-262 |
| 1545 | CGPG8995.pep | Porin_3 | 54-326 |
| 1546 | CGPG90.pep | MFS_1 | 68-427 |
| 1547 | CGPG900.pep | DUF231 | 241-420 |
| 1548 | CGPG9002.pep | CTP_transf_1 | 51-382 |
| 1549 | CGPG9009.pep | Alg6_Alg8 | 22-514 |
| 1550 | CGPG9011.pep | OTCace_N::OTCace | 70-212::216-369 |
| 1551 | CGPG9012.pep | FolB | 16-129 |
| 1552 | CGPG9017.pep | DMRL_synthase | 70-213 |
| 1553 | CGPG9025.pep | Glyco_transf_29 | 105-355 |
| 1554 | CGPG9026.pep | Adap_comp_sub | 160-428 |
| 1555 | CGPG9032.pep | RNase_PH::RNase_PH_C | 33-165::194-262 |
| 1556 | CGPG9040.pep | Sec1 | 35-592 |
| 1557 | CGPG9044.pep | Syntaxin::SNARE | 57-163::256-318 |
| 1558 | CGPG9048.pep | RNase_PH | 15-135 |
| 1559 | CGPG9049.pep | Glycos_transf_1 | 244-442 |
| 1560 | CGPG9058.pep | RNA_pol_N | 1-60 |
| 1561 | CGPG906.pep | PPR::PPR | 210-244::245-279 |
| 1562 | CGPG9070.pep | ATP-synt_C::ATP-synt_C | 20-85::104-169 |
| 1564 | CGPG9084.pep | CH::EB1 | 15-116::209-255 |
| 1566 | CGPG9098.pep | DUF6::DUF6 | 32-165::208-337 |
| 1567 | CGPG9099.pep | Rick_17kDa_Anti | 66-110 |
| 1568 | CGPG9110.pep | RALF | 53-118 |
| 1569 | CGPG9119.pep | PTR2 | 115-504 |
| 1570 | CGPG9125.pep | ThiF | 98-233 |
| 1571 | CGPG913.pep | PPR::PPR::PPR::PPR::PPR::PPR | 86-120::188-222::223-257::289-323::325-358::361-395 |
| 1574 | CGPG9164.pep | DHBP_synthase::GTP_cyclohydro2 | 5-202::207-377 |
| 1575 | CGPG9172.pep | Sec61_beta | 32-77 |
| 1577 | CGPG9185.pep | DUF423 | 10-115 |
| 1578 | CGPG9187.pep | Pkinase | 12-263 |
| 1579 | CGPG9190.pep | DREPP | 2-203 |
| 1580 | CGPG9193.pep | GATase::GMP_synt_C | 11-196::432-524 |
| 1581 | CGPG9195.pep | DUF1279 | 91-193 |
| 1582 | CGPG9203.pep | Na_H_Exchanger::TrkA_C | 13-391::418-486 |
| 1583 | CGPG9209.pep | GATase::GMP_synt_C | 9-197::423-515 |
| 1585 | CGPG9210.pep | Na_H_Exchanger::TrkA_N | 10-376::402-517 |
| 1586 | CGPG9211.pep | NTP_transferase::MannoseP_isomer | 7-296::307-473 |
| 1587 | CGPG9212.pep | ATP-synt_ab_N::ATP-synt_ab | 22-87::143-353 |
| 1588 | CGPG9216.pep | DHBP_synthase::GTP_cyclohydro2 | 10-206::211-379 |
| 1589 | CGPG9226.pep | Carboxyl_trans | 40-541 |
| 1590 | CGPG9252.pep | CDC48_N::AAA::AAA | 28-114::245-429::518-705 |
| 1592 | CGPG9289.pep | LSM | 10-75 |
| 1593 | CGPG9298.pep | p450 | 41-516 |

TABLE 20-continued

| PEP Seq ID No. | Construct ID | Pfam_module | Position |
|---|---|---|---|
| 1594 | CGPG9299.pep | ThiF | 82-227 |
| 1597 | CGPG9316.pep | ATP-grasp_2::Ligase_CoA | 34-242::285-421 |
| 1598 | CGPG9317.pep | DUF163 | 43-196 |
| 1599 | CGPG9318.pep | Aldo_ket_red | 20-285 |
| 1600 | CGPG9324.pep | Pkinase | 158-706 |
| 1601 | CGPG9357.pep | Raffinose_syn | 7-757 |
| 1602 | CGPG965.pep | Hexapep::Hexapep::Hexapep::Hexapep | 70-87::119-136::142-159::160-177 |
| 1603 | CGPG970.pep | NPH3 | 206-441 |
| 1604 | CGPG982.pep | p450 | 29-495 |
| 1605 | CGPG994.pep | adh_short | 50-218 |
| 1606 | CGPG996.pep | DUF866 | 1-167 |

TABLE 21

| PEP Seq ID No. | Construct ID | Pfam domain name | Begin | Stop | score | E-value |
|---|---|---|---|---|---|---|
| 806 | CGPG1023.pep | Na_Ca_ex | 104 | 255 | 94.2 | 4.10E-25 |
| 806 | CGPG1023.pep | Na_Ca_ex | 299 | 432 | 128.4 | 2.10E-35 |
| 807 | CGPG1038.pep | DUF1475 | 1 | 256 | 709.5 | 2.40E-210 |
| 812 | CGPG1113.pep | DUF1350 | 49 | 370 | 64.5 | 3.50E-16 |
| 814 | CGPG1163.pep | DSPc | 49 | 182 | 103 | 9.00E-28 |
| 817 | CGPG1205.pep | Arm | 94 | 134 | 37.2 | 5.90E-08 |
| 817 | CGPG1205.pep | Arm | 135 | 175 | 32.9 | 1.10E-06 |
| 817 | CGPG1205.pep | Arm | 176 | 216 | 31.7 | 2.60E-06 |
| 817 | CGPG1205.pep | Arm | 258 | 298 | 18.8 | 0.02 |
| 818 | CGPG1207.pep | NifU_N | 26 | 105 | 78.3 | 2.60E-20 |
| 820 | CGPG1223.pep | ATP_bind_1 | 7 | 250 | 425.9 | 5.70E-125 |
| 821 | CGPG1250.pep | DUF822 | 12 | 160 | 323.6 | 3.70E-94 |
| 824 | CGPG1319.pep | DUF599 | 10 | 233 | 464.2 | 1.70E-136 |
| 826 | CGPG1329.pep | Cullin | 29 | 631 | 966.3 | 1.20E-287 |
| 827 | CGPG133.pep | Cyclin_N | 168 | 293 | 232.6 | 9.20E-67 |
| 827 | CGPG133.pep | Cyclin_C | 295 | 422 | 170.5 | 4.50E-48 |
| 828 | CGPG1332.pep | Cullin | 12 | 646 | 709.1 | 3.20E-210 |
| 829 | CGPG1343.pep | LRR_1 | 389 | 412 | 9.2 | 6 |
| 830 | CGPG1348.pep | Lectin_legB | 27 | 248 | 295 | 1.40E-85 |
| 830 | CGPG1348.pep | Pkinase | 334 | 604 | 170.2 | 5.30E-48 |
| 830 | CGPG1348.pep | Pkinase_Tyr | 334 | 604 | 134.8 | 2.50E-37 |
| 831 | CGPG1349.pep | B_lectin | 65 | 171 | 95.8 | 1.30E-25 |
| 831 | CGPG1349.pep | S_locus_glycop | 180 | 312 | 105 | 2.40E-28 |
| 831 | CGPG1349.pep | PAN_1 | 327 | 404 | 38.5 | 2.40E-08 |
| 831 | CGPG1349.pep | Pkinase | 484 | 731 | 167.1 | 4.70E-47 |
| 831 | CGPG1349.pep | Pkinase_Tyr | 484 | 731 | 89.6 | 1.00E-23 |
| 832 | CGPG1373.pep | Pkinase | 12 | 291 | 356.7 | 3.80E-104 |
| 833 | CGPG1377.pep | Pkinase | 4 | 258 | 247.3 | 3.30E-71 |
| 834 | CGPG1412.pep | TPP_enzyme_N | 45 | 221 | 286.5 | 5.40E-83 |
| 834 | CGPG1412.pep | TPP_enzyme_M | 243 | 376 | 82.9 | 1.00E-21 |
| 834 | CGPG1412.pep | TPP_enzyme_C | 431 | 578 | 35 | 3.50E-09 |
| 835 | CGPG1421.pep | Biotin_lipoyl | 76 | 149 | 85.1 | 2.30E-22 |
| 835 | CGPG1421.pep | E3_binding | 180 | 218 | 58.5 | 2.20E-14 |
| 835 | CGPG1421.pep | 2-oxoacid_dh | 249 | 480 | 358.5 | 1.10E-104 |
| 836 | CGPG1426.pep | Aminotran_1_2 | 48 | 432 | 525 | 8.50E-155 |
| 837 | CGPG1433.pep | HI0933_like | 44 | 365 | -247.2 | 0.002 |
| 837 | CGPG1433.pep | GIDA | 45 | 369 | -206 | 0.00022 |
| 837 | CGPG1433.pep | Pyr_redox_2 | 45 | 359 | 241.5 | 1.90E-69 |
| 837 | CGPG1433.pep | Pyr_redox | 216 | 313 | 115.7 | 1.40E-31 |
| 837 | CGPG1433.pep | Pyr_redox_dim | 388 | 497 | 213.1 | 6.50E-61 |
| 838 | CGPG1453.pep | malic | 171 | 360 | 412.3 | 7.10E-121 |
| 838 | CGPG1453.pep | Malic_M | 362 | 615 | 468.8 | 7.10E-138 |
| 839 | CGPG1454.pep | Ribul_P_3_epim | 7 | 207 | 331.5 | 1.50E-96 |
| 840 | CGPG1463.pep | Alpha-amylase | 26 | 361 | 224.3 | 2.80E-64 |
| 840 | CGPG1463.pep | Alpha-amyl_C2 | 362 | 422 | 132.9 | 9.40E-37 |
| 841 | CGPG1464.pep | Glycolytic | 11 | 358 | 852.5 | 2.20E-253 |
| 842 | CGPG1471.pep | IF4E | 1 | 198 | 287.7 | 2.20E-83 |
| 843 | CGPG1481.pep | Pkinase | 4 | 260 | 292.7 | 7.40E-85 |
| 844 | CGPG1499.pep | PPDK_N | 85 | 445 | 654.8 | 6.90E-194 |
| 844 | CGPG1499.pep | PEP-utilizers | 496 | 586 | 165.9 | 1.10E-46 |
| 844 | CGPG1499.pep | PEP-utilizers_C | 598 | 955 | 688.7 | 4.30E-204 |
| 845 | CGPG150.pep | p450 | 30 | 507 | 128 | 2.80E-35 |
| 846 | CGPG1536.pep | CRAL_TRIO_N | 73 | 142 | 46.4 | 1.00E-10 |
| 846 | CGPG1536.pep | CRAL_TRIO | 159 | 345 | 145.1 | 2.00E-40 |
| 847 | CGPG1539.pep | UPF0139 | 8 | 107 | 215.9 | 9.60E-62 |
| 848 | CGPG155.pep | GlutR_N | 100 | 251 | 288.2 | 1.70E-83 |
| 848 | CGPG155.pep | Shikimate_DH | 255 | 407 | 208.3 | 1.80E-59 |

TABLE 21-continued

| PEP Seq ID No. | Construct ID | Pfam domain name | Begin | Stop | score | E-value |
|---|---|---|---|---|---|---|
| 848 | CGPG155.pep | GlutR_dimer | 420 | 526 | 180.6 | 4.10E−51 |
| 849 | CGPG1583.pep | PLAC8 | 88 | 187 | 176.8 | 5.40E−50 |
| 850 | CGPG1588.pep | PLAC8 | 75 | 214 | 156.3 | 8.30E−44 |
| 851 | CGPG16.pep | MIP | 14 | 235 | 396.7 | 3.60E−116 |
| 852 | CGPG1609.pep | MMR_HSR1 | 54 | 190 | 118.9 | 1.50E−32 |
| 852 | CGPG1609.pep | DUF933 | 337 | 420 | 205.4 | 1.40E−58 |
| 853 | CGPG1629.pep | WD40 | 262 | 301 | 31.1 | 4.20E−06 |
| 853 | CGPG1629.pep | WD40 | 307 | 346 | 36 | 1.30E−07 |
| 853 | CGPG1629.pep | WD40 | 356 | 395 | 41.3 | 3.50E−09 |
| 854 | CGPG1637.pep | DUF220 | 163 | 262 | 148.5 | 1.80E−41 |
| 855 | CGPG1653.pep | TBC | 200 | 415 | −15 | 1.60E−06 |
| 856 | CGPG1658.pep | Nodulin-like | 14 | 260 | 516.4 | 3.30E−152 |
| 857 | CGPG1663.pep | MFS_1 | 22 | 387 | 26.3 | 0.00011 |
| 857 | CGPG1663.pep | BT1 | 30 | 441 | 633.5 | 1.90E−187 |
| 858 | CGPG1682.pep | OPT | 62 | 685 | 688.8 | 4.20E−204 |
| 859 | CGPG1701.pep | Glyco_transf_8 | 76 | 299 | 13.5 | 1.90E−07 |
| 861 | CGPG1724.pep | Per1 | 63 | 334 | 669.6 | 2.50E−198 |
| 862 | CGPG1726.pep | DUF607 | 111 | 291 | 388.6 | 9.80E−114 |
| 863 | CGPG1736.pep | Usp | 1 | 148 | 64.9 | 2.70E−16 |
| 864 | CGPG1741.pep | mTERF | 279 | 627 | 84.1 | 4.40E−22 |
| 865 | CGPG1783.pep | PB1 | 42 | 132 | 85 | 2.40E−22 |
| 866 | CGPG1790.pep | PB1 | 59 | 153 | 109.6 | 9.20E−30 |
| 868 | CGPG1845.pep | TFIID-18 kDa | 29 | 119 | 145.5 | 1.50E−40 |
| 869 | CGPG1855.pep | CAF1 | 3 | 227 | 330.9 | 2.30E−96 |
| 870 | CGPG1870.pep | Pkinase | 406 | 572 | 74.8 | 2.90E−19 |
| 871 | CGPG1879.pep | Pkinase | 21 | 277 | 357.5 | 2.30E−104 |
| 871 | CGPG1879.pep | Pkinase_Tyr | 21 | 275 | 88.2 | 2.60E−23 |
| 871 | CGPG1879.pep | NAF | 303 | 364 | 98.7 | 1.80E−26 |
| 872 | CGPG1886.pep | Pkinase | 26 | 325 | 337.3 | 2.70E−98 |
| 873 | CGPG1903.pep | F-box | 320 | 367 | 41 | 4.30E−09 |
| 874 | CGPG1905.pep | F-box | 4 | 51 | 41.7 | 2.60E−09 |
| 874 | CGPG1905.pep | Kelch_2 | 104 | 150 | 27.4 | 5.30E−05 |
| 874 | CGPG1905.pep | Kelch_2 | 255 | 306 | 41.6 | 2.80E−09 |
| 875 | CGPG1914.pep | F-box | 42 | 89 | 39.8 | 9.50E−09 |
| 875 | CGPG1914.pep | Kelch_2 | 170 | 215 | 26.3 | 0.00011 |
| 875 | CGPG1914.pep | Kelch_1 | 170 | 215 | 52.2 | 1.80E−12 |
| 875 | CGPG1914.pep | Kelch_2 | 217 | 266 | 31.3 | 3.60E−06 |
| 875 | CGPG1914.pep | Kelch_1 | 217 | 266 | 59.1 | 1.50E−14 |
| 876 | CGPG193.pep | WD40 | 167 | 205 | 28.5 | 2.40E−05 |
| 876 | CGPG193.pep | WD40 | 268 | 307 | 24.4 | 0.00041 |
| 876 | CGPG193.pep | WD40 | 318 | 355 | 25.1 | 0.00026 |
| 876 | CGPG193.pep | WD40 | 363 | 401 | 39.3 | 1.40E−08 |
| 877 | CGPG1939.pep | F-box | 66 | 113 | 36.2 | 1.20E−07 |
| 877 | CGPG1939.pep | WD40 | 152 | 190 | 26.2 | 0.00012 |
| 877 | CGPG1939.pep | WD40 | 247 | 283 | 33.6 | 7.10E−07 |
| 877 | CGPG1939.pep | WD40 | 325 | 364 | 22.9 | 0.0012 |
| 878 | CGPG1949.pep | YDG_SRA | 360 | 519 | 403.5 | 3.10E−118 |
| 878 | CGPG1949.pep | Pre-SET | 543 | 639 | 156.7 | 6.30E−44 |
| 878 | CGPG1949.pep | SET | 641 | 771 | 178.4 | 1.80E−50 |
| 879 | CGPG1959.pep | PHD | 34 | 82 | 54.3 | 4.30E−13 |
| 879 | CGPG1959.pep | SET | 208 | 344 | 105.1 | 2.20E−28 |
| 880 | CGPG197.pep | p450 | 40 | 481 | 169.2 | 1.10E−47 |
| 882 | CGPG1981.pep | MT-A70 | 476 | 636 | 321.4 | 1.70E−93 |
| 883 | CGPG1999.pep | Nfu_N | 78 | 193 | 145 | 2.10E−40 |
| 883 | CGPG1999.pep | NifU | 221 | 291 | 121.1 | 3.30E−33 |
| 884 | CGPG2.pep | p450 | 71 | 531 | 324.3 | 2.20E−94 |
| 885 | CGPG2006.pep | RCC1 | 32 | 82 | 31.3 | 3.60E−06 |
| 885 | CGPG2006.pep | RCC1 | 138 | 187 | 40 | 8.30E−09 |
| 885 | CGPG2006.pep | RCC1 | 190 | 239 | 33 | 1.10E−06 |
| 885 | CGPG2006.pep | RCC1 | 294 | 343 | 42.8 | 1.20E−09 |
| 886 | CGPG2010.pep | Aminotran_5 | 74 | 448 | 681.1 | 8.90E−202 |
| 886 | CGPG2010.pep | Beta_elim_lyase | 77 | 389 | −107.3 | 0.0021 |
| 887 | CGPG2011.pep | X8 | 128 | 209 | 153.5 | 5.60E−43 |
| 888 | CGPG2014.pep | Pkinase | 28 | 282 | 339.2 | 7.00E−99 |
| 888 | CGPG2014.pep | NAF | 341 | 398 | 86.9 | 6.70E−23 |
| 889 | CGPG2023.pep | Zip | 48 | 352 | 371 | 1.90E−108 |
| 890 | CGPG2026.pep | Pkinase | 38 | 324 | 328.9 | 9.40E−96 |
| 892 | CGPG2064.pep | Cenp-O | 123 | 201 | 107.6 | 3.80E−29 |
| 894 | CGPG2077.pep | NAC | 88 | 147 | 81.6 | 2.50E−21 |
| 894 | CGPG2077.pep | UBA | 195 | 232 | 29.8 | 1.00E−05 |
| 895 | CGPG2095.pep | AARP2CN | 228 | 309 | 121.6 | 2.30E−33 |
| 895 | CGPG2095.pep | DUF663 | 483 | 780 | 615.9 | 3.60E−182 |
| 896 | CGPG2105.pep | Pkinase | 102 | 404 | 274.6 | 2.00E−79 |
| 896 | CGPG2105.pep | Pkinase_C | 422 | 471 | 39.6 | 1.10E−08 |
| 897 | CGPG2108.pep | Response_reg | 64 | 180 | 86.8 | 6.80E−23 |
| 897 | CGPG2108.pep | CCT | 442 | 484 | 65 | 2.50E−16 |
| 898 | CGPG2111.pep | polyprenyl_synt | 74 | 324 | 156.4 | 7.70E−44 |
| 899 | CGPG2124.pep | UIM | 139 | 156 | 20.6 | 0.0057 |

TABLE 21-continued

| PEP Seq ID No. | Construct ID | Pfam domain name | Begin | Stop | score | E-value |
|---|---|---|---|---|---|---|
| 899 | CGPG2124.pep | efhand | 220 | 248 | 35.7 | 1.70E−07 |
| 900 | CGPG2125.pep | Glutaredoxin | 44 | 110 | 40.7 | 5.10E−09 |
| 903 | CGPG2134.pep | ATP-synt_G | 8 | 122 | 170.2 | 5.30E−48 |
| 904 | CGPG2139.pep | DUF1517 | 94 | 391 | 709.7 | 2.10E−210 |
| 905 | CGPG2140.pep | PhzC-PhzF | 6 | 282 | 506.2 | 3.90E−149 |
| 907 | CGPG2163.pep | Cupin_1 | 5 | 157 | 105.9 | 1.20E−28 |
| 907 | CGPG2163.pep | Cupin_1 | 190 | 339 | 83.5 | 6.80E−22 |
| 908 | CGPG2165.pep | ClpS | 76 | 152 | 131.5 | 2.40E−36 |
| 910 | CGPG2218.pep | Spc97_Spc98 | 67 | 555 | 750.6 | 1.10E−222 |
| 912 | CGPG2225.pep | EMP24_GP25L | 52 | 116 | 55.6 | 1.80E−13 |
| 913 | CGPG2229.pep | Subtilisin_N | 30 | 106 | 89.6 | 9.70E−24 |
| 913 | CGPG2229.pep | Peptidase_S8 | 119 | 600 | 52.4 | 1.60E−12 |
| 913 | CGPG2229.pep | PA | 362 | 461 | 112 | 1.80E−30 |
| 915 | CGPG2254.pep | Ribosomal_L7Ae | 20 | 114 | 110.3 | 5.80E−30 |
| 916 | CGPG2268.pep | CBS | 66 | 188 | 107.9 | 3.00E−29 |
| 917 | CGPG227.pep | p450 | 37 | 494 | 364.2 | 2.20E−106 |
| 918 | CGPG2312.pep | UPF0061 | 75 | 571 | 361.8 | 1.20E−105 |
| 919 | CGPG2315.pep | SIP1 | 286 | 514 | 516.5 | 3.10E−152 |
| 920 | CGPG2316.pep | PTPA | 98 | 396 | 696.6 | 1.80E−206 |
| 922 | CGPG235.pep | p450 | 74 | 510 | 203.2 | 6.10E−58 |
| 923 | CGPG2358.pep | Branch | 54 | 278 | 425.3 | 8.70E−125 |
| 925 | CGPG2361.pep | Metallophos | 9 | 231 | 49.7 | 1.00E−11 |
| 926 | CGPG2365.pep | Epimerase | 3 | 211 | −25.8 | 3.00E−05 |
| 927 | CGPG2372.pep | Pribosyltran | 29 | 169 | 147.9 | 2.70E−41 |
| 928 | CGPG2374.pep | Aminotran_5 | 8 | 370 | −92.6 | 4.20E−07 |
| 929 | CGPG2377.pep | DAO | 69 | 466 | 243.4 | 5.00E−70 |
| 929 | CGPG2377.pep | FAD_binding_2 | 69 | 457 | −124 | 0.0024 |
| 930 | CGPG2387.pep | H_PPase | 1 | 239 | −188.8 | 6.80E−17 |
| 931 | CGPG2389.pep | Carb_anhydrase | 52 | 275 | 117.4 | 4.30E−32 |
| 932 | CGPG2395.pep | AA_permease | 89 | 526 | −4.2 | 1.30E−05 |
| 934 | CGPG2409.pep | DUF862 | 17 | 154 | 252.5 | 8.90E−73 |
| 935 | CGPG2410.pep | GST_N | 5 | 79 | 68.9 | 1.70E−17 |
| 935 | CGPG2410.pep | GST_C | 101 | 204 | 30.1 | 8.30E−06 |
| 937 | CGPG2416.pep | Hin1 | 97 | 235 | 198.2 | 2.10E−56 |
| 938 | CGPG2441.pep | Sina | 5 | 205 | 188 | 2.30E−53 |
| 939 | CGPG2450.pep | adh_short | 112 | 282 | −38.2 | 0.004 |
| 939 | CGPG2450.pep | Epimerase | 114 | 371 | 191.5 | 2.10E−54 |
| 939 | CGPG2450.pep | 3Beta_HSD | 115 | 402 | −72.8 | 1.60E−05 |
| 939 | CGPG2450.pep | NAD_binding_4 | 116 | 342 | −62.5 | 9.90E−05 |
| 940 | CGPG2451.pep | RALF | 57 | 129 | 123.9 | 4.80E−34 |
| 941 | CGPG2492.pep | Pribosyltran | 80 | 216 | 144.1 | 3.80E−40 |
| 942 | CGPG2495.pep | ADH_N | 25 | 134 | 143.2 | 7.40E−40 |
| 942 | CGPG2495.pep | ADH_zinc_N | 165 | 307 | 138 | 2.60E−38 |
| 943 | CGPG2506.pep | PfkB | 5 | 289 | 140.3 | 5.30E−39 |
| 944 | CGPG2515.pep | TIM | 5 | 244 | 446 | 5.10E−131 |
| 945 | CGPG2531.pep | Redoxin | 4 | 160 | 43.7 | 6.60E−10 |
| 945 | CGPG2531.pep | AhpC-TSA | 5 | 138 | 178.9 | 1.30E−50 |
| 946 | CGPG2581.pep | SeIR | 12 | 133 | 289.3 | 7.50E−84 |
| 947 | CGPG2584.pep | zf-Tim10_DDP | 22 | 86 | 115.1 | 2.00E−31 |
| 948 | CGPG2592.pep | TFIID_30 kDa | 30 | 80 | 135.9 | 1.10E−37 |
| 949 | CGPG2612.pep | RRM_1 | 65 | 132 | 43 | 1.10E−09 |
| 949 | CGPG2612.pep | RRM_1 | 150 | 225 | 83.9 | 5.30E−22 |
| 949 | CGPG2612.pep | RRM_1 | 275 | 343 | 53.1 | 9.50E−13 |
| 950 | CGPG2660.pep | B3 | 17 | 115 | 77.8 | 3.60E−20 |
| 950 | CGPG2660.pep | B3 | 211 | 301 | 61.4 | 3.10E−15 |
| 951 | CGPG2663.pep | NTF2 | 15 | 131 | 168.8 | 1.50E−47 |
| 951 | CGPG2663.pep | RRM_1 | 295 | 365 | 45.3 | 2.10E−10 |
| 952 | CGPG2679.pep | ACBP | 104 | 190 | 54.4 | 3.80E−13 |
| 952 | CGPG2679.pep | Ank | 265 | 297 | 49.7 | 1.00E−11 |
| 952 | CGPG2679.pep | Ank | 298 | 330 | 35.5 | 2.00E−07 |
| 953 | CGPG2696.pep | zf-C3HC4 | 177 | 218 | 43.9 | 5.70E−10 |
| 954 | CGPG2772.pep | Mov34 | 6 | 136 | 111.9 | 1.90E−30 |
| 955 | CGPG2773.pep | Asp | 161 | 498 | −73.6 | 3.00E−09 |
| 956 | CGPG281.pep | TLC | 91 | 574 | 1046.6 | 0 |
| 957 | CGPG2846.pep | Aldo_ket_red | 49 | 365 | 248 | 2.00E−71 |
| 958 | CGPG2852.pep | Glyoxalase | 9 | 132 | 37.4 | 5.20E−08 |
| 960 | CGPG2870.pep | zf-CCCH | 111 | 137 | 49.3 | 1.30E−11 |
| 960 | CGPG2870.pep | zf-CCCH | 159 | 185 | 34.6 | 3.60E−07 |
| 960 | CGPG2870.pep | zf-CCCH | 205 | 231 | 49.5 | 1.20E−11 |
| 960 | CGPG2870.pep | zf-CCCH | 347 | 373 | 29.9 | 9.60E−06 |
| 960 | CGPG2870.pep | zf-CCCH | 393 | 419 | 42.5 | 1.50E−09 |
| 961 | CGPG2877.pep | LAG1 | 96 | 307 | 430.8 | 1.90E−126 |
| 962 | CGPG289.pep | Cellulose_synt | 243 | 1060 | 2161.1 | 0 |
| 963 | CGPG2924.pep | zf-C3HC4 | 138 | 179 | 33.3 | 9.10E−07 |
| 964 | CGPG2947.pep | Acetyltransf_1 | 265 | 343 | 50.6 | 5.60E−12 |
| 964 | CGPG2947.pep | Bromodomain | 460 | 548 | 122.2 | 1.50E−33 |
| 965 | CGPG2963.pep | C1_3 | 80 | 108 | 35.7 | 1.60E−07 |
| 965 | CGPG2963.pep | C1_2 | 81 | 108 | 37.1 | 6.10E−08 |

TABLE 21-continued

| PEP Seq ID No. | Construct ID | Pfam domain name | Begin | Stop | score | E-value |
|---|---|---|---|---|---|---|
| 965 | CGPG2963.pep | C1_1 | 122 | 172 | 14.3 | 0.00058 |
| 965 | CGPG2963.pep | C1_3 | 136 | 164 | 36.3 | 1.10E-07 |
| 965 | CGPG2963.pep | C1_3 | 194 | 223 | 27.2 | 6.10E-05 |
| 965 | CGPG2963.pep | C1_2 | 305 | 335 | 40.5 | 5.90E-09 |
| 965 | CGPG2963.pep | C1_3 | 391 | 420 | 40.1 | 8.20E-09 |
| 965 | CGPG2963.pep | C1_3 | 494 | 522 | 25.6 | 0.00018 |
| 965 | CGPG2963.pep | C1_3 | 551 | 581 | 27.5 | 5.00E-05 |
| 965 | CGPG2963.pep | C1_2 | 552 | 581 | 47.9 | 3.50E-11 |
| 966 | CGPG2987.pep | SRF-TF | 11 | 66 | 24.4 | 0.00041 |
| 968 | CGPG3045.pep | Pkinase | 82 | 356 | 192 | 1.50E-54 |
| 968 | CGPG3045.pep | Pkinase_Tyr | 82 | 356 | 254 | 3.20E-73 |
| 969 | CGPG3046.pep | AAA | 121 | 305 | 245.7 | 1.00E-70 |
| 970 | CGPG3060.pep | p450 | 67 | 528 | 268 | 1.90E-77 |
| 971 | CGPG3075.pep | Auxin_inducible | 7 | 106 | 121 | 3.50E-33 |
| 972 | CGPG310.pep | Cyclin_N | 18 | 143 | 31.8 | 1.80E-07 |
| 973 | CGPG3103.pep | PPR | 14 | 48 | 10.8 | 0.4 |
| 973 | CGPG3103.pep | PPR | 49 | 83 | 37.5 | 4.80E-08 |
| 973 | CGPG3103.pep | PPR | 84 | 118 | 38.8 | 1.90E-08 |
| 973 | CGPG3103.pep | PPR | 119 | 153 | 11.8 | 0.31 |
| 973 | CGPG3103.pep | PPR | 155 | 188 | 27.6 | 4.50E-05 |
| 973 | CGPG3103.pep | PPR | 189 | 223 | 34.8 | 3.20E-07 |
| 973 | CGPG3103.pep | PPR | 224 | 258 | 36.8 | 7.80E-08 |
| 973 | CGPG3103.pep | PPR | 259 | 293 | 7.7 | 0.95 |
| 973 | CGPG3103.pep | PPR | 295 | 329 | 39.7 | 1.10E-08 |
| 973 | CGPG3103.pep | PPR | 330 | 364 | 12.6 | 0.25 |
| 973 | CGPG3103.pep | PPR | 365 | 398 | 30.4 | 6.70E-06 |
| 974 | CGPG315.pep | p450 | 29 | 491 | 346.8 | 3.80E-101 |
| 976 | CGPG3189.pep | RRM_1 | 115 | 186 | 101.9 | 2.00E-27 |
| 976 | CGPG3189.pep | RRM_1 | 209 | 280 | 104.9 | 2.40E-28 |
| 977 | CGPG3204.pep | KH_1 | 45 | 104 | 53.4 | 7.60E-13 |
| 977 | CGPG3204.pep | KH_1 | 151 | 221 | 58.6 | 2.20E-14 |
| 977 | CGPG3204.pep | KH_1 | 318 | 381 | 44.6 | 3.60E-10 |
| 977 | CGPG3204.pep | KH_2 | 318 | 365 | 11.3 | 0.019 |
| 977 | CGPG3204.pep | KH_1 | 400 | 467 | 63.4 | 7.50E-16 |
| 977 | CGPG3204.pep | KH_1 | 575 | 637 | 53.3 | 8.70E-13 |
| 978 | CGPG3208.pep | MATH | 26 | 153 | 47.1 | 6.00E-11 |
| 978 | CGPG3208.pep | MATH | 180 | 302 | 18.3 | 0.0015 |
| 979 | CGPG3219.pep | 2OG-FeII_Oxy | 220 | 320 | 161.1 | 2.90E-45 |
| 980 | CGPG3233.pep | PPR | 160 | 194 | 21.8 | 0.0026 |
| 980 | CGPG3233.pep | PPR | 195 | 229 | 9.6 | 0.56 |
| 980 | CGPG3233.pep | PPR | 231 | 265 | 24.1 | 0.00052 |
| 980 | CGPG3233.pep | PPR | 266 | 300 | 40.7 | 5.10E-09 |
| 980 | CGPG3233.pep | PPR | 301 | 335 | 44 | 5.30E-10 |
| 980 | CGPG3233.pep | PPR | 336 | 370 | 45.3 | 2.20E-10 |
| 980 | CGPG3233.pep | PPR | 371 | 405 | 44.7 | 3.30E-10 |
| 980 | CGPG3233.pep | PPR | 406 | 440 | 7.4 | 1 |
| 981 | CGPG3263.pep | Tryp_alpha_amyl | 28 | 104 | 36.6 | 8.90E-08 |
| 982 | CGPG3276.pep | ECH | 11 | 186 | 48.1 | 3.10E-11 |
| 984 | CGPG3282.pep | Steroid_dh | 117 | 268 | 65.5 | 1.80E-16 |
| 985 | CGPG3300.pep | zf-CCHC | 55 | 72 | 30.4 | 6.40E-06 |
| 985 | CGPG3300.pep | zf-CCHC | 74 | 91 | 26.8 | 7.80E-05 |
| 985 | CGPG3300.pep | zf-CCHC | 93 | 110 | 29.8 | 1.00E-05 |
| 985 | CGPG3300.pep | zf-CCHC | 112 | 129 | 27.3 | 5.70E-05 |
| 985 | CGPG3300.pep | zf-CCHC | 138 | 155 | 23.8 | 0.00038 |
| 985 | CGPG3300.pep | zf-CCHC | 157 | 174 | 24.9 | 0.00026 |
| 985 | CGPG3300.pep | zf-CCHC | 229 | 246 | 26.5 | 9.70E-05 |
| 986 | CGPG3318.pep | Peptidase_C14 | 3 | 416 | 273.4 | 4.50E-79 |
| 987 | CGPG3319.pep | AP2 | 28 | 79 | 61.2 | 3.40E-15 |
| 988 | CGPG3326.pep | zf-C3HC4 | 259 | 299 | 36.8 | 7.90E-08 |
| 989 | CGPG333.pep | PTS_2-RNA | 48 | 239 | 409.9 | 3.80E-120 |
| 990 | CGPG3338.pep | Alba | 17 | 87 | 114.8 | 2.50E-31 |
| 991 | CGPG334.pep | Mov34 | 20 | 128 | 65.2 | 2.20E-16 |
| 992 | CGPG3374.pep | peroxidase | 42 | 286 | 426.2 | 4.60E-125 |
| 993 | CGPG3402.pep | Dimerisation | 30 | 89 | 93.1 | 8.60E-25 |
| 993 | CGPG3402.pep | Methyltransf_2 | 99 | 342 | 287.6 | 2.40E-83 |
| 995 | CGPG3413.pep | WD40 | 168 | 207 | 41.5 | 3.10E-09 |
| 995 | CGPG3413.pep | U3_snoRNA_C | 377 | 523 | 212.3 | 1.10E-60 |
| 996 | CGPG3422.pep | WD40 | 241 | 279 | 41.2 | 3.70E-09 |
| 996 | CGPG3422.pep | WD40 | 387 | 425 | 35.3 | 2.20E-07 |
| 996 | CGPG3422.pep | WD40 | 519 | 559 | 21.9 | 0.0024 |
| 997 | CGPG3436.pep | DUF6 | 17 | 144 | 33.8 | 6.40E-07 |
| 997 | CGPG3436.pep | DUF6 | 198 | 327 | 50.4 | 6.10E-12 |
| 998 | CGPG3539.pep | Mito_carr | 11 | 105 | 84.6 | 3.10E-22 |
| 998 | CGPG3539.pep | Mito_carr | 113 | 209 | 115.7 | 1.40E-31 |
| 998 | CGPG3539.pep | Mito_carr | 214 | 303 | 102.2 | 1.60E-27 |
| 999 | CGPG3550.pep | FAE1_CUT1_RppA | 81 | 370 | 700.9 | 9.60E-208 |
| 999 | CGPG3550.pep | Chal_sti_synt_C | 327 | 470 | 2.6 | 0.0011 |
| 999 | CGPG3550.pep | ACP_syn_III_C | 384 | 468 | 21.5 | 8.90E-08 |

TABLE 21-continued

| PEP Seq ID No. | Construct ID | Pfam domain name | Begin | Stop | score | E-value |
|---|---|---|---|---|---|---|
| 1000 | CGPG3551.pep | Pkinase | 9 | 273 | 145.9 | 1.10E−40 |
| 1001 | CGPG3552.pep | Aldedh | 23 | 441 | 176.5 | 6.90E−50 |
| 1002 | CGPG3572.pep | FA_hydroxylase | 112 | 225 | 133.2 | 7.50E−37 |
| 1004 | CGPG3599.pep | DUF579 | 51 | 289 | 588.5 | 6.70E−174 |
| 1008 | CGPG364.pep | zf-C3HC4 | 97 | 137 | 51 | 4.30E−12 |
| 1010 | CGPG3679.pep | malic | 36 | 179 | 249.1 | 9.50E−72 |
| 1010 | CGPG3679.pep | Malic_M | 181 | 418 | 426.3 | 4.30E−125 |
| 1010 | CGPG3679.pep | PTA_PTB | 446 | 768 | 457.7 | 1.60E−134 |
| 1011 | CGPG3686.pep | Gp_dh_N | 2 | 150 | 334.5 | 1.80E−97 |
| 1011 | CGPG3686.pep | Gp_dh_C | 155 | 312 | 388.4 | 1.10E−113 |
| 1012 | CGPG3694.pep | LRRNT_2 | 38 | 78 | 64.2 | 4.40E−16 |
| 1012 | CGPG3694.pep | LRR_1 | 106 | 128 | 11.7 | 2.1 |
| 1012 | CGPG3694.pep | LRR_1 | 130 | 152 | 14.2 | 0.48 |
| 1012 | CGPG3694.pep | LRR_1 | 154 | 176 | 16.7 | 0.089 |
| 1012 | CGPG3694.pep | LRR_1 | 178 | 201 | 11.7 | 2.1 |
| 1012 | CGPG3694.pep | Pkinase | 312 | 583 | 104.7 | 2.80E−28 |
| 1012 | CGPG3694.pep | Pkinase_Tyr | 312 | 583 | 110.8 | 4.20E−30 |
| 1013 | CGPG3696.pep | MMR_HSR1 | 136 | 257 | 120.2 | 5.90E−33 |
| 1014 | CGPG3698.pep | WD40 | 104 | 142 | 31.6 | 2.80E−06 |
| 1014 | CGPG3698.pep | WD40 | 234 | 272 | 22.5 | 0.0016 |
| 1015 | CGPG3699.pep | adh_short | 19 | 187 | 111.6 | 2.30E−30 |
| 1015 | CGPG3699.pep | KR | 19 | 203 | −54.2 | 0.00034 |
| 1016 | CGPG3702.pep | SAM_2 | 227 | 293 | 48.9 | 1.80E−11 |
| 1016 | CGPG3702.pep | SAM_1 | 228 | 291 | 52.7 | 1.30E−12 |
| 1017 | CGPG3703.pep | ENOD93 | 25 | 103 | 190.1 | 5.50E−54 |
| 1018 | CGPG3707.pep | Pkinase | 42 | 333 | 296.2 | 6.30E−86 |
| 1019 | CGPG3710.pep | VQ | 118 | 148 | 45.7 | 1.60E−10 |
| 1020 | CGPG3730.pep | DUF167 | 140 | 216 | 99.7 | 9.10E−27 |
| 1021 | CGPG3731.pep | DUF616 | 194 | 508 | 769.9 | 1.60E−228 |
| 1022 | CGPG3734.pep | PRK | 46 | 233 | 177.1 | 4.40E−50 |
| 1022 | CGPG3734.pep | Pribosyltran | 280 | 425 | 5.8 | 0.00083 |
| 1023 | CGPG3745.pep | RRM_1 | 386 | 455 | 66.7 | 7.80E−17 |
| 1023 | CGPG3745.pep | RRM_1 | 481 | 553 | 49.6 | 1.10E−11 |
| 1024 | CGPG3764.pep | Response_reg | 20 | 145 | 67.1 | 5.90E−17 |
| 1026 | CGPG3851.pep | SH3_1 | 284 | 338 | 42.4 | 1.60E−09 |
| 1026 | CGPG3851.pep | SH3_2 | 285 | 338 | 30.1 | 8.10E−06 |
| 1027 | CGPG3911.pep | Aldedh | 104 | 587 | 526.9 | 2.20E−155 |
| 1028 | CGPG3948.pep | NAP | 50 | 295 | 467.9 | 1.30E−137 |
| 1031 | CGPG3996.pep | Inositol_P | 6 | 267 | 363.1 | 4.60E−106 |
| 1032 | CGPG4006.pep | ENT | 1 | 74 | 140.3 | 5.60E−39 |
| 1033 | CGPG4025.pep | SQS_PSY | 44 | 331 | 455.8 | 5.80E−134 |
| 1034 | CGPG4028.pep | Transket_pyr | 398 | 565 | 233 | 6.90E−67 |
| 1034 | CGPG4028.pep | Transketolase_C | 579 | 702 | 152.2 | 1.40E−42 |
| 1035 | CGPG403.pep | Pkinase | 78 | 336 | 354.1 | 2.40E−103 |
| 1036 | CGPG4041.pep | DEAD | 141 | 315 | 219 | 1.10E−62 |
| 1036 | CGPG4041.pep | Helicase_C | 386 | 462 | 120.8 | 4.10E−33 |
| 1037 | CGPG4078.pep | GST_C | 180 | 283 | 23.1 | 0.00038 |
| 1038 | CGPG4079.pep | RRS1 | 1 | 178 | 271.1 | 2.30E−78 |
| 1041 | CGPG4104.pep | LRRNT_2 | 30 | 67 | 33.1 | 1.00E−06 |
| 1041 | CGPG4104.pep | LRR_1 | 95 | 117 | 11.4 | 2.3 |
| 1041 | CGPG4104.pep | LRR_1 | 119 | 141 | 15.5 | 0.21 |
| 1041 | CGPG4104.pep | LRR_1 | 143 | 165 | 12.1 | 1.8 |
| 1041 | CGPG4104.pep | LRR_1 | 167 | 188 | 16.1 | 0.13 |
| 1041 | CGPG4104.pep | Pkinase | 367 | 633 | 99.2 | 1.30E−26 |
| 1042 | CGPG4127.pep | Hydrolase | 43 | 239 | 93.3 | 7.50E−25 |
| 1043 | CGPG4135.pep | Pkinase | 118 | 376 | 357.9 | 1.70E−104 |
| 1043 | CGPG4135.pep | efhand | 423 | 451 | 41.5 | 3.10E−09 |
| 1043 | CGPG4135.pep | efhand | 459 | 487 | 24.8 | 0.00033 |
| 1043 | CGPG4135.pep | efhand | 495 | 523 | 30.6 | 5.70E−06 |
| 1043 | CGPG4135.pep | efhand | 529 | 557 | 40.3 | 7.00E−09 |
| 1044 | CGPG4161.pep | Methyltransf_11 | 56 | 159 | 48 | 3.30E−11 |
| 1044 | CGPG4161.pep | Methyltransf_12 | 56 | 157 | 31.8 | 2.40E−06 |
| 1045 | CGPG4180.pep | GHMP_kinases_N | 152 | 219 | 64.2 | 4.40E−16 |
| 1045 | CGPG4180.pep | GHMP_kinases_C | 382 | 466 | 58.4 | 2.50E−14 |
| 1046 | CGPG4191.pep | Bombesin | 163 | 176 | 14.8 | 0.16 |
| 1047 | CGPG4199.pep | Copine | 117 | 265 | 295.3 | 1.20E−85 |
| 1047 | CGPG4199.pep | zf-C3HC4 | 385 | 417 | 16.2 | 0.0013 |
| 1048 | CGPG4241.pep | GASA | 3 | 99 | 179.9 | 6.40E−51 |
| 1049 | CGPG427.pep | Pkinase | 8 | 262 | 210 | 5.80E−60 |
| 1049 | CGPG427.pep | Pkinase_Tyr | 8 | 262 | 248 | 2.10E−71 |
| 1050 | CGPG4273.pep | dsrm | 2 | 68 | 70 | 7.70E−18 |
| 1050 | CGPG4273.pep | dsrm | 88 | 153 | 66.9 | 6.90E−17 |
| 1051 | CGPG4301.pep | 2OG-FeII_Oxy | 151 | 253 | 97 | 6.00E−26 |
| 1052 | CGPG4303.pep | Rhodanese | 13 | 114 | 64.9 | 2.70E−16 |
| 1053 | CGPG4313.pep | G6PD_N | 94 | 273 | 322.4 | 8.50E−94 |
| 1053 | CGPG4313.pep | G6PD_C | 276 | 573 | 522.2 | 6.00E−154 |
| 1054 | CGPG4314.pep | AWPM-19 | 15 | 156 | 335.5 | 9.50E−98 |
| 1055 | CGPG4329.pep | AA_kinase | 86 | 324 | 201.9 | 1.60E−57 |

TABLE 21-continued

| PEP Seq ID No. | Construct ID | Pfam domain name | Begin | Stop | score | E-value |
|---|---|---|---|---|---|---|
| 1056 | CGPG4330.pep | PALP | 53 | 341 | 418.6 | 9.40E−123 |
| 1057 | CGPG4338.pep | Proteasome | 21 | 217 | 157.3 | 4.00E−44 |
| 1058 | CGPG4341.pep | Mito_carr | 51 | 134 | 78 | 3.10E−20 |
| 1058 | CGPG4341.pep | Mito_carr | 158 | 246 | 81.5 | 2.80E−21 |
| 1058 | CGPG4341.pep | Mito_carr | 252 | 343 | 82.8 | 1.10E−21 |
| 1061 | CGPG4386.pep | GHMP_kinases_N | 113 | 171 | 55.4 | 1.90E−13 |
| 1061 | CGPG4386.pep | GHMP_kinases_C | 245 | 338 | 29.5 | 1.20E−05 |
| 1062 | CGPG4394.pep | p450 | 39 | 503 | 389.1 | 7.00E−114 |
| 1063 | CGPG4396.pep | p450 | 39 | 504 | 355.6 | 8.20E−104 |
| 1064 | CGPG4400.pep | p450 | 32 | 474 | 146.7 | 6.70E−41 |
| 1065 | CGPG4401.pep | p450 | 47 | 511 | 383.1 | 4.60E−112 |
| 1066 | CGPG441.pep | Chalcone | 14 | 225 | 498.4 | 8.60E−147 |
| 1067 | CGPG4413.pep | p450 | 32 | 547 | 286.5 | 5.20E−83 |
| 1068 | CGPG4427.pep | p450 | 57 | 530 | 225.1 | 1.60E−64 |
| 1069 | CGPG4446.pep | p450 | 43 | 504 | 275.6 | 1.00E−79 |
| 1070 | CGPG4448.pep | p450 | 32 | 486 | 332.3 | 8.70E−97 |
| 1071 | CGPG4474.pep | Band_7 | 33 | 212 | 136.8 | 5.90E−38 |
| 1072 | CGPG4482.pep | peroxidase | 47 | 291 | 314.4 | 2.10E−91 |
| 1073 | CGPG4511.pep | VHS | 36 | 166 | 58.2 | 2.80E−14 |
| 1073 | CGPG4511.pep | GAT | 227 | 315 | 18.1 | 2.80E−05 |
| 1074 | CGPG4517.pep | Aldo_ket_red | 5 | 292 | 460.6 | 2.10E−135 |
| 1075 | CGPG4551.pep | XS | 30 | 148 | 250.2 | 4.60E−72 |
| 1075 | CGPG4551.pep | XH | 418 | 557 | 251.6 | 1.70E−72 |
| 1077 | CGPG4567.pep | SRF-TF | 3 | 53 | 85.4 | 1.80E−22 |
| 1078 | CGPG4586.pep | RRM_1 | 8 | 73 | 41.5 | 2.90E−09 |
| 1079 | CGPG4600.pep | zf-CCCH | 13 | 39 | 35.4 | 2.00E−07 |
| 1079 | CGPG4600.pep | zf-CCCH | 149 | 174 | 24.1 | 0.00053 |
| 1080 | CGPG4631.pep | C1_3 | 87 | 115 | 40.8 | 4.80E−09 |
| 1080 | CGPG4631.pep | C1_2 | 88 | 115 | 41.2 | 3.80E−09 |
| 1080 | CGPG4631.pep | C1_3 | 208 | 237 | 39.4 | 1.30E−08 |
| 1080 | CGPG4631.pep | C1_2 | 209 | 237 | 45.5 | 1.80E−10 |
| 1080 | CGPG4631.pep | C1_3 | 264 | 292 | 48.3 | 2.70E−11 |
| 1080 | CGPG4631.pep | C1_2 | 319 | 349 | 41.5 | 2.90E−09 |
| 1080 | CGPG4631.pep | C1_3 | 404 | 433 | 55.4 | 1.90E−13 |
| 1080 | CGPG4631.pep | C1_2 | 566 | 595 | 40.8 | 4.70E−09 |
| 1081 | CGPG4642.pep | Pyridoxal_deC | 63 | 412 | 126.5 | 7.90E−35 |
| 1082 | CGPG4645.pep | Cu-oxidase_3 | 31 | 148 | 198.9 | 1.30E−56 |
| 1082 | CGPG4645.pep | Cu-oxidase | 157 | 325 | 222.3 | 1.10E−63 |
| 1082 | CGPG4645.pep | Cu-oxidase_2 | 414 | 551 | 155.1 | 2.00E−43 |
| 1083 | CGPG4646.pep | efhand_like | 27 | 105 | 109.6 | 9.60E−30 |
| 1083 | CGPG4646.pep | PI-PLC-X | 108 | 251 | 143.6 | 5.60E−40 |
| 1083 | CGPG4646.pep | PI-PLC-Y | 332 | 450 | 93.9 | 5.20E−25 |
| 1083 | CGPG4646.pep | C2 | 471 | 563 | 82.3 | 1.50E−21 |
| 1084 | CGPG4649.pep | SMP | 14 | 72 | 102 | 1.90E−27 |
| 1084 | CGPG4649.pep | SMP | 130 | 191 | 127.6 | 3.60E−35 |
| 1084 | CGPG4649.pep | SMP | 195 | 256 | 62.7 | 1.30E−15 |
| 1085 | CGPG4653.pep | DUF1637 | 47 | 280 | 366.2 | 5.30E−107 |
| 1087 | CGPG4668.pep | SYF2 | 140 | 306 | 301.7 | 1.50E−87 |
| 1088 | CGPG469.pep | tRNA-synt_1c | 213 | 518 | 428.8 | 7.70E−126 |
| 1088 | CGPG469.pep | tRNA-synt_1c_C | 520 | 697 | 229.4 | 8.00E−66 |
| 1089 | CGPG4708.pep | Sulfate_transp | 172 | 482 | 504.9 | 9.60E−149 |
| 1089 | CGPG4708.pep | STAS | 505 | 623 | 142.8 | 9.80E−40 |
| 1090 | CGPG4712.pep | Mem_trans | 9 | 565 | 715.3 | 4.30E−212 |
| 1091 | CGPG4714.pep | DUF231 | 248 | 423 | 336.8 | 3.80E−98 |
| 1092 | CGPG4719.pep | Response_reg | 37 | 153 | 91.6 | 2.50E−24 |
| 1092 | CGPG4719.pep | CCT | 417 | 461 | 85 | 2.40E−22 |
| 1093 | CGPG473.pep | Peptidase_M16 | 88 | 234 | 184 | 3.90E−52 |
| 1093 | CGPG473.pep | Peptidase_M16_C | 239 | 423 | 161.3 | 2.70E−45 |
| 1094 | CGPG4734.pep | Auxin_inducible | 19 | 119 | 55.4 | 1.90E−13 |
| 1095 | CGPG4736.pep | Pribosyltran | 225 | 358 | 139.9 | 7.20E−39 |
| 1096 | CGPG474.pep | Pro_isomerase | 6 | 172 | 426 | 5.20E−125 |
| 1102 | CGPG4850.pep | PMEI | 25 | 174 | 138.8 | 1.60E−38 |
| 1103 | CGPG4868.pep | PsbW | 1 | 133 | 333 | 5.40E−97 |
| 1104 | CGPG4871.pep | Tryp_alpha_amyl | 52 | 133 | 98.3 | 2.30E−26 |
| 1105 | CGPG488.pep | Histone | 19 | 92 | 110.5 | 5.00E−30 |
| 1105 | CGPG488.pep | CBFD_NFYB_HMF | 25 | 89 | 20.6 | 0.002 |
| 1106 | CGPG4908.pep | WD40 | 16 | 54 | 22.1 | 0.002 |
| 1106 | CGPG4908.pep | WD40 | 63 | 101 | 22.2 | 0.002 |
| 1108 | CGPG4921.pep | WD40 | 202 | 241 | 26.8 | 7.90E−05 |
| 1108 | CGPG4921.pep | WD40 | 253 | 291 | 41.3 | 3.40E−09 |
| 1108 | CGPG4921.pep | WD40 | 295 | 333 | 33.5 | 7.40E−07 |
| 1108 | CGPG4921.pep | WD40 | 337 | 375 | 47.3 | 5.20E−11 |
| 1108 | CGPG4921.pep | WD40 | 472 | 510 | 25.7 | 0.00017 |
| 1109 | CGPG4954.pep | LRRNT_2 | 33 | 72 | 38.6 | 2.20E−08 |
| 1109 | CGPG4954.pep | LRR_1 | 76 | 98 | 9 | 6.5 |
| 1109 | CGPG4954.pep | LRR_1 | 100 | 122 | 12.7 | 1.4 |
| 1109 | CGPG4954.pep | LRR_1 | 124 | 145 | 8 | 10 |
| 1110 | CGPG4956.pep | Asp | 141 | 482 | −61.6 | 5.90E−10 |

TABLE 21-continued

| PEP Seq ID No. | Construct ID | Pfam domain name | Begin | Stop | score | E-value |
|---|---|---|---|---|---|---|
| 1111 | CGPG4959.pep | adh_short | 15 | 183 | 94.8 | 2.80E−25 |
| 1111 | CGPG4959.pep | KR | 16 | 200 | −64.6 | 0.0014 |
| 1112 | CGPG4965.pep | zf-A20 | 15 | 39 | 32.9 | 1.20E−06 |
| 1112 | CGPG4965.pep | zf-AN1 | 114 | 154 | 64.5 | 3.50E−16 |
| 1113 | CGPG4970.pep | GASA | 1 | 108 | 225.3 | 1.40E−64 |
| 1114 | CGPG4980.pep | U-box | 73 | 147 | 95.4 | 1.80E−25 |
| 1114 | CGPG4980.pep | Arm | 246 | 287 | 20.1 | 0.0085 |
| 1114 | CGPG4980.pep | Arm | 288 | 328 | 22.4 | 0.0017 |
| 1115 | CGPG4982.pep | F-box | 2 | 49 | 42.8 | 1.20E−09 |
| 1115 | CGPG4982.pep | FBA_1 | 209 | 387 | 313.8 | 3.20E−91 |
| 1116 | CGPG4985.pep | CPSase_sm_chain | 56 | 203 | 298.5 | 1.30E−86 |
| 1116 | CGPG4985.pep | GATase | 245 | 422 | 238.5 | 1.50E−68 |
| 1117 | CGPG4990.pep | LRRNT_2 | 73 | 112 | 28.9 | 1.90E−05 |
| 1117 | CGPG4990.pep | LRR_1 | 139 | 161 | 13.9 | 0.59 |
| 1117 | CGPG4990.pep | LRR_1 | 163 | 183 | 13.6 | 0.73 |
| 1117 | CGPG4990.pep | LRR_1 | 187 | 206 | 13.9 | 0.62 |
| 1117 | CGPG4990.pep | LRR_1 | 210 | 232 | 8.2 | 9.1 |
| 1117 | CGPG4990.pep | LRR_1 | 306 | 328 | 9.8 | 4.6 |
| 1118 | CGPG4991.pep | PALP | 164 | 473 | 254.7 | 2.00E−73 |
| 1119 | CGPG5007.pep | adh_short | 21 | 192 | 65.9 | 1.30E−16 |
| 1119 | CGPG5007.pep | Epimerase | 23 | 271 | −42.4 | 0.00053 |
| 1120 | CGPG5015.pep | adh_short | 13 | 126 | −22.3 | 0.00036 |
| 1121 | CGPG5026.pep | adh_short | 46 | 221 | 22.7 | 4.00E−07 |
| 1122 | CGPG5029.pep | adh_short | 80 | 252 | 70.7 | 4.90E−18 |
| 1123 | CGPG5046.pep | LRRNT_2 | 30 | 70 | 51.2 | 3.60E−12 |
| 1123 | CGPG5046.pep | LRR_1 | 99 | 121 | 9.2 | 6 |
| 1123 | CGPG5046.pep | LRR_1 | 123 | 145 | 10.5 | 3.4 |
| 1123 | CGPG5046.pep | LRR_1 | 147 | 169 | 15.8 | 0.16 |
| 1123 | CGPG5046.pep | Pkinase_Tyr | 306 | 573 | 109.4 | 1.10E−29 |
| 1123 | CGPG5046.pep | Pkinase | 306 | 573 | 145.6 | 1.40E−40 |
| 1124 | CGPG508.pep | Na_sulph_symp | 93 | 563 | 619 | 4.30E−183 |
| 1125 | CGPG5103.pep | C2 | 9 | 95 | 64.8 | 3.00E−16 |
| 1126 | CGPG511.pep | Rho_GDI | 22 | 222 | 43.8 | 6.70E−12 |
| 1127 | CGPG5121.pep | efhand_like | 30 | 113 | 41.4 | 3.20E−09 |
| 1127 | CGPG5121.pep | PI-PLC-X | 116 | 258 | 140.7 | 4.20E−39 |
| 1127 | CGPG5121.pep | PI-PLC-Y | 331 | 449 | 88.6 | 2.00E−23 |
| 1127 | CGPG5121.pep | C2 | 470 | 562 | 81.3 | 3.00E−21 |
| 1128 | CGPG5126.pep | peroxidase | 54 | 303 | 312 | 1.10E−90 |
| 1129 | CGPG5136.pep | p450 | 35 | 500 | 88.4 | 2.30E−23 |
| 1130 | CGPG5146.pep | p450 | 45 | 501 | 209 | 1.10E−59 |
| 1131 | CGPG5149.pep | p450 | 31 | 478 | 306.7 | 4.40E−89 |
| 1132 | CGPG5181.pep | Pkinase | 278 | 540 | 112.7 | 1.10E−30 |
| 1133 | CGPG52.pep | Sugar_tr | 32 | 472 | −75.6 | 5.00E−06 |
| 1134 | CGPG5206.pep | UDPG_MGDP_dh_N | 2 | 200 | 331.6 | 1.40E−96 |
| 1134 | CGPG5206.pep | UDPG_MGDP_dh | 209 | 306 | 189.1 | 1.10E−53 |
| 1134 | CGPG5206.pep | UDPG_MGDP_dh_C | 328 | 452 | 183.7 | 4.70E−52 |
| 1136 | CGPG5232.pep | Pkinase | 71 | 328 | 295.9 | 8.10E−86 |
| 1137 | CGPG5239.pep | Copine | 136 | 284 | 331.7 | 1.30E−96 |
| 1138 | CGPG5246.pep | ABC_tran | 94 | 285 | 132.8 | 9.70E−37 |
| 1138 | CGPG5246.pep | ABC_tran | 406 | 571 | 146.2 | 9.10E−41 |
| 1139 | CGPG525.pep | CDP-OH_P_transf | 138 | 277 | 132.1 | 1.60E−36 |
| 1140 | CGPG5268.pep | CDC50 | 65 | 368 | 681.3 | 7.50E−202 |
| 1141 | CGPG5272.pep | AA_permease | 153 | 621 | 569.2 | 4.10E−168 |
| 1142 | CGPG5333.pep | MFS_1 | 55 | 468 | 76 | 1.30E−19 |
| 1142 | CGPG5333.pep | Sugar_tr | 89 | 515 | 21.1 | 8.20E−10 |
| 1143 | CGPG5338.pep | RRM_1 | 8 | 77 | 90.6 | 5.10E−24 |
| 1143 | CGPG5338.pep | RRM_1 | 108 | 178 | 82.6 | 1.30E−21 |
| 1144 | CGPG5341.pep | F-box | 33 | 79 | 31.7 | 2.60E−06 |
| 1145 | CGPG5369.pep | AA_kinase | 83 | 366 | 213.4 | 5.30E−61 |
| 1145 | CGPG5369.pep | ACT | 400 | 469 | 20.9 | 0.0047 |
| 1145 | CGPG5369.pep | ACT | 477 | 539 | 9.7 | 0.71 |
| 1146 | CGPG5372.pep | SBF | 142 | 322 | 125.7 | 1.30E−34 |
| 1147 | CGPG5380.pep | Tyr-DNA_phospho | 137 | 581 | 1043.5 | 0 |
| 1148 | CGPG5386.pep | MOSC_N | 4 | 132 | 245 | 1.70E−70 |
| 1148 | CGPG5386.pep | MOSC | 138 | 296 | 66.5 | 8.80E−17 |
| 1149 | CGPG5396.pep | PALP | 9 | 297 | 469.3 | 5.00E−138 |
| 1150 | CGPG5397.pep | PDT | 128 | 307 | 347.9 | 1.70E−101 |
| 1151 | CGPG5421.pep | Pre-SET | 119 | 267 | 14.7 | 2.20E−05 |
| 1151 | CGPG5421.pep | SET | 269 | 414 | 151.3 | 2.60E−42 |
| 1152 | CGPG5433.pep | MtN3_slv | 10 | 98 | 144.3 | 3.30E−40 |
| 1152 | CGPG5433.pep | MtN3_slv | 132 | 218 | 145.4 | 1.50E−40 |
| 1153 | CGPG5439.pep | LANC_like | 69 | 410 | 459.8 | 3.60E−135 |
| 1154 | CGPG5453.pep | Mito_carr | 14 | 116 | 102 | 1.80E−27 |
| 1154 | CGPG5453.pep | Mito_carr | 125 | 215 | 98.8 | 1.60E−26 |
| 1154 | CGPG5453.pep | Mito_carr | 233 | 334 | 104 | 4.60E−28 |
| 1155 | CGPG5456.pep | Mito_carr | 78 | 175 | 128.9 | 1.50E−35 |
| 1155 | CGPG5456.pep | Mito_carr | 183 | 279 | 100.4 | 5.50E−27 |
| 1155 | CGPG5456.pep | Mito_carr | 283 | 373 | 91.5 | 2.70E−24 |

TABLE 21-continued

| PEP Seq ID No. | Construct ID | Pfam domain name | Begin | Stop | score | E-value |
|---|---|---|---|---|---|---|
| 1156 | CGPG5483.pep | PP2C | 66 | 369 | 92.8 | 1.10E−24 |
| 1157 | CGPG5492.pep | FAE1_CUT1_RppA | 61 | 358 | 683.7 | 1.40E−202 |
| 1157 | CGPG5492.pep | Chal_sti_synt_C | 312 | 458 | −1.1 | 0.0023 |
| 1157 | CGPG5492.pep | ACP_syn_III_C | 372 | 456 | 4.3 | 5.30E−06 |
| 1158 | CGPG5508.pep | RCC1 | 310 | 359 | 23.9 | 0.00059 |
| 1158 | CGPG5508.pep | RCC1 | 413 | 462 | 39 | 1.70E−08 |
| 1158 | CGPG5508.pep | RCC1 | 478 | 526 | 32.5 | 1.50E−06 |
| 1158 | CGPG5508.pep | RCC1 | 582 | 630 | 28.9 | 1.80E−05 |
| 1158 | CGPG5508.pep | FYVE | 633 | 701 | 44.7 | 3.30E−10 |
| 1158 | CGPG5508.pep | DZC | 967 | 1002 | 74 | 4.80E−19 |
| 1159 | CGPG5520.pep | TFIID-31 kDa | 19 | 152 | 319.5 | 6.10E−93 |
| 1160 | CGPG5525.pep | PRMT5 | 187 | 679 | 1145.5 | 0 |
| 1161 | CGPG5526.pep | Pkinase | 8 | 295 | 335.7 | 8.20E−98 |
| 1162 | CGPG5530.pep | Response_reg | 504 | 644 | 85.4 | 1.80E−22 |
| 1163 | CGPG5534.pep | Y_phosphatase2 | 3 | 169 | 331.1 | 2.00E−96 |
| 1164 | CGPG5537.pep | TBP | 62 | 147 | 136.9 | 5.90E−38 |
| 1164 | CGPG5537.pep | TBP | 152 | 238 | 157.1 | 4.70E−44 |
| 1165 | CGPG5545.pep | CBS | 35 | 175 | 26.9 | 7.50E−05 |
| 1165 | CGPG5545.pep | CBS | 193 | 318 | 80.7 | 4.60E−21 |
| 1166 | CGPG555.pep | PALP | 104 | 396 | 325.8 | 7.90E−95 |
| 1166 | CGPG555.pep | Thr_dehydrat_C | 409 | 498 | 105.4 | 1.70E−28 |
| 1166 | CGPG555.pep | Thr_dehydrat_C | 504 | 591 | 126.4 | 8.20E−35 |
| 1167 | CGPG5558.pep | Cyclin_N | 212 | 337 | 208.5 | 1.60E−59 |
| 1167 | CGPG5558.pep | Cyclin_C | 339 | 458 | 141 | 3.30E−39 |
| 1168 | CGPG5559.pep | Suc_Fer-like | 69 | 311 | 370.5 | 2.70E−108 |
| 1169 | CGPG5562.pep | Suc_Fer-like | 59 | 308 | 60.7 | 4.90E−15 |
| 1170 | CGPG5592.pep | Rho_GDI | 35 | 239 | 71.2 | 3.40E−18 |
| 1171 | CGPG5625.pep | LRR_1 | 433 | 455 | 20.5 | 0.0061 |
| 1171 | CGPG5625.pep | LRR_1 | 457 | 476 | 11.7 | 2.1 |
| 1171 | CGPG5625.pep | Pkinase | 586 | 854 | 138.6 | 1.80E−38 |
| 1171 | CGPG5625.pep | Pkinase_Tyr | 587 | 854 | 123.3 | 7.00E−34 |
| 1172 | CGPG5631.pep | WAK | 171 | 270 | 186.4 | 7.00E−53 |
| 1172 | CGPG5631.pep | Pkinase_Tyr | 390 | 660 | 146.8 | 5.90E−41 |
| 1172 | CGPG5631.pep | Pkinase | 390 | 658 | 159.5 | 9.00E−45 |
| 1173 | CGPG5632.pep | Aldedh | 29 | 491 | 831.6 | 4.30E−247 |
| 1174 | CGPG5636.pep | Aldedh | 15 | 476 | 794.5 | 6.10E−236 |
| 1175 | CGPG5637.pep | Aldedh | 32 | 493 | 925.9 | 1.70E−275 |
| 1176 | CGPG564.pep | Aminotran_3 | 80 | 413 | 293.8 | 3.30E−85 |
| 1177 | CGPG5641.pep | Aldedh | 14 | 472 | 720.7 | 1.10E−213 |
| 1178 | CGPG5650.pep | Aminotran_3 | 32 | 374 | 476.5 | 3.50E−140 |
| 1179 | CGPG5653.pep | Aminotran_1_2 | 32 | 383 | 268.2 | 1.70E−77 |
| 1180 | CGPG5657.pep | Aldedh | 15 | 474 | 701.6 | 5.70E−208 |
| 1181 | CGPG5671.pep | Gp_dh_N | 3 | 151 | 356.5 | 4.40E−104 |
| 1181 | CGPG5671.pep | Gp_dh_C | 156 | 313 | 350.1 | 3.90E−102 |
| 1182 | CGPG5672.pep | Glutaminase | 24 | 309 | 615.7 | 4.20E−182 |
| 1183 | CGPG5677.pep | PGAM | 4 | 165 | 177.7 | 3.10E−50 |
| 1184 | CGPG5678.pep | Aminotran_1_2 | 35 | 385 | 204 | 3.60E−58 |
| 1185 | CGPG5679.pep | TIM | 7 | 248 | 398.9 | 8.00E−117 |
| 1186 | CGPG5682.pep | Aminotran_3 | 31 | 384 | 432.3 | 7.00E−127 |
| 1187 | CGPG5691.pep | PK | 5 | 350 | 699.4 | 2.60E−207 |
| 1187 | CGPG5691.pep | PK_C | 362 | 478 | 198.7 | 1.40E−56 |
| 1188 | CGPG5699.pep | Gp_dh_N | 3 | 155 | 274 | 3.00E−79 |
| 1188 | CGPG5699.pep | Gp_dh_C | 160 | 316 | 231.1 | 2.60E−66 |
| 1189 | CGPG5705.pep | NDK | 3 | 137 | 354.1 | 2.40E−103 |
| 1190 | CGPG5722.pep | Pyrophosphatase | 17 | 175 | 197.9 | 2.50E−56 |
| 1191 | CGPG5734.pep | Cyclin_N | 232 | 357 | 208.7 | 1.40E−59 |
| 1191 | CGPG5734.pep | Cyclin_C | 359 | 478 | 150 | 6.70E−42 |
| 1192 | CGPG5736.pep | PP2C | 22 | 280 | 398.6 | 9.20E−117 |
| 1193 | CGPG5744.pep | CDC50 | 63 | 365 | 697.3 | 1.20E−206 |
| 1194 | CGPG5747.pep | Pkinase | 23 | 318 | 294 | 2.90E−85 |
| 1195 | CGPG5748.pep | NAD_Gly3P_dh_N | 84 | 259 | 271 | 2.50E−78 |
| 1195 | CGPG5748.pep | NAD_Gly3P_dh_C | 282 | 432 | 282.8 | 6.90E−82 |
| 1198 | CGPG577.pep | Thioredoxin | 7 | 111 | 138.6 | 1.70E−38 |
| 1199 | CGPG5780.pep | AA_permease | 68 | 517 | −83.3 | 0.0017 |
| 1200 | CGPG5793.pep | AA_permease | 285 | 815 | 226.5 | 5.90E−65 |
| 1201 | CGPG5795.pep | Sugar_tr | 123 | 565 | 30.1 | 3.70E−10 |
| 1202 | CGPG5796.pep | Sugar_tr | 43 | 466 | 340.9 | 2.30E−99 |
| 1202 | CGPG5796.pep | MFS_1 | 47 | 417 | 74.4 | 3.70E−19 |
| 1203 | CGPG5800.pep | AA_permease | 86 | 546 | 489 | 5.90E−144 |
| 1204 | CGPG5812.pep | Pkinase | 22 | 273 | 334.2 | 2.30E−97 |
| 1204 | CGPG5812.pep | Pkinase_Tyr | 22 | 271 | 85.2 | 2.10E−22 |
| 1205 | CGPG5815.pep | Pkinase | 9 | 272 | 136.6 | 6.90E−38 |
| 1206 | CGPG5838.pep | Pkinase | 1 | 264 | 137.8 | 3.10E−38 |
| 1207 | CGPG5844.pep | Pkinase | 78 | 351 | 159.7 | 7.80E−45 |
| 1207 | CGPG5844.pep | Pkinase_Tyr | 78 | 351 | 122.7 | 1.10E−33 |
| 1208 | CGPG5846.pep | Pkinase_Tyr | 92 | 376 | 128.5 | 2.00E−35 |
| 1208 | CGPG5846.pep | Pkinase | 99 | 376 | 136.1 | 9.90E−38 |
| 1209 | CGPG5851.pep | Pkinase_Tyr | 121 | 401 | 138.2 | 2.30E−38 |

TABLE 21-continued

| PEP Seq ID No. | Construct ID | Pfam domain name | Begin | Stop | score | E-value |
|---|---|---|---|---|---|---|
| 1209 | CGPG5851.pep | Pkinase | 121 | 401 | 139.5 | 9.70E−39 |
| 1210 | CGPG5857.pep | Pkinase | 19 | 273 | 159.1 | 1.20E−44 |
| 1211 | CGPG5862.pep | Pkinase | 181 | 447 | 99.8 | 8.50E−27 |
| 1211 | CGPG5862.pep | Pkinase_Tyr | 181 | 447 | 95.5 | 1.70E−25 |
| 1212 | CGPG5863.pep | Pkinase | 52 | 330 | 86.5 | 8.60E−23 |
| 1213 | CGPG5867.pep | Pkinase_Tyr | 142 | 423 | 94.1 | 4.50E−25 |
| 1213 | CGPG5867.pep | Pkinase | 142 | 423 | 104 | 4.70E−28 |
| 1214 | CGPG5872.pep | Pkinase_Tyr | 18 | 288 | 125.8 | 1.20E−34 |
| 1214 | CGPG5872.pep | Pkinase | 18 | 288 | 153 | 7.90E−43 |
| 1215 | CGPG5913.pep | ADH_N | 28 | 109 | 95.4 | 1.80E−25 |
| 1215 | CGPG5913.pep | ADH_zinc_N | 140 | 284 | 151 | 3.30E−42 |
| 1217 | CGPG5961.pep | Biotin_lipoyl | 94 | 167 | 79.7 | 9.50E−21 |
| 1217 | CGPG5961.pep | 2-oxoacid_dh | 232 | 462 | 478 | 1.20E−140 |
| 1219 | CGPG5968.pep | Pribosyltran | 36 | 172 | 151.2 | 2.90E−42 |
| 1220 | CGPG5984.pep | Pkinase | 115 | 443 | 246.8 | 4.70E−71 |
| 1221 | CGPG5991.pep | LRR_1 | 266 | 293 | 9.3 | 5.7 |
| 1222 | CGPG6006.pep | RRM_1 | 19 | 89 | 81.3 | 3.10E−21 |
| 1223 | CGPG6015.pep | La | 14 | 85 | 101.3 | 3.00E−27 |
| 1223 | CGPG6015.pep | RRM_1 | 118 | 188 | 37.1 | 6.40E−08 |
| 1223 | CGPG6015.pep | RRM_3 | 302 | 404 | 142.2 | 1.40E−39 |
| 1224 | CGPG603.pep | G6PD_N | 35 | 222 | 342 | 1.00E−99 |
| 1224 | CGPG603.pep | G6PD_C | 224 | 508 | 655.5 | 4.50E−194 |
| 1225 | CGPG6046.pep | Str_synth | 179 | 266 | 137.2 | 4.80E−38 |
| 1226 | CGPG6063.pep | Nramp | 88 | 451 | 733.6 | 1.40E−217 |
| 1228 | CGPG6092.pep | SRPRB | 53 | 235 | 117.6 | 3.70E−32 |
| 1229 | CGPG6104.pep | Steroid_dh | 111 | 262 | 337.7 | 2.00E−98 |
| 1230 | CGPG6106.pep | LEA_5 | 1 | 92 | 209.3 | 9.10E−60 |
| 1231 | CGPG6111.pep | PP-binding | 48 | 115 | 75.2 | 2.10E−19 |
| 1232 | CGPG6113.pep | UQ_con | 7 | 143 | 205.4 | 1.40E−58 |
| 1234 | CGPG6132.pep | SMP | 13 | 71 | 121.1 | 3.30E−33 |
| 1234 | CGPG6132.pep | SMP | 135 | 196 | 113.9 | 4.90E−31 |
| 1234 | CGPG6132.pep | SMP | 200 | 262 | 105 | 2.30E−28 |
| 1236 | CGPG6147.pep | Redoxin | 74 | 234 | 181.5 | 2.20E−51 |
| 1236 | CGPG6147.pep | AhpC-TSA | 75 | 214 | 65.2 | 2.30E−16 |
| 1237 | CGPG6152.pep | Arf | 5 | 177 | 434.6 | 1.40E−127 |
| 1237 | CGPG6152.pep | SRPRB | 15 | 177 | −23.5 | 7.20E−06 |
| 1237 | CGPG6152.pep | Miro | 19 | 129 | 20.4 | 0.00012 |
| 1237 | CGPG6152.pep | Ras | 19 | 179 | −47.2 | 8.20E−06 |
| 1238 | CGPG6154.pep | Ion_trans_2 | 122 | 204 | 70 | 7.90E−18 |
| 1238 | CGPG6154.pep | Ion_trans_2 | 253 | 328 | 48.9 | 1.80E−11 |
| 1239 | CGPG6170.pep | UQ_con | 19 | 158 | 187.1 | 4.50E−53 |
| 1240 | CGPG6171.pep | Thioredoxin | 120 | 227 | 55.8 | 1.50E−13 |
| 1241 | CGPG6177.pep | AIG1 | 39 | 236 | 212.9 | 7.60E−61 |
| 1241 | CGPG6177.pep | MMR_HSR1 | 39 | 154 | 31.5 | 1.40E−06 |
| 1242 | CGPG6181.pep | Peptidase_C12 | 2 | 214 | 311.3 | 1.80E−90 |
| 1243 | CGPG6188.pep | Di19 | 10 | 217 | 479 | 6.00E−141 |
| 1244 | CGPG6202.pep | TB2_DP1_HVA22 | 9 | 106 | 191.2 | 2.60E−54 |
| 1245 | CGPG6217.pep | MFS_1 | 40 | 460 | 86.7 | 7.20E−23 |
| 1245 | CGPG6217.pep | Sugar_tr | 90 | 507 | −7.3 | 1.10E−08 |
| 1246 | CGPG623.pep | SATase_N | 45 | 149 | 210 | 5.60E−60 |
| 1246 | CGPG623.pep | Hexapep | 203 | 220 | 19.7 | 0.011 |
| 1246 | CGPG623.pep | Hexapep | 229 | 246 | 15.6 | 0.18 |
| 1246 | CGPG623.pep | Hexapep | 247 | 264 | 8 | 16 |
| 1247 | CGPG6239.pep | Sugar_tr | 27 | 458 | 289.4 | 7.10E−84 |
| 1247 | CGPG6239.pep | MFS_1 | 32 | 413 | 90.4 | 5.50E−24 |
| 1248 | CGPG6244.pep | Pkinase | 39 | 303 | 81.8 | 2.10E−21 |
| 1249 | CGPG6254.pep | Pkinase | 12 | 264 | 310.9 | 2.40E−90 |
| 1249 | CGPG6254.pep | Pkinase_Tyr | 12 | 261 | 75.1 | 2.20E−19 |
| 1249 | CGPG6254.pep | NAF | 292 | 352 | 103 | 9.50E−28 |
| 1251 | CGPG627.pep | His_biosynth | 48 | 289 | 33.3 | 4.00E−12 |
| 1252 | CGPG6271.pep | Pkinase | 191 | 527 | 227.5 | 3.00E−65 |
| 1253 | CGPG6278.pep | Pkinase_Tyr | 86 | 365 | 146.9 | 5.60E−41 |
| 1253 | CGPG6278.pep | Pkinase | 86 | 368 | 158.7 | 1.60E−44 |
| 1254 | CGPG6288.pep | Pkinase | 207 | 463 | 183.7 | 4.70E−52 |
| 1254 | CGPG6288.pep | Pkinase_Tyr | 207 | 463 | 207.1 | 4.10E−59 |
| 1255 | CGPG6309.pep | PRA1 | 29 | 181 | 233.1 | 6.50E−67 |
| 1256 | CGPG633.pep | DCP1 | 12 | 134 | 258.3 | 1.70E−74 |
| 1257 | CGPG635.pep | RmlD_sub_bind | 7 | 338 | −145.7 | 0.00034 |
| 1257 | CGPG635.pep | adh_short | 7 | 177 | −35.3 | 0.0026 |
| 1257 | CGPG635.pep | Epimerase | 9 | 273 | 226.4 | 6.40E−65 |
| 1257 | CGPG635.pep | Polysacc_synt_2 | 9 | 319 | −162.6 | 0.0011 |
| 1257 | CGPG635.pep | 3Beta_HSD | 10 | 299 | −79 | 3.60E−05 |
| 1257 | CGPG635.pep | NAD_binding_4 | 11 | 240 | −73 | 0.00047 |
| 1258 | CGPG6350.pep | LRRNT_2 | 32 | 78 | 22.6 | 0.0015 |
| 1258 | CGPG6350.pep | LRR_1 | 105 | 127 | 20.8 | 0.0051 |
| 1258 | CGPG6350.pep | LRR_1 | 129 | 151 | 13.6 | 0.74 |
| 1258 | CGPG6350.pep | LRR_1 | 153 | 175 | 13.4 | 0.84 |
| 1258 | CGPG6350.pep | LRR_1 | 177 | 196 | 10.9 | 2.9 |

TABLE 21-continued

| PEP Seq ID No. | Construct ID | Pfam domain name | Begin | Stop | score | E-value |
|---|---|---|---|---|---|---|
| 1260 | CGPG6365.pep | Aminotran_1_2 | 32 | 384 | 403.5 | 3.20E−118 |
| 1261 | CGPG6374.pep | Gln-synt_C | 120 | 380 | 370.8 | 2.30E−108 |
| 1262 | CGPG6377.pep | PGK | 2 | 383 | 466.4 | 3.70E−137 |
| 1263 | CGPG638.pep | PA | 51 | 163 | 106 | 1.10E−28 |
| 1264 | CGPG6397.pep | NAD_binding_2 | 1 | 157 | −57 | 0.00027 |
| 1264 | CGPG6397.pep | NAD_Gly3P_dh_N | 2 | 121 | −33.4 | 0.0009 |
| 1264 | CGPG6397.pep | F420_oxidored | 3 | 246 | 249.4 | 7.60E−72 |
| 1265 | CGPG6398.pep | Enolase_N | 5 | 135 | 212.4 | 1.10E−60 |
| 1265 | CGPG6398.pep | Enolase_C | 140 | 430 | 405 | 1.10E−118 |
| 1266 | CGPG6408.pep | ADH_N | 25 | 155 | 153.5 | 6.00E−43 |
| 1266 | CGPG6408.pep | ADH_zinc_N | 185 | 350 | 101.5 | 2.50E−27 |
| 1267 | CGPG6415.pep | NTP_transferase | 4 | 271 | 71.9 | 2.10E−18 |
| 1268 | CGPG6421.pep | ADH_N | 25 | 148 | 131.4 | 2.60E−36 |
| 1268 | CGPG6421.pep | ADH_zinc_N | 179 | 318 | 163.9 | 4.30E−46 |
| 1269 | CGPG6442.pep | iPGM_N | 2 | 363 | 870.1 | 1.10E−258 |
| 1269 | CGPG6442.pep | Metalloenzyme | 373 | 488 | 191.4 | 2.20E−54 |
| 1270 | CGPG6443.pep | PGK | 1 | 391 | 727.8 | 7.60E−216 |
| 1271 | CGPG6446.pep | PK | 106 | 453 | 901.2 | 4.70E−268 |
| 1271 | CGPG6446.pep | PK_C | 467 | 587 | 259.4 | 7.60E−75 |
| 1272 | CGPG6453.pep | Aminotran_1_2 | 41 | 402 | 404.3 | 1.80E−118 |
| 1273 | CGPG6466.pep | ADH_N | 27 | 153 | 129.2 | 1.20E−35 |
| 1273 | CGPG6466.pep | ADH_zinc_N | 184 | 322 | 135.3 | 1.80E−37 |
| 1274 | CGPG6467.pep | Aminotran_3 | 19 | 366 | 361.7 | 1.20E−105 |
| 1275 | CGPG6470.pep | PfkB | 1 | 302 | 230 | 5.40E−66 |
| 1276 | CGPG6475.pep | NTP_transferase | 10 | 282 | 35.5 | 1.90E−09 |
| 1277 | CGPG6477.pep | NDK | 4 | 138 | 268.7 | 1.20E−77 |
| 1278 | CGPG6478.pep | PfkB | 1 | 308 | 70.6 | 5.30E−18 |
| 1279 | CGPG6493.pep | AA_permease | 94 | 561 | 594.7 | 9.00E−176 |
| 1280 | CGPG6506.pep | Asparaginase | 140 | 457 | 525.4 | 6.50E−155 |
| 1281 | CGPG6518.pep | NAD_binding_2 | 2 | 173 | 303 | 5.60E−88 |
| 1281 | CGPG6518.pep | 6PGD | 177 | 467 | 700.7 | 1.10E−207 |
| 1282 | CGPG6546 pep | PK | 3 | 348 | 560.5 | 1.80E−165 |
| 1282 | CGPG6546.pep | PK_C | 360 | 477 | 86.8 | 6.80E−23 |
| 1283 | CGPG6556.pep | Aminotran_1_2 | 124 | 475 | 223.7 | 4.30E−64 |
| 1284 | CGPG6562.pep | Aminotran_3 | 116 | 451 | 628.8 | 4.90E−186 |
| 1285 | CGPG6566.pep | NTP_transferase | 95 | 350 | 301.4 | 1.80E−87 |
| 1285 | CGPG6566.pep | Hexapep | 398 | 415 | 6.4 | 25 |
| 1285 | CGPG6566.pep | Hexapep | 432 | 449 | 16.6 | 0.097 |
| 1285 | CGPG6566.pep | Hexapep | 460 | 477 | 5.5 | 31 |
| 1286 | CGPG6571.pep | Aldedh | 102 | 560 | 720.7 | 1.10E−213 |
| 1287 | CGPG6576.pep | Aldedh | 99 | 565 | 569.2 | 4.30E−168 |
| 1288 | CGPG659.pep | G_glu_transpept | 48 | 567 | 839.1 | 2.30E−249 |
| 1289 | CGPG6594.pep | DAO | 94 | 524 | −28.6 | 0.00082 |
| 1289 | CGPG6594.pep | GIDA | 94 | 429 | −226.6 | 0.0045 |
| 1289 | CGPG6594.pep | Pyr_redox_2 | 94 | 419 | 229.8 | 6.20E−66 |
| 1289 | CGPG6594.pep | Pyr_redox | 278 | 374 | 119.5 | 9.90E−33 |
| 1289 | CGPG6594.pep | Pyr_redox_dim | 450 | 559 | 194.7 | 2.20E−55 |
| 1290 | CGPG6603.pep | Pyr_redox_2 | 94 | 397 | 239.1 | 9.60E−69 |
| 1290 | CGPG6603.pep | Pyr_redox | 257 | 350 | 101.2 | 3.10E−27 |
| 1290 | CGPG6603.pep | Pyr_redox_dim | 427 | 538 | 189.7 | 7.10E−54 |
| 1291 | CGPG6608.pep | DAO | 93 | 497 | −33.9 | 0.0018 |
| 1291 | CGPG6608.pep | Pyr_redox_2 | 93 | 394 | 145.4 | 1.60E−40 |
| 1291 | CGPG6608.pep | Pyr_redox | 256 | 348 | 92.2 | 1.70E−24 |
| 1291 | CGPG6608.pep | Pyr_redox_dim | 423 | 532 | 89.3 | 1.20E−23 |
| 1292 | CGPG6634.pep | DUF177 | 100 | 252 | 152.3 | 1.30E−42 |
| 1294 | CGPG6667.pep | Invertase_neut | 89 | 577 | 1313.4 | 0 |
| 1295 | CGPG6678.pep | Biotin_lipoyl | 92 | 165 | 75.9 | 1.30E−19 |
| 1295 | CGPG6678.pep | E3_binding | 225 | 263 | 51.7 | 2.60E−12 |
| 1295 | CGPG6678.pep | 2-oxoacid_dh | 281 | 512 | 374.6 | 1.60E−109 |
| 1296 | CGPG6695.pep | GIDA | 97 | 428 | −211.9 | 0.00053 |
| 1296 | CGPG6695.pep | Pyr_redox_2 | 97 | 408 | 266.1 | 7.40E−77 |
| 1296 | CGPG6695.pep | Pyr_redox | 266 | 361 | 90.1 | 7.20E−24 |
| 1296 | CGPG6695.pep | Pyr_redox_dim | 436 | 545 | 184.3 | 3.20E−52 |
| 1297 | CGPG6699.pep | Ribul_P_3_epim | 94 | 295 | 491.3 | 1.20E−144 |
| 1298 | CGPG670.pep | Fer2 | 60 | 135 | 120.2 | 6.20E−33 |
| 1299 | CGPG6705.pep | PK | 89 | 433 | 788.8 | 3.30E−234 |
| 1299 | CGPG6705.pep | PK_C | 445 | 559 | 164.3 | 3.30E−46 |
| 1299 | CGPG6705.pep | PEP-utilizers | 584 | 663 | 122.9 | 9.40E−34 |
| 1300 | CGPG6735.pep | FBPase | 93 | 413 | 525 | 8.60E−155 |
| 1301 | CGPG6744.pep | Glycolytic | 92 | 429 | 576.6 | 2.40E−170 |
| 1302 | CGPG6753.pep | Pyr_redox | 236 | 328 | 10.7 | 0.00051 |
| 1302 | CGPG6753.pep | Pyr_redox_2 | 236 | 538 | 72.9 | 1.10E−18 |
| 1303 | CGPG6757.pep | Aminotran_1_2 | 127 | 473 | 234 | 3.30E−67 |
| 1305 | CGPG6806.pep | mTERF | 110 | 457 | 550.4 | 2.00E−162 |
| 1306 | CGPG6811.pep | GH3 | 10 | 567 | 1341 | 0 |
| 1308 | CGPG6815.pep | V-ATPase_G | 5 | 109 | 183.9 | 4.00E−52 |
| 1310 | CGPG6830.pep | Tbf5 | 13 | 76 | 113.7 | 5.40E−31 |
| 1313 | CGPG6864.pep | DUF620 | 190 | 438 | 698.7 | 4.50E−207 |

TABLE 21-continued

| PEP Seq ID No. | Construct ID | Pfam domain name | Begin | Stop | score | E-value |
|---|---|---|---|---|---|---|
| 1314 | CGPG6877.pep | Hep_59 | 101 | 194 | 198.3 | 1.90E−56 |
| 1315 | CGPG6878.pep | Peptidase_M24 | 107 | 343 | 229.5 | 7.80E−66 |
| 1316 | CGPG6880.pep | PAP_fibrillin | 72 | 232 | 178.2 | 2.20E−50 |
| 1318 | CGPG6887.pep | AIG2 | 12 | 111 | 89.1 | 1.40E−23 |
| 1319 | CGPG6895.pep | zf-CCHC | 166 | 183 | 26 | 0.00014 |
| 1319 | CGPG6895.pep | zf-CCHC | 208 | 225 | 24.9 | 0.00026 |
| 1319 | CGPG6895.pep | zf-CCHC | 325 | 342 | 38.1 | 3.30E−08 |
| 1319 | CGPG6895.pep | zf-CCHC | 356 | 373 | 32 | 2.20E−06 |
| 1322 | CGPG6912.pep | zf-DHHC | 149 | 213 | 119.1 | 1.30E−32 |
| 1324 | CGPG6942.pep | RNA_pol_Rpb5_N | 18 | 108 | 174.3 | 3.20E−49 |
| 1324 | CGPG6942.pep | RNA_pol_Rpb5_C | 149 | 222 | 68.2 | 2.80E−17 |
| 1327 | CGPG6969.pep | 2OG-FeII_Oxy | 223 | 323 | 152.3 | 1.30E−42 |
| 1329 | CGPG6991.pep | Glyco_tran_28_C | 11 | 170 | 171.7 | 1.90E−48 |
| 1332 | CGPG7037.pep | Sad1_UNC | 313 | 416 | −3.4 | 0.0011 |
| 1333 | CGPG7051.pep | PAP_fibrillin | 84 | 236 | 218.7 | 1.40E−62 |
| 1336 | CGPG7086.pep | SFT2 | 44 | 163 | 182.6 | 9.70E−52 |
| 1339 | CGPG7136.pep | NOI | 1 | 72 | 159.7 | 8.10E−45 |
| 1340 | CGPG7147.pep | RAMP4 | 1 | 64 | 152.5 | 1.20E−42 |
| 1343 | CGPG7222.pep | Branch | 49 | 274 | 399.8 | 4.00E−117 |
| 1345 | CGPG7233.pep | eIF2A | 214 | 407 | 415.3 | 8.90E−122 |
| 1346 | CGPG7238.pep | UPF0185 | 5 | 80 | 214.1 | 3.30E−61 |
| 1347 | CGPG7253.pep | ArfGap | 15 | 117 | 58.4 | 2.40E−14 |
| 1348 | CGPG7255.pep | Arf | 5 | 177 | 365.3 | 1.00E−106 |
| 1348 | CGPG7255.pep | SRPRB | 15 | 200 | −3.7 | 2.60E−07 |
| 1348 | CGPG7255.pep | Miro | 19 | 129 | 40.3 | 7.10E−09 |
| 1348 | CGPG7255.pep | Ras | 19 | 179 | −43.7 | 4.50E−06 |
| 1349 | CGPG7286.pep | ORC2 | 20 | 345 | 558.7 | 6.00E−165 |
| 1350 | CGPG7292.pep | Methyltransf_11 | 38 | 135 | 44.1 | 5.00E−10 |
| 1350 | CGPG7292.pep | Methyltransf_12 | 38 | 133 | 38.4 | 2.60E−08 |
| 1351 | CGPG7301.pep | ELFV_dehydrog_N | 57 | 187 | 294.9 | 1.50E−85 |
| 1351 | CGPG7301.pep | ELFV_dehydrog | 202 | 445 | 484.3 | 1.50E−142 |
| 1352 | CGPG7305.pep | DAO | 126 | 401 | −31.6 | 0.0013 |
| 1352 | CGPG7305.pep | Pyr_redox_2 | 126 | 386 | 66.3 | 1.00E−16 |
| 1352 | CGPG7305.pep | Pyr_redox | 255 | 345 | 55.7 | 1.60E−13 |
| 1353 | CGPG7307.pep | Gp_dh_N | 11 | 163 | 300.6 | 3.00E−87 |
| 1353 | CGPG7307.pep | Gp_dh_C | 168 | 324 | 258.5 | 1.50E−74 |
| 1354 | CGPG7318.pep | MIP | 1 | 142 | −31.2 | 9.10E−08 |
| 1355 | CGPG7319.pep | SNF5 | 172 | 400 | 471.8 | 9.00E−139 |
| 1356 | CGPG7345.pep | Lipase_3 | 97 | 237 | 131.1 | 3.30E−36 |
| 1357 | CGPG7368.pep | MT-A70 | 516 | 676 | 316.4 | 5.20E−92 |
| 1358 | CGPG7385.pep | FHA | 32 | 107 | 51 | 4.10E−12 |
| 1359 | CGPG7391.pep | G-patch | 6 | 50 | 71.2 | 3.40E−18 |
| 1360 | CGPG7405.pep | TATA_RF | 1 | 216 | 160.8 | 3.70E−45 |
| 1361 | CGPG7415.pep | IU_nuc_hydro | 1 | 312 | 255.3 | 1.30E−73 |
| 1362 | CGPG7416.pep | GLTP | 52 | 233 | 208 | 2.30E−59 |
| 1363 | CGPG7420.pep | PRK | 95 | 302 | 426.6 | 3.60E−125 |
| 1366 | CGPG7445.pep | PRC | 92 | 169 | 37.2 | 5.70E−08 |
| 1366 | CGPG7445.pep | PRC | 171 | 252 | 48.6 | 2.20E−11 |
| 1367 | CGPG7465.pep | Aldedh | 103 | 567 | 834.4 | 6.30E−248 |
| 1368 | CGPG7473.pep | F-box | 273 | 320 | 35.1 | 2.60E−07 |
| 1368 | CGPG7473.pep | WD40 | 412 | 449 | 41.5 | 2.90E−09 |
| 1368 | CGPG7473.pep | WD40 | 453 | 493 | 49.7 | 1.00E−11 |
| 1368 | CGPG7473.pep | WD40 | 520 | 556 | 30.6 | 5.70E−06 |
| 1368 | CGPG7473.pep | WD40 | 560 | 598 | 41.7 | 2.70E−09 |
| 1369 | CGPG7489.pep | UBX | 295 | 376 | 70.8 | 4.50E−18 |
| 1370 | CGPG7492.pep | Pescadillo_N | 8 | 291 | 519 | 5.30E−153 |
| 1370 | CGPG7492.pep | BRCT | 337 | 414 | 50.7 | 5.00E−12 |
| 1371 | CGPG7499.pep | G-alpha | 423 | 839 | 50.2 | 3.20E−22 |
| 1374 | CGPG7508.pep | Smg4_UPF3 | 1 | 170 | 236.2 | 7.10E−68 |
| 1375 | CGPG7509.pep | SSB | 76 | 187 | 95.3 | 1.90E−25 |
| 1376 | CGPG7511.pep | GFA | 31 | 125 | 74.2 | 4.20E−19 |
| 1377 | CGPG7515.pep | Brix | 45 | 297 | 232.5 | 9.60E−67 |
| 1378 | CGPG7521.pep | G-alpha | 23 | 386 | 560.5 | 1.80E−165 |
| 1380 | CGPG7547.pep | PAD_porph | 14 | 368 | 695.7 | 3.40E−206 |
| 1381 | CGPG7561.pep | Snf7 | 17 | 187 | 219.6 | 7.40E−63 |
| 1382 | CGPG7562.pep | Sybindin | 6 | 136 | 253.6 | 4.30E−73 |
| 1382 | CGPG7562.pep | Sedlin_N | 11 | 135 | −21.6 | 0.00015 |
| 1383 | CGPG7563.pep | DUF887 | 40 | 279 | 394.2 | 2.10E−115 |
| 1384 | CGPG7567.pep | Peptidase_M18 | 14 | 461 | 680 | 1.90E−201 |
| 1389 | CGPG7597.pep | zf-AN1 | 76 | 116 | 78.4 | 2.40E−20 |
| 1390 | CGPG7606.pep | Pentapeptide | 127 | 166 | 29.2 | 1.50E−05 |
| 1390 | CGPG7606.pep | Pentapeptide | 172 | 211 | 42.7 | 1.30E−09 |
| 1392 | CGPG7637.pep | DAD | 2 | 112 | 168.4 | 1.90E−47 |
| 1393 | CGPG7649.pep | YgbB | 71 | 227 | 244.8 | 2.00E−70 |
| 1394 | CGPG7658.pep | Cyclase | 56 | 256 | 109.9 | 7.70E−30 |
| 1395 | CGPG7664.pep | Aldedh | 9 | 463 | 801 | 7.20E−238 |
| 1396 | CGPG7666.pep | Aminotran_1_2 | 26 | 392 | 491 | 1.50E−144 |
| 1397 | CGPG7668.pep | DUF594 | 660 | 719 | 97.6 | 3.90E−26 |

TABLE 21-continued

| PEP Seq ID No. | Construct ID | Pfam domain name | Begin | Stop | score | E-value |
|---|---|---|---|---|---|---|
| 1399 | CGPG7746.pep | UPF0153 | 49 | 139 | 59.7 | 9.90E−15 |
| 1400 | CGPG7747.pep | Copine | 113 | 261 | 308.5 | 1.30E−89 |
| 1401 | CGPG7752.pep | zf-MYND | 176 | 214 | 48.9 | 1.80E−11 |
| 1401 | CGPG7752.pep | PDCD2_C | 241 | 403 | 38.2 | 1.00E−10 |
| 1403 | CGPG7770.pep | YTH | 263 | 353 | 218.6 | 1.40E−62 |
| 1406 | CGPG7778.pep | Ubie_methyltran | 51 | 304 | 393.3 | 3.70E−115 |
| 1406 | CGPG7778.pep | Methyltransf_11 | 105 | 222 | 75 | 2.50E−19 |
| 1406 | CGPG7778.pep | Methyltransf_12 | 105 | 220 | 43.1 | 1.00E−09 |
| 1407 | CGPG7786.pep | KH_1 | 141 | 193 | 27.6 | 4.60E−05 |
| 1408 | CGPG7788.pep | YIF1 | 34 | 263 | 341.8 | 1.20E−99 |
| 1410 | CGPG78.pep | Hpt | 46 | 132 | 55.5 | 1.80E−13 |
| 1411 | CGPG783.pep | RRM_1 | 288 | 354 | 40 | 8.40E−09 |
| 1411 | CGPG783.pep | RRM_2 | 682 | 778 | 232.4 | 1.00E−66 |
| 1412 | CGPG7832.pep | STT3 | 26 | 670 | 626.4 | 2.50E−185 |
| 1413 | CGPG7841.pep | ECH | 17 | 186 | 192.8 | 8.40E−55 |
| 1413 | CGPG7841.pep | 3HCDH_N | 311 | 490 | 295.4 | 1.10E−85 |
| 1413 | CGPG7841.pep | 3HCDH | 492 | 585 | 116.2 | 9.50E−32 |
| 1414 | CGPG7845.pep | LRRNT_2 | 23 | 64 | 49.2 | 1.50E−11 |
| 1414 | CGPG7845.pep | LRR_1 | 97 | 119 | 10.5 | 3.5 |
| 1414 | CGPG7845.pep | LRR_1 | 121 | 143 | 14.5 | 0.39 |
| 1414 | CGPG7845.pep | LRR_1 | 145 | 167 | 12.1 | 1.7 |
| 1414 | CGPG7845.pep | LRR_1 | 169 | 192 | 13.1 | 1.1 |
| 1414 | CGPG7845.pep | LRR_1 | 194 | 216 | 14 | 0.55 |
| 1415 | CGPG7847.pep | Peptidase_C48 | 30 | 225 | −1.9 | 0.00023 |
| 1417 | CGPG7853.pep | LRR_1 | 142 | 164 | 17.4 | 0.052 |
| 1417 | CGPG7853.pep | LRR_1 | 166 | 188 | 9.9 | 4.4 |
| 1417 | CGPG7853.pep | LRR_1 | 190 | 212 | 10 | 4.3 |
| 1417 | CGPG7853.pep | LRR_1 | 214 | 235 | 13.8 | 0.65 |
| 1417 | CGPG7853.pep | LRR_1 | 258 | 280 | 10.5 | 3.5 |
| 1417 | CGPG7853.pep | LRR_1 | 282 | 304 | 14 | 0.56 |
| 1417 | CGPG7853.pep | LRR_1 | 306 | 325 | 11.7 | 2.1 |
| 1418 | CGPG7857.pep | Response_reg | 79 | 195 | 89.7 | 9.40E−24 |
| 1418 | CGPG7857.pep | CCT | 689 | 736 | 62.1 | 1.80E−15 |
| 1420 | CGPG7869.pep | Acyltransferase | 117 | 264 | 81.9 | 2.00E−21 |
| 1421 | CGPG7891.pep | FMO-like | 11 | 427 | −207 | 1.20E−16 |
| 1421 | CGPG7891.pep | DAO | 13 | 268 | −9.4 | 4.70E−05 |
| 1422 | CGPG7892.pep | FMO-like | 9 | 416 | −157.4 | 2.80E−19 |
| 1423 | CGPG7906.pep | Skp1_POZ | 4 | 65 | 96.7 | 7.50E−26 |
| 1423 | CGPG7906.pep | Skp1 | 76 | 153 | 154.3 | 3.40E−43 |
| 1424 | CGPG7924.pep | AAA | 249 | 462 | 54.2 | 4.60E−13 |
| 1428 | CGPG7964.pep | IQ | 108 | 128 | 25.7 | 0.00017 |
| 1428 | CGPG7964.pep | IQ | 130 | 150 | 12.2 | 1.9 |
| 1429 | CGPG7968.pep | FMO-like | 13 | 427 | −229.9 | 2.10E−15 |
| 1429 | CGPG7968.pep | DAO | 15 | 291 | −34.2 | 0.0019 |
| 1429 | CGPG7968.pep | Pyr_redox_2 | 15 | 321 | −18 | 0.00054 |
| 1431 | CGPG7972.pep | FAD_binding_3 | 5 | 372 | −97.4 | 5.20E−06 |
| 1432 | CGPG7982.pep | Tetraspannin | 4 | 241 | 241.9 | 1.40E−69 |
| 1433 | CGPG7985.pep | BT1 | 57 | 469 | 419.2 | 6.00E−123 |
| 1434 | CGPG7993.pep | F-box | 27 | 73 | 15.1 | 0.26 |
| 1434 | CGPG7993.pep | LRR_2 | 278 | 304 | 16.8 | 0.084 |
| 1435 | CGPG8.pep | p450 | 39 | 503 | 399 | 7.30E−117 |
| 1436 | CGPG80.pep | Pkinase | 68 | 328 | 277.6 | 2.60E−80 |
| 1437 | CGPG8001.pep | FMO-like | 13 | 433 | −243.5 | 1.10E−14 |
| 1437 | CGPG8001.pep | Pyr_redox | 215 | 295 | 5.3 | 0.0016 |
| 1438 | CGPG8009.pep | BT1 | 41 | 511 | 517.8 | 1.30E−152 |
| 1440 | CGPG8049.pep | BT1 | 1 | 436 | 331.8 | 1.20E−96 |
| 1441 | CGPG806.pep | Synaptobrevin | 127 | 215 | 146.7 | 6.20E−41 |
| 1442 | CGPG8060.pep | DUF829 | 161 | 425 | 426 | 5.30E−125 |
| 1446 | CGPG81.pep | Pkinase | 70 | 330 | 287.7 | 2.30E−83 |
| 1452 | CGPG8125.pep | zf-C3HC4 | 46 | 86 | 31.1 | 4.00E−06 |
| 1453 | CGPG8134.pep | DEK_C | 3 | 57 | 60.4 | 6.10E−15 |
| 1453 | CGPG8134.pep | SWIB | 197 | 272 | 140.9 | 3.60E−39 |
| 1453 | CGPG8134.pep | SWIB | 305 | 382 | 112.9 | 9.40E−31 |
| 1455 | CGPG8156.pep | PCI | 258 | 362 | 69.4 | 1.20E−17 |
| 1456 | CGPG8159.pep | ACT | 77 | 141 | 51.9 | 2.10E−12 |
| 1456 | CGPG8159.pep | ACT | 308 | 374 | 51.5 | 3.00E−12 |
| 1458 | CGPG8179.pep | WD40 | 138 | 177 | 23.7 | 0.00069 |
| 1458 | CGPG8179.pep | WD40 | 264 | 305 | 42.5 | 1.50E−09 |
| 1459 | CGPG8193.pep | Ank | 22 | 54 | 5.5 | 5.2 |
| 1459 | CGPG8193.pep | Ank | 55 | 87 | 36.4 | 1.00E−07 |
| 1460 | CGPG8197.pep | F-box | 5 | 53 | 22 | 0.0022 |
| 1461 | CGPG8198.pep | F-box | 74 | 119 | 15 | 0.28 |
| 1461 | CGPG8198.pep | Kelch_2 | 174 | 221 | 19.7 | 0.011 |
| 1461 | CGPG8198.pep | Kelch_1 | 223 | 278 | 15.6 | 0.041 |
| 1461 | CGPG8198.pep | Kelch_2 | 329 | 369 | 14.2 | 0.51 |
| 1463 | CGPG8211.pep | F-box | 182 | 229 | 48.8 | 2.00E−11 |
| 1463 | CGPG8211.pep | WD40 | 292 | 328 | 30.3 | 6.90E−06 |
| 1463 | CGPG8211.pep | WD40 | 332 | 368 | 37.7 | 4.30E−08 |

TABLE 21-continued

| PEP Seq ID No. | Construct ID | Pfam domain name | Begin | Stop | score | E-value |
|---|---|---|---|---|---|---|
| 1463 | CGPG8211.pep | WD40 | 372 | 408 | 43.4 | 8.30E−10 |
| 1463 | CGPG8211.pep | WD40 | 411 | 449 | 40.9 | 4.60E−09 |
| 1463 | CGPG8211.pep | WD40 | 453 | 538 | 32.2 | 1.90E−06 |
| 1463 | CGPG8211.pep | WD40 | 542 | 578 | 38.9 | 1.80E−08 |
| 1464 | CGPG823.pep | Ribosomal_S6e | 1 | 129 | 258.3 | 1.70E−74 |
| 1466 | CGPG8238.pep | PGI | 49 | 537 | 857.4 | 7.40E−255 |
| 1467 | CGPG8260.pep | Iso_dh | 4 | 331 | 460.7 | 1.90E−135 |
| 1468 | CGPG8267.pep | Pyridoxal_deC | 34 | 383 | 352.2 | 8.70E−103 |
| 1469 | CGPG8268.pep | NIR_SIR_ferr | 62 | 131 | 43.9 | 5.60E−10 |
| 1469 | CGPG8268.pep | NIR_SIR | 164 | 345 | 193.4 | 5.50E−55 |
| 1469 | CGPG8268.pep | NIR_SIR_ferr | 360 | 432 | 76.9 | 6.80E−20 |
| 1470 | CGPG8274.pep | PK | 5 | 347 | 589.9 | 2.50E−174 |
| 1470 | CGPG8274.pep | PK_C | 363 | 476 | 81.9 | 2.10E−21 |
| 1471 | CGPG8277.pep | Rib_5-P_isom_A | 55 | 229 | 345 | 1.30E−100 |
| 1472 | CGPG8279.pep | F-box | 22 | 69 | 43 | 1.10E−09 |
| 1472 | CGPG8279.pep | Kelch_1 | 124 | 168 | 35.2 | 2.40E−07 |
| 1472 | CGPG8279.pep | Kelch_1 | 170 | 213 | 29.4 | 1.40E−05 |
| 1472 | CGPG8279.pep | Kelch_2 | 170 | 213 | 24.3 | 0.00045 |
| 1475 | CGPG8408.pep | DUF641 | 60 | 192 | 237.3 | 3.40E−68 |
| 1476 | CGPG842.pep | Redoxin | 5 | 162 | 182.6 | 9.80E−52 |
| 1476 | CGPG842.pep | AhpC-TSA | 6 | 142 | 38.6 | 2.20E−08 |
| 1477 | CGPG8421.pep | NOSIC | 121 | 173 | 90.1 | 6.90E−24 |
| 1477 | CGPG8421.pep | Nop | 213 | 361 | 257.3 | 3.20E−74 |
| 1478 | CGPG8435.pep | NHL | 55 | 82 | 5.9 | 3.4 |
| 1478 | CGPG8435.pep | NHL | 115 | 142 | 37.2 | 5.80E−08 |
| 1479 | CGPG8440.pep | U-box | 242 | 316 | 70.2 | 6.80E−18 |
| 1479 | CGPG8440.pep | Arm | 372 | 413 | 47.5 | 4.70E−11 |
| 1479 | CGPG8440.pep | Arm | 455 | 495 | 32.1 | 2.00E−06 |
| 1479 | CGPG8440.pep | Arm | 496 | 537 | 22.3 | 0.0018 |
| 1479 | CGPG8440.pep | Arm | 538 | 578 | 25.5 | 0.0002 |
| 1480 | CGPG8453.pep | ACT | 36 | 99 | 33.5 | 7.90E−07 |
| 1480 | CGPG8453.pep | ACT | 129 | 201 | 54.1 | 4.90E−13 |
| 1480 | CGPG8453.pep | ACT | 265 | 332 | 28.6 | 2.40E−05 |
| 1480 | CGPG8453.pep | ACT | 343 | 406 | 43.5 | 7.50E−10 |
| 1481 | CGPG8470.pep | DUF89 | 18 | 357 | −103.6 | 0.0022 |
| 1482 | CGPG8479.pep | F-box | 31 | 78 | 22.6 | 0.0015 |
| 1482 | CGPG8479.pep | Kelch_1 | 124 | 170 | 35.4 | 2.00E−07 |
| 1482 | CGPG8479.pep | Kelch_1 | 172 | 216 | 44.6 | 3.40E−10 |
| 1482 | CGPG8479.pep | Kelch_2 | 172 | 216 | 21.7 | 0.0027 |
| 1483 | CGPG8489.pep | F-box | 3 | 50 | 44.4 | 3.90E−10 |
| 1483 | CGPG8489.pep | FBA_1 | 219 | 384 | 291.3 | 2.00E−84 |
| 1484 | CGPG8498.pep | Fcf1 | 87 | 185 | 245.9 | 9.10E−71 |
| 1485 | CGPG85.pep | Aa_trans | 19 | 454 | 556.5 | 2.80E−164 |
| 1486 | CGPG8501.pep | PPR | 149 | 183 | 11.6 | 0.32 |
| 1486 | CGPG8501.pep | PPR | 189 | 223 | 29 | 1.70E−05 |
| 1486 | CGPG8501.pep | PPR | 224 | 258 | 25.6 | 0.00019 |
| 1486 | CGPG8501.pep | PPR | 259 | 292 | 6.5 | 1.3 |
| 1486 | CGPG8501.pep | PPR | 330 | 364 | 4.2 | 2.5 |
| 1486 | CGPG8501.pep | PPR | 401 | 435 | 12.3 | 0.27 |
| 1487 | CGPG8507.pep | DUF588 | 31 | 185 | 202.1 | 1.30E−57 |
| 1488 | CGPG8509.pep | Pro_isomerase | 80 | 233 | 18.3 | 3.90E−10 |
| 1490 | CGPG8517.pep | B_lectin | 84 | 197 | 191 | 2.90E−54 |
| 1490 | CGPG8517.pep | S_locus_glycop | 211 | 339 | 250 | 5.20E−72 |
| 1490 | CGPG8517.pep | PAN_2 | 356 | 422 | 105.1 | 2.10E−28 |
| 1492 | CGPG852.pep | Ribosomal_S5 | 94 | 160 | 140.9 | 3.60E−39 |
| 1492 | CGPG852.pep | Ribosomal_S5_C | 177 | 250 | 134.4 | 3.30E−37 |
| 1498 | CGPG8567.pep | TB2_DP1_HVA22 | 3 | 98 | 59.4 | 1.20E−14 |
| 1499 | CGPG8580.pep | Caleosin | 22 | 195 | 434.3 | 1.70E−127 |
| 1501 | CGPG8590.pep | DUF579 | 42 | 289 | 571.9 | 6.60E−169 |
| 1503 | CGPG8594.pep | DUF584 | 1 | 139 | 248.7 | 1.30E−71 |
| 1504 | CGPG8606.pep | Exo_endo_phos | 56 | 327 | 125 | 2.30E−34 |
| 1505 | CGPG8628.pep | DUF584 | 32 | 203 | 125.8 | 1.30E−34 |
| 1507 | CGPG8654.pep | PPR | 73 | 107 | 13.2 | 0.21 |
| 1507 | CGPG8654.pep | PPR | 141 | 175 | 38.6 | 2.30E−08 |
| 1508 | CGPG8668.pep | TATA_RF | 1 | 200 | 306.9 | 3.90E−89 |
| 1511 | CGPG8702.pep | RPE65 | 50 | 622 | 19.9 | 1.70E−17 |
| 1514 | CGPG8748.pep | AAA | 201 | 357 | 13.1 | 1.30E−06 |
| 1516 | CGPG8770.pep | DUF543 | 1 | 73 | 107.6 | 3.90E−29 |
| 1517 | CGPG8777.pep | DUF569 | 1 | 144 | 377.9 | 1.70E−110 |
| 1517 | CGPG8777.pep | DUF569 | 227 | 368 | 391.4 | 1.40E−114 |
| 1519 | CGPG8786.pep | DUF260 | 13 | 113 | 247.6 | 2.70E−71 |
| 1520 | CGPG8792.pep | Abhydrolase_3 | 75 | 290 | 228.4 | 1.60E−65 |
| 1521 | CGPG8801.pep | PPR | 110 | 144 | 18.7 | 0.022 |
| 1521 | CGPG8801.pep | PPR | 145 | 179 | 9.1 | 0.64 |
| 1521 | CGPG8801.pep | PPR | 181 | 215 | 42.6 | 1.40E−09 |
| 1521 | CGPG8801.pep | PPR | 216 | 250 | 19.5 | 0.012 |
| 1521 | CGPG8801.pep | PPR | 251 | 285 | 23.6 | 0.00076 |
| 1521 | CGPG8801.pep | PPR | 286 | 320 | 37.2 | 6.10E−08 |

TABLE 21-continued

| PEP Seq ID No. | Construct ID | Pfam domain name | Begin | Stop | score | E-value |
|---|---|---|---|---|---|---|
| 1521 | CGPG8801.pep | PPR | 321 | 355 | 12 | 0.3 |
| 1522 | CGPG8809.pep | Ribosomal_L12 | 141 | 208 | 61.2 | 3.50E−15 |
| 1523 | CGPG8840.pep | CLP_protease | 115 | 289 | 45.1 | 1.30E−11 |
| 1524 | CGPG8850.pep | PPR | 189 | 223 | 17.3 | 0.057 |
| 1524 | CGPG8850.pep | PPR | 224 | 258 | 48.5 | 2.40E−11 |
| 1524 | CGPG8850.pep | PPR | 297 | 331 | 34.6 | 3.50E−07 |
| 1524 | CGPG8850.pep | PPR | 332 | 366 | 46.2 | 1.20E−10 |
| 1524 | CGPG8850.pep | PPR | 367 | 401 | 40.7 | 5.40E−09 |
| 1524 | CGPG8850.pep | PPR | 402 | 436 | 50 | 8.00E−12 |
| 1524 | CGPG8850.pep | PPR | 437 | 470 | 36.5 | 9.50E−08 |
| 1524 | CGPG8850.pep | PPR | 471 | 505 | 39.8 | 9.60E−09 |
| 1524 | CGPG8850.pep | PPR | 506 | 540 | 23.2 | 0.00094 |
| 1524 | CGPG8850.pep | PPR | 542 | 576 | 46.6 | 8.80E−11 |
| 1525 | CGPG8870.pep | Fructosamin_kin | 54 | 339 | 208 | 2.30E−59 |
| 1525 | CGPG8870.pep | APH | 69 | 308 | 80.1 | 7.30E−21 |
| 1526 | CGPG8871.pep | DUF59 | 36 | 115 | 57.6 | 4.20E−14 |
| 1527 | CGPG8872.pep | RRM_1 | 138 | 205 | 78 | 3.00E−20 |
| 1527 | CGPG8872.pep | RRM_1 | 214 | 288 | 32.4 | 1.70E−06 |
| 1527 | CGPG8872.pep | RRM_1 | 308 | 378 | 60 | 8.10E−15 |
| 1528 | CGPG8876.pep | SFT2 | 43 | 162 | 194.7 | 2.40E−55 |
| 1529 | CGPG8902.pep | RNA_pol_I_A49 | 31 | 415 | 702.7 | 2.70E−208 |
| 1530 | CGPG8904.pep | G-alpha | 103 | 447 | 513.2 | 3.10E−151 |
| 1531 | CGPG8907.pep | DnaJ | 4 | 67 | 128.7 | 1.70E−35 |
| 1531 | CGPG8907.pep | zf-C2H2 | 338 | 362 | 28 | 3.40E−05 |
| 1532 | CGPG8914.pep | Whi5 | 181 | 205 | 50.1 | 7.80E−12 |
| 1533 | CGPG8931.pep | eIF3_subunit | 1 | 231 | 272.1 | 1.20E−78 |
| 1534 | CGPG8933.pep | MACPF | 126 | 322 | 60.6 | 5.20E−15 |
| 1535 | CGPG8935.pep | Pkinase | 33 | 324 | 308.5 | 1.30E−89 |
| 1536 | CGPG8938.pep | Pkinase | 71 | 348 | 187.5 | 3.40E−53 |
| 1536 | CGPG8938.pep | Pkinase_Tyr | 71 | 348 | 128.4 | 2.10E−35 |
| 1537 | CGPG8944.pep | PH | 31 | 134 | 48.5 | 2.40E−11 |
| 1538 | CGPG895.pep | DUF231 | 251 | 427 | 223.7 | 4.30E−64 |
| 1540 | CGPG8961.pep | Dus | 59 | 392 | 236.5 | 5.90E−68 |
| 1541 | CGPG8963.pep | Pkinase | 319 | 612 | 332 | 1.10E−96 |
| 1542 | CGPG898.pep | DUF231 | 276 | 448 | 289.8 | 5.30E−84 |
| 1543 | CGPG8993.pep | AAA | 44 | 226 | 54.9 | 2.80E−13 |
| 1543 | CGPG8993.pep | Rep_fac_C | 237 | 326 | 113.5 | 6.50E−31 |
| 1544 | CGPG8994.pep | Brix | 86 | 262 | 264.3 | 2.50E−76 |
| 1545 | CGPG8995.pep | Porin_3 | 54 | 326 | 280.1 | 4.30E−81 |
| 1546 | CGPG90.pep | MFS_1 | 68 | 427 | 55 | 2.50E−13 |
| 1547 | CGPG900.pep | DUF231 | 241 | 420 | 229.6 | 6.90E−66 |
| 1548 | CGPG9002.pep | CTP_transf_1 | 51 | 382 | 443.1 | 3.90E−130 |
| 1549 | CGPG9009.pep | Alg6_Alg8 | 22 | 514 | 439.6 | 4.30E−129 |
| 1550 | CGPG9011.pep | OTCace_N | 70 | 212 | 188.6 | 1.60E−53 |
| 1550 | CGPG9011.pep | OTCace | 216 | 369 | 198.1 | 2.20E−56 |
| 1551 | CGPG9012.pep | FolB | 16 | 129 | 125 | 2.10E−34 |
| 1552 | CGPG9017.pep | DMRL_synthase | 70 | 213 | 195.5 | 1.30E−55 |
| 1553 | CGPG9025.pep | Glyco_transf_29 | 105 | 355 | −11 | 1.90E−06 |
| 1554 | CGPG9026.pep | Adap_comp_sub | 160 | 428 | 469.4 | 4.70E−138 |
| 1555 | CGPG9032.pep | RNase_PH | 33 | 165 | 135.6 | 1.40E−37 |
| 1555 | CGPG9032.pep | RNase_PH_C | 194 | 262 | 44.9 | 2.70E−10 |
| 1556 | CGPG9040.pep | Sec1 | 35 | 592 | 217.7 | 2.70E−62 |
| 1557 | CGPG9044.pep | Syntaxin | 57 | 163 | 93.9 | 5.10E−25 |
| 1557 | CGPG9044.pep | SNARE | 256 | 318 | 79.5 | 1.10E−20 |
| 1558 | CGPG9048.pep | RNase_PH | 15 | 135 | 53.3 | 8.30E−13 |
| 1559 | CGPG9049.pep | Glycos_transf_1 | 244 | 442 | 16 | 3.70E−05 |
| 1560 | CGPG9058.pep | RNA_pol_N | 1 | 60 | 125.6 | 1.40E−34 |
| 1561 | CGPG906.pep | PPR | 210 | 244 | 28.2 | 3.10E−05 |
| 1561 | CGPG906.pep | PPR | 245 | 279 | 13.7 | 0.19 |
| 1562 | CGPG9070.pep | ATP-synt_C | 20 | 85 | 42.4 | 1.60E−09 |
| 1562 | CGPG9070.pep | ATP-synt_C | 104 | 169 | 21.7 | 0.00014 |
| 1564 | CGPG9084.pep | CH | 15 | 116 | 47.4 | 5.20E−11 |
| 1564 | CGPG9084.pep | EB1 | 209 | 255 | 79.7 | 9.20E−21 |
| 1566 | CGPG9098.pep | DUF6 | 32 | 165 | 22.6 | 0.0015 |
| 1566 | CGPG9098.pep | TPT | 199 | 337 | −10.3 | 0.0023 |
| 1566 | CGPG9098.pep | DUF6 | 208 | 337 | 66.1 | 1.20E−16 |
| 1567 | CGPG9099.pep | Rick_17kDa_Anti | 66 | 110 | 24.9 | 0.00029 |
| 1568 | CGPG9110.pep | RALF | 53 | 118 | 122.9 | 9.30E−34 |
| 1569 | CGPG9119.pep | PTR2 | 115 | 504 | 350.4 | 3.10E−102 |
| 1570 | CGPG9125.pep | ThiF | 98 | 233 | 171.7 | 1.90E−48 |
| 1571 | CGPG913.pep | PPR | 86 | 120 | 32.9 | 1.20E−06 |
| 1571 | CGPG913.pep | PPR | 188 | 222 | 51.1 | 4.00E−12 |
| 1571 | CGPG913.pep | PPR | 223 | 257 | 7.4 | 1 |
| 1571 | CGPG913.pep | PPR | 289 | 323 | 26 | 0.00014 |
| 1571 | CGPG913.pep | PPR | 325 | 358 | 12 | 0.29 |
| 1571 | CGPG913.pep | PPR | 361 | 395 | 12.8 | 0.24 |
| 1574 | CGPG9164.pep | DHBP_synthase | 5 | 202 | 475.9 | 5.10E−140 |
| 1574 | CGPG9164.pep | GTP_cyclohydro2 | 207 | 377 | 431.4 | 1.30E−126 |

TABLE 21-continued

| PEP Seq ID No. | Construct ID | Pfam domain name | Begin | Stop | score | E-value |
|---|---|---|---|---|---|---|
| 1575 | CGPG9172.pep | Sec61_beta | 32 | 77 | 83 | 9.60E−22 |
| 1577 | CGPG9185.pep | DUF423 | 10 | 115 | 84.7 | 2.90E−22 |
| 1578 | CGPG9187.pep | Pkinase | 12 | 263 | 298.2 | 1.60E−86 |
| 1579 | CGPG9190.pep | DREPP | 2 | 203 | 280.3 | 3.80E−81 |
| 1580 | CGPG9193.pep | GATase | 11 | 196 | 175.1 | 1.90E−49 |
| 1580 | CGPG9193.pep | GMP_synt_C | 432 | 524 | 172.7 | 9.30E−49 |
| 1581 | CGPG9195.pep | DUF1279 | 91 | 193 | 127 | 5.60E−35 |
| 1582 | CGPG9203.pep | Na_H_Exchanger | 13 | 391 | 242.3 | 1.00E−69 |
| 1582 | CGPG9203.pep | TrkA_C | 418 | 486 | 58.4 | 2.50E−14 |
| 1583 | CGPG9209.pep | GATase | 9 | 197 | 199.6 | 7.80E−57 |
| 1583 | CGPG9209.pep | GMP_synt_C | 423 | 515 | 201.4 | 2.20E−57 |
| 1585 | CGPG9210.pep | Na_H_Exchanger | 10 | 376 | 229 | 1.10E−65 |
| 1585 | CGPG9210.pep | TrkA_N | 402 | 517 | 131 | 3.50E−36 |
| 1586 | CGPG9211.pep | NTP_transferase | 7 | 296 | 508.1 | 1.00E−149 |
| 1586 | CGPG9211.pep | MannoseP_isomer | 307 | 473 | 454 | 2.00E−133 |
| 1586 | CGPG9211.pep | Cupin_2 | 388 | 458 | 48.1 | 3.10E−11 |
| 1587 | CGPG9212.pep | ATP-synt_ab_N | 22 | 87 | 53.4 | 7.60E−13 |
| 1587 | CGPG9212.pep | ATP-synt_ab | 143 | 353 | 429.3 | 5.40E−126 |
| 1588 | CGPG9216.pep | DHBP_synthase | 10 | 206 | 377.8 | 1.70E−110 |
| 1588 | CGPG9216.pep | GTP_cyclohydro2 | 211 | 379 | 395.3 | 9.20E−116 |
| 1589 | CGPG9226.pep | Carboxyl_trans | 40 | 541 | 967.5 | 5.20E−288 |
| 1590 | CGPG9252.pep | CDC48_N | 28 | 114 | 132.1 | 1.60E−36 |
| 1590 | CGPG9252.pep | AAA | 245 | 429 | 330.3 | 3.40E−96 |
| 1590 | CGPG9252.pep | AAA_5 | 245 | 377 | 9.8 | 0.00052 |
| 1590 | CGPG9252.pep | AAA | 518 | 705 | 344.1 | 2.40E−100 |
| 1592 | CGPG9289.pep | LSM | 10 | 75 | 64.8 | 3.00E−16 |
| 1593 | CGPG9298.pep | p450 | 41 | 516 | 138.8 | 1.60E−38 |
| 1594 | CGPG9299.pep | ThiF | 82 | 227 | 145.2 | 1.80E−40 |
| 1597 | CGPG9316.pep | ATP-grasp_2 | 34 | 242 | 405.7 | 7.10E−119 |
| 1597 | CGPG9316.pep | Ligase_CoA | 285 | 421 | 229 | 1.10E−65 |
| 1598 | CGPG9317.pep | DUF163 | 43 | 196 | 205.3 | 1.50E−58 |
| 1599 | CGPG9318.pep | Aldo_ket_red | 20 | 285 | 408 | 1.40E−119 |
| 1600 | CGPG9324.pep | Pkinase | 158 | 706 | 150.9 | 3.40E−42 |
| 1601 | CGPG9357.pep | Raffinose_syn | 7 | 757 | 1669.7 | 0 |
| 1602 | CGPG965.pep | Hexapep | 70 | 87 | 10.5 | 6.4 |
| 1602 | CGPG965.pep | Hexapep | 119 | 136 | 16.4 | 0.11 |
| 1602 | CGPG965.pep | Hexapep | 142 | 159 | 5.9 | 28 |
| 1602 | CGPG965.pep | Hexapep | 160 | 177 | 2.6 | 71 |
| 1603 | CGPG970.pep | NPH3 | 206 | 441 | 272 | 1.20E−78 |
| 1604 | CGPG982.pep | p450 | 29 | 495 | 389.8 | 4.30E−114 |
| 1605 | CGPG994.pep | adh_short | 50 | 218 | 46.7 | 8.30E−11 |
| 1606 | CGPG996.pep | DUF866 | 1 | 167 | 456.5 | 3.60E−134 |

TABLE 22

| Pfam domain name | Accession # | gathering cutoff | domain description |
|---|---|---|---|
| 2OG-FeII_Oxy | PF03171.11 | 11.5 | 2OG-Fe(II) oxygenase superfamily |
| 3Beta_HSD | PF01073.10 | −135.9 | 3-beta hydroxysteroid dehydrogenase/isomerase family |
| 3HCDH | PF00725.13 | −8.9 | 3-hydroxyacyl-CoA dehydrogenase, C-terminal domain |
| 3HCDH_N | PF02737.9 | −82.1 | 3-hydroxyacyl-CoA dehydrogenase, NAD binding domain |
| 6PGD | PF00393.10 | −232.3 | 6-phosphogluconate dehydrogenase, C-terminal domain |
| AAA | PF00004.20 | 12.3 | ATPase family associated with various cellular activities (AAA) |
| AAA_5 | PF07728.5 | 4 | ATPase family associated with various cellular activities (AAA) |
| AARP2CN | PF08142.3 | 25 | AARP2CN (NUC121) domain |
| AA_kinase | PF00696.19 | −40 | Amino acid kinase family |
| AA_permease | PF00324.12 | −120.8 | Amino acid permease |
| ABC_tran | PF00005.18 | 9.5 | ABC transporter |
| ACBP | PF00887.10 | −14 | Acyl CoA binding protein |
| ACP_syn_III_C | PF08541.1 | −21.6 | 3-Oxoacyl-[acyl-carrier-protein (ACP)] synthase III C terminal |
| ACT | PF01842.16 | 0.7 | ACT domain |
| ADH_N | PF08240.3 | −14.5 | Alcohol dehydrogenase GroES-like domain |
| ADH_zinc_N | PF00107.17 | 23.8 | Zinc-binding dehydrogenase |
| AIG1 | PF04548.7 | −40 | AIG1 family |
| AIG2 | PF06094.3 | 12.7 | AIG2-like family |
| AP2 | PF00847.11 | 21.7 | AP2 domain |
| APH | PF01636.14 | 32.5 | Phosphotransferase enzyme family |
| ATP-grasp_2 | PF08442.1 | −118.8 | ATP-grasp domain |
| ATP-synt_C | PF00137.12 | 5 | ATP synthase subunit C |
| ATP-synt_G | PF04718.6 | −7.9 | Mitochondrial ATP synthase g subunit |
| ATP-synt_ab | PF00006.16 | −37.5 | ATP synthase alpha/beta family, nucleotide-binding domain |
| ATP-synt_ab_N | PF02874.14 | 17 | ATP synthase alpha/beta family, beta-barrel domain |
| ATP_bind_1 | PF03029.8 | −19 | Conserved hypothetical ATP binding protein |
| AWPM-19 | PF05512.2 | 25 | AWM-19-like family |

TABLE 22-continued

| Pfam domain name | Accession # | gathering cutoff | domain description |
|---|---|---|---|
| Aa_trans | PF01490.9 | −128.4 | Transmembrane amino acid transporter protein |
| Abhydrolase_3 | PF07859.4 | 25.8 | alpha/beta hydrolase fold |
| Acetyltransf_1 | PF00583.15 | 18.6 | Acetyltransferase (GNAT) family |
| Acyltransferase | PF01553.12 | 22 | Acyltransferase |
| Adap_comp_sub | PF00928.12 | −5.4 | Adaptor complexes medium subunit family |
| AhpC-TSA | PF00578.12 | 4.8 | AhpC/TSA family |
| Alba | PF01918.12 | 20 | Alba |
| Aldedh | PF00171.13 | −208.2 | Aldehyde dehydrogenase family |
| Aldo_ket_red | PF00248.12 | −97 | Aldo/keto reductase family |
| Alg6_Alg8 | PF03155.6 | −235.5 | ALG6, ALG8 glycosyltransferase family |
| Alpha-amyl_C2 | PF07821.3 | 25 | Alpha-amylase C-terminal beta-sheet domain |
| Alpha-amylase | PF00128.15 | −92.6 | Alpha amylase, catalytic domain |
| Aminotran_1_2 | PF00155.12 | −57.5 | Aminotransferase class I and II |
| Aminotran_3 | PF00202.12 | −206.1 | Aminotransferase class-III |
| Aminotran_5 | PF00266.10 | −164.4 | Aminotransferase class-V |
| Ank | PF00023.21 | 0 | Ankyrin repeat |
| Arf | PF00025.12 | 40 | ADP-ribosylation factor family |
| ArfGap | PF01412.9 | −17 | Putative GTPase activating protein for Arf |
| Arm | PF00514.14 | 17 | Armadillo/beta-catenin-like repeat |
| Asp | PF00026.14 | −153.8 | Eukaryotic aspartyl protease |
| Asparaginase | PF00710.11 | 25 | Asparaginase |
| Auxin_inducible | PF02519.5 | −15 | Auxin responsive protein |
| B3 | PF02362.12 | 26.5 | B3 DNA binding domain |
| BRCT | PF00533.17 | 27.8 | BRCA1 C Terminus (BRCT) domain |
| BT1 | PF03092.7 | −148.6 | BT1 family |
| B_lectin | PF01453.15 | 28.2 | D-mannose binding lectin |
| Band_7 | PF01145.16 | 10.3 | SPFH domain/Band 7 family |
| Beta_elim_lyase | PF01212.12 | −110.3 | Beta-eliminating lyase |
| Biotin_lipoyl | PF00364.13 | −2.3 | Biotin-requiring enzyme |
| Bombesin | PF02044.8 | 11.4 | Bombesin-like peptide |
| Branch | PF02485.12 | −83.5 | Core-2/I-Branching enzyme |
| Brix | PF04427.9 | 11.4 | Brix domain |
| Bromodomain | PF00439.16 | 8.9 | Bromodomain |
| C1_1 | PF00130.13 | 11.4 | Phorbol esters/diacylglycerol binding domain (C1 domain) |
| C1_2 | PF03107.7 | 26.4 | C1 domain |
| C1_3 | PF07649.3 | 25 | C1-like domain |
| C2 | PF00168.21 | 3.7 | C2 domain |
| CAF1 | PF04857.11 | −100.5 | CAF1 family ribonuclease |
| CBFD_NFYB_HMF | PF00808.14 | 18.4 | Histone-like transcription factor (CBF/NF-Y) and archaeal histone |
| CBS | PF00571.19 | 17.5 | CBS domain pair |
| CCT | PF06203.5 | 25 | CCT motif |
| CDC48_N | PF02359.9 | −2 | Cell division protein 48 (CDC48), N-terminal domain |
| CDC50 | PF03381.6 | 25 | LEMS (ligand-effect modulator 3) family/CDC50 family |
| CDP-OH_P_transf | PF01066.12 | 0 | CDP-alcohol phosphatidyltransferase |
| CH | PF00307.22 | 22.5 | Calponin homology (CH) domain |
| CLP_protease | PF00574.14 | −77.2 | Clp protease |
| CPSase_sm_chain | PF00988.13 | 25 | Carbamoyl-phosphate synthase small chain, CPSase domain |
| CRAL_TRIO | PF00650.11 | −26 | CRAL/TRIO domain |
| CRAL_TRIO_N | PF03765.6 | 16 | CRAL/TRIO, N-terminus |
| CTP_transf_1 | PF01148.11 | −35.9 | Cytidylyltransferase family |
| Caleosin | PF05042.4 | 25 | Caleosin related protein |
| Carb_anhydrase | PF00194.12 | −105 | Eukaryotic-type carbonic anhydrase |
| Carboxyl_trans | PF01039.13 | −262.3 | Carboxyl transferase domain |
| Cellulose_synt | PF03552.5 | −257.9 | Cellulose synthase |
| Cenp-O | PF09496.1 | 25 | Cenp-O kinetochore centromere component |
| Chal_sti_synt_C | PF02797.6 | −6.1 | Chalcone and stilbene synthases, C-terminal domain |
| Chalcone | PF02431.6 | 25 | Chalcone-flavanone isomerase |
| ClpS | PF02617.8 | −15 | ATP-dependent Clp protease adaptor protein ClpS |
| Copine | PF07002.7 | −36.5 | Copine |
| Cu-oxidase | PF00394.13 | −18.9 | Multicopper oxidase |
| Cu-oxidase_2 | PF07731.5 | −5.8 | Multicopper oxidase |
| Cu-oxidase_3 | PF07732.6 | 10 | Multicopper oxidase |
| Cullin | PF00888.13 | −33.3 | Cullin family |
| Cupin_1 | PF00190.13 | −13 | Cupin |
| Cupin_2 | PF07883.2 | 19.4 | Cupin domain |
| Cyclase | PF04199.4 | −31.7 | Putative cyclase |
| Cyclin_C | PF02984.10 | −13 | Cyclin, C-terminal domain |
| Cyclin_N | PF00134.14 | −14.7 | Cyclin, N-terminal domain |
| DAD | PF02109.7 | 25 | DAD family |
| DAO | PF01266.15 | −34.9 | FAD dependent oxidoreductase |
| DCP1 | PF06058.4 | −16.8 | Dcp1-like decapping family |
| DEAD | PF00270.20 | 7.2 | DEAD/DEAH box helicase |
| DEK_C | PF08766.2 | 25 | DEK C terminal domain |
| DHBP_synthase | PF00926.10 | −95.1 | 3,4-dihydroxy-2-butanone 4-phosphate synthase |
| DMRL_synthase | PF00885.10 | −43 | 6,7-dimethyl-8-ribityllumazine synthase |
| DREPP | PF05558.3 | 25 | DREPP plasma membrane polypeptide |
| DSPc | PF00782.11 | −21.8 | Dual specificity phosphatase, catalytic domain |

TABLE 22-continued

| Pfam domain name | Accession # | gathering cutoff | domain description |
|---|---|---|---|
| DUF1279 | PF06916.4 | 25 | Protein of unknown function (DUF1279) |
| DUF1350 | PF07082.2 | −145.7 | Protein of unknown function (DUF1350) |
| DUF1475 | PF07343.2 | 25 | Protein of unknown function (DUF1475) |
| DUF1517 | PF07466.2 | 25 | Protein of unknown function (DUF1517) |
| DUF163 | PF02590.8 | −48.6 | Uncharacterized ACR, COG1576 |
| DUF1637 | PF07847.3 | 25 | Protein of unknown function (DUF1637) |
| DUF167 | PF02594.7 | −3.4 | Uncharacterised ACR, YggU family COG1872 |
| DUF177 | PF02620.8 | 25 | Uncharacterized ACR, COG1399 |
| DUF220 | PF02713.5 | 25 | Domain of unknown function DUF220 |
| DUF231 | PF03005.6 | −58 | Arabidopsis proteins of unknown function |
| DUF260 | PF03195.5 | 0.8 | Protein of unknown function DUF260 |
| DUF423 | PF04241.6 | −17.6 | Protein of unknown function (DUF423) |
| DUF543 | PF04418.3 | 25 | Domain of unknown function (DUF543) |
| DUF569 | PF04601.4 | −47.6 | Protein of unknown function (DUF569) |
| DUF579 | PF04669.4 | 25 | Protein of unknown function (DUF579) |
| DUF584 | PF04520.4 | 25 | Protein of unknown function, DUF584 |
| DUF588 | PF04535.3 | 25 | Domain of unknown function (DUF588) |
| DUF59 | PF01883.10 | −7.9 | Domain of unknown function DUF59 |
| DUF594 | PF04578.4 | 25 | Protein of unknown function, DUF594 |
| DUF599 | PF04654.3 | 25 | Protein of unknown function, DUF599 |
| DUF6 | PF00892.11 | 21.7 | Integral membrane protein DUF6 |
| DUF607 | PF04678.4 | 25 | Protein of unknown function, DUF607 |
| DUF616 | PF04765.4 | 25 | Protein of unknown function (DUF616) |
| DUF620 | PF04788.3 | 25 | Protein of unknown function (DUF620) |
| DUF641 | PF04859.3 | 25 | Plant protein of unknown function (DUF641) |
| DUF663 | PF04950.3 | 25 | Protein of unknown function (DUF663) |
| DUF822 | PF05687.4 | 25 | Plant protein of unknown function (DUF822) |
| DUF829 | PF05705.5 | 25 | Eukaryotic protein of unknown function (DUF829) |
| DUF862 | PF05903.5 | −21.4 | PPPDE putative peptidase domain |
| DUF866 | PF05907.4 | 30.1 | Eukaryotic protein of unknown function (DUF866) |
| DUF887 | PF05967.2 | −72.3 | Eukaryotic protein of unknown function (DUF887) |
| DUF89 | PF01937.10 | −113.8 | Protein of unknown function DUF89 |
| DUF933 | PF06071.4 | 20 | Protein of unknown function (DUF933) |
| DZC | PF08381.2 | 15.3 | Disease resistance/zinc finger/chromosome condensation-like region |
| Di19 | PF05605.3 | 25 | Drought induced 19 protein (Di19) |
| Dimerisation | PF08100.2 | 25 | Dimerisation domain |
| DnaJ | PF00226.22 | −8 | DnaJ domain |
| Dus | PF01207.8 | −82.1 | Dihydrouridine synthase (Dus) |
| E3_binding | PF02817.8 | 10 | e3 binding domain |
| EB1 | PF03271.8 | 25 | EB1-like C-terminal motif |
| ECH | PF00378.11 | −57.6 | Enoyl-CoA hydratase/isomerase family |
| ELFV_dehydrog | PF00208.12 | −26.4 | Glutamate/Leucine/Phenylalanine/Valine dehydrogenase |
| ELFV_dehydrog_N | PF02812.9 | 31.8 | Glu/Leu/Phe/Val dehydrogenase, dimerisation domain |
| EMP24_GP25L | PF01105.15 | 10.4 | emp24/gp25L/p24 family/GOLD |
| ENOD93 | PF03386.5 | 25 | Early nodulin 93 ENOD93 protein |
| ENT | PF03735.5 | 25 | ENT domain |
| Enolase_C | PF00113.13 | −71.2 | Enolase, C-terminal TIM barrel domain |
| Enolase_N | PF03952.7 | 11.3 | Enolase, N-terminal domain |
| Epimerase | PF01370.12 | −46.3 | NAD dependent epimerase/dehydratase family |
| Exo_endo_phos | PF03372.14 | 11 | Endonuclease/Exonuclease/phosphatase family |
| F-box | PF00646.24 | 14.4 | F-box domain |
| F420_oxidored | PF03807.8 | −34.5 | NADP oxidoreductase coenzyme F420-dependent |
| FAD_binding_2 | PF00890.15 | −124.8 | FAD binding domain |
| FAD_binding_3 | PF01494.10 | −136.6 | FAD binding domain |
| FAE1_CUT1_RppA | PF08392.3 | −192.7 | FAE1/Type III polyketide synthase-like protein |
| FA_hydroxylase | PF04116.4 | −15.3 | Fatty acid hydroxylase superfamily |
| FBA_1 | PF07734.4 | −39.4 | F-box associated |
| FBPase | PF00316.11 | −170.3 | Fructose-1-6-bisphosphatase |
| FHA | PF00498.17 | 25 | FHA domain |
| FMO-like | PF00743.10 | −381.6 | Flavin-binding monooxygenase-like |
| FYVE | PF01363.12 | 28.5 | FYVE zinc finger |
| Fcf1 | PF04900.3 | −7.6 | Fcf1 |
| Fer2 | PF00111.18 | 7 | 2Fe-2S iron-sulfur cluster binding domain |
| FolB | PF02152.9 | 25 | Dihydroneopterin aldolase |
| Fructosamin_kin | PF03881.5 | −125.6 | Fructosamine kinase |
| G-alpha | PF00503.11 | −230 | G-protein alpha subunit |
| G-patch | PF01585.14 | 18.4 | G-patch domain |
| G6PD_C | PF02781.7 | −175 | Glucose-6-phosphate dehydrogenase, C-terminal domain |
| G6PD_N | PF00479.13 | −99 | Glucose-6-phosphate dehydrogenase, NAD binding domain |
| GASA | PF02704.5 | 25 | Gibberellin regulated protein |
| GAT | PF03127.5 | −7 | GAT domain |
| GATase | PF00117.19 | −38.1 | Glutamine amidotransferase class-I |
| GFA | PF04828.5 | 12.4 | Glutathione-dependent formaldehyde-activating enzyme |
| GH3 | PF03321.4 | −336 | GH3 auxin-responsive promoter |
| GHMP_kinases_C | PF08544.4 | 20.8 | GHMP kinases C terminal |
| GHMP_kinases_N | PF00288.17 | 17.1 | GHMP kinases N terminal domain |
| GIDA | PF01134.13 | −226.7 | Glucose inhibited division protein A |

TABLE 22-continued

| Pfam domain name | Accession # | gathering cutoff | domain description |
|---|---|---|---|
| GLTP | PF08718.2 | −71.1 | Glycolipid transfer protein (GLTP) |
| GMP_synt_C | PF00958.13 | 25 | GMP synthase C terminal domain |
| GST_C | PF00043.16 | 22.3 | Glutathione S-transferase, C-terminal domain |
| GST_N | PF02798.11 | 14.6 | Glutathione S-transferase, N-terminal domain |
| GTP_cyclohydro2 | PF00925.11 | −49 | GTP cyclohydrolase II |
| G_glu_transpept | PF01019.12 | −236.1 | Gamma-glutamyltranspeptidase |
| Gln-synt_C | PF00120.15 | −124 | Glutamine synthetase, catalytic domain |
| GlutR_N | PF05201.6 | −37.8 | Glutamyl-tRNAGlu reductase, N-terminal domain |
| GlutR_dimer | PF00745.11 | 25 | Glutamyl-tRNAGlu reductase, dimerisation domain |
| Glutaminase | PF04960.6 | −143.6 | Glutaminase |
| Glutaredoxin | PF00462.15 | 17.2 | Glutaredoxin |
| Glyco_tran_28_C | PF04101.7 | −10.4 | Glycosyltransferase family 28 C-terminal domain |
| Glyco_transf_29 | PF00777.9 | −74 | Glycosyltransferase family 29 (sialyltransferase) |
| Glyco_transf_8 | PF01501.11 | −43.2 | Glycosyl transferase family 8 |
| Glycolytic | PF00274.10 | −174.5 | Fructose-bisphosphate aldolase class-I |
| Glycos_transf_1 | PF00534.11 | −7.3 | Glycosyl transferases group 1 |
| Glyoxalase | PF00903.16 | 12.1 | Glyoxalase/Bleomycin resistance protein/Dioxygenase superfamily |
| Gp_dh_C | PF02800.11 | −64.1 | Glyceraldehyde 3-phosphate dehydrogenase, C-terminal domain |
| Gp_dh_N | PF00044.15 | −74.2 | Glyceraldehyde 3-phosphate dehydrogenase, NAD binding domain |
| HI0933_like | PF03486.5 | −255.8 | HI0933-like protein |
| H_PPase | PF03030.7 | −377 | Inorganic H+ pyrophosphatase |
| Helicase_C | PF00271.22 | 2.4 | Helicase conserved C-terminal domain |
| Hep_59 | PF07052.2 | 25 | Hepatocellular carcinoma-associated antigen 59 |
| Hexapep | PF00132.15 | 0.3 | Bacterial transferase hexapeptide (three repeats) |
| Hin1 | PF07320.4 | 25 | Harpin-induced protein 1 (Hin1) |
| His_biosynth | PF00977.12 | −102.4 | Histidine biosynthesis protein |
| Histone | PF00125.15 | 17.4 | Core histone H2A/H2B/H3/H4 |
| Hpt | PF01627.14 | 25 | Hpt domain |
| Hydrolase | PF00702.17 | 13.6 | haloacid dehalogenase-like hydrolase |
| IF4E | PF01652.9 | −35 | Eukaryotic initiation factor 4E |
| IQ | PF00612.18 | 11.9 | IQ calmodulin-binding motif |
| IU_nuc_hydro | PF01156.10 | −154 | Inosine-uridine preferring nucleoside hydrolase |
| Inositol_P | PF00459.16 | −55.6 | Inositol monophosphatase family |
| Invertase_neut | PF04853.3 | −233.6 | Plant neutral invertase |
| Ion_trans_2 | PF07885.7 | 24.9 | Ion channel |
| Iso_dh | PF00180.11 | −97 | Isocitrate/isopropylmalate dehydrogenase |
| KH_1 | PF00013.20 | 12.5 | KH domain |
| KH_2 | PF07650.8 | 5 | KH domain |
| KR | PF08659.1 | −74.3 | KR domain |
| Kelch_1 | PF01344.16 | 11.7 | Kelch motif |
| Kelch_2 | PF07646.6 | 14 | Kelch motif |
| LAG1 | PF03798.7 | −57.5 | Longevity-assurance protein (LAG1) |
| LANC_like | PF05147.4 | −76.9 | Lanthionine synthetase C-like protein |
| LEA_5 | PF00477.8 | 25 | Small hydrophilic plant seed protein |
| LRRNT_2 | PF08263.3 | 18.6 | Leucine rich repeat N-terminal domain |
| LRR_1 | PF00560.24 | 7.7 | Leucine Rich Repeat |
| LRR_2 | PF07723.4 | 6 | Leucine Rich Repeat |
| LSM | PF01423.13 | 13.7 | LSM domain |
| La | PF05383.8 | 25 | La domain |
| Lectin_legB | PF00139.10 | −110.1 | Legume lectin domain |
| Ligase_CoA | PF00549.10 | −43.3 | CoA-ligase |
| Lipase_3 | PF01764.16 | −8 | Lipase (class 3) |
| MACPF | PF01823.10 | −24.6 | MAC/Perforin domain |
| MATH | PF00917.17 | 0.5 | MATH domain |
| MFS_1 | PF07690.7 | 23.5 | Major Facilitator Superfamily |
| MIP | PF00230.11 | −62 | Major intrinsic protein |
| MMR_HSR1 | PF01926.14 | 31.2 | GTPase of unknown function |
| MOSC | PF03473.8 | 25 | MOSC domain |
| MOSC_N | PF03476.7 | 25 | MOSC N-terminal beta barrel domain |
| MT-A70 | PF05063.5 | −40.8 | MT-A70 |
| Malic_M | PF03949.6 | −143.9 | Malic enzyme, NAD binding domain |
| MannoseP_isomer | PF01050.9 | −70 | Mannose-6-phosphate isomerase |
| Mem_trans | PF03547.9 | −73.4 | Membrane transport protein |
| Metalloenzyme | PF01676.9 | −14.4 | Metalloenzyme superfamily |
| Metallophos | PF00149.19 | 22 | Calcineurin-like phosphoesterase |
| Methyltransf_11 | PF08241.3 | 21 | Methyltransferase domain |
| Methyltransf_12 | PF08242.3 | 23 | Methyltransferase domain |
| Methyttransf_2 | PF00891.9 | −103.8 | O-methyltransferase |
| Miro | PF08477.4 | 10.8 | Miro-like protein |
| Mito_carr | PF00153.18 | 0 | Mitochondrial carrier protein |
| Mov34 | PF01398.12 | 0.9 | Mov34/MPN/PAD-1 family |
| MtN3_slv | PF03083.7 | 9.7 | MtN3/saliva family |
| NAC | PF01849.9 | 0 | NAC domain |
| NAD_Gly3P_dh_C | PF07479.5 | −50.8 | NAD-dependent glycerol-3-phosphate dehydrogenase C-terminus |
| NAD_Gly3P_dh_N | PF01210.14 | −44 | NAD-dependent glycerol-3-phosphate dehydrogenase N-terminus |
| NAD_binding_2 | PF03446.6 | −63.5 | NAD binding domain of 6-phosphogluconate dehydrogenase |
| NAD_binding_4 | PF07993.3 | −87.7 | Male sterility protein |

TABLE 22-continued

| Pfam domain name | Accession # | gathering cutoff | domain description |
|---|---|---|---|
| NAF | PF03822.5 | 4.5 | NAF domain |
| NAP | PF00956.9 | −122 | Nucleosome assembly protein (NAP) |
| NDK | PF00334.10 | −59.9 | Nucleoside diphosphate kinase |
| NHL | PF01436.12 | 3.8 | NHL repeat |
| NIR_SIR | PF01077.13 | −19.6 | Nitrite and sulphite reductase 4Fe-4S domain |
| NIR_SIR_ferr | PF03460.8 | 2.4 | Nitrite/Sulfite reductase ferredoxin-like half domain |
| NOI | PF05627.2 | 0.3 | Nitrate-induced NOI protein |
| NOSIC | PF08060.4 | 25 | NOSIC (NUC001) domain |
| NPH3 | PF03000.5 | 25 | NPH3 family |
| NTF2 | PF02136.11 | 6 | Nuclear transport factor 2 (NTF2) domain |
| NTP_transferase | PF00483.14 | −39.9 | Nucleotidyl transferase |
| Na_Ca_ex | PF01699.15 | 25 | Sodium/calcium exchanger protein |
| Na_H_Exchanger | PF00999.12 | −67.9 | Sodium/hydrogen exchanger family |
| Na_sulph_symp | PF00939.10 | −259 | Sodium: sulfate symporter transmembrane region |
| Nfu_N | PF08712.2 | 20 | Scaffold protein Nfu/NifU N terminal |
| NifU | PF01106.8 | −5.6 | NifU-like domain |
| NifU_N | PF01592.7 | −27.4 | NifU-like N terminal domain |
| Nodulin-like | PF06813.4 | −57.8 | Nodulin-like |
| Nop | PF01798.9 | 25 | Putative snoRNA binding domain |
| Nramp | PF01566.9 | −171.4 | Natural resistance-associated macrophage protein |
| OPT | PF03169.6 | −238.6 | OPT oligopeptide transporter protein |
| ORC2 | PF04084.5 | −181.2 | Origin recognition complex subunit 2 |
| OTCace | PF00185.15 | −42 | Aspartate/ornithine carbamoyltransferase, Asp/Orn binding domain |
| OTCace_N | PF02729.12 | −55 | Aspartate/ornithine carbamoyltransferase, carbamoyl-P binding domain |
| PA | PF02225.13 | 13 | PA domain |
| PAD_porph | PF04371.6 | −180.8 | Porphyromonas-type peptidyl-arginine deiminase |
| PALP | PF00291.16 | −70 | Pyridoxal-phosphate dependent enzyme |
| PAN_1 | PF00024.17 | 1.4 | PAN domain |
| PAN_2 | PF08276.2 | −4.9 | PAN-like domain |
| PAP_fibrillin | PF04755.3 | 25 | PAP_fibrillin |
| PB1 | PF00564.15 | 12.3 | PB1 domain |
| PCI | PF01399.18 | 25 | PCI domain |
| PDCD2_C | PF04194.4 | −40.9 | Programmed cell death protein 2, C-terminal putative domain |
| PDT | PF00800.9 | 25 | Prephenate dehydratase |
| PEP-utilizers | PF00391.14 | 0.6 | PEP-utilising enzyme, mobile domain |
| PEP-utilizers_C | PF02896.9 | −173 | PEP-utilising enzyme, TIM barrel domain |
| PGAM | PF00300.13 | −3 | Phosphoglycerate mutase family |
| PGI | PF00342.10 | −168.9 | Phosphoglucose isomerase |
| PGK | PF00162.10 | −39.3 | Phosphoglycerate kinase |
| PH | PF00169.20 | 25.1 | PH domain |
| PHD | PF00628.20 | 26.2 | PHD-finger |
| PI-PLC-X | PF00388.10 | 18.8 | Phosphatidylinositol-specific phospholipase C, X domain |
| PI-PLC-Y | PF00387.10 | −11 | Phosphatidylinositol-specific phospholipase C, Y domain |
| PK | PF00224.12 | −244 | Pyruvate kinase, barrel domain |
| PK_C | PF02887.7 | −44 | Pyruvate kinase, alpha/beta domain |
| PLAC8 | PF04749.8 | −1.1 | PLAC8 family |
| PMEI | PF04043.6 | 25 | Plant invertase/pectin methylesterase inhibitor |
| PP-binding | PF00550.16 | 25.3 | Phosphopantetheine attachment site |
| PP2C | PF00481.12 | −36.3 | Protein phosphatase 2C |
| PPDK_N | PF01326.10 | −150.2 | Pyruvate phosphate dikinase, PEP/pyruvate binding domain |
| PPR | PF01535.11 | 0 | PPR repeat |
| PRA1 | PF03208.10 | 25 | PRA1 family protein |
| PRC | PF05239.7 | 25 | PRC-barrel domain |
| PRK | PF00485.9 | −28.5 | Phosphoribulokinase/Uridine kinase family |
| PRMT5 | PF05185.7 | 25 | PRMT5 arginine-N-methyltransferase |
| PTA_PTB | PF01515.10 | −165.5 | Phosphate acetyl/butaryl transferase |
| PTPA | PF03095.6 | −106 | Phosphotyrosyl phosphate activator (PTPA) protein |
| PTR2 | PF00854.12 | −50 | POT family |
| PTS_2-RNA | PF01885.7 | −48 | RNA 2'-phosphotransferase, Tpt1/KptA family |
| Pentapeptide | PF00805.13 | 0 | Pentapeptide repeats (8 copies) |
| Peptidase_C12 | PF01088.12 | 10 | Ubiquitin carboxyl-terminal hydrolase, family 1 |
| Peptidase_C14 | PF00656.13 | −22.5 | Caspase domain |
| Peptidase_C48 | PF02902.10 | −13.1 | Ulp1 protease family, C-terminal catalytic domain |
| Peptidase_M16 | PF00675.11 | −38 | Insulinase (Peptidase family M16) |
| Peptidase_M16_C | PF05193.12 | 7.9 | Peptidase M16 inactive domain |
| Peptidase_M18 | PF02127.6 | −250.8 | Aminopeptidase I zinc metalloprotease (M18) |
| Peptidase_M24 | PF00557.15 | −70.7 | metallopeptidase family M24 |
| Peptidase_S8 | PF00082.13 | −51 | Subtilase family |
| Per1 | PF04080.4 | 25 | Per1-like |
| Pescadillo_N | PF06732.2 | −167.1 | Pescadillo N-terminus |
| PfkB | PF00294.15 | −67.8 | pfkB family carbohydrate kinase |
| PhzC-PhzF | PF02567.7 | −66 | Phenazine biosynthesis-like protein |
| Pkinase | PF00069.16 | 70.3 | Protein kinase domain |
| Pkinase_C | PF00433.15 | 14.1 | Protein kinase C terminal domain |
| Pkinase_Tyr | PF07714.8 | 65 | Protein tyrosine kinase |
| Polysacc_synt_2 | PF02719.6 | −176 | Polysaccharide biosynthesis protein |
| Porin_3 | PF01459.13 | −53 | Eukaryotic porin |

TABLE 22-continued

| Pfam domain name | Accession # | gathering cutoff | domain description |
|---|---|---|---|
| Pre-SET | PF05033.7 | 3.9 | Pre-SET motif |
| Pribosyltran | PF00156.18 | 2 | Phosphoribosyl transferase domain |
| Pro_isomerase | PF00160.12 | −37 | Cyclophilin type peptidyl-prolyl cis-trans isomerase/CLD |
| Proteasome | PF00227.17 | −36.7 | Proteasome A-type and B-type |
| PsbW | PF07123.3 | 6.7 | Photosystem II reaction centre W protein (PsbW) |
| Pyr_redox | PF00070.18 | 5 | Pyridine nucleotide-disulphide oxidoreductase |
| Pyr_redox_2 | PF07992.5 | −20 | Pyridine nucleotide-disulphide oxidoreductase |
| Pyr_redox_dim | PF02852.13 | −13 | Pyridine nucleotide-disulphide oxidoreductase, dimerisation domain |
| Pyridoxal_deC | PF00282.10 | −158.6 | Pyridoxal-dependent decarboxylase conserved domain |
| Pyrophosphatase | PF00719.10 | −41 | Inorganic pyrophosphatase |
| RALF | PF05498.2 | 25 | Rapid ALkalinization Factor (RALF) |
| RAMP4 | PF06624.3 | 25 | Ribosome associated membrane protein RAMP4 |
| RCC1 | PF00415.9 | 21.2 | Regulator of chromosome condensation (RCC1) |
| RNA_pol_I_A49 | PF06870.3 | 25 | A49-like RNA polymerase I associated factor |
| RNA_pol_N | PF01194.8 | 25 | RNA polymerases N/8 kDa subunit |
| RNA_pol_Rpb5_C | PF01191.10 | 25 | RNA polymerase Rpb5, C-terminal domain |
| RNA_pol_Rpb5_N | PF03871.5 | −8.9 | RNA polymerase Rpb5, N-terminal domain |
| RNase_PH | PF01138.12 | 4 | 3' exoribonuclease family, domain 1 |
| RNase_PH_C | PF03725.6 | 20 | 3' exoribonuclease family, domain 2 |
| RPE65 | PF03055.6 | −156.5 | Retinal pigment epithelial membrane protein |
| RRM_1 | PF00076.13 | 17.7 | RNA recognition motif, (a.k.a. RRM, RBD, or RNP domain) |
| RRM_2 | PF04059.3 | 25 | RNA recognition motif 2 |
| RRM_3 | PF08777.2 | 0.5 | RNA binding motif |
| RRS1 | PF04939.3 | −60.5 | Ribosome biogenesis regulatory protein (RRS1) |
| Raffinose_syn | PF05691.3 | −395.7 | Raffinose synthase or seed imbibition protein Sip1 |
| Ras | PF00071.13 | −69.9 | Ras family |
| Redoxin | PF08534.1 | −1 | Redoxin |
| Rep_fac_C | PF08542.2 | −0.4 | Replication factor C |
| Response_reg | PF00072.15 | 4 | Response regulator receiver domain |
| Rho_GDI | PF02115.8 | −55 | RHO protein GDP dissociation inhibitor |
| Rhodanese | PF00581.11 | 25 | Rhodanese-like domain |
| Rib_5-P_isom_A | PF06026.5 | −84.5 | Ribose 5-phosphate isomerase A (phosphoriboisomerase A) |
| Ribosomal_L12 | PF00542.10 | 25 | Ribosomal protein L7/L12 C-terminal domain |
| Ribosomal_L7Ae | PF01248.17 | 6 | Ribosomal protein L7Ae/L30e/S12e/Gadd45 family |
| Ribosomal_S5 | PF00333.11 | 25 | Ribosomal protein S5, N-terminal domain |
| Ribosomal_S5_C | PF03719.6 | 0 | Ribosomal protein S5, C-terminal domain |
| Ribosomal_S6e | PF01092.10 | 25 | Ribosomal protein S6e |
| Ribul_P_3_epim | PF00834.10 | −97.3 | Ribulose-phosphate 3 epimerase family |
| Rick_17kDa_Anti | PF05433.6 | 23.2 | Rickettsia 17 kDa surface antigen |
| RmlD_sub_bind | PF04321.8 | −171.8 | RmlD substrate binding domain |
| SAM_1 | PF00536.21 | 11.3 | SAM domain (Sterile alpha motif) |
| SAM_2 | PF07647.8 | 0 | SAM domain (Sterile alpha motif) |
| SATase_N | PF06426.5 | 25 | Serine acetyltransferase, N-terminal |
| SBF | PF01758.7 | −27.8 | Sodium Bile acid symporter family |
| SET | PF00856.19 | 23.5 | SET domain |
| SFT2 | PF07770.3 | −14.4 | SFT2-like protein |
| SH3_1 | PF00018.19 | −8 | SH3 domain |
| SH3_2 | PF07653.8 | 0 | Variant SH3 domain |
| SIP1 | PF04938.3 | 25 | Survival motor neuron (SMN) interacting protein 1 (SIP1) |
| SMP | PF04927.3 | 25 | Seed maturation protein |
| SNARE | PF05739.10 | 23.8 | SNARE domain |
| SNF5 | PF04855.3 | 25 | SNF5/SMARCB1/INI1 |
| SQS_PSY | PF00494.10 | −78 | Squalene/phytoene synthase |
| SRF-TF | PF00319.9 | 11 | SRF-type transcription factor (DNA-binding and dimerisation domain) |
| SRPRB | PF09439.1 | −45.6 | Signal recognition particle receptor beta subunit |
| SSB | PF00436.16 | 0.4 | Single-strand binding protein family |
| STAS | PF01740.12 | 0 | STAS domain |
| STT3 | PF02516.5 | −175 | Oligosaccharyl transferase STT3 subunit |
| SWIB | PF02201.9 | −5.7 | SWIB/MDM2 domain |
| SYF2 | PF08231.3 | 25 | SYF2 splicing factor |
| S_locus_glycop | PF00954.11 | −12.7 | S-locus glycoprotein family |
| Sad1_UNC | PF07738.4 | −20.4 | Sad1/UNC-like C-terminal |
| Sec1 | PF00995.14 | −272 | Sec1 family |
| Sec61_beta | PF03911.7 | 25 | Sec61beta family |
| Sedlin_N | PF04628.4 | −22.1 | Sedlin, N-terminal conserved region |
| SeIR | PF01641.9 | −66.5 | SeIR domain |
| Shikimate_DH | PF01488.11 | −4.4 | Shikimate/quinate 5-dehydrogenase |
| Sina | PF03145.7 | −48.4 | Seven in absentia protein family |
| Skp1 | PF01463.10 | −2 | Skp1 family, dimerisation domain |
| Skp1_POZ | PF03931.6 | 14.9 | Skp1 family, tetramerisation domain |
| Smg4_UPF3 | PF03467.6 | −27.5 | Smg-4/UPF3 family |
| Snf7 | PF03357.12 | −22.9 | Snf7 |
| Spc97_Spc98 | PF04130.4 | −136.8 | Spc97/Spc98 family |
| Steroid_dh | PF02544.7 | −44.7 | 3-oxo-5-alpha-steroid 4-dehydrogenase |
| Str_synth | PF03088.7 | 4.7 | Strictosidine synthase |
| Subtilisin_N | PF05922.7 | 26.1 | Subtilisin N-terminal Region |
| Suc_Fer-like | PF06999.3 | −42.4 | Sucrase/ferredoxin-like |

TABLE 22-continued

| Pfam domain name | Accession # | gathering cutoff | domain description |
|---|---|---|---|
| Sugar_tr | PF00083.15 | −85 | Sugar (and other) transporter |
| Sulfate_transp | PF00916.11 | −131.5 | Sulfate transporter family |
| Sybindin | PF04099.3 | −44.4 | Sybindin-like family |
| Synaptobrevin | PF00957.12 | 25 | Synaptobrevin |
| Syntaxin | PF00804.16 | 11.4 | Syntaxin |
| TATA_RF | PF08612.2 | 25 | TATA-binding related factor (TRF) |
| TB2_DP1_HVA22 | PF03134.10 | −6.9 | TB2/DP1, HVA22 family |
| TBC | PF00566.9 | −58 | TBC domain |
| TBP | PF00352.12 | −8 | Transcription factor TFIID for TATA-binding protein, TBP) |
| TFIID-18kDa | PF02269.7 | −7.3 | Transcription initiation factor IID, 18 kD subunit |
| TFIID-31kDa | PF02291.6 | 25 | Transcription initiation factor IID, 31 kD subunit |
| TFIID_30kDa | PF03540.4 | 25 | Transcription initiation factor TFIID 23-30 kDa subunit |
| TIM | PF00121.9 | −97 | Triosephosphate isomerase |
| TLC | PF03219.5 | 25 | TLC ATP/ADP transporter |
| TPP_enzyme_C | PF02775.12 | 19.7 | Thiamine pyrophosphate enzyme, C-terminal TPP binding domain |
| TPP_enzyme_M | PF00205.13 | −8.1 | Thiamine pyrophosphate enzyme, central domain |
| TPP_enzyme_N | PF02776.9 | −70 | Thiamine pyrophosphate enzyme, N-terminal TPP binding domain |
| TPT | PF03151.7 | −15.3 | Triose-phosphate Transporter family |
| Tbf5 | PF06331.3 | 25 | Transcription factor TFIIH complex subunit Tfb5 |
| Tetraspannin | PF00335.11 | −15.4 | Tetraspanin family |
| ThiF | PF00899.12 | −38.4 | ThiF family |
| Thioredoxin | PF00085.11 | −25.7 | Thioredoxin |
| Thr_dehydrat_C | PF00585.9 | −7.9 | C-terminal regulatory domain of Threonine dehydratase |
| Transket_pyr | PF02779.15 | −49 | Transketolase, pyrimidine binding domain |
| Transketolase_C | PF02780.11 | −15.5 | Transketolase, C-terminal domain |
| TrkA_C | PF02080.12 | 25 | TrkA-C domain |
| TrkA_N | PF02254.9 | 4.7 | TrkA-N domain |
| Tryp_alpha_amyl | PF00234.13 | −0.2 | Protease inhibitor/seed storage/LTP family |
| Tyr-DNA_phospho | PF06087.3 | −152.8 | Tyrosyl-DNA phosphodiesterase |
| U-box | PF04564.6 | −7.6 | U-box domain |
| U3_snoRNA_C | PF09384.1 | 25 | U3 small nucleolar RNA C terminal |
| UBA | PF00627.22 | 20.7 | UBA/TS-N domain |
| UBX | PF00789.11 | 10 | UBX domain |
| UDPG_MGDP_dh | PF00984.10 | −6.9 | UDP-glucose/GDP-mannose dehydrogenase family, central domain |
| UDPG_MGDP_dh_C | PF03720.6 | 0.8 | UDP-glucose/GDP-mannose dehydrogenase family, UDP binding domain |
| UDPG_MGDP_dh_N | PF03721.5 | −74.8 | UDP-glucose/GDP-mannose dehydrogenase family, NAD binding domain |
| UIM | PF02809.11 | 16.6 | Ubiquitin interaction motif |
| UPF0061 | PF02696.5 | −200 | Uncharacterized ACR, YdiU/UPF0061 family |
| UPF0139 | PF03669.4 | 25 | Uncharacterised protein family (UPF0139) |
| UPF0153 | PF03692.6 | 11.7 | Uncharacterised protein family (UPF0153) |
| UPF0185 | PF03671.5 | 11.6 | Uncharacterised protein family (UPF0185) |
| UQ_con | PF00179.17 | −30 | Ubiquitin-conjugating enzyme |
| Ubie_methyltran | PF01209.9 | −117 | ubiE/COQ5 methyltransferase family |
| Usp | PF00582.17 | 21.6 | Universal stress protein family |
| V-ATPase_G | PF03179.6 | −19.8 | Vacuolar (H+)-ATPase G subunit |
| VHS | PF00790.10 | −13.2 | VHS domain |
| VQ | PF05678.5 | 25 | VQ motif |
| WAK | PF08488.2 | 25 | Wall-associated kinase |
| WD40 | PF00400.23 | 21.5 | WD domain, G-beta repeat |
| Whi5 | PF08528.2 | 25 | Whi5 like |
| X8 | PF07983.4 | −28.8 | X8 domain |
| XH | PF03469.5 | 25 | XH domain |
| XS | PF03468.5 | 25 | XS domain |
| YDG_SRA | PF02182.8 | 25 | YDG/SRA domain |
| YIF1 | PF03878.6 | −81.2 | YIF1 |
| YTH | PF04146.6 | 25 | YT521-B-like family |
| Y_phosphatase2 | PF03162.4 | −47.6 | Tyrosine phosphatase family |
| YgbB | PF02542.7 | 25 | YgbB family |
| Zip | PF02535.13 | −25.8 | ZIP Zinc transporter |
| adh_short | PF00106.16 | −40.2 | short chain dehydrogenase |
| dsrm | PF00035.16 | 24.6 | Double-stranded RNA binding motif |
| eIF2A | PF08662.2 | 0 | Eukaryotic translation initiation factor eIF2A |
| eIF3_subunit | PF08597.1 | 11.9 | Translation initiation factor eIF3 subunit |
| efhand | PF00036.23 | 21.7 | EF hand |
| efhand_like | PF09279.2 | 8.8 | Phosphoinositide-specific phospholipase C, efhand-like |
| iPGM_N | PF06415.4 | −263.4 | BPG-independent PGAM N-terminus (iPGM_N) |
| mTERF | PF02536.5 | −60 | mTERF |
| malic | PF00390.10 | 25 | Malic enzyme, N-terminal domain |
| p450 | PF00067.13 | −105 | Cytochrome P450 |
| peroxidase | PF00141.14 | −10 | Peroxidase |
| polyprenyl_synt | PF00348.8 | −43 | Polyprenyl synthetase |
| tRNA-synt_1c | PF00749.12 | −130.2 | tRNA synthetases class I (E and Q), catalytic domain |
| tRNA-synt_1c_C | PF03950.9 | 25 | tRNA synthetases class I (E and Q), anti-codon binding domain |
| zf-A20 | PF01754.7 | 25 | A20-like zinc finger |
| zf-AN1 | PF01428.7 | 0 | AN1-like Zinc finger |

TABLE 22-continued

| Pfam domain name | Accession # | gathering cutoff | domain description |
|---|---|---|---|
| zf-C2H2 | PF00096.17 | 17.7 | Zinc finger, C2H2 type |
| zf-C3HC4 | PF00097.16 | 16 | Zinc finger, C3HC4 type (RING finger) |
| zf-CCCH | PF00642.15 | 0 | Zinc finger C-x8-C-x5-C-x3-H type (and similar) |
| zf-CCHC | PF00098.14 | 17.9 | Zinc knuckle |
| zf-DHHC | PF01529.11 | −11 | DHHC zinc finger domain |
| zf-MYND | PF01753.9 | 11 | MYND finger |
| zf-Tim10_DDP | PF02953.6 | −5 | Tim10/DDP family zinc finger |

Example 10. Selection of Transgenic Plants with Enhanced Agronomic Trait(s)

This example illustrates identification of plant cells of the invention by screening derived plants and seeds for enhanced trait. Transgenic seed and plants in corn, soybean, cotton or canola with recombinant DNA identified in Table 2 are prepared by plant cells transformed with DNA that is stably integrated into the genome of the corn cell. Transgenic corn plant cells are transformed with recombinant DNA from each of the genes identified in Table 2. Progeny transgenic plants and seed of the transformed plant cells are screened for enhanced water use efficiency, enhanced cold tolerance, increased yield, enhanced nitrogen use efficiency, enhanced seed protein and enhanced seed oil as compared to control plants A. Selection for Enhanced Nitrogen Use Efficiency Transgenic corn seeds provided by the present invention are planted in fields with three levels of nitrogen (N) fertilizer being applied, e.g. low level (0 N), medium level (80 lb/ac) and high level (180 lb/ac). A variety of physiological traits are monitored. Plants with enhanced NUE provide higher yield as compared to control plants.

B. Selection for Increased Yield

Effective selection of enhanced yielding transgenic plants uses hybrid progeny of the transgenic plants for corn, cotton, and canola, or inbred progeny of transgenic plants for soybean plants plant such as corn, cotton, canola, or inbred plant such as soy, canola and cottoncotton over multiple locations with plants grown under optimal production management practices, and maximum pest control. A target for improved yield is about a 5% to 10% increase or more in yield as compared to yield produced by plants grown from seed for a control plant. Selection methods can be applied in multiple and diverse geographic locations, for example up to 16 or more locations, over one or more planting seasons, for example at least two planting seasons, to statistically distinguish yield improvement from natural environmental effects.

C. Selection for Enhanced Water Use Efficiency (WUE)

The selection process imposes a water withholding period to induce stressdrought followed by watering. For example, for corn, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

D. Selection for Growth Under Cold Stress (1) Cold germination assay—Trays of transgenic and control seeds are placed in a growth chamber at 9.7° C. for 24 days (no light). Seeds having higher germination rates as compared to the control are identified.

(2) Cold field efficacy trial—A cold field efficacy trial is used to identify gene constructs that confer enhanced cold vigor at germination and early seedling growth under early spring planting field conditions in conventional-till and simulated no-till environments. Seeds are planted into the ground around two weeks before local farmers begin to plant corn so that a significant cold stress is exerted onto the crop, named as cold treatment. Seeds also are planted under local optimal planting conditions such that the crop has little or no exposure to cold condition, named as normal treatment. At each location, seeds are planted under both cold and normal conditions with 3 repetitions per treatment. Two temperature monitors are set up at each location to monitor both air and soil temperature daily.

Seed emergence is defined as the point when the growing shoot breaks the soil surface. The number of emerged seedlings in each plot is counted everyday from the day the earliest plot begins to emerge until no significant changes in emergence occur. In addition, for each planting date, the latest date when emergence is 0 in all plots is also recorded. Seedling vigor is also rated at V3-V4 stage before the average of corn plant height reaches 10 inches, with 1=excellent early growth, 5=Average growth and 9=poor growth. Days to 50% emergence, maximum percent emergence and seedling vigor are used to determine plants with enhanced cold tolerance.

E. Screens for Transgenic Plant Seeds with Increased Protein and/or Oil Levels

This example sets forth a high-throughput selection for identifying plant seeds with improvement in seed composition using the Infratec 1200 series Grain Analyzer, which is a near-infrared transmittance spectrometer used to determine the composition of a bulk seed sample (Table 26). Near infrared analysis is a non-destructive, high-throughput method that can analyze multiple traits in a single sample scan. An NIR calibration for the analytes of interest is used to predict the values of an unknown sample. The NIR spectrum is obtained for the sample and compared to the calibration using a complex chemometric software package that provides predicted values as well as information on how well the sample fits in the calibration.

Infratec Model 1221, 1225, or 1227 with transport module by Foss North America is used with cuvette, item #1000-4033, Foss North America or for small samples with small cell cuvette, Foss standard cuvette modified by Leon Girard Co. Corn and soy check samples of varying composition maintained in check cell cuvettes are supplied by Leon Girard Co. NIT collection software is provided by Maximum Consulting Inc. Software. Calculations are performed automatically by the software. Seed samples are received in packets or containers with barcode labels from the customer. The seed is poured into the cuvettes and analyzed as received.

TABLE 23

| | |
|---|---|
| Typical sample(s): | Whole grain corn and soybean seeds |
| Analytical time to run method: | Less than 0.75 min per sample |
| Total elapsed time per run: | 1.5 minute per sample |
| Typical and minimum sample size: | Corn typical: 50 cc; minimum 30 cc |
| | Soybean typical: 50 cc; minimum 5 cc |
| Typical analytical range: | Determined in part by the specific calibration. |
| | Corn - moisture 5-15%, oil 5-20%, protein 5-30%, starch 50-75%, and density 1.0-1.3%. |
| | Soybean - moisture 5-15%, oil 15-25%, and protein 35-50%. |

Example 11. Cotton Transgenic Plants with Enhanced Agronomic Traits

Cotton transformation is performed as generally described in WO0036911 and in U.S. Pat. No. 5,846,797. Transgenic cotton plants containing each of the recombinant DNA having a sequence of SEQ ID NO: 1 through SEQ ID NO: 803 are obtained by transforming with recombinant DNA from each of the genes identified in Table 2. Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, e.g. cotton variety ST474, cotton variety FM 958, and cotton variety Siokra L-23, are used to compare the relative performance of the transgenic cotton plants containing the recombinant DNA. The specified culture conditions are growing a first set of transgenic and control plants under "wet" conditions, e.g. irrigated in the range of 85 to 100 percent of evapotranspiration to provide leaf water potential of −14 to −18 bars, and growing a second set of transgenic and control plants under "dry" conditions, e.g. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates; and improved fiber parameters.

The transgenic cotton plants of this invention are identified from among the transgenic cotton plants by agronomic trait screening as having increased yield and enhanced water use efficiency.

Example 12. Canola Plants with Enhanced Agrominic Traits

This example illustrates plant transformation in producing the transgenic canola plants of this invention and the production and identification of transgenic seed for transgenic canola having enhanced water use efficiency, enhanced cold tolerance, increased yield, enhanced nitrogen use efficiency, enhanced seed protein and enhanced seed oil.

Tissues from in vitro grown canola seedlings are prepared and inoculated with a suspension of overnight grown *Agrobacterium* containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterizations are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant Transgenic canola plant cells are transformed with recombinant DNA from each of the genes identified in Table 2. Transgenic progeny plants and seed of the transformed plant cells are screened for enhanced water use efficiency, enhanced cold tolerance, increased yield, enhanced nitrogen use efficiency, enhanced seed protein and enhanced seed oil.

Example 13. Selection of Transgenic Plants with Enhanced Agronomic Trait(s)

This example illustrates the preparation and identification by selection of transgenic seeds and plants derived from transgenic plant cells of this invention where the plants and seed are identified by screening for a transgenic plant having an enhanced agronomic trait imparted by expression or suppression of a protein selected from the group including the homologous proteins identified in Example 7. Transgenic plant cells of corn, soybean, cotton, canola, alfalfa, wheat and rice are transformed with recombinant DNA for expressing or suppressing each of the homologs identified in Example 7, Plants are regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. Plants are identified exhibiting enhanced traits imparted by expression or suppression of the homologous proteins.

Example 14. Monocot and Dicot Plant Transformation for the Suppression of Endogeneous Protein This example illustrates monocot and dicot plant transformation to produce nuclei of this invention in cells of a transgenic plant by transformation where the recombinant DNA suppresses the expression of an endogenous protein identified in Table 24.

Corn, soybean, cotton, or canola tissue are transformed as described in Examples 2-5 using recombinant DNA in the nucleus with DNA that is transcribed into RNA that forms double-stranded RNA targeted to an endogenous gene with DNA encoding the protein. The genes for which the double-stranded RNAs are targeted are the native gene in corn, soybean, cotton or canola that are homologs of the genes encoding the protein that has the function of the protein of *Arabidopsis thaliana* as identified in Table 24.

Populations of transgenic plants prepared in Examples 3, 4, 5, 6, or 13 with DNA for suppressing a gene identified in Table 2 as providing an enhanced trait by gene suppression are screened to identify an event from those plants with a nucleus of the invention by selecting the trait identified in this specification.

TABLE 24

| PEP SEQ ID | Pfam module | Construct ID | Traits |
|---|---|---|---|
| 115 | AP2 | 10177 | LN |
| 116 | zf-C2H2 | 12155 | CS SS |
| 118 | F-box::Tub | 11873 | LN PEG |
| 154 | Pex2_Pex12::zf-C3HC4 | 11113 | CS |
| 188 | Myb_DNA-binding::Myb_DNA-binding | 12325 | LN |
| 200 | bZIP_1 | 71228 | CK |

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11274312B2). An electronic copy of the "Sequence Listing" will also be available from the USPTO upon request and payment of the fee set forth in 37 CFR 1.19(b)(3).

What is claimed is:

1. A method for manufacturing non-natural, transgenic seed that can be used to produce a crop of transgenic plants with an enhanced trait resulting from expression of recombinant DNA in a plant cell nucleus, wherein said method for manufacturing said transgenic seed comprises:
   (a) screening a population of plants for said enhanced trait and said recombinant DNA, wherein individual plants in said population can exhibit said trait at a level less than, essentially the same as or greater than the level that said trait is exhibited in control plants which do not contain the recombinant DNA, wherein said enhanced trait is selected from the group of enhanced traits consisting of enhanced late stage growth and increased yield,
   (b) selecting from said population one or more plants that exhibit said trait at a level greater than the level that said trait is exhibited in control plants, and
   (c) collecting seeds from said one or more plants selected from step b, wherein the plant cell nucleus of said one or more plants comprises stably integrated, recombinant DNA comprising a promoter that is functional in said plant cell and that is operably linked to a protein coding DNA encoding a protein having at least 95% amino acid sequence identity to SEQ ID NO:1261.

2. The method of claim 1 wherein said method for manufacturing said transgenic seed further comprises
   (a) verifying that said recombinant DNA is stably integrated in said one or more selected plants, and
   (b) analyzing tissue of said one or more selected plants to determine the expression of a protein having the function of a protein having SEQ ID NO:1261.

3. The method of claim 1 wherein said seed is corn, soybean, cotton, alfalfa, canola wheat or rice seed.

4. A method of producing hybrid corn seed comprising:
   (a) acquiring hybrid corn seed from a herbicide tolerant corn plant which also has stably-integrated, recombinant DNA in a plant cell nucleus;
   (b) producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA;
   (c) selecting corn plants which are homozygous and hemizygous for said recombinant DNA by treating with an herbicide;
   (d) collecting seed from herbicide-treated-surviving corn plants and planting said seed to produce further progeny corn plants;
   (e) repeating steps (c) and (d) at least once to produce an inbred corn line; and
   (f) crossing said inbred corn line with a second corn line to produce hybrid seed, wherein the plant cell nucleus of said hybrid seed comprises stably integrated, recombinant DNA comprising a promoter that is functional in said plant cell and that is operably linked to a protein coding DNA encoding a protein having at least 95% amino acid sequence identity to SEQ ID NO: 1261, and wherein the herbicide tolerant hybrid corn plant is selected to have an enhanced trait relative to control plants which do not contain the recombinant DNA, wherein said enhanced trait is selected from the group of enhanced traits consisting of enhanced late stage growth and increased yield.

5. The method of claim 1 wherein said protein coding DNA encodes a protein having at least 98% amino acid sequence identity to SEQ ID NO:1261.

6. The method of claim 1 wherein the plant cell nucleus further comprises DNA expressing a protein that provides tolerance from exposure to an herbicide applied at levels that are lethal to a wild type of said plant cell.

7. The method of claim 6 wherein said herbicide is a glyphosate, dicamba, or glufosinate compound.

8. The method of claim 4 wherein said protein coding DNA encodes a protein having at least 98% amino acid sequence identity to SEQ ID NO:1261.

9. The method of claim 4 wherein the plant cell nucleus further comprises DNA expressing a protein that provides tolerance from exposure to an herbicide applied at levels that are lethal to a wild type of said plant cell.

10. The method of claim 9 wherein said herbicide is a glyphosate, dicamba, or glufosinate compound.

* * * * *